United States Patent
Alipour et al.

(10) Patent No.: US 11,298,402 B2
(45) Date of Patent: Apr. 12, 2022

(54) LYSOSOMAL DEGRADATION OF LIPIDS AND PROTEINS AND METHOD OF USE THEREOF

(71) Applicant: University of Ottawa, Ottawa (CA)

(72) Inventors: Mohsen Amir Alipour, Ottawa (CA); Zemin Yao, Orleans (CA)

(73) Assignee: University of Ottawa, Ottawa (CA)

( * ) Notice: Subject to any disclaimer, the term of this patent is extended or adjusted under 35 U.S.C. 154(b) by 221 days.

(21) Appl. No.: 15/743,213

(22) PCT Filed: Jul. 8, 2016

(86) PCT No.: PCT/CA2016/000192
§ 371 (c)(1),
(2) Date: Jan. 9, 2018

(87) PCT Pub. No.: WO2017/008141
PCT Pub. Date: Jan. 19, 2017

(65) Prior Publication Data
US 2019/0125827 A1    May 2, 2019

Related U.S. Application Data

(60) Provisional application No. 62/191,274, filed on Jul. 10, 2015.

(51) Int. Cl.
| | | |
|---|---|---|
| *A61K 38/17* | (2006.01) | |
| *A61K 31/202* | (2006.01) | |
| *A61K 31/7088* | (2006.01) | |
| *A61K 39/395* | (2006.01) | |
| *A61P 3/06* | (2006.01) | |
| *A61P 3/00* | (2006.01) | |
| *C07K 14/47* | (2006.01) | |
| *C12N 15/113* | (2010.01) | |

(52) U.S. Cl.
CPC ........ *A61K 38/1709* (2013.01); *A61K 31/202* (2013.01); *A61K 31/7088* (2013.01); *A61K 39/395* (2013.01); *A61P 3/00* (2018.01); *A61P 3/06* (2018.01); *C07K 14/4702* (2013.01); *C12N 15/113* (2013.01); *C12N 2310/14* (2013.01)

(58) Field of Classification Search
None
See application file for complete search history.

(56) References Cited

FOREIGN PATENT DOCUMENTS

WO    WO 2005/056049 A1    6/2005

OTHER PUBLICATIONS

Medline Plus (https://medlineplus.gov/fattyliverdisease.html; Apr. 26, 2017).*
Medline Plus (https://medlineplus.gov/fattyliverdisease.html; Apr. 26, 2017) teaches.*
Bagshaw et al. ("The Arf-family protein, Arl8b, is involved in the special distribution of lysosomes" Biochemical and Biophysical Reseach communications 344 (2006) 1186-1191).*
Ferreira et al. ("Arl8b and SKIP act together to link lysosomes to kinesin-1" Developmental Cell 21, 1171-1178, 2011).*
Khatter et al. (The small GTPase Arl8b regulates assembly of mammalian HOPS complex on lysosomes 2015; Journal of Cell Science 128; 1746-1761).*
Extended European Search Report for EP 16823576.0, dated Feb. 25, 2019.
Khatter et al., Arf-like GTPase Arl8: Moving from the periphery to the center of lysosomal biology. Cellular Logistics 2015;5:3. DOI: 10.1080/21592799.2015.1086501.
Khatter et al., The small GTPase Arl8b regulates assembly of the mammalian HOPS complex on lysosomes. J Cell Sci 2015;128:1746-1761. doi: 10.1242/jcs.162651.
Numrich et al., The I-BAR protein Ivy1 is an effector of the Rab7 GTPase Ypt7 involved in vacuole membrane homeostasis. J Cell Sci 2015;128:2278-2292. doi: 10.1242/jcs.164905.
Sahu et al., Microautophagy of cytosolic proteins by late endosomes. Dev Cell. Jan. 18, 2011;20(1):131-9. doi: 10.1016/j.devcel.2010.12.003.
Sundaram et al., Recent progress in understanding protein and lipid factors affecting hepatic VLDL assembly and secretion. Nutrition & Metabolism 2010;7:35. https://doi.org/10.1186/1743-7075-7-35.
Wartosch et al., Recruitment of VPS33A to HOPS by VPS16 Is Required for Lysosome Fusion with Endosomes and Autophagosomes. Traffic. Jul. 2015;16(7):727-42. doi: 10.1111/tra.12283. Epub Apr. 30, 2015.
International Search Report and Written Opinion for PCT/CA2016/000192, dated Sep. 28, 2016.
International Preliminary Report on Patentability for PCT/CA2016/000192, dated Jan. 25, 2018.
Numrich et al., The I-BAR protein Ivy1 is an effector of the Rab7 GTPase Ypt7 involved in vacuole membrane homeostasis. *J. Cell Sci.* Jul. 1, 2015;128(13):2278-92. doi: 10.1242/jcs.164905. Epub May 21, 2015.

* cited by examiner

*Primary Examiner* — James H Alstrum-Acevedo
*Assistant Examiner* — Tara L Martinez
(74) *Attorney, Agent, or Firm* — Wolf, Greenfield & Sacks, P.C.

(57) ABSTRACT

Methods for modulating lysosome-mediated microautophagy of a lipid or protein substrate in a cell are provided herein. In certain embodiments, said methods may comprise increasing lysosome-mediated microautophagy by treating the cell with a microautophagy-enhancing agent which increases lysosomal association-dissociation events between lysosomes and the cellular lipid or protein substrate and/or increases lysosomal degradation capacity; or decreasing lysosome-mediated microautophagy by treating the cell with a microautophagy-reducing agent which reduces lysosomal association-dissociation events between lysosomes and the cellular lipid or protein substrate and/or decreases lysosomal degradation capacity; thereby modulating lysosome-mediated microautophagy of the lipid or protein substrate.

2 Claims, 76 Drawing Sheets

Specification includes a Sequence Listing.

FIGURE 10
LDs, Lysotracker Blue, Peroxisome        LDs, Lysotracker Blue, Peroxisome
(a)                                       (b)
Oleate overnight, Control                 +EPA, 1HR
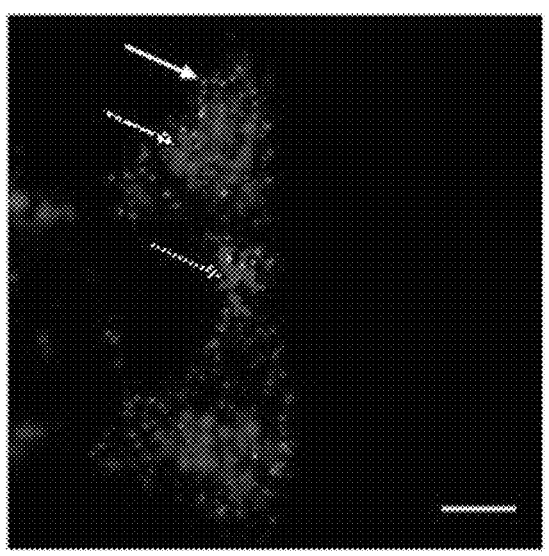 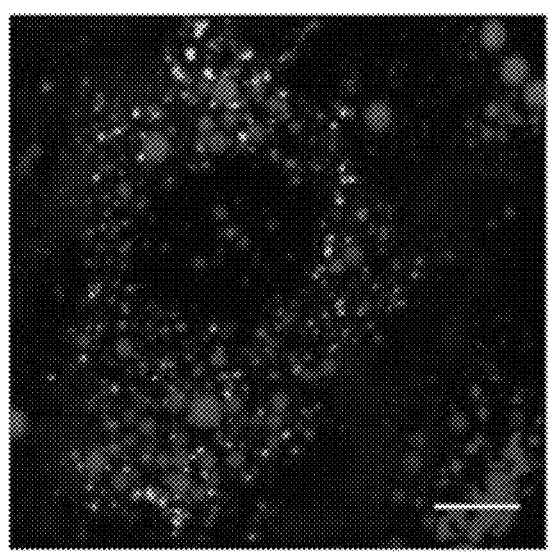

FIGURE 13
A 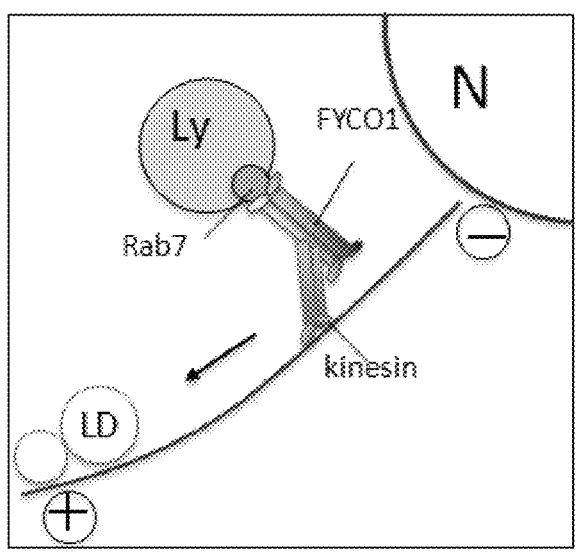
B 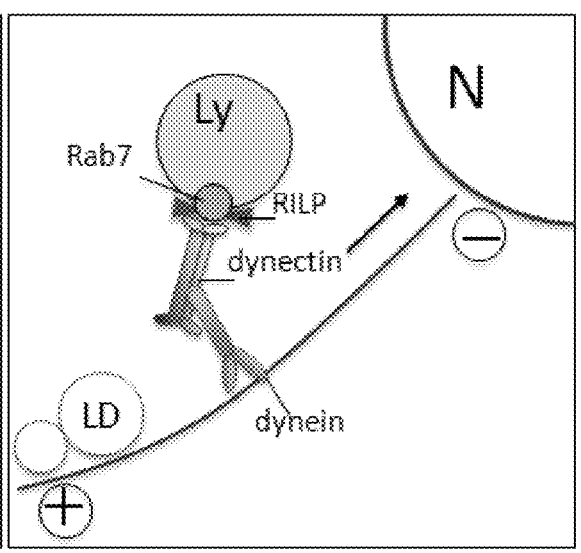

FIGURE 16
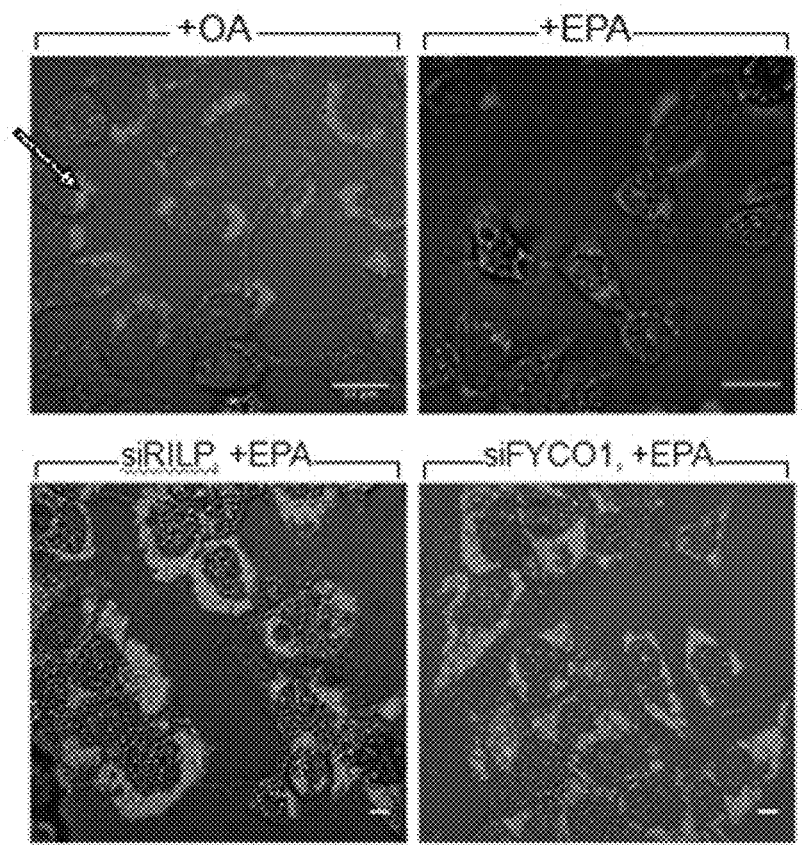
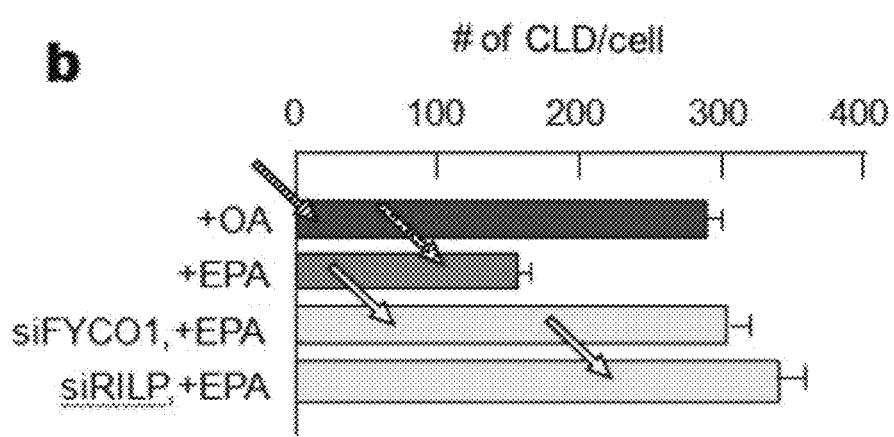

FIGURE 32A

Arl8bwt-GFP plasmid DNA (sequencing data obtained using CMV forward primer)
---
TTCCCCAAATTATAGGAGCAGAGCTCTCTGGCTACTAGAGAACCCACTGCTTACTGGCTTATCGAAATTAATACGAC
TCACTATAGGGAGACCCAAGCTGGCTAGTTAAGCTTGGTACCGAGCTCGGATCCACTAGTCCAGTGTGGTGGAATTG
CCCTTCACCATGCTGGCGCTCATCTCCCGCCTGCTGGACTGGTTCCGTTCGCTCTTCTGGAAGGAAGAGATGGAGCT
GACGCTCGTGGGGCTGCAGTACTCGGGCAAGACCACCTTCGTCAATGTCATCGCGTCAGGTCAATTCAGTGAAGATA
TGATACCCACAGTGGGCTTCAACATGAGGAAGGTAACTAAAGGTAACGTCACAATAAAGATCTGGGACATAGGAGGA
CAACCCGATTTCGAAGTATGTGGGAGCGGTATTGCAGAGGAGTCAATGCTATTGTTTACATGATAGATGCTGCAGA
TCGTGAAAAGATAGAAGCTTCCCGAAATGAGCTACATAATCTTCTAGATAAACCACAGTTACAAGGAATTCCAGTGC
TAGTGCTTGGAAACAAGAGAGATCTTCCTAATGCCTTGGATGAGAAACAGCTAATTGAAAAAATGAATCTGTCTGCT
ATTCAGGATAGAGAAATTTGCTGCTATTCAATTTCTTGCAAAGAAAAGGATAATATAGATATCACACTTCAGTGGCT
TATTCAGCATTCAAAATCTAGAAGAAGCGAAGGGCAATTCTGCAGATATCCAGCACAGTGGCGGCCGCTCGAGTCTA
GAATGGCTAGCAAAGGAGAAGAACTTTTCACTGGAGTTGTCCCAATTCTTGTTTGAATTAGATGGTGATGTTAATGG
GCACAAATTTTCTGTCAGTGGAGAGGGTGAAGGTGAATGCTACATACGGAAAGCTTACCCTTAAATTTATTTTGCAC
TACTGGAAAACTACCTGTTCCATGGGCCAATACTTGTCACTACTTTCTCTTATGTTGTCCATGCTTTTTCCGTTAT
CCGGATAATATGAAACGGCATGACTTTTCCAGAGTGCCATGGCCCGAAGGGTTATGTTCTAGGAACGCACTTATATC
TTTCAAGATGACGGGAACTAACAAGAACCCGTGCTGAAGTCAAGTTTGAAGGGGATACCTTGGTTTATCGTACGAGT
TTAAAGGGTATTGATTTTAAAGAAATAGGAATACCATCCTCCGGACTCCTACTTCTGTAGTTCCACTCTATTACCTC
CCCACCATTGTGTTATATTCCATGTGCCGGCTCACCAAGTGAATGGTATTACTAAGCTAATACTCTCATCAATCTTC
CTCCACCAACACACTGAG Arl8bwt-GFP (sequence data annotated by M.Sundaram)
---

```
                          10        20        30        40        50
                  ....|....|....|....|....|....|....|....|....|....|
Arl8b-GFP(CMV-F)  1   TTCCCCAAATTATAGGAGCAGAGCTCTCTGGCTACTAGAGAACCCACTGC  50

60        70        80        90       100
                  ....|....|....|....|....|....|....|....|....|....|
Arl8b-GFP(CMV-F)  51  TTACTGGCTTATCGAAATTAATACGACTCACTATAGGGAGACCCAAGCTG  100

110       120       130       140       150
                  ....|....|....|....|....|....|....|....|....|....|
Arl8b-GFP(CMV-F)  101 GCTAGTTAAGCTTGGTACCGAGCTCGGATCCACTAGTCCAGTGTGGTGGA  150
                                   KpnI         BamHI 160       170       180       190       200
                  ....|....|....|....|....|....|....|....|....|....|
Arl8b-GFP(CMV-F)  151 ATTGCCCTTCACCATGCTGGCGCTCATCTCCCGCCTGCTGGACTGGTTCC  200
                                     M  L  A  L  I  S  R  L  L  D  W  F 210       220       230       240       250
                  ....|....|....|....|....|....|....|....|....|....|
Arl8b-GFP(CMV-F)  201 GTTCGCTCTTCTGGAAGGAAGAGATGGAGCTGACGCTCGTGGGGCTGCAG  250
                      R  S  L  F  W  K  E  E  M  E  L  T  L  V  G  L  Q 260       270       280       290       300
                  ....|....|....|....|....|....|....|....|....|....|
Arl8b-GFP(CMV-F)  251 TACTCGGGCAAGACCACCTTCGTCAATGTCATCGCGTCAGGTCAATTCAG  300
                      Y  S  G  K  T  T  F  V  N  V  I  A  S  G  Q  F  S
```

Arl8b translated amino acid sequence

FIGURE 32B

```
                        310        320        330        340        350
                   ....|....|....|....|....|....|....|....|....|....|
Arl8b-GFP(CMV-F)  301  TGAAGATATGATACCCACAGTGGGCTTCAACATGAGGAAGGTAACTAAAG  350
                        E  D  M  I  P  T  V  G  F  N  M  R  K  V  T  K 360        370        380        390        400
                   ....|....|....|....|....|....|....|....|....|....|
Arl8b-GFP(CMV-F)  351  GTAACGTCACAATAAAGATCTGGGACATAGGAGGACAACCCCGATTTCGA  400
                        G  N  V  T  I  K  I  W  D  I  G  G  Q  P  R  F  R 410        420        430        440        450
                   ....|....|....|....|....|....|....|....|....|....|
Arl8b-GFP(CMV-F)  401  AGCATGTGGGAGCGGTATTGCAGAGGAGTCAATGCTATTGTTTACATGAT  450
                        S  M  W  E  R  Y  C  R  G  V  N  A  I  V  Y  M  I 460        470        480        490        500
                   ....|....|....|....|....|....|....|....|....|....|
Arl8b-GFP(CMV-F)  451  AGATGCTGCAGATCGTGAAAAGATAGAAGCTTCCCGAAATGAGCTACATA  500
                        D  A  A  D  R  E  K  I  E  A  S  R  N  E  L  H 510        520        530        540        550
                   ....|....|....|....|....|....|....|....|....|....|
Arl8b-GFP(CMV-F)  501  ATCTTCTAGATAAACCACAGTTACAAGGAATTCCAGTGCTAGTGCTTGGA  550
                        I  L  L  D  K  P  Q  L  Q  G  I  P  V  L  V  L  G 560        570        580        590        600
                   ....|....|....|....|....|....|....|....|....|....|
Arl8b-GFP(CMV-F)  551  AACAAGAGAGATCTTCCTAATGCCTTGGATGAGAAACAGCTAATTGAAAA  600
                        N  K  R  D  L  P  N  A  L  D  E  K  Q  L  I  E  K 610        620        630        640        650
                   ....|....|....|....|....|....|....|....|....|....|
Arl8b-GFP(CMV-F)  601  AATGAATCTGTCTGCTATTCAGGATAGAGAAATTTGCTGCTATTCAATTT  650
                        M  N  L  S  A  I  Q  D  R  E  I  C  C  Y  S  I 660        670        680        690        700
                   ....|....|....|....|....|....|....|....|....|....|
Arl8b-GFP(CMV-F)  651  CTTGCAAAGAAAAGGATAATATAGATATCACACTTCAGTGGCTTATTCAG  700
                        S  C  K  E  K  D  N  I  D  I  T  L  Q  W  L  I  Q 710        720        730        740        750
                   ....|....|....|....|....|....|....|....|....|....|
Arl8b-GFP(CMV-F)  701  CATTCAAAATCTAGAAGAAGCGAAGGGCAATTCTGCAGATATCCAGCACA  750
                        H  S  K  S  R  R  S  E  G  Q  F  C  R  Y  P  A  Q 760        770        780        790        800
                   ....|....|....|....|....|....|....|....|....|....|
Arl8b-GFP(CMV-F)  751  GTGGCGGCCGCTCGAGTCTAGAATGGTTAGCAAAGGAGAAGAACTTTTCA  800
                        V  A  A  A  L  E  S  R  M  V  S  K  G  E  E  L  F
                                  XhoI            NheI 810        820        830        840        850
                   ....|....|....|....|....|....|....|....|....|....|
```

GFP variant tag

FIGURE 32C

```
                      ....|....|....|....|....|....|....|....|....|....|
Arl8b-GFP(CMV-F)  801 CTGGAGTTGTCCCAATTCTTGTT  ATTAGATGGTGATG   TGGGCA 850
                      T   G  V  V  P  I  L  V   *                MseI
                            860       870       880       890       900
                      ....|....|....|....|....|....|....|....|....|....|
Arl8b-GFP(CMV-F)  851 CAAATTTTCTGTCAGTGGAGAGGGTGAAGGTGAATGCTACATACGGAAAG 900

910       920       930       940       950
                      ....|....|....|....|....|....|....|....|....|....|
Arl8b-GFP(CMV-F)  901 CTTACCCTTAAATTTATTTTGCACTACTGGAAAACTACCTGTTCCATGGG 950

960       970       980       990      1000
                      ....|....|....|....|....|....|....|....|....|....|
Arl8b-GFP(CMV-F)  951 CCAATACTTGTCACTACTTTCTCTTATGTTGTCCATGCTTTTTCCCGTTA
                 1000

1010      1020      1030      1040      1050
                      ....|....|....|....|....|....|....|....|....|....|
Arl8b-GFP(CMV-F) 1001 TCCGGATAATATGAAACGGCATGACTTTTCCAGAGTGCCATGGCCCGAAG
                 1050

1060      1070      1080      1090      1100
                      ....|....|....|....|....|....|....|....|....|....|
Arl8b-GFP(CMV-F) 1051 GGTTATGTTCTAGGAACGCACTTATATCTTTCAAGATGACGGGAACTAAC
                 1100

1110      1120      1130      1140      1150
                      ....|....|....|....|....|....|....|....|....|....|
Arl8b-GFP(CMV-F) 1101 AAGAACCCGTGCTGAAGTCAAGTTTGAAGGGGATACCTTGGTTTATCGTA
                 1150

1160      1170      1180      1190      1200
                      ....|....|....|....|....|....|....|....|....|....|
Arl8b-GFP(CMV-F) 1151 CGAGTTTAAAGGGTATTGATTTTAAAGAAATAGGAATACCATCCTCCGGA
                 1200

1210      1220      1230      1240      1250
                      ....|....|....|....|....|....|....|....|....|....|
Arl8b-GFP(CMV-F) 1201 CTCCTACTTCTGTAGTTCCACTCTATTACCTCCCCACCATTGTGTTATAT
                 1250

1260      1270      1280      1290      1300
                      ....|....|....|....|....|....|....|....|....|....|
Arl8b-GFP(CMV-F) 1251 TCCATGTGCCGGCTCACCAAGTGAATGGTATTACTAAGCTAATACTCTCA
                 1300
```

FIGURE 32D

```
                            1310       1320
                    ....|....|....|....|....|..
Arl8b-GFP(CMV-F)  1301 TCAATCTTCCTCCACCAACACACTGAG 1327
```

Figure 33A

Arl8bwt-mcherry plasmid DNA (sequencing data obtained using CMV forward primer)

```
CACCCAAGACAAAAGCAGAGCTGGTTTAGTGACCGTCAGATCCGCTAGCGCTACCGGACTCAGATCTCGAGATGCTG
GCGCTCATCTCCCGCCTGCTGGACTGGTTCCGTTCGCTCTTCTGGAAGGAAGAGATGGAGCTGACGCTCGTGGGGCT
GCAGTACTCGGGCAAGACCACCTTCGTCAATGTCATCGCGTCAGGTCAATTCAGTGAAGATATGATACCCACAGTGG
GCTTCAACATGAGGAAGGTAACTAAAGGTAACGTCACAATAAAGATCTGGGACATAGGAGGACAACCCCGATTTCGA
AGCATGTGGGAGCGGTATTGCAGAGGAGTCAATGCTATTGTTTACATGATAGATGCTGCAGATCGTGAAAAGATAGA
AGCTTCCCGAAATGAGCTACATAATCTTCTAGATAAACCACAGTTACAAGGAATTCCAGTGCTAGTGCTTGGAAACA
AGAGAGATCTTCCTAATGCCTTGGATGAGAAACAGCTAATTGAAAAAATGAATCTGTCTGCTATTCAGGATAGAGAA
ATTTGCTGCTATTCAATTTCTTGCAAAGAAAAGGATAATATAGATATCACACTTCAGTGGCTTATTCAGCATTCAAA
ATCTAGAAGAAGCCGGGATCCGATGGTGAGCAAGGGCGAGGAGGATAACATGGCCATCATCAAGGAGTTCATGCGCT
TCAAGGTGCACATGGAGGGCTCCGTGAACGGCCACGAGTTCGAGATCGAGGGCGAGGGCGAGGGCCGCCCCTACGAG
GGCACCCAGACCGCCAAGCTGAAGGTGACCAAGGGTGGCCCCCTGCCCTTCGCCTGGGACATCCTGTCCCCTCAGTT
CATGTACGGCTCCAAGGCCTACGTGAAGCACCCCGCCGACATCCCCGACTACTTGAAGCTGTCCTTCCCCGAGGGCT
TCAAGTGGGAGCGCGTGATGAACTTCGAGGACGGCGGCGTGGTGACCGTGACCCAGGACTCCTCCCTGCAGGACGGC
GAGTTCATCTACAAGTGAAGCTGCGCGGCACCAACTTCCCCTCCGACGGCCCCGTAATGCAGAAGAGGACCATGGGC
TGGGAGGCCTCCTCGAGCGATGTACCCCGAGGACGCGCCCTGAGGCGAGATCAGCAGAGGCTGAGCTGAGACGCCGCC
ACTACGACGCTGAGTCAGAACTACTACAAGTCAGAGCCGGCAGCTGCTGGCCTACACGTCACTTCAGTGGAACTTAA
CTTCACAAAGCGAGGAAC
```

Arl8bwt-mcherry (sequence data annotated by M.Sundaram)

```
                        10         20         30         40         50
                ....|....|....|....|....|....|....|....|....|....|
Arl8b-mcherry  1  CACCCAAGACAAAAGCAGAGCTGGTTTAGTGACCGTCAGATCCGCTAGCG  50
                                                            XbaI 60         70         80         90        100
                ....|....|....|....|....|....|....|....|....|....|
Arl8b-mcherry  51 CTACCGGACTCAGATCTCGAGATGCTGGCGCTCATCTCCCGCCTGCTGGA  100
                      PasRI  M  L  A  L  I  S  R  L  L  D 110        120        130        140        150
                ....|....|....|....|....|....|....|....|....|....|
Arl8b-mcherry 101 CTGGTTCCGTTCGCTCTTCTGGAAGGAAGAGATGGAGCTGACGCTCGTGG  150
                   W  F  R  S  L  F  W  K  E  E  M  E  L  T  L  V 160        170        180        190        200
                ....|....|....|....|....|....|....|....|....|....|
Arl8b-mcherry 151 GGCTGCAGTACTCGGGCAAGACCACCTTCGTCAATGTCATCGCGTCAGGT  200
                   G  L  Q  Y  S  G  K  T  T  F  V  N  V  I  A  S 210        220        230        240        250
                ....|....|....|....|....|....|....|....|....|....|
Arl8b-mcherry 201 CAATTCAGTGAAGATATGATACCCACAGTGGGCTTCAACATGAGGAAGGT  250
                   Q  F  S  E  D  M  I  P  T  V  G  F  N  M  R  K 260        270        280        290        300
                ....|....|....|....|....|....|....|....|....|....|
Arl8b-mcherry 251 AACTAAAGGTAACGTCACAATAAAGATCTGGGACATAGGAGGACAACCCC  300
                   T  K  G  N  V  T  I  K  I  W  D  I  G  G  Q  P
```

Arl8b translated amino acid sequence

Figure 33B

```
                       310        320        330        340        350
                  ....|....|....|....|....|....|....|....|....|....|
Arl8b-mcherry 301 GATTTCGAAGCATGTGGGAGCGGTATTGCAGAGGAGTCAATGCTATTGTT 350
                   R  F  E  A  C  G  S  G  I  A  E  E  S  M  L  L 360        370        380        390        400
                  ....|....|....|....|....|....|....|....|....|....|
Arl8b-mcherry 351 TACATGATAGATGCTGCAGATCGTGAAAAGATAGAAGCTTCCCGAAATGA 400
                   Y  M  I  D  A  A  D  R  E  K  I  E  A  S  R  N  E 410        420        430        440        450
                  ....|....|....|....|....|....|....|....|....|....|
Arl8b-mcherry 401 GCTACATAATCTTCTAGATAAACCACAGTTACAAGGAATTCCAGTGCTAG 450
                   L  H  N  L  L  D  K  P  Q  L  Q  G  I  P  V  L 460        470        480        490        500
                  ....|....|....|....|....|....|....|....|....|....|
Arl8b-mcherry 451 TGCTTGGAAACAAGAGAGATCTTCCTAATGCCTTGGATGAGAAACAGCTA 500
                   V  L  G  N  K  R  D  L  P  N  A  L  D  E  K  Q  L 510        520        530        540        550
                  ....|....|....|....|....|....|....|....|....|....|
Arl8b-mcherry 501 ATTGAAAAAATGAATCTGTCTGCTATTCAGGATAGAGAAATTTGCTGCTA 550
                   I  E  K  M  N  L  S  A  I  Q  D  R  E  I  C  C  Y 560        570        580        590        600
                  ....|....|....|....|....|....|....|....|....|....|
Arl8b-mcherry 551 TTCAATTTCTTGCAAAGAAAAGGATAATATAGATATCACACTTCAGTGGC 600
                   S  I  S  C  K  E  K  D  N  I  D  I  T  L  Q  W 610        620        630        640        650
                  ....|....|....|....|....|....|....|....|....|....|
Arl8b-mcherry 601 TTATTCAGCATTCAAAATCTAGAAGAAGCCGGATCCGATGGTGAGCAAG 650
                   L  I  Q  H  S  K  S  R  R  S        R  D  P  M  V  S  K
                                              BamHI 660        670        680        690        700
                  ....|....|....|....|....|....|....|....|....|....|
Arl8b-mcherry 651 GGCGAGGAGGATAACATGGCCATCATCAAGGAGTTCATGCGCTTCAAGGT 700
                   G  E  E  D  N  M  A  I  I  K  E  F  M  R  F  K  V 710        720        730        740        750
                  ....|....|....|....|....|....|....|....|....|....|
Arl8b-mcherry 701 GCACATGGAGGGCTCCGTGAACGGCCACGAGTTCGAGATCGAGGGCGAGG 750
                   H  M  E  G  S  V  N  G  H  E  F  E  I  E  G  E 760        770        780        790        800
                  ....|....|....|....|....|....|....|....|....|....|
Arl8b-mcherry 751 GCGAGGGCCGCCCCTACGAGGGCACCCAGACCGCCAAGCTGAAGGTGACC 800
                   G  E  G  R  P  Y  E  G  T  Q  T  A  K  L  K  V  T 810        820        830        840        850
                  ....|....|....|....|....|....|....|....|....|....|
Arl8b-mcherry 801 AAGGGTGGCCCCCTGCCCTTCGCCTGGGACATCCTGTCCCCTCAGTTCAT 850
```

Figure 33C

```
                              K  G  G  P  L  P  F  A  W  D  I  L  S  P  Q  F  M
                             860        870        880        890        900
                       ....|....|....|....|....|....|....|....|....|....|
Arl8b-mcherry   851    GTACGGCTCCAAGGCCTACGTGAAGCACCCCGCCGACATCCCCGACTACT  900
                        Y  G  S  K  A  Y  V  K  H  P  A  D  I  P  D  Y 910        920        930        940        950
                       ....|....|....|....|....|....|....|....|....|....|
Arl8b-mcherry   901    TGAAGCTGTCCTTCCCCGAGGGCTTCAAGTGGGAGCGCGTGATGAACTTC  950
                        L  K  L  S  F  P  E  G  F  K  W  E  R  V  M  N  F 960        970        980        990       1000
                       ....|....|....|....|....|....|....|....|....|....|
Arl8b-mcherry   951    GAGGACGGCGGCGTGGTGACCGTGACCCAGGACTCCTCCCTGCAGGACGG 1000
                        E  D  G  G  V  V  T  V  T  Q  D  S  S  L  Q  D  G 1010       1020       1030       1040       1050
                       ....|....|....|....|....|....|....|....|....|....|
Arl8b-mcherry  1001    CGAGTTCATCTACAAGGTGAAGCTGCGCGGCACCAACTTCCCCTCCGACGG 1050
                        E  F  I  Y  K  V                      BsaXI 1060       1070       1080       1090       1100
                       ....|....|....|....|....|....|....|....|....|....|
Arl8b-mcherry  1051    CCCCGTAATGCAGAAGAGGACCATGGGCTGGAGGCCTCCTCGAGCGATGT 1100

1110       1120       1130       1140       1150
                       ....|....|....|....|....|....|....|....|....|....|
Arl8b-mcherry  1101    ACCCCGAGGACGCGCCCTGAGGCGAGATCAGCAGAGGCTGAGCTGAGACG 1150

1160       1170       1180       1190       1200
                       ....|....|....|....|....|....|....|....|....|....|
Arl8b-mcherry  1151    CCGCCACTACGACGCTGAGTCAGAACTACTACAAGTCAGAGCCGGCAGCT 1200

1210       1220       1230       1240       1250
                       ....|....|....|....|....|....|....|....|....|....|
Arl8b-mcherry  1201    GCTGGCCTACACGTCACTTCAGTGGAACTTAACTTCACAAAGCGAGGAAC 1250
```

FIGURE 34A

Arl8b-DA-mCherry plasmid DNA (sequencing data obtained using CMV forward primer)

TTTCAACGGAATACAAATAGCGAGCTGGTTTAGTGACCGTCAGATCCGCTAGCGCTACCGGACTCAGATCTCGAGAT
GCTGGCGCTCATCTCCCGCCTGCTGGACTGGTTCCGTTCGCTCTTCTGGAAGGAAGAGATGGAGCTGACGCTCGTGG
GGCTGCAGTACTCGGGCAAGACCACCTTCGTCAATGTCATCGCGTCAGGTCAATTCAGTGAAGATATGATACCCACA
GTGGGCTTCAACATGAGGAAGGTAACTAAAGGTAACGTCACAATAAAGATCTGGGACATAGGAGGACTACCCCGATT
TCGAAGCATGTGGGAGCGGTATTGCAGAGGAGTCAATGCTATTGTTTACATGATAGATGCTGCAGATCGTGAAAAGA
TAGAAGCTTCCCGAAATGAGCTACATAATCTTCTAGATAAACCACAGTTACAAGGAATTCCAGTGCTAGTGCTTGGA
AACAAGAGAGATCTTCCTAATGCCTTGGATGAGAAACAGCTAATTGAAAAAATGAATCTGTCTGCTATTCAGGATAG
AGAAATTTGCTGCTATTCAATTTCTTGCAAAGAAAAGGATAATATAGATATCACACTTCAGTGGCTTATTCAGCATT
CAAAATCTAGAAGAAGCCGGATCCGATGGTGAGCAAGGGCGAGGAGGATAACATGGCCATCATCAAGGAGTTCATG
CGCTTCAAGGTGCACATGGAGGGCTCCGTGAACGGCCACGAGTTCGAGATCGAGGGCGAGGGCGAGGGCCGCCCTA
CGAGGGCACCCAGACCGCCAAGCTGAAGGTGACCAAGGGTGGCCCCCTGCCCTTCGCCTGGGACATCCTGTCCCCTC
AGTTCATGTACGGCTCCAAGGCCTACGTGAAGCACCCCGCCGACATCCCCGACTACTTGAAGCTGTCCTTCCCCGAG
GGCTTCAAGTGGGAGCGCGTGATGAACTTCGAGGACGGCGGCGTGGTGACCGTGACCCAGGACTCCTCCCTGCAGGA
CGGCGAGTTCATCTACAGTGAAGCTGCGCGGCACCAACTTCCCCTCCGACGCTCGTATGCAGAGAGACATGGGCTGG
GAGCTCTCGAGCGATGTACCCGAGACGCGCCTGAGGCGAGATCAGCAGAGCTGAGCTGAGGACGCGCACTACGACGC
TGAAGTCAGACACTACAGTCAGAAGCCGTTCAGCTGCC

Arl8b-DA-mCherry (sequence data annotated by M.Sundaram)

```
                   10        20        30        40        50
                ....|....|....|....|....|....|....|....|....|....|
Arl8b-DA(CMV-F)  1  TTTCAACGGAATACAAATAGCGAGCTGGTTTAGTGACCGTCAGATCC       50
                                                                  NheI 60        70        80        90       100
                ....|....|....|....|....|....|....|....|....|....|
Arl8b-DA(CMV-F) 51  GCTACCGGACTCAGATCTCGAGATGCTGGCGCTCATCTCCCGCCTGC     100
                                    PaeR7I   M  L  A  L  I  S  R  L 110       120       130       140       150
                ....|....|....|....|....|....|....|....|....|....|
Arl8b-DA(CMV-F) 101 TGGACTGGTTCCGTTCGCTCTTCTGGAAGGAAGAGATGGAGCTGACGCTC 150
                    L  D  W  F  R  S  L  F  W  K  E  E  M  E  L  T  L 160       170       180       190       200
                ....|....|....|....|....|....|....|....|....|....|
Arl8b-DA(CMV-F) 151 GTGGGGCTGCAGTACTCGGGCAAGACCACCTTCGTCAATGTCATCGCGTC 200
                    V  G  L  Q  Y  S  G  K  T  T  F  V  N  V  I  A  S 210       220       230       240       250
                ....|....|....|....|....|....|....|....|....|....|
Arl8b-DA(CMV-F) 201 AGGTCAATTCAGTGAAGATATGATACCCACAGTGGGCTTCAACATGAGGA 250
                    G  Q  F  S  E  D  M  I  P  T  V  G  F  N  M  R 260       270       280       290       300
                ....|....|....|....|....|....|....|....|....|....|
Arl8b-DA(CMV-F) 251 AGGTAACTAAAGGTAACGTCACAATAAAGATCTGGGACATAGGAGGACTA 300
                    K  V  T  K  G  N  V  T  I  K  I  W  D  I  G  G  L
                                                                ***
```

Arl8b-DA translated amino acid sequence

*** mutation Q75 → L

Figure 34B

```
                          310        320        330        340        350
                     ....|....|....|....|....|....|....|....|....|....|
Arl8b-DA(CMV-F)  301 CCCCGATTTCGAAGCATGTGGGAGCGGTATTGCAGAGGAGTCAATGCTAT 350
                      P  R  F  E  A  C  G  S  G  I  A  E  E  S  M  L
                          360        370        380        390        400
                     ....|....|....|....|....|....|....|....|....|....|
Arl8b-DA(CMV-F)  351 TGTTTACATGATAGATGCTGCAGATCGTGAAAAGATAGAAGCTTCCCGAA 400
                      C  L  H  D  R  C  C  R  S  V  K  D  R  S  L  P 410        420        430        440        450
                     ....|....|....|....|....|....|....|....|....|....|
Arl8b-DA(CMV-F)  401 ATGAGCTACATAATCTTCTAGATAAACCACAGTTACAAGGAATTCCAGTG 450
                      N  E  L  H  N  L  L  D  K  P  Q  L  Q  G  I  P  V 460        470        480        490        500
                     ....|....|....|....|....|....|....|....|....|....|
Arl8b-DA(CMV-F)  451 CTAGTGCTTGGAAACAAGAGAGATCTTCCTAATGCCTTGGATGAGAAACA 500
                      L  V  L  G  N  K  R  D  L  P  N  A  L  D  E  K  Q 510        520        530        540        550
                     ....|....|....|....|....|....|....|....|....|....|
Arl8b-DA(CMV-F)  501 GCTAATTGAAAAAATGAATCTGTCTGCTATTCAGGATAGAGAAATTTGCT 550
                      L  I  E  K  M  N  L  S  A  I  Q  D  R  E  I  C 560        570        580        590        600
                     ....|....|....|....|....|....|....|....|....|....|
Arl8b-DA(CMV-F)  551 GCTATTCAATTTCTTGCAAAGAAAAGGATAATATAGATATCACACTTCAG 600
                      C  Y  S  I  S  C  K  E  K  D  N  I  D  I  T  L  Q 610        620        630        640        650
                     ....|....|....|....|....|....|....|....|....|....|
Arl8b-DA(CMV-F)  601 TGGCTTATTCAGCATTCAAAATCTAGAAGAAGCCGGATCCGATGGTGAG 650
                      W  L  I  Q  H  S  K  S  R  R  S    R  D  P  M
                                                    BamHI 660        670        680        690        700
                     ....|....|....|....|....|....|....|....|....|....|
Arl8b-DA(CMV-F)  651 CAAGGGCGAGGAGGATAACATGGCCATCATCAAGGAGTTCATGCGCTTCA 700

710        720        730        740        750
                     ....|....|....|....|....|....|....|....|....|....|
Arl8b-DA(CMV-F)  701 AGGTGCACATGGAGGGCTCCGTGAACGGCCACGAGTTCGAGATCGAGGGC 750

760        770        780        790        800
                     ....|....|....|....|....|....|....|....|....|....|
Arl8b-DA(CMV-F)  751 GAGGGCGAGGGCCGCCCCTACGAGGGCACCCAGACCGCCAAGCTGAAGGT 800

810        820        830        840        850
                     ....|....|....|....|....|....|....|....|....|....|
Arl8b-DA(CMV-F)  801 GACCAAGGGTGGCCCCCTGCCCTTCGCCTGGGACATCCTGTCCCCTCAGT 850
```

Figure 34C

```
                          860        870        880        890        900
                     ....|....|....|....|....|....|....|....|....|....|
Arl8b-DA(CMV-F)  851 TCATGTACGGCTCCAAGGCCTACGTGAAGCACCCCGCCGACATCCCCGAC 900
                      M  Y  G  S  K  A  Y  V  K  H  P  A  D  I  P  D 910        920        930        940        950
                     ....|....|....|....|....|....|....|....|....|....|
Arl8b-DA(CMV-F)  901 TACTTGAAGCTGTCCTTCCCCGAGGGCTTCAAGTGGGAGCGCGTGATGAA 950
                      Y  L  K  L  S  F  P  E  G  F  K  W  E  R  V  M  N 960        970        980        990        1000
                     ....|....|....|....|....|....|....|....|....|....|
Arl8b-DA(CMV-F)  951 CTTCGAGGACGGCGGCGTGGTGACCGTGACCCAGGACTCCTCCCTGCAGG 1000
                      F  E  D  G  G  V  V  T  V  T  Q  D  S  S  L  Q 1010       1020       1030       1040       1050
                     ....|....|....|....|....|....|....|....|....|....|
Arl8b-DA(CMV-F) 1001 ACGGCGAGTTCATCTACAGTGAAGCTGCGCGGCACCAACTTCCCCTCCGA 1050
                      D  G  E  F  I  Y  S  E  A  A  R  H  Q  L  P  R 1060       1070       1080       1090       1100
                     ....|....|....|....|....|....|....|....|....|....|
Arl8b-DA(CMV-F) 1051 CGCTCGTATGCAGAGAGACATGGGCTGGAGCTCTCGAGCGATGTACCCG 1100
                      R  S  Y  A  E  R  H  G  L  E  A  L  E  R  C  T
                                                      SacI 1110       1120       1130       1140       1150
                     ....|....|....|....|....|....|....|....|....|....|
Arl8b-DA(CMV-F) 1101 AGACGCGCCTGAGGCGAGATCAGCAGAGCTGAGCGAGGACGCGCACTAC 1150
                      D  A  P  E  A  R  Q  A  E  L  S  E  D  A  H  Y 1160       1170       1180       1190
                     ....|....|....|....|....|....|....|....|...
Arl8b-DA(CMV-F) 1151 GACGCTGAAGTCAGACACTACAGTCAGAAGCCGTTCAGCTGCC 1193
                                                          PvuII
```

FIGURE 35A

Arl8b-DN-mcherry plasmid DNA (sequencing data obtained using CMV forward primer)

ATAACCCCAATACAAAAGCAGAGCTGGTTTAGTGACCGTCAGATCCGCTAGCGCTACCGGACTCAGATCTCGAGATG
CTGGCGCTCATCTCCCGCCTGCTGGACTGGTTCCGTTCGCTCTTCTGGAAGGAAGAGATGGAGCTGACGCTCGTGGG
GCTGCAGTACTCGGGCAAGAACACCTTCGTCAATGTCATCGCGTCAGGTCAATTCAGTGAAGATATGATACCCACAG
TGGGCTTCAACATGAGGAAGGTAACTAAAGGTAACGTCACAATAAAGATCTGGGACATAGGAGGACAACCCCGATTT
CGAAGCATGTGGGAGCGGTATTGCAGAGGAGTCAATGCTATTGTTTACATGATAGATGCTGCAGATCGTGAAAGAT
AGAAGCTTCCCGAAATGAGCTACATAATCTTCTAGATAAACCACAGTTACAAGGAATTCCAGTGCTAGTGCTTGGAA
ACAAGAGAGATCTTCCTAATGCCTTGGATGAGAAACAGCTAATTGAAAAGATGAATCTGTCTGCTATTCAGGATAGA
GAAATTTGCTGCTATTCAATTTCTTGCAAAGAAAAGGATAATATAGATATCACACTTCAGTGGCTTATTCAGCATTC
AAAATCTAGAAGAAGCCGGATCCGATGGTGAGCAAGGGCGAGGAGGATAACATGGCCATCATCAAGGAGTTCATGC
GCTTCAAGGTGCACATGGAGGGCTCCGTGAACGGCCACGAGTTCGAGATCGAGGGCGAGGGCGAGGGCCGCCCCTAC
GAGGGCACCCAGACCGCCAAGCTGAAGGTGACCAAGGGTGGCCCCCTGCCCTTCGCCTGGGACATCCTGTCCCCTCA
GTTCATGTACGGCTCCAAGGCCTACGTGAAGCACCCCGCCGACATCCCCGACTACTTGAAGCTGTCCTTCCCCGAGG
GCTTCAAGTGGGAGCGCGTGATGAACTTCCAGGACGGCGGCGTGGTGACCGTGACCCAGGACTTCCTCCCCCTGCAGG
ACGGCGAGTTCATCTACAAAGTGAAGCTGCGCGGGCACCAACTTCCCCCTCCGACGGCCCCGTAATGCAGAAGAAAG
ACCATGGGCCTGGAAGGCCTTCCTCGAGCGATGTTACCCGAAGACGGCGTCCCTGAAAGGCGAGATATCAGCATGAA
GCTGAAGCTTGAAGATCGGCGTCACTTACGTACTGCCTTGAGTCATAGACCAACTTACAAGCCATAGAAGTCGGTGC
AGCTTGTCCTGTCCTTTACACATGCTCTATAACTATCTAAGTTTGGAAACATTCACTACGGTCTACACAGCAGGATG
AC

Arl8b-DN-mcherry (sequence data annotated by M.Sundaram)

```
                    10         20         30         40         50
                ....|....|....|....|....|....|....|....|....|....|
Arl8b-DN(CMV-F)  1  ATAACCCCAATACAAAAGCAGAGCTGGTTTAGTGACCGTCAGATCCGCTA  50
                                                              NheI 60         70         80         90         100
                ....|....|....|....|....|....|....|....|....|....|
Arl8b-DN(CMV-F) 51  CCGCTACCGGACTCAGATCTCGAGATGCTGGCGCTCATCTCCCGCCTGCT  100
                             SmaI          M  L  A  L  I  S  R  L  L 110        120        130        140        150
                ....|....|....|....|....|....|....|....|....|....|
Arl8b-DN(CMV-F) 101 GGACTGGTTCCGTTCGCTCTTCTGGAAGGAAGAGATGGAGCTGACGCTCG  150
                    D  W  F  R  S  L  F  W  K  E  E  M  E  L  T  L 160        170        180        190        200
                ....|....|....|....|....|....|....|....|....|....|
Arl8b-DN(CMV-F) 151 TGGGGCTGCAGTACTCGGGCAAGAACACCTTCGTCAATGTCATCGCGTCA  200
                    V  G  L  Q  Y  S  G  K  N  T  F  V  N  V  I  A  S
                                            ***

210        220        230        240        250
                ....|....|....|....|....|....|....|....|....|....|
Arl8b-DN(CMV-F) 201 GGTCAATTCAGTGAAGATATGATACCCACAGTGGGCTTCAACATGAGGAA  250
                    G  Q  F  S  E  D  M  I  P  T  V  G  F  N  M  R  K 260        270        280        290        300
                ....|....|....|....|....|....|....|....|....|....|
```

Arl8b-DN translated amino acid sequence

*** mutation T34→N

Figure 35B

```
Arl8b-DN(CMV-F)  251  GGTAACTAAAGGTAACGTCACAATAAAGATCTGGGACATAGGAGGACAAC  300
                        V  T  K  G  N  V  T  I  K  I  W  D  I  G  G  Q 310       320       330       340       350
                      ....|....|....|....|....|....|....|....|....|....|
Arl8b-DN(CMV-F)  301  CCCGATTTCGAAGCATGTGGGAGCGGTATTGCAGAGGAGTCAATGCTATT  350
                       P  D  F  E  A  C  G  S  G  I  A  E  E  S  N  A  I 360       370       380       390       400
                      ....|....|....|....|....|....|....|....|....|....|
Arl8b-DN(CMV-F)  351  GTTTACATGATAGATGCTGCAGATCGTGAAAAGATAGAAGCTTCCCGAAA  400
                       V  Y  M  I  D  A  A  D  R  E  K  I  E  A  S  R  N 410       420       430       440       450
                      ....|....|....|....|....|....|....|....|....|....|
Arl8b-DN(CMV-F)  401  TGAGCTACATAATCTTCTAGATAAACCACAGTTACAAGGAATTCCAGTGC  450
                       E  L  H  N  L  L  D  K  P  Q  L  Q  G  I  P  V 460       470       480       490       500
                      ....|....|....|....|....|....|....|....|....|....|
Arl8b-DN(CMV-F)  451  TAGTGCTTGGAAACAAGAGAGATCTTCCTAATGCCTTGGATGAGAAACAG  500
                       L  V  L  G  N  K  R  D  L  P  N  A  L  D  E  K  Q 510       520       530       540       550
                      ....|....|....|....|....|....|....|....|....|....|
Arl8b-DN(CMV-F)  501  CTAATTGAAAAGATGAATCTGTCTGCTATTCAGGATAGAGAAATTTGCTG  550
                       L  I  E  K  M  N  L  S  A  I  Q  D  R  E  I  C  C 560       570       580       590       600
                      ....|....|....|....|....|....|....|....|....|....|
Arl8b-DN(CMV-F)  551  CTATTCAATTTCTTGCAAAGAAAAGGATAATATAGATATCACACTTCAGT  600
                       Y  S  I  S  C  K  E  K  D  N  I  D  I  T  L  Q 610       620       630       640       650
                      ....|....|....|....|....|....|....|....|....|....|
Arl8b-DN(CMV-F)  601  GGCTTATTCAGCATTCAAAATCTAGAAGAAGCCGGATCCGATGGTGAGC  650
                       W  L  I  Q  H  S  K  S  R  R  S  R  D  P  M  V
                                                          BamHI 660       670       680       690       700
                      ....|....|....|....|....|....|....|....|....|....|
Arl8b-DN(CMV-F)  651  AAGGGCGAGGAGGATAACATGGCCATCATCAAGGAGTTCATGCGCTTCAA  700
                       K  G  E  E  D  N  M  A  I  I  K  E  F  M  R  F  K 710       720       730       740       750
                      ....|....|....|....|....|....|....|....|....|....|
Arl8b-DN(CMV-F)  701  GGTGCACATGGAGGGCTCCGTGAACGGCCACGAGTTCGAGATCGAGGGCG  750
                       V  H  M  E  G  S  V  N  G  H  E  F  E  I  E  G 760       770       780       790       800
                      ....|....|....|....|....|....|....|....|....|....|
Arl8b-DN(CMV-F)  751  AGGGCGAGGGCCGCCCCTACGAGGGCACCCAGACCGCCAAGCTGAAGGTG  800
```

Figure 35C

```
                            E G G R P Y F G T Q T A K L K Y
                  810       820       830       840       850
              ....|....|....|....|....|....|....|....|....|....|
Arl8b-DN(CMV-F)  801 ACCAAGGGTGGCCCCCTGCCCTTCGCCTGGGACATCCTGTCCCCTCAGTT 850
                      T K G G P L P F A W D I L S P Q F 860       870       880       890       900
              ....|....|....|....|....|....|....|....|....|....|
Arl8b-DN(CMV-F)  851 CATGTACGGCTCCAAGGCCTACGTGAAGCACCCCGCCGACATCCCCGACT 900
                      M Y G S K A Y V K H P A D I P D 910       920       930       940       950
              ....|....|....|....|....|....|....|....|....|....|
Arl8b-DN(CMV-F)  901 ACTTGAAGCTGTCCTTCCCCGAGGGCTTCAAGTGGGAGCGCGTGATGAAC 950
                      Y L K L S F P E G F K W E R V M N 960       970       980       990       1000
              ....|....|....|....|....|....|....|....|....|....|
Arl8b-DN(CMV-F)  951 TTCCAGGACGGCGGCGTGGTGACCGTGACCCAGGACTTCCTCCCCTGCAG 1000
                      F Q D G G V V T V T Q D F L P C R 1010      1020      1030      1040      1050
              ....|....|....|....|....|....|....|....|....|....|
Arl8b-DN(CMV-F) 1001 GACGGCGAGTTCATCTACAAAG  AAGCTGCGCGGGCACCAACTTCCCCC 1050
                      T A E F I Y K    *

1060      1070      1080      1090      1100
              ....|....|....|....|....|....|....|....|....|....|
Arl8b-DN(CMV-F) 1051 TCCGACGGCCCCGTAATGCAGAAGAAAGA CCATGG GCCTGGAAGGCCTTC 1100
                                                    NcoI 1110      1120      1130      1140      1150
              ....|....|....|....|....|....|....|....|....|....|
Arl8b-DN(CMV-F) 1101 CTCGAGCGATGTTACCCGAAGACGGCGTCCCTGAAAGGCGAGATATCAGC 1150

1160      1170      1180      1190      1200
              ....|....|....|....|....|....|....|....|....|....|
Arl8b-DN(CMV-F) 1151 ATGAAGCTGAAGCTTGAAGATCGGCGTCACTTACGTACTGCCTTGAGTCA 1200

1210      1220      1230      1240      1250
              ....|....|....|....|....|....|....|....|....|....|
Arl8b-DN(CMV-F) 1201 TAGACCAACTTACAAGCCATAGAAGTCGGTGCAGCTTGTCCTGTCCTTTA 1250

1260      1270      1280      1290      1300
              ....|....|....|....|....|....|....|....|....|....|
Arl8b-DN(CMV-F) 1251 CACATGCTCTATAACTATCTAAGTTTGGAAACATTCACTACGGTCTACAC 1300

```
         ....|....|.
Arl8b-DN(CMV-F)  1301 AGCAGGATGAC 1311
```

*SEQ ID NO: 1 (Human Arl8b/Arl10c):*

MLALISRLLDWFRSLFWKEEMELTLVGLQYSGKTTFVNVIASGQFSEDMIPTVGFNMRK
VTKGNVTIKIWDIGGQPRFRSMWERYCRGVNAIVYMIDAADREKIEASRNELHNLLDKP
QLQGIPVLVLGNKRDLPNALDEKQLIEKMNLSAIQDREICCYSISCKEKDNIDITLQWLIQ
HSKSRRS

*SEQ ID NO: 2: (human Vps39, protein, GenBank: AAH68559.1):*

>gi|46250447|gb|AAH68559.1| Vacuolar protein sorting 39 homolog (S. cerevisiae) [Homo sapiens]
MHDAFEPVPILEKLPLQIDCLAAWEEWLLVGTKQGHLLLYRIRKDVGCNRFEVTLEKSNKNFSKKIQQIH
VVSQFKILVSLLENNIYVHDLLTFQQITTVSKAKGASLFTCDLQHTETGEEVLRMCVAVKKKLQLYFWKD
REFHELQGDFSVPDVPKSMAWCENSICVGFKRDYYLIRVDGKGSIKELFPTGKQLEPLVAPLADGKVAVG
QDDLTVVLNEEGICTQKCALNWTDIPVAMEHQPPYIIAVLPRYVEIRTFEPRLLVQSIELQRPRFITSGG
SNIIYVASNHFVWRLIPVPMATQIQQLLQDKQFELALQLAEMKDDSDSEKQQQIHHIKNLYAFNLFCQKR
FDESMQVFAKLGTDPTHVMGLYPDLLPTDYRKQLQYPNPLPVLSGAELEKAHLALIDYLTQKRSQLVKKL
NDSDHQSSTSPLMEGTPTIKSKKKLLQIIDTTLLKCYLHTNVALVAPLLRLENNHCHIEESEHVLKKAHK
YSELIILYEKKGLHEKALQVLVDQSKKANSPLKGHERTVQYLQHLGTENLHLIFSYSVWVLRDFPEDGLK
IFTEDLPEVESLPRDRVLGFLIENFKGLAIPYLEHIIHVWEETGSRFHNCLIQLYCEKVQGLMKEYLLSF
PAGKTPVPAGEEEGELGEYRQKLLMFLEISSYYDPGRLICDFPFDGLLEERALLLGRMGKHEQALFIYVH
ILKDTRMAEEYCHKHYDRNKDGNKDVYLSLLRMYLSPPSIHCLGPIKLELLEPKANLQAALQVLELHHSK
LDTTKALNLLPANTQINDIRIFLEKVLEENAQKKRFNQVLKNLLHAEFLRVQEERILHQQVKCIITEEKV
CMVCKKKIGNSAFARYPNGVVVHYFCSKEVNPADT

*SEQ ID NO: 3 and 4: (human Vps41, protein):*

Isoform 1 (NCBI Reference Sequence: NP_055211.2) (SEQ ID NO:3):
>gi|114199475|ref|NP_055211.2| vacuolar protein sorting-associated protein 41 homolog isoform 1 [Homo sapiens]
MAEAEEQETGSLEESTDESEEEESEEEPKLKYERLSNGVTEILQKDAASCMTVHDKFLALGTHYGKVYLL
DVQGNITQKFDVSPVKINQISLDESGEHMGVCSEDGKVQVFGLYSGEEFHETFDCPIKIIAVHPHFVRSS
CKQFVTGGKKLLLFERSWMNRWKSAVLHEGEGNIRSVKWRGHLIAWANNMGVKIFDIISKQRITNVPRDD
ISLRPDMYPCSLCWKDNVTLIIGWGTSVKVCSVKERHASEMRDLPSRYVEIVSQFETEFYISGLAPLCDQ

FIGURE 46B

LVVLSYVKEISEKTEREYCARPRLDIIQPLSETCEEISSDALTVRGFQENECRDYHLEYSEGESLFYIVS
PRDVVVAKERDQDDHIDWLLEKKKYEEALMAAEISQKNIKRHKILDIGLAYINHLVERGDYDIAARKCQK
ILGKNAALWEYEVYKFKEIGQLKAISPYLPRGDPVLKPLIYEMILHEFLESDYEGFATLIREWPGDLYNN
SVIVQAVRDHLKKDSQNKTLLKTLAELYTYDKNYGNALEIYLTLRHKDVFQLIHKHNLFSSIKDKIVLLM
DFDSEKAVDMLLDNEDKISIKKVVEELEDRPELQHVYLHKLFKRDHHKGQRYHEKQISLYAEYDRPNLLP
FLRDSTHCPLEKALEICQQRNFVEETVYLLSRMGNSRSALKMIMEELHDVDKAIEFAKEQDDGELWEDLI
LYSIDKPPFITGLLNNIGTHVDPILLIHRIKEGMEIPNLRDSLVKILQDYNLQILLREGCKKILVADSLS
LLKKMHRTQMKGVLVDEENICESCLSPILPSDAAKPFSVVVFHCRHMFHKECLPMPSMNSAAQFCNICSA
KNRGPGSAILEMKK

Isoform 2 (NCBI Reference Sequence: NP_542198.2) (SEQ ID NO: 4):
>gi|114199473|ref|NP_542198.2| vacuolar protein sorting-associated protein 41 homolog isoform 2 [Homo sapiens]
MAEAEEQETGSLEESTDESEEEESEEEPKLKYERLSNGVTEILQKDAASCMTVHDKFLALGTHYGKVYLL
DVQGNITQKFDVVQVFGLYSGEEFHETFDCPIKIIAVHPHFVRSSCKQFVTGGKKLLLFERSWMNRWKSA
VLHEGEGNIRSVKWRGHLIAWANNMGVKIFDIISKQRITNVPRDDISLRPDMYPCSLCWKDNVTLIIGWG
TSVKVCSVKERHASEMRDLPSRYVEIVSQFETEFYISGLAPLCDQLVVLSYVKEISEKTEREYCARPRLD
IIQPLSETCEEISSDALTVRGFQENECRDYHLEYSEGESLFYIVSPRDVVVAKERDQDDHIDWLLEKKKY
EEALMAAEISQKNIKRHKILDIGLAYINHLVERGDYDIAARKCQKILGKNAALWEYEVYKFKEIGQLKAI
SPYLPRGDPVLKPLIYEMILHEFLESDYEGFATLIREWPGDLYNNSVIVQAVRDHLKKDSQNKTLLKTLA
ELYTYDKNYGNALEIYLTLRHKDVFQLIHKHNLFSSIKDKIVLLMDFDSEKAVDMLLDNEDKISIKKVVE
ELEDRPELQHVYLHKLFKRDHHKGQRYHEKQISLYAEYDRPNLLPFLRDSTHCPLEKALEICQQRNFVEE
TVYLLSRMGNSRSALKMIMEELHDVDKAIEFAKEQDDGELWEDLILYSIDKPPFITGLLNNIGTHVDPIL
LIHRIKEGMEIPNLRDSLVKILQDYNLQILLREGCKKILVADSLSLLKKMHRTQMKGVLVDEENICESCL
SPILPSDAAKPFSVVVFHCRHMFHKECLPMPSMNSAAQFCNICSAKNRGPGSAILEMKK

*SEQ ID NO: 5 and 6: (human Vps11, protein):*
Isoform 1 (NCBI Reference Sequence: NP_068375.3) (SEQ ID NO:5):
>gi|17978477|ref|NP_068375.3| vacuolar protein sorting-associated protein 11 homolog isoform 1 [Homo sapiens]
MAAYLQWRRFVFFDKELVKEPLSNDGAAPGATPASGSAASKFLCLPPGITVCDSGRGSLVFGDMEGQIWF
LPRSLQLTGFQAYKLRVTHLYQLKQHNILASVGEDEEGINPLVKIWNLEKRDGGNPLCTRIFPAIPGTEP
TVVSCLTVHENLNFMAIGFTDGSVTLNKGDITRDRHSKTQILHKGNYPVTGLAFRQAGKTTHLFVVTTEN
VQSYIVSGKDYPRVELDTHGCGLRCSALSDPSQDLQFIVAGDECVYLQPDERGPCFAFEGHKLIAHWFR
GYLIIVSRDRKVSPKSEFTSRDSQSSDKQILNIYDLCNKFIAYSTVFEDVVDVLAEWGSLYVLTRDGRVH
ALQEKDTQTKLEMLFKKNLFEMAINLAKSQHLDSDGLAQIFMQYGDHLYSKGNHDGAVQQYIRTIGKLEP
SYVIRKFLDAQRIHNLTAYLQTLHRQSLANADHTTLLLNCYTKLKDSSKLEEFIKKKSESEVHFDVETAI

FIGURE 46C

KVLRQAGYYSHALYLAENHAHHEWYLKIQLEDIKNYQEALRYIGKLPFEQAESNMKRYGKILMHHIPEQT
TQLLKGLCTDYRPSLEGRSDREAPGCRANSEEFIPIFANNPRELKAFLEHMSEVQPDSPQGIYDTLLELR
LQNWAHEKDPQVKEKLHAEAISLLKSGRFCDVFDKALVLCQMHDFQDGVLYLYEQGKLFQQIMHYHMQHE
QYRQVISVCERHGEQDPSLWEQALSYFARKEEDCKEYVAAVLKHIENKNLMPPLLVVQTLAHNSTATLSV
IRDYLVQKLQKQSQQIAQDELRVRRYREETTRIRQEIQELKASPKIFQKTKCSICNSALELPSVHFLCGH
SFHQHCFESYSESDADCPTCLPENRKVMDMIRAQEQKRDLHDQFQHQLKCSNDSFSVIADYFGRGVFNKL
TLLTDPPTARLTSSLEAGLQRDLLMHSRRGT

Isoform 2 (NCBI Reference Sequence: NP_001277114.1) (SEQ ID NO:6):
>gi|589058161|ref|NP_001277114.1| vacuolar protein sorting-associated protein 11 homolog isoform 2 [Homo sapiens]
MKSVCRRGPCRAPLWFSWSSRVVLWSTGRKKEVHLLTCYQLSNPGRLLDYPAHMEGQIWFLPRSLQLTGF
QAYKLRVTHLYQLKQHNILASVGEDEEGINPLVKIWNLEKRDGGNPLCTRIFPAIPGTEPTVVSCLTVHE
NLNFMAIGFTDGSVTLNKGDITRDRHSKTQILHKGNYPVTGLAFRQAGKTTHLFVVTTENVQSYIVSGKD
YPRVELDTHGCGLRCSALSDPSQDLQFIVAGDECVYLYQPDERGPCFAFEGHKLIAHWFRGYLIIVSRDR
KVSPKSEFTSRDSQSSDKQILNIYDLCNKFIAYSTVFEDVVDVLAEWGSLYVLTRDGRVHALQEKDTQTK
LEMLFKKNLFEMAINLAKSQHLDSDGLAQIFMQYGDHLYSKGNHDGAVQQYIRTIGKLEPSYVIRKFLDA
QRIHNLTAYLQTLHRQSLANADHTTLLLNCYTKLKDSSKLEEFIKKKSESEVHFDVETAIKVLRQAGYYS
HALYLAENHAHHEWYLKIQLEDIKNYQEALRYIGKLPFEQAESNMKRYGKILMHHIPEQTTQLLKGLCTD
YRPSLEGRSDREAPGCRANSEEFIPIFANNPRELKAFLEHMSEVQPDSPQGIYDTLLELRLQNWAHEKDP
QVKEKLHAEAISLLKSGRFCDVFDKALVLCQMHDFQDGVLYLYEQGKLFQQIMHYHMQHEQYRQVISVCE
RHGEQDPSLWEQALSYFARKEEDCKEYVAAVLKHIENKNLMPPLLVVQTLAHNSTATLSVIRDYLVQKLQ
KQSQQIAQDELRVRRYREETTRIRQEIQELKASPKIFQKTKCSICNSALELPSVHFLCGHSFHQHCFESY
SESDADCPTCLPENRKVMDMIRAQEQKRDLHDQFQHQLKCSNDSFSVIADYFGRGVFNKLTLLTDPPTAR
LTSSLEAGLQRDLLMHSRRGT

*SEQ ID NO: 7: (human Vps41, isoform 1, NCBI Reference Sequence: NP_055211.2, protein):*
>gi|114199475|ref|NP_055211.2| vacuolar protein sorting-associated protein 41 homolog isoform 1 [Homo sapiens]
MAEAEEQETGSLEESTDESEEEESEEEPKLKYERLSNGVTEILQKDAASCMTVHDKFLALGTHYGKVYLL
DVQGNITQKFDVSPVKINQISLDESGEHMGVCSEDGKVQVFGLYSGEEFHETFDCPIKIIAVHPHFVRSS
CKQFVTGGKKLLLFERSWMNRWKSAVLHEGEGNIRSVKWRGHLIAWANNMGVKIFDIISKQRITNVPRDD
ISLRPDMYPCSLCWKDNVTLIIGWGTSVKVCSVKERHASEMRDLPSRYVEIVSQFETEFYISGLAPLCDQ
LVVLSYVKEISEKTEREYCARPRLDIIQPLSETCEEISSDALTVRGFQENECRDYHLEYSEGESLFYIVS
PRDVVVAKERDQDDHIDWLLEKKKYEEALMAAEISQKNIKRHKILDIGLAYINHLVERGDYDIAARKCQK
ILGKNAALWEYEVYKFKEIGQLKAISPYLPRGDPVLKPLIYEMILHEFLESDYEGFATLIREWPGDLYNN
SVIVQAVRDHLKKDSQNKTLLKTLAELYTYDKNYGNALEIYLTLRHKDVFQLIHKHNLFSSIKDKIVLLM
DFDSEKAVDMLLDNEDKISIKKVVEELEDRPELQHVYLHKLFKRDHHKGQRYHEKQISLYAEYDRPNLLP

FIGURE 46D

FLRDSTHCPLEKALEICQQRNFVEETVYLLSRMGNSRSALKMIMEELHDVDKAIEFAKEQDDGELWEDLI
LYSIDKPPFITGLLNNIGTHVDPILLIHRIKEGMEIPNLRDSLVKILQDYNLQILLREGCKKILVADSLS
LLKKMHRTQMKGVLVDEENICESCLSPILPSDAAKPFSVVVFHCRHMFHKECLPMPSMNSAAQFCNICSA
KNRGPGSAILEMKK

SEQ ID NO: 8: (human Vps41, isoform 2, NCBI Reference Sequence: NP_542198.2, protein):

>gi|114199473|ref|NP_542198.2| vacuolar protein sorting-associated protein 41 homolog isoform 2 [Homo sapiens]
MAEAEEQETGSLEESTDESEEEESEEEPKLKYERLSNGVTEILQKDAASCMTVHDKFLALGTHYGKVYLL
DVQGNITQKFDVVQVFGLYSGEEFHETFDCPIKIIAVHPHFVRSSCKQFVTGGKKLLLFERSWMNRWKSA
VLHEGEGNIRSVKWRGHLIAWANNMGVKIFDIISKQRITNVPRDDISLRPDMYPCSLCWKDNVTLIIGWG
TSVKVCSVKERHASEMRDLPSRYVEIVSQFETEFYISGLAPLCDQLVVLSYVKEISEKTEREYCARPRLD
IIQPLSETCEEISSDALTVRGFQENECRDYHLEYSEGESLFYIVSPRDVVVAKERDQDDHIDWLLEKKKY
EEALMAAEISQKNIKRHKILDIGLAYINHLVERGDYDIAARKCQKILGKNAALWEYEVYKFKEIGQLKAI
SPYLPRGDPVLKPLIYEMILHEFLESDYEGFATLIREWPGDLYNNSVIVQAVRDHLKKDSQNKTLLKTLA
ELYTYDKNYGNALEIYLTLRHKDVFQLIHKHNLFSSIKDKIVLLMDFDSEKAVDMLLDNEDKISIKKVVE
ELEDRPELQHVYLHKLFKRDHHKGQRYHEKQISLYAEYDRPNLLPFLRDSTHCPLEKALEICQQRNFVEE
TVYLLSRMGNSRSALKMIMEELHDVDKAIEFAKEQDDGELWEDLILYSIDKPPFITGLLNNIGTHVDPIL
LIHRIKEGMEIPNLRDSLVKILQDYNLQILLREGCKKILVADSLSLLKKMHRTQMKGVLVDEENICESCL
SPILPSDAAKPFSVVVFHCRHMFHKECLPMPSMNSAAQFCNICSAKNRGPGSAILEMKK

SEQ ID NO: 9: (human Vps11, isoform 1, NCBI Reference Sequence: NP_068375.3, protein):

>gi|17978477|ref|NP_068375.3| vacuolar protein sorting-associated protein 11 homolog isoform 1 [Homo sapiens]
MAAYLQWRRFVFFDKELVKEPLSNDGAAPGATPASGSAASKFLCLPPGITVCDSGRGSLVFGDMEGQIWF
LPRSLQLTGFQAYKLRVTHLYQLKQHNILASVGEDEEGINPLVKIWNLEKRDGGNPLCTRIFPAIPGTEP
TVVSCLTVHENLNFMAIGFTDGSVTLNKGDITRDRHSKTQILHKGNYPVTGLAFRQAGKTTHLFVVTTEN
VQSYIVSGKDYPRVELDTHGCGLRCSALSDPSQDLQFIVAGDECVYLYQPDERGPCFAFEGHKLIAHWFR
GYLIIVSRDRKVSPKSEFTSRDSQSSDKQILNIYDLCNKFIAYSTVFEDVVDVLAEWGSLYVLTRDGRVH
ALQEKDTQTKLEMLFKKNLFEMAINLAKSQHLDSDGLAQIFMQYGDHLYSKGNHDGAVQQYIRTIGKLEP
SYVIRKFLDAQRIHNLTAYLQTLHRQSLANADHTTLLLNCYTKLKDSSKLEEFIKKKSESEVHFDVETAI
KVLRQAGYYSHALYLAENHAHHEWYLKIQLEDIKNYQEALRYIGKLPFEQAESNMKRYGKILMHHIPEQT
TQLLKGLCTDYRPSLEGRSDREAPGCRANSEEFIPIFANNPRELKAFLEHMSEVQPDSPQGIYDTLLELR
LQNWAHEKDPQVKEKLHAEAISLLKSGRFCDVFDKALVLCQMHDFQDGVLYLYEQGKLFQQIMHYHMQHE
QYRQVISVCERHGEQDPSLWEQALSYFARKEEDCKEYVAAVLKHIENKNLMPPLLVVQTLAHNSTATLSV
IRDYLVQKLQKQSQQIAQDELRVRRYREETTRIRQEIQELKASPKIFQKTKCSICNSALELPSVHFLCGH
SFHQHCFESYSESDADCPTCLPENRKVMDMIRAQEQKRDLHDQFQHQLKCSNDSFSVIADYFGRGVFNKL
TLLTDPPTARLTSSLEAGLQRDLLMHSRRGT

FIGURE 46E

SEQ ID NO: 10: (human Vps11, isoform 2, NCBI Reference Sequence: NP_001277114.1, protein):

>gi|589058161|ref|NP_001277114.1| vacuolar protein sorting-associated protein 11 homolog isoform 2 [Homo sapiens]

MKSVCRRGPCRAPLWFSWSSRVVLWSTGRKKEVHLLTCYQLSNPGRLLDYPAHMEGQIWFLPRSLQLTGF
QAYKLRVTHLYQLKQHNILASVGEDEEGINPLVKIWNLEKRDGGNPLCTRIFPAIPGTEPTVVSCLTVHE
NLNFMAIGFTDGSVTLNKGDITRDRHSKTQILHKGNYPVTGLAFRQAGKTTHLFVVTTENVQSYIVSGKD
YPRVELDTHGCGLRCSALSDPSQDLQFIVAGDECVYLYQPDERGPCFAFEGHKLIAHWFRGYLIIVSRDR
KVSPKSEFTSRDSQSSDKQILNIYDLCNKFIAYSTVFEDVVDVLAEWGSLYVLTRDGRVHALQEKDTQTK
LEMLFKKNLFEMAINLAKSQHLDSDGLAQIFMQYGDHLYSKGNHDGAVQQYIRTIGKLEPSYVIRKFLDA
QRIHNLTAYLQTLHRQSLANADHTTLLLNCYTKLKDSSKLEEFIKKKSESEVHFDVETAIKVLRQAGYYS
HALYLAENHAHHEWYLKIQLEDIKNYQEALRYIGKLPFEQAESNMKRYGKILMHHIPEQTTQLLKGLCTD
YRPSLEGRSDREAPGCRANSEEFIPIFANNPRELKAFLEHMSEVQPDSPQGIYDTLLELRLQNWAHEKDP
QVKEKLHAEAISLLKSGRFCDVFDKALVLCQMHDFQDGVLYLYEQGKLFQQIMHYHMQHEQYRQVISVCE
RHGEQDPSLWEQALSYFARKEEDCKEYVAAVLKHIENKNLMPPLLVVQTLAHNSTATLSVIRDYLVQKLQ
KQSQQIAQDELRVRRYREETTRIRQEIQELKASPKIFQKTKCSICNSALELPSVHFLCGHSFHQHCFESY
SESDADCPTCLPENRKVMDMIRAQEQKRDLHDQFQHQLKCSNDSFSVIADYFGRGVFNKLTLLTDPPTAR
LTSSLEAGLQRDLLMHSRRGT

SEQ ID NO: 11: (human Vps39, protein, GenBank: AAH68559.1):

>gi|46250447|gb|AAH68559.1| Vacuolar protein sorting 39 homolog (S. cerevisiae) [Homo sapiens]

MHDAFEPVPILEKLPLQIDCLAAWEEWLLVGTKQGHLLLYRIRKDVGCNRFEVTLEKSNKNFSKKIQQIH
VVSQFKILVSLLENNIYVHDLLTFQQITTVSKAKGASLFTCDLQHTETGEEVLRMCVAVKKKLQLYFWKD
REFHELQGDFSVPDVPKSMAWCENSICVGFKRDYYLIRVDGKGSIKELFPTGKQLEPLVAPLADGKVAVG
QDDLTVVLNEEGICTQKCALNWTDIPVAMEHQPPYIIAVLPRYVEIRTFEPRLLVQSIELQRPRFITSGG
SNIIYVASNHFVWRLIPVPMATQIQQLLQDKQFELALQLAEMKDDSDSEKQQQIHHIKNLYAFNLFCQKR
FDESMQVFAKLGTDPTHVMGLYPDLLPTDYRKQLQYPNPLPVLSGAELEKAHLALIDYLTQKRSQLVKKL
NDSDHQSSTSPLMEGTPTIKSKKKLLQIIDTTLLKCYLHTNVALVAPLLRLENNHCHIEESEHVLKKAHK
YSELIILYEKKGLHEKALQVLVDQSKKANSPLKGHERTVQYLQHLGTENLHLIFSYSVWVLRDFPEDGLK
IFTEDLPEVESLPRDRVLGFLIENFKGLAIPYLEHIIHVWEETGSRFHNCLIQLYCEKVQGLMKEYLLSF
PAGKTPVPAGEEEGELGEYRQKLLMFLEISSYYDPGRLICDFPFDGLLEERALLLGRMGKHEQALFIYVH
ILKDTRMAEEYCHKHYDRNKDGNKDVYLSLLRMYLSPPSIHCLGPIKLELLEPKANLQAALQVLELHHSK
LDTTKALNLLPANTQINDIRIFLEKVLEENAQKKRFNQVLKNLLHAEFLRVQEERILHQQVKCIITEEKV
CMVCKKKIGNSAFARYPNGVVVHYFCSKEVNPADT

FIGURE 46F

_SEQ ID NO: 12: Arl8b<sup>T34N</sup> amino acid sequence:_
MLALISRLLDWFRSLFWKEEMELTLVGLQYSGKNTFVNVIASGQFSEDMIPTVGFNMRK
VTKGNVTIKIWDIGGQPRFRSMWERYCRGVNAIVYMIDAADREKIEASRNELHNLLDKP
QLQGIPVLVLGNKRDLPNALDEKQLIEKMNLSAIQDREICCYSISCKEKDNIDITLQWLIQ
HSKSRRS _SEQ ID NO: 13: Arl8b<sup>Q75L</sup> amino acid sequence:_
MLALISRLLDWFRSLFWKEEMELTLVGLQYSGKTTFVNVIASGQFSEDMIPTVGFNMRK
VTKGNVTIKIWDIGGLPRFRSMWERYCRGVNAIVYMIDAADREKIEASRNELHNLLDKP
QLQGIPVLVLGNKRDLPNALDEKQLIEKMNLSAIQDREICCYSISCKEKDNIDITLQWLIQ
HSKSRRS _SEQ ID NO: 14: Arl8b<sup>WT</sup>-GFP plasmid DNA sequence:_
TTCCCCAAATTATAGGAGCAGAGCTCTCTGGCTACTAGAGAACCCACTGCTTACTGG
CTTATCGAAATTAATACGACTCACTATAGGGAGACCCAAGCTGGCTAGTTAAGCTTG
GTACCGAGCTCGGATCCACTAGTCCAGTGTGGTGGAATTGCCCTTCACCATGCTGGC
GCTCATCTCCCGCCTGCTGGACTGGTTCCGTTCGCTCTTCTGGAAGGAAGAGATGGA
GCTGACGCTCGTGGGGCTGCAGTACTCGGGCAAGACCACCTTCGTCAATGTCATCGC
GTCAGGTCAATTCAGTGAAGATATGATACCCACAGTGGGCTTCAACATGAGGAAGG
TAACTAAAGGTAACGTCACAATAAAGATCTGGGACATAGGAGGACAACCCCGATTT
CGAAGCATGTGGGAGCGGTATTGCAGAGGAGTCAATGCTATTGTTTACATGATAGAT
GCTGCAGATCGTGAAAAGATAGAAGCTTCCCGAAATGAGCTACATAATCTTCTAGAT
AAACCACAGTTACAAGGAATTCCAGTGCTAGTGCTTGGAAACAAGAGAGATCTTCC
TAATGCCTTGGATGAGAAACAGCTAATTGAAAAATGAATCTGTCTGCTATTCAGGA
TAGAGAAATTTGCTGCTATTCAATTTCTTGCAAAGAAAGGATAATATAGATATCAC
ACTTCAGTGGCTTATTCAGCATTCAAAATCTAGAAGAAGCGAAGGGCAATTCTGCAG
ATATCCAGCACAGTGGCGGCCGCTCGAGTCTAGAATGGCTAGCAAAGGAGAAGAAC
TTTTCACTGGAGTTGTCCCAATTCTTGTTTGAATTAGATGGTGATGTTAATGGGCACA
AATTTTCTGTCAGTGGAGAGGGTGAAGGTGAATGCTACATACGGAAAGCTTACCCTT
AAATTTATTTTGCACTACTGGAAAACTACCTGTTCCATGGGCCAATACTTGTCACTAC

FIGURE 46G

TTTCTCTTATGTTGTCCATGCTTTTTCCCGTTATCCGGATAATATGAAACGGCATGAC
TTTTCCAGAGTGCCATGGCCCGAAGGGTTATGTTCTAGGAACGCACTTATATCTTTC
AAGATGACGGGAACTAACAAGAACCCGTGCTGAAGTCAAGTTTGAAGGGGATACCT
TGGTTTATCGTACGAGTTTAAAGGGTATTGATTTTAAGAAATAGGAATACCATCCT
CCGGACTCCTACTTCTGTAGTTCCACTCTATTACCTCCCCACCATTGTGTTATATTCC
ATGTGCCGGCTCACCAAGTGAATGGTATTACTAAGCTAATACTCTCATCAATCTTCC
TCCACCAACACACTGAG

_SEQ ID NO: 15: Arl8b$^{WT}$-mcherry plasmid DNA sequence:_
CACCCAAGACAAAAGCAGAGCTGGTTTAGTGACCGTCAGATCCGCTAGCGCTACCG
GACTCAGATCTCGAGATGCTGGCGCTCATCTCCCGCCTGCTGGACTGGTTCCGTTCG
CTCTTCTGGAAGGAAGAGATGGAGCTGACGCTCGTGGGGCTGCAGTACTCGGGCAA
GACCACCTTCGTCAATGTCATCGCGTCAGGTCAATTCAGTGAAGATATGATACCCAC
AGTGGGCTTCAACATGAGGAAGGTAACTAAAGGTAACGTCACAATAAAGATCTGGG
ACATAGGAGGACAACCCCGATTTCGAAGCATGTGGGAGCGGTATTGCAGAGGAGTC
AATGCTATTGTTTACATGATAGATGCTGCAGATCGTGAAAGATAGAAGCTTCCCGA
AATGAGCTACATAATCTTCTAGATAAACCACAGTTACAAGGAATTCCAGTGCTAGTG
CTTGGAAACAAGAGAGATCTTCCTAATGCCTTGGATGAGAAACAGCTAATTGAAAA
AATGAATCTGTCTGCTATTCAGGATAGAGAAATTTGCTGCTATTCAATTTCTTGCAA
AGAAAAGGATAATATAGATATCACACTTCAGTGGCTTATTCAGCATTCAAAATCTAG
AAGAAGCCGGGATCCGATGGTGAGCAAGGGCGAGGAGGATAACATGGCCATCATC
AAGGAGTTCATGCGCTTCAAGGTGCACATGGAGGGCTCCGTGAACGGCCACGAGTT
CGAGATCGAGGGCGAGGGCGAGGGCCGCCCCTACGAGGGCACCCAGACCGCCAAG
CTGAAGGTGACCAAGGGTGGCCCCCTGCCCTTCGCCTGGGACATCCTGTCCCCTCAG
TTCATGTACGGCTCCAAGGCCTACGTGAAGCACCCCGCCGACATCCCCGACTACTTG
AAGCTGTCCTTCCCCGAGGGCTTCAAGTGGGAGCGCGTGATGAACTTCGAGGACGG
CGGCGTGGTGACCGTGACCCAGGACTCCTCCCTGCAGGACGGCGAGTTCATCTACA
AGTGAAGCTGCGCGGCACCAACTTCCCCTCCGACGGCCCCGTAATGCAGAAGAGGA
CCATGGGCTGGAGGCCTCCTCGAGCGATGTACCCCGAGGACGCGCCCTGAGGCGAG
ATCAGCAGAGGCTGAGCTGAGACGCCGCCACTACGACGCTGAGTCAGAACTACTAC

FIGURE 46H

AAGTCAGAGCCGGCAGCTGCTGGCCTACACGTCACTTCAGTGGAACTTAACTTCACA
AAGCGAGGAAC

SEQ ID NO: 16: Arl8b$^{Q75L}$-mcherry plasmid DNA sequence:

TTTCAACGGAATACAAATAGCGAGCTGGTTTAGTGACCGTCAGATCCGCTAGCGCTA
CCGGACTCAGATCTCGAGATGCTGGCGCTCATCTCCCGCCTGCTGGACTGGTTCCGT
TCGCTCTTCTGGAAGGAAGAGATGGAGCTGACGCTCGTGGGGCTGCAGTACTCGGG
CAAGACCACCTTCGTCAATGTCATCGCGTCAGGTCAATTCAGTGAAGATATGATACC
CACAGTGGGCTTAACATGAGGAAGGTAACTAAAGGTAACGTCACAATAAAGATCT
GGGACATAGGAGGACTACCCCGATTTCGAAGCATGTGGGAGCGGTATTGCAGAGGA
GTCAATGCTATTGTTTACATGATAGATGCTGCAGATCGTGAAAGATAGAAGCTTCC
CGAAATGAGCTACATAATCTTCTAGATAAACCACAGTTACAAGGAATTCCAGTGCTA
GTGCTTGGAAACAAGAGAGATCTTCCTAATGCCTTGGATGAGAAACAGCTAATTGA
AAAAATGAATCTGTCTGCTATTCAGGATAGAGAAATTTGCTGCTATTCAATTTCTTG
CAAAGAAAGGATAATATAGATATCACACTTCAGTGGCTTATTCAGCATTCAAAATC
TAGAAGAAGCCGGGATCCGATGGTGAGCAAGGGCGAGGAGGATAACATGGCCATC
ATCAAGGAGTTCATGCGCTTCAAGGTGCACATGGAGGGCTCCGTGAACGGCCACGA
GTTCGAGATCGAGGGCGAGGGCGAGGGCCGCCCCTACGAGGGCACCCAGACCGCCA
AGCTGAAGGTGACCAAGGGTGGCCCCCTGCCCTTCGCCTGGGACATCCTGTCCCCTC
AGTTCATGTACGGCTCCAAGGCCTACGTGAAGCACCCCGCCGACATCCCCGACTACT
TGAAGCTGTCCTTCCCCGAGGGCTTCAAGTGGGAGCGCGTGATGAACTTCGAGGAC
GGCGGCGTGGTGACCGTGACCCAGGACTCCTCCCTGCAGGACGGCGAGTTCATCTA
CAGTGAAGCTGCGCGGCACCAACTTCCCCTCCGACGCTCGTATGCAGAGAGACATG
GGCTGGGAGCTCTCGAGCGATGTACCCGAGACGCGCCTGAGGCGAGATCAGCAGAG
CTGAGCTGAGGACGCGCACTACGACGCTGAAGTCAGACACTACAGTCAGAAGCCGT
TCAGCTGCC

SEQ ID NO: 17: Arl8b$^{T34N}$-mcherry plasmid DNA sequence:

ATAACCCCAATACAAAAGCAGAGCTGGTTTAGTGACCGTCAGATCCGCTAGCGCTA
CCGGACTCAGATCTCGAGATGCTGGCGCTCATCTCCCGCCTGCTGGACTGGTTCCGT

FIGURE 46I

TCGCTCTTCTGGAAGGAAGAGATGGAGCTGACGCTCGTGGGGCTGCAGTACTCGGG
CAAGAACACCTTCGTCAATGTCATCGCGTCAGGTCAATTCAGTGAAGATATGATACC
CACAGTGGGCTTCAACATGAGGAAGGTAACTAAAGGTAACGTCACAATAAAGATCT
GGGACATAGGAGGACAACCCCGATTTCGAAGCATGTGGGAGCGGTATTGCAGAGGA
GTCAATGCTATTGTTTACATGATAGATGCTGCAGATCGTGAAAGATAGAAGCTTCC
CGAAATGAGCTACATAATCTTCTAGATAAACCACAGTTACAAGGAATTCCAGTGCTA
GTGCTTGGAAACAAGAGAGATCTTCCTAATGCCTTGGATGAGAAACAGCTAATTGA
AAAGATGAATCTGTCTGCTATTCAGGATAGAGAAATTTGCTGCTATTCAATTTCTTG
CAAAGAAAGGATAATATAGATATCACACTTCAGTGGCTTATTCAGCATTCAAAATC
TAGAAGAAGCCGGGATCCGATGGTGAGCAAGGGCGAGGAGGATAACATGGCCATC
ATCAAGGAGTTCATGCGCTTCAAGGTGCACATGGAGGGCTCCGTGAACGGCCACGA
GTTCGAGATCGAGGGCGAGGGCGAGGGCCGCCCCTACGAGGGCACCCAGACCGCCA
AGCTGAAGGTGACCAAGGGTGGCCCCCTGCCCTTCGCCTGGGACATCCTGTCCCTC
AGTTCATGTACGGCTCCAAGGCCTACGTGAAGCACCCCGCCGACATCCCCGACTACT
TGAAGCTGTCCTTCCCCGAGGGCTTCAAGTGGGAGCGCGTGATGAACTTCCAGGACG
GCGGCGTGGTGACCGTGACCCAGGACTTCCTCCCCTGCAGGACGGCGAGTTCATCTA
CAAAGTGAAGCTGCGCGGGCACCAACTTCCCCCTCCGACGGCCCCGTAATGCAGAA
GAAAGACCATGGGCCTGGAAGGCCTTCCTCGAGCGATGTTACCCGAAGACGGCGTC
CCTGAAAGGCGAGATATCAGCATGAAGCTGAAGCTTGAAGATCGGCGTCACTTACG
TACTGCCTTGAGTCATAGACCAACTTACAAGCCATAGAAGTCGGTGCAGCTTGTCCT
GTCCTTTACACATGCTCTATAACTATCTAAGTTTGGAAACATTCACTACGGTCTACAC
AGCAGGATGAC

*SEQ ID NO: 18: MG1021 DNA Sequence*

CACCCAAGACAAAAGCAGAGCTGGTTTAGTGACCGTCAGATCCGCTAGCGCTACCG
GACTCAGATCTCGAGATGCTGGCGCTCATCTCCCGCCTGCTGGACTGGTTCCGTTCG
CTCTTCTGGAAGGAAGAGATGGAGCTGACGCTCGTGGGGCTGCAGTACTCGGGCAA
GACCACCTTCGTCAATGTCATCGCGTCAGGTCAATTCAGTGAAGATATGATACCCAC
AGTGGGCTTCAACATGAGGAAGGTAACTAAAGGTAACGTCACAATAAAGATCTGGG
ACATAGGAGGACAACCCCGATTTCGAAGCATGTGGGAGCGGTATTGCAGAGGAGTC

FIGURE 46J

AATGCTATTGTTTACATGATAGATGCTGCAGATCGTGAAAGATAGAAGCTTCCCGA
ATGAGCTACATAATCTTCTAGATAAACCACAGTTACAAGGAATTCCAGTGCTAGTG
CTTGGAAACAAGAGAGATCTTCCTAATGCCTTGGATGAGAAACAGCTAATTGAAAA
ATGAATCTGTCTGCTATTCAGGATAGAGAAATTTGCTGCTATTCAATTTCTTGCAA
AGAAAAGGATAATATAGATATCACACTTCAGTGGCTTATTCAGCATTCAAAATCTAG
AAGAAGCCGGGATCCGATGGTGAGCAAGGGCGAGGAGGATAACATGGCCATCATC
AAGGAGTTCATGCGCTTCAAGGTGCACATGGAGGGCTCCGTGAACGGCCACGAGTT
CGAGATCGAGGGCGAGGGCGAGGGCCGCCCCTACGAGGGCACCCAGACCGCCAAG
CTGAAGGTGACCAAGGGTGGCCCCCTGCCCTTCGCCTGGGACATCCTGTCCCTCAG
TTCATGTACGGCTCCAAGGCCTACGTGAAGCACCCCGCCGACATCCCCGACTACTTG
AAGCTGTCCTTCCCCGAGGGCTTCAAGTGGGAGCGCGTGATGAACTTCGAGGACGG
CGGCGTGGTGACCGTGACCCAGGACTCCTCCCTGCAGGACGGCGAGTTCATCTACA
AGTGAAGCTGCGCGGCACCAACTTCCCCTCCGACGGCCCCGTAATGCAGAAGAGGA
CCATGGGCTGGAGGCCTCCTCGAGCGATGTACCCCGAGGACGCGCCCTGAGGCGAG
ATCAGCAGAGGCTGAGCTGAGACGCCGCCACTACGACGCTGAGTCAGAACTACTAC
AAGTCAGAGCCGGCAGCTGCTGGCCTACACGTCACTTCAGTGGAACTTAACTTCACA
AAGCGAGGAAC

*SEQ ID NO: 19: MG1022 DNA Sequence*
TTTCAACGGAATACAAATAGCGAGCTGGTTTAGTGACCGTCAGATCCGCTAGCGCTA
CCGGACTCAGATCTCGAGATGCTGGCGCTCATCTCCCGCCTGCTGGACTGGTTCCGT
TCGCTCTTCTGGAAGGAAGAGATGGAGCTGACGCTCGTGGGGCTGCAGTACTCGGG
CAAGACCACCTTCGTCAATGTCATCGCGTCAGGTCAATTCAGTGAAGATATGATACC
CACAGTGGGCTTCAACATGAGGAAGGTAACTAAAGGTAACGTCACAATAAAGATCT
GGGACATAGGAGGACTACCCCGATTTCGAAGCATGTGGGAGCGGTATTGCAGAGGA
GTCAATGCTATTGTTTACATGATAGATGCTGCAGATCGTGAAAGATAGAAGCTTCC
CGAAATGAGCTACATAATCTTCTAGATAAACCACAGTTACAAGGAATTCCAGTGCTA
GTGCTTGGAAACAAGAGAGATCTTCCTAATGCCTTGGATGAGAAACAGCTAATTGA
AAAAATGAATCTGTCTGCTATTCAGGATAGAGAAATTTGCTGCTATTCAATTTCTTG
CAAAGAAAAGGATAATATAGATATCACACTTCAGTGGCTTATTCAGCATTCAAAATC

FIGURE 46K

TAGAAGAAGCCGGGATCCGATGGTGAGCAAGGGCGAGGAGGATAACATGGCCATC
ATCAAGGAGTTCATGCGCTTCAAGGTGCACATGGAGGGCTCCGTGAACGGCCACGA
GTTCGAGATCGAGGGCGAGGGCGAGGGCCGCCCCTACGAGGGCACCCAGACCGCCA
AGCTGAAGGTGACCAAGGGTGGCCCCCTGCCCTTCGCCTGGGACATCCTGTCCCTC
AGTTCATGTACGGCTCCAAGGCCTACGTGAAGCACCCCGCCGACATCCCCGACTACT
TGAAGCTGTCCTTCCCCGAGGGCTTCAAGTGGGAGCGCGTGATGAACTTCGAGGAC
GGCGGCGTGGTGACCGTGACCCAGGACTCCTCCTGCAGGACGGCGAGTTCATCTA
CAGTGAAGCTGCGCGGCACCAACTTCCCCTCCGACGCTCGTATGCAGAGAGACATG
GGCTGGGAGCTCTCGAGCGATGTACCCGAGACGCGCCTGAGGCGAGATCAGCAGAG
CTGAGCTGAGGACGCGCACTACGACGCTGAAGTCAGACACTACAGTCAGAAGCCGT
TCAGCTGCC

SEQ ID NO: 20: MG1023 DNA Sequence

ATAACCCCAATACAAAAGCAGAGCTGGTTTAGTGACCGTCAGATCCGCTAGCGCTA
CCGGACTCAGATCTCGAGATGCTGGCGCTCATCTCCCGCCTGCTGGACTGGTTCCGT
TCGCTCTTCTGGAAGGAAGAGATGGAGCTGACGCTCGTGGGCTGCAGTACTCGGG
CAAGAACACCTTCGTCAATGTCATCGCGTCAGGTCAATTCAGTGAAGATATGATACC
CACAGTGGGCTTCAACATGAGGAAGGTAACTAAAGGTAACGTCACAATAAAGATCT
GGGACATAGGAGGACAACCCCGATTTCGAAGCATGTGGGAGCGGTATTGCAGAGGA
GTCAATGCTATTGTTTACATGATAGATGCTGCAGATCGTGAAAAGATAGAAGCTTCC
CGAAATGAGCTACATAATCTTCTAGATAAACCACAGTTACAAGGAATTCCAGTGCTA
GTGCTTGGAAACAAGAGAGATCTTCCTAATGCCTTGGATGAGAAACAGCTAATTGA
AAAGATGAATCTGTCTGCTATTCAGGATAGAGAAATTTGCTGCTATTCAATTTCTTG
CAAAGAAAAGGATAATATAGATATCACACTTCAGTGGCTTATTCAGCATTCAAAATC
TAGAAGAAGCCGGGATCCGATGGTGAGCAAGGGCGAGGAGGATAACATGGCCATC
ATCAAGGAGTTCATGCGCTTCAAGGTGCACATGGAGGGCTCCGTGAACGGCCACGA
GTTCGAGATCGAGGGCGAGGGCGAGGGCCGCCCCTACGAGGGCACCCAGACCGCCA
AGCTGAAGGTGACCAAGGGTGGCCCCCTGCCCTTCGCCTGGGACATCCTGTCCCTC
AGTTCATGTACGGCTCCAAGGCCTACGTGAAGCACCCCGCCGACATCCCCGACTACT
TGAAGCTGTCCTTCCCCGAGGGCTTCAAGTGGGAGCGCGTGATGAACTTCCAGGACG

FIGURE 46L

GCGGCGTGGTGACCGTGACCCAGGACTTCCTCCCCTGCAGGACGGCGAGTTCATCTA
CAAAGTGAAGCTGCGCGGGCACCAACTTCCCCCTCCGACGGCCCCGTAATGCAGAA
GAAAGACCATGGGCCTGGAAGGCCTTCCTCGAGCGATGTTACCCGAAGACGGCGTC
CCTGAAAGGCGAGATATCAGCATGAAGCTGAAGCTTGAAGATCGGCGTCACTTACG
TACTGCCTTGAGTCATAGACCAACTTACAAGCCATAGAAGTCGGTGCAGCTTGTCCT
GTCCTTTACACATGCTCTATAACTATCTAAGTTTGGAAACATTCACTACGGTCTACAC
AGCAGGATGAC

Adenovirus Vector Details of MG1021, MG1022, and MG1023:

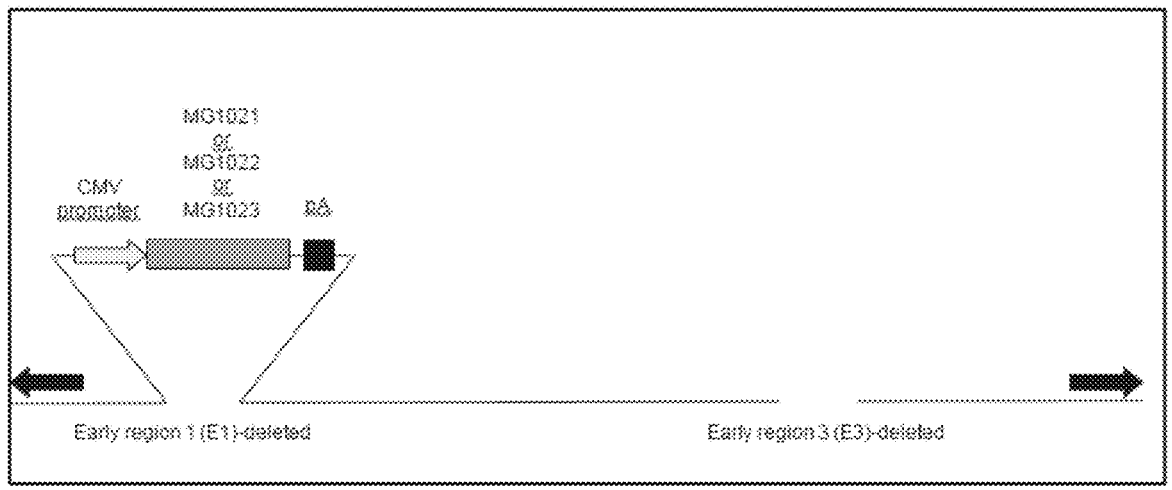

AdMG1021, AdMG1022, and AdMG1023 are early region 1 (E1) and early region 3 (E3) deleted adenovirus vectors. These vectors cannot replicate in most cell lines and tissues; they can replicate and grow in E1-complementing cell lines such as 293 cells. Expression of genes contained in these vectors is under regulation by the human cytomegalovirus immediate-early enhancer promoter (designated as CMV promoter) and human growth hormone polyadenylation sequence pA. All three genes encode fusion proteins, and contain a carboxy-terminal mCherry fluorescent gene (not shown).

AdMG1021, AdMG1022, and AdMG1023 are replication-defective adenovirus vectors based on human adenovirus serotype 5. Such viruses are non-toxic and non-oncogenic.

A

Figure 48 (Continued)
B
Liver sections stained with Oil Red O
HFD fed mouse - EV injected (control)
HFD fed mouse - MG1023 injected
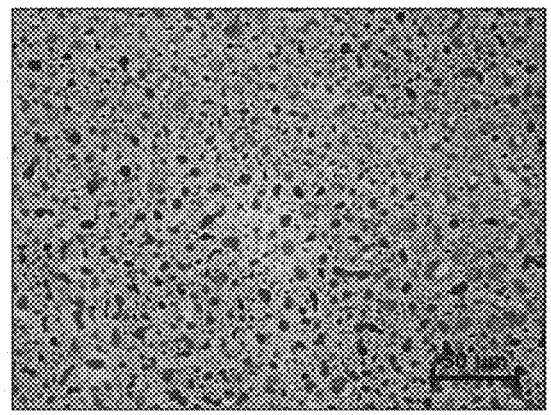
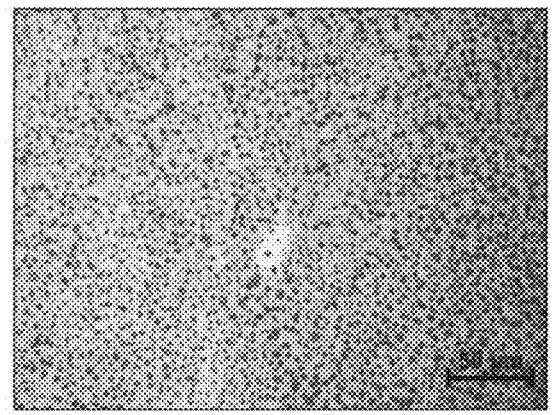

A

B

A

LYSOSOMAL DEGRADATION OF LIPIDS AND PROTEINS AND METHOD OF USE THEREOF

RELATED APPLICATIONS

This application is a national stage filing under 35 U.S.C. § 371 of international PCT application, PCT/CA2016/000192, filed Jul. 8, 2016, which claims priority under 35 U.S.C. § 119(e) to U.S. Provisional Application, U.S. Ser. No. 62/191,274, filed Jul. 10, 2015, each of which is incorporated herein by reference.

FIELD OF INVENTION

The present invention relates generally to lysosomal motility, microautophagy, and lysosome-mediated reduction of cellular lipid or protein content.

BACKGROUND

Triglycerides (TG), comprising one glycerol and three fatty acid moieties linked through ester linkages, are an important source of energy in the body. Within cells, TG may be stored in cytosolic lipid droplets (CLDs), which play an important role in intracellular lipid storage. CLDs comprise an inner lipid core including TG, which is surrounded by an outer phospholipid monolayer. The surface of CLDs typically feature functional proteins. Within cells, CLDs may serve as a storage depot of TG, and may act to increase cellular resistance to lipotoxicity, helping cells to tolerate reasonable levels of TG.

High levels of TG and related metabolites such as diglycerides and fatty acids, however, may lead to cellular lipotoxicity and/or organ damage. High levels of TG and these metabolites are often associated with several important liver and cardiovascular conditions. For example, hypertriglyceridemia (which involves elevated TG levels in the blood stream) may be associated with increased risk of diseases including fatty liver disease, pancreatitis, and cardiovascular disease, to name a few. Dietary and/or genetic factors may contribute to the development of hypertriglyceridemia, which represents an important health concern.

Omega-3 fatty acids (such as eicosapentaenoic acid (EPA) and docosahexaenoic acid (DHA), present in foodstuffs such as fish, whole grains, fresh fruit, and vegetables) may be useful in ameliorating circulating levels of TG, and may reduce the risk of hypertriglyceridemia. Indeed, Omega-3 fatty acids have been suspected to have applications in reducing the risk of selected metabolic abnormalities, such as atherosclerosis, hypertriglyceridemia, and perhaps non-alcoholic fatty liver disease.

The lipid-lowering effect of omega-3s has been attributed to decreased production of very low density lipoproteins (VLDL) by the liver[1] and increased intracellular degradation of apolipoprotein B-100, which is a structural constituent of VLDL.[2,3] It has also been shown that omega-3s can act as a ligand of several key factors of hepatic gene transcription, with SREBP-1c and PPARα being well known[4]. Suppressed SREBP-1c expression, combined with PPARα activation has been demonstrated to ameliorate steatohepatitis and the associated development of hepatocellular carcinoma in cancer-prone[5] or atherosclerosis-prone[6] mouse models treated with omega-3s. An anti-inflammatory effect of omega-3s is mediated through a cell surface G protein coupled receptor, GPR120[7] and a group of bioactive derivatives termed resolvins, docosatrienes, and protectins[8].

However, the cellular pathway(s) through which omega-3 fatty acids reduce lipid levels remain unclear, hindering the development of therapeutic treatments effective against conditions related to those cellular pathways, such as those associated with elevated cytosolic lipid droplet (CLD) and/or TG levels.

Alternative, additional, and/or improved compounds, compositions, and methods for reduction, turnover, and/or modulation of cellular lipid or protein content are desirable.

SUMMARY OF INVENTION

In an embodiment, there is provided herein a method for increasing lysosome-mediated microautophagy of a lipid or protein substrate in a cell, said method comprising:
  treating the cell with a microautophagy-enhancing agent which increases lysosomal association-dissociation events between lysosomes and the lipid or protein substrate;
  thereby increasing lysosome-mediated microautophagy of the lipid or protein substrate.

In a further embodiment of a method as described above, the microautophagy-enhancing agent may comprise an omega-3 fatty acid, or a GDP-bound form of Arl8b ($Arl8b^{GDP}$) protein, or a combination thereof.

In still a further embodiment of a method or methods as described above, the microautophagy-enhancing agent may comprise an omega-3 fatty acid which is eicosapentaenoic acid (EPA) or docosahexaenoic acid (DHA), an $Arl8b^{GDP}$ protein which is $Arl8b^{T34N}$ or a functional equivalent thereof, or a combination thereof.

In another embodiment of a method or methods as described above, the microautophagy-enhancing agent may comprise, or further comprise, one or more nucleic acids which decrease cellular levels of a GTP-bound form of Arl8b (e.g. $Arl8b^{Q75L}$), Vps41, Vps11, or any combination thereof. In yet another embodiment, the one or more nucleic acids may be gene silencing nucleic acids.

In still another embodiment of a method or methods as described above, the microautophagy-enhancing agent may comprise, or further comprise, one or more expression vectors or mRNAs which increase cellular levels of $Arl8b^{WT}$, a GDP-bound form of Arl8b (e.g. $Arl8b^{T34N}$), Vps39, or any combination thereof. In an embodiment, an expression vector may include an AAV vector, for example. In another embodiment, the mRNA may be a chemically modified mRNA, for example.

In certain embodiments of a method or methods as described herein, the microautophagy-enhancing agent may comprise, or further comprise, an expression vector which comprises a nucleic acid sequence encoding $Arl8b^{WT}$, a GDP-bound form of Arl8b (e.g. $Arl8b^{T34N}$), Vps39, or any combination thereof.

In a further embodiment, the microautophagy-enhancing agent may comprise, or further comprise, an expression vector or mRNA encoding $Arl8b^{T34N}$, or $Arl8b^{T34N}$ protein or a peptide derived therefrom.

In yet another embodiment, the microautophagy-enhancing agent may comprise, or further comprise, a combination of expression vectors or mRNAs encoding $Arl8b^{T34N}$ and Vps39.

In certain embodiments of a method or methods as described herein, the lipid or protein substrate may be a lipid droplet (LD) or cytosolic lipid droplet (CLD).

In a further embodiment of a method or methods as described herein, the cell may be a hepatic cell of a subject having hypertriglyceridemia, hepatosteatosis, fatty liver disease, non-alcoholic fatty liver disease (NAFLD), non-alcoholic steatosis (NASH) or hepatitis C virus (HCV) infection, or a cell of a subject having obesity.

In yet another embodiment of a method or methods as described herein, the lipid or protein substrate may be alpha-synuclein.

In still another embodiment of a method or methods as described herein, the cell may be a neuron of a subject having Parkinson's disease.

In another embodiment, the cell may be a hepatic cell of a subject having hyperglycemia or hepatic insulin insensitivity.

In an embodiment, there is provided herein a method for decreasing lysosome-mediated microautophagy of a lipid or protein substrate in a cell, said method comprising:
   treating the cell with a microautophagy-reducing agent which decreases lysosomal association-dissociation events between lysosomes and the lipid or protein substrate;
   thereby decreasing lysosome-mediated microautophagy of the lipid or protein substrate.

In another embodiment of a method as described above, the microautophagy-reducing agent may comprise one or more nucleic acids which decrease cellular levels of $Arl8b^{WT}$, a GDP-bound form of Arl8b (e.g. $Arl8b^{T34N}$), Rab 5, Rab7, Rab9, LAL (lysosomal acidic lipase), LAMP1 (lysosome-associated proteins), KIFbβ, FYCO1, RILP, Vps39, or any combination thereof. In still another embodiment, the one or more nucleic acids may be gene silencing nucleic acids.

In yet another embodiment of a method or methods as described above, the microautophagy-reducing agent may comprise, or further comprise, a GTP-bound form of Arl8b ($Arl8b^{GTP}$) protein, one or more expression vectors or mRNAs which increase cellular levels of a GTP-bound form of Arl8b (e.g. $Arl8b^{Q75L}$), Vps41, or Vps11, or any combination thereof.

In still another embodiment, the microautophagy-reducing agent may comprise or further comprise $Arl8b^{Q75L}$ protein or a functional equivalent thereof, one or more expression vectors or mRNAs which comprise a nucleic acid sequence encoding a GTP-bound form of Arl8b (e.g. $Arl8b^{Q75L}$), Vps41, or Vps11, or any combination thereof.

In a further embodiment of a method or methods as described above, the microautophagy-reducing agent may comprise, or further comprise, an expression vector or mRNA encoding $Arl8b^{Q75L}$, or $Arl8b^{Q75L}$ protein or a peptide derived therefrom. In an embodiment, an expression vector may include an AAV vector, for example. In another embodiment, the mRNA may be a chemically modified mRNA, for example.

In still a further embodiment of a method for decreasing lysosome-mediated microautophagy of a lipid or protein substrate in a cell, the lipid or protein substrate may be a lipid droplet (LD) or cytosolic lipid droplet (CLD).

In yet another embodiment of a method for decreasing lysosome-mediated microautophagy of a lipid or protein substrate in a cell, the cell may be a hepatocellular carcinoma cell of a subject having liver cancer.

In another embodiment, there is provided herein a method for modulating lysosome-mediated microautophagy of a lipid or protein substrate in a cell, said method comprising:
   increasing lysosome-mediated microautophagy by treating the cell with a microautophagy-enhancing agent which increases lysosomal association-dissociation events between lysosomes and the cellular lipid or protein substrate; or
   decreasing lysosome-mediated microautophagy by treating the cell with a microautophagy-reducing agent which reduces lysosomal association-dissociation events between lysosomes and the cellular lipid or protein substrate;
   thereby modulating lysosome-mediated microautophagy of the lipid or protein substrate.

In an embodiment, there is provided herein a use of one or more gene silencing nucleic acids which decrease cellular levels of a GTP-bound form of Arl8b (e.g. $Arl8b^{Q75L}$), Vps41, Vps11, or any combination thereof, for increasing lysosome-mediated microautophagy of a lipid or protein substrate in a cell.

In another embodiment, there is provided herein a use of one or more expression vectors, mRNAs, or proteins which increase cellular levels of $Arl8b^{WT}$, a GDP-bound form of Arl8b (e.g. $Arl8b^{T34N}$), Vps39, or any combination thereof, for increasing lysosome-mediated microautophagy of a lipid or protein substrate in a cell.

In still another embodiment of a use for increasing lysosome-mediated microautophagy of a lipid or protein substrate in a cell, the cell may be a hepatic cell of a subject having hypertriglyceridemia, hepatosteatosis, fatty liver disease, non-alcoholic fatty liver disease (NAFLD), non-alcoholic steatohepatitis (NASH) hyperglycemia, hepatic insulin insensitivity, or hepatitis C virus (HCV) infection, or a neuron of a subject having Parkinson's disease, or a cell of a subject having obesity.

In still another embodiment, there is provided herein a use of one or more gene silencing nucleic acids which decrease cellular levels of $Arl8b^{WT}$, a GDP-bound form of Arl8b (e.g. $Arl8b^{T34N}$), Rab 5, Rab7, Rab9, LAL (lysosomal acidic lipase), LAMP1 (lysosome-associated proteins), KIFbβ, FYCO1, RILP, Vps39, or any combination thereof, for decreasing lysosome-mediated microautophagy of a lipid or protein substrate in a cell.

In yet another embodiment, there is provided herein a use of one or more expression vectors, mRNAs, or proteins, which increase cellular levels of a GTP-bound form of Arl8b (e.g. $Arl8b^{Q75L}$), Vps41, Vps11, or any combination thereof, for decreasing lysosome-mediated microautophagy of a lipid or protein substrate in a cell.

In another embodiment of a use for decreasing lysosome-mediated microautophagy of a lipid or protein substrate in a cell, the cell may be a hepatocellular carcinoma cell of a subject having liver cancer.

In an embodiment, there is provided herein a method for identifying a microautophagy-enhancing agent, said method comprising:
   treating a hepatic liver cell with a candidate agent; and
   determining whether lysosome-mediated microautophagy of cytosolic lipid droplets is increased relative to an untreated control cell;
wherein determination of an increase in lysosome-mediated microautophagy of cytosolic lipid droplets indicates that the candidate agent is a microautophagy-enhancing agent.

In yet another embodiment, there is provided herein a method for identifying a microautophagy-reducing agent, said method comprising:
   treating a hepatic liver cell with a candidate agent; and
   determining whether lysosome-mediated microautophagy of cytosolic lipid droplets is decreased relative to an untreated control cell;
wherein determination of a decrease in lysosome-mediated microautophagy of cytosolic lipid droplets indicates that the candidate agent is a microautophagy-reducing agent.

In an embodiment, there is provided herein a use of a cell culture or animal model having a hepatosteatosis level which is controllable by modulation of Arl8b$^{Q75L}$/Arl8b$^{T34N}$ levels for identifying biomarkers for hepatosteatosis-related diseases, therapeutic treatments for hepatosteatosis-related diseases (such as, for example, small molecules, antibodies, DNA, RNA, or modified nucleic acids, or proteins), or delivery agents for hepatosteatosis therapeutics (such as, for example, microvesicles, exosomes, ectosomes). In a further embodiment, the hepatosteatosis-related disease may be fibrosis or non-alcoholic steatohepatitis (NASH).

In an embodiment, there is provided herein a microautophagy-enhancing agent which increases lysosome-mediated microautophagy of a lipid or protein substrate in a cell, comprising at least one of:
- an omega-3 fatty acid;
- a nucleic acid which decreases cellular levels of a GTP-bound form of Arl8b (e.g. Arl8b$^{Q75L}$), Vps41, or Vps11; or
- an expression vector, mRNA, or protein which increases cellular levels of Arl8b$^{WT}$, a GDP-bound form of Arl8b (e.g. Arl8b$^{T34N}$), or Vps39;

or any combination thereof.

In a further embodiment, there is provided herein a microautophagy-reducing agent which decreases lysosome-mediated microautophagy of a lipid or protein substrate in a cell, comprising at least one of
- oleate (OA);
- a nucleic acid which decreases cellular levels of Arl8b$^{WT}$, a GDP-bound form of Arl8b (e.g. Arl8b$^{T34N}$), Rab5, Rab7, Rab9, LAL (lysosomal acidic lipase), LAMP1 (lysosome-associated proteins), KIFbβ, FYCO1, RILP, or Vps39;
- an expression vector, mRNA, or protein, which increases cellular levels of a GTP-bound form of Arl8b (e.g. Arl8b$^{Q75L}$), Vps41, or Vps11;

or any combination thereof.

In still another embodiment, there is provided herein a polypeptide comprising the amino acid sequence:

(Arl8b$^{T34N}$; SEQ ID NO: 12)
MLALISRLLDWFRSLFWKEEMELTLVGLQYSGKNTFVNVIASGQFSEDMI

PTVGFNMRKVTKGNVTIKIWDIGGQPRFRSMWERYCRGVNAIVYMIDAA

DREKIEASRNELHNLLDKPQLQGIPVLVLGNKRDLPNALDEKQLIEKMNL

SAIQDREICCYSISCKEKDNIDITLQWLIQHSKSRRS for use in increasing lysosome-mediated microautophagy of a lipid or protein substrate in a cell. In another embodiment, there is provided herein a nucleic acid encoding said polypeptide.

In yet another embodiment, there is provided herein a composition comprising a polypeptide or nucleic acid as described above and a pharmaceutically acceptable carrier. In a further embodiment, the composition may further comprise Vps39 or a Vps39 expression vector or mRNA.

In an embodiment, there is provided herein a use of a polypeptide as described above, a composition as described above, or a nucleic acid as described above, for the treatment of hypertriglyceridemia, hepatosteatosis, fatty liver disease, non-alcoholic fatty liver disease (NAFLD), hepatitis C virus (HCV) infection, Parkinson's disease, hyperglycemia, hepatic insulin insensitivity, or obesity.

In another embodiment, there is provided herein a polypeptide comprising the amino acid sequence:

(Arl8b$^{Q75L}$; SEQ ID NO: 13)
MLALISRLLDWFRSLFWKEEMELTLVGLQYSGKTTFVNVIASGQFSEDMI

PTVGFNMRKVTKGNVTIKIWDIGGLPRFRSMWERYCRGVNAIVYMIDAA

DREKIEASRNELHNLLDKPQLQGIPVLVLGNKRDLPNALDEKQLIEKMNL

SAIQDREICCYSISCKEKDNIDITLQWLIQHSKSRRS for use in decreasing lysosome-mediated microautophagy of a lipid or protein substrate in a cell. In a further embodiment, there is provided herein a nucleic acid sequence encoding said polypeptide.

In yet another embodiment, there is provided herein a composition comprising a polypeptide or nucleic acid as described above and a pharmaceutically acceptable carrier.

In still another embodiment, there is provided herein a use of an Arl8b$^{Q75L}$ polypeptide as described above, a composition as described above, or a nucleic acid as described above, for the treatment of cancer. In a further embodiment, the cancer may be liver cancer.

In yet another embodiment, there is provided herein a microautophagy-enhancing agent comprising Arl8b$^{T34N}$, or an expression vector or mRNA encoding Arl8b$^{T34N}$, and Vps39, or an expression vector or mRNA encoding Vps39.

In an embodiment, there is provided herein a method for increasing lysosomal motility (for example, lysosomal bidirectional motility), or microautophagy capacity, or engulfment/degradation capacity, or any combination thereof, in a cell, said method comprising:
- treating the cell with a microautophagy-enhancing agent which increases lysosomal association-dissociation events and/or engulfment events between lysosomes and the lipid or protein substrate;
- thereby increasing lysosomal motility (for example, lysosomal bidirectional motility), or microautophagy capacity, or engulfment/degradation capacity, or any combination thereof.

In a further embodiment of a method for increasing lysosomal motility (for example, lysosomal bidirectional motility), or microautophagy capacity, or engulfment/degradation capacity, or any combination thereof, in a cell, increasing lysosomal motility (for example, lysosomal bidirectional motility), or microautophagy capacity, or engulfment/degradation capacity, or any combination thereof, may increase lysosome-mediated microautophagy, lysosome-mediated macroautophagy, lysosomal maturation processes, or a combination thereof in the cell.

In another embodiment, there is provided herein a method for decreasing lysosomal motility (for example, lysosomal bidirectional motility), or microautophagy capacity, or engulfment/degradation capacity, or any combination thereof, in a cell, said method comprising:
- treating the cell with a microautophagy-reducing agent which decreases lysosomal association-dissociation events and/or engulfment events between lysosomes and the lipid or protein substrate;
- thereby decreasing lysosomal motility (for example, lysosomal bidirectional motility), or microautophagy capacity, or engulfment/degradation capacity, or any combination thereof.

In a further embodiment of a method for decreasing lysosomal motility (for example, lysosomal bidirectional motility), or microautophagy capacity, or engulfment/degradation capacity, or any combination thereof, in a cell, decreasing lysosomal motility (for example, lysosomal bidirectional motility), or microautophagy capacity, or engulfment/degradation capacity, or any combination thereof, may decrease lysosome-mediated microautophagy, lysosome-mediated macroautophagy, lysosomal maturation processes, or a combination thereof in the cell.

BRIEF DESCRIPTION OF DRAWINGS

FIG. 10 illustrates that peroxisomal interaction with CLD is independent of EPA treatment. Imaging of OA- (a) or EPA-treated cells (b) expressing Peroxisome-GFP (green), a peroxisome marker. Lipid droplets are red, lysosomes are blue (lysotracker blue);

FIG. 13 illustrates models for anterograde (a) and retrograde (b) lysosomal motility;

FIG. 16 illustrates that silencing FYCO1 or RILP abolished EPA-induced lipid degradation. (a) Images of CLD in cells 6 h post-oleate (OA) or EPA treatment, or in cells that had been transfected with siRNA specific for RIPL (siRILP) or FYCO1 (siFYCO1) prior to the EPA treatment. Scale bars, 22 µm. (b) Quantification of CLD as represented in (a);

FIGS. 32A-32D provide a $^{GFP}$Arl8b$^{WT}$ plasmid DNA sequence encoding a $^{GFP}$Arl8b$^{WT}$ fusion protein, including annotations indicating the nucleic acid sequence encoding Arl8b$^{WT}$, the translated amino acid sequence of Arl8b$^{WT}$, the nucleic acid sequence encoding the GFP tag, and the translated amino acid sequence of the GFP tag;

FIGS. 33A-33C provide a $^{mCherry}$Arl8b$^{WT}$ plasmid DNA sequence encoding a $^{mCherry}$Arl8b$^{WT}$ fusion protein, including annotations indicating the nucleic acid sequence encoding Arl8b$^{WT}$, the translated amino acid sequence of Arl8b$^{WT}$, the nucleic acid sequence encoding the mCherry tag, and the translated amino acid sequence of the mCherry tag;

FIGS. 34A-34C provide a $^{mCherry}$Arl8b$^{Q75L}$ (Arl8b$^{Q75L}$ is the putative GTP-bound form, or dominant-active "DA" form, of Arl8b) plasmid DNA sequence encoding a $^{mCherry}$Arl8b$^{Q75L}$ fusion protein, including annotations indicating the nucleic acid sequence encoding Arl8b$^{Q75L}$, the translated amino acid sequence of Arl8b$^{Q75L}$, the nucleic acid sequence encoding the mCherry tag, and the translated amino acid sequence of the mCherry tag;

FIGS. 35A-35D provide a $^{mCherry}$Arl8b$^{T34N}$ (Arl8b$^{T34N}$ is the putative GDP-bound form, or dominant negative "DN" form, of Arl8b) plasmid DNA sequence encoding a $^{mCherry}$Arl8b$^{T34N}$ fusion protein, including annotations indicating the nucleic acid sequence encoding Arl8b$^{T34N}$, the translated amino acid sequence of Arl8b$^{T34N}$, the nucleic acid sequence encoding the mCherry tag, and the translated amino acid sequence of the mCherry tag;

FIG. 44 shows an alignment of Arl8b amino acid sequences from examples of various animals (along with associated Uniprot identifier numbers). Note that Arl8b is highly conserved in mammals, thus the amino acid sequence of human and rodent (e.g. mouse and rat) Arl8b have 100% sequence identity;

FIGS. 46A-46L show the amino acid sequences of human Arl8b/Arl10c; human Vps39; human Vps41; human Vps11; human Vps41; human Vps11; and human Vps39 proteins, as well as other nucleic acid and amino acid sequences as described herein;

Figure 1:
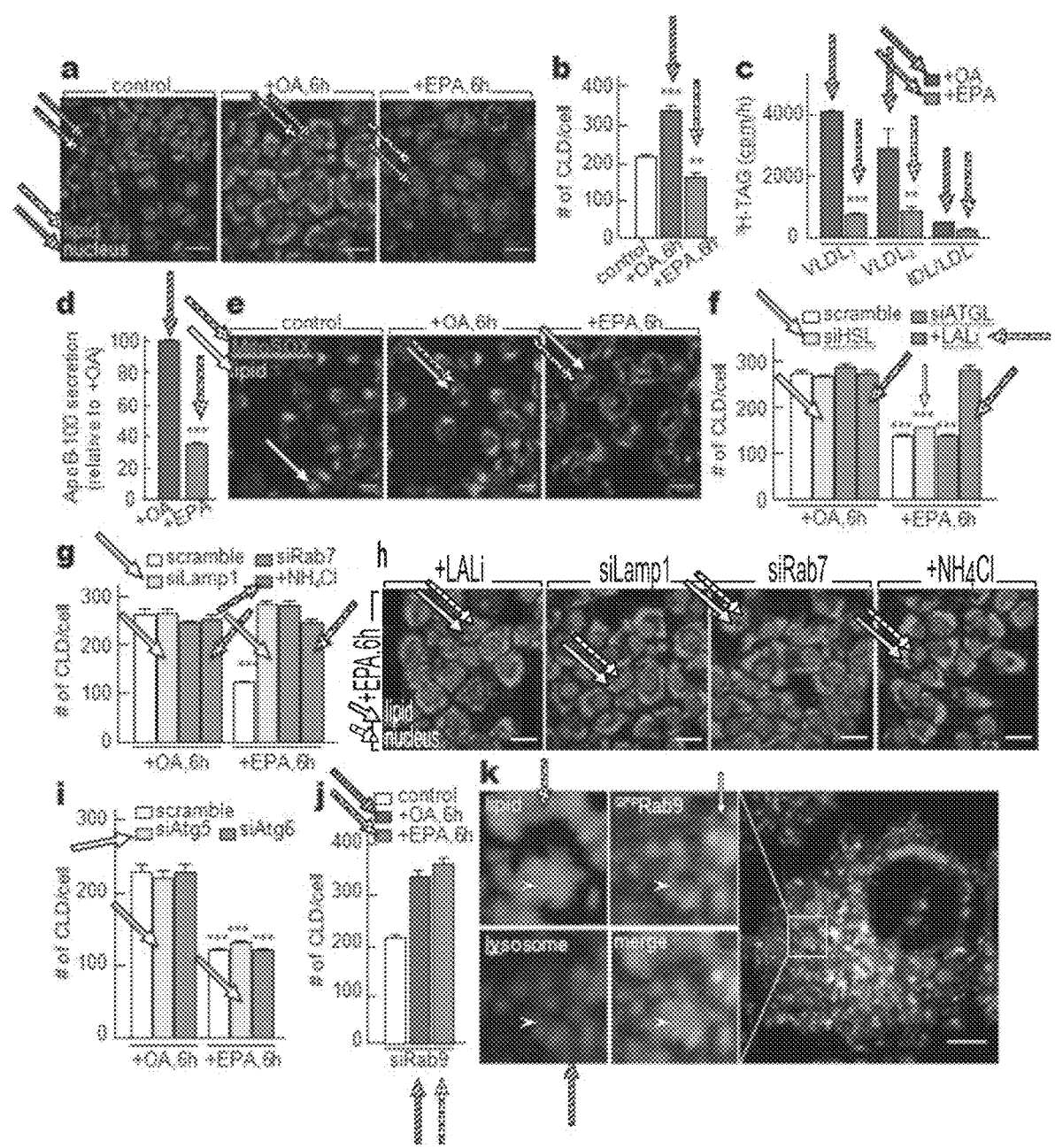
FIG. 1 illustrates that EPA-induced lipid degradation is achieved through Atg5-independent autophagy. (a) Images of cells in baseline (control) and 6 h post-oleate (OA) or EPA treatment. Scale bar, 22 μm. (b) Quantification of CLD as represented in (a). (c) Secretion of metabolically labeled TG associated with $VLDL_1$, $VLDL_2$, and intermediate density lipoproteins (IDL)/low density lipoproteins (LDL). (d) Secretion of apoB-100. (e) Imaging of mitochondrial superoxide formation in situ using MitoSOX Red. Scale bar, 16 μm. (f) and (g) Quantification of CLD 6 h post-OA or EPA treatment in cells transfected with HSL- or ATGL-specific siRNA or treated with LAL inhibitor (LALi) (f), or transfected with Rab7- or LAMP1-specific siRNA or treated with $NH_4Cl$ (g). (h) Representative images of CLD 6 h post-EPA treatment as used for quantification in (f) and (g). Scale bar, 22 μm. (i) Quantification of CLD 6 h post-OA or EPA treatment in cells transfected with control (scramble), Atg5-, or Atg6-specific siRNA. (j) Quantification of CLD in baseline (control) and 6 h post-OA or EPA treatment of cells transfected with Rab9-specific siRNA. (k) Imaging of lysosome and CLD distribution 6 h post-EPA treatment in cells transfected with $^{GFP}$Rab9. Scale bar, 8 μm. All quantification data are presented as mean±SEM. p<0.01, * p<0.001. $VLDL_1$, large TG-rich VLDL that is produced under hypertriglyceridemia conditions; $VLDL_2$, VLDL that is produced under normal physiological conditions; HSL, hormone sensitive lipase; ATGL, adipose triglyceride lipase; LAL, lysosomal acidic lipase; LAMP1, lysosomal-associated membrane protein 1.

It will be understood that several of the figures provided herein include photographs of stained cells, or other depictions in which elements may be distinguished from one another by color. To enhance clarity of such figures, arrows indicating color have been included in the drawings as follows: Blue (lined arrow); Red (dotted arrow); Green (solid arrow).

DETAILED DESCRIPTION

Described herein are compounds, compositions, methods, and uses relating to the reduction, turnover, and/or modulation of cellular lipid or protein content, as well as compounds, compositions, methods, and uses relating to the treatment or prevention of diseases or conditions relating to lysosomal function, lysosomal motility, lysosomal degradation capacity, autophagy, and/or cellular protein or lipid accumulation. It will be appreciated that embodiments and examples provided herein are for illustrative purposes intended for those skilled in the art, and are not meant to be limiting in any way.

Although the beneficial effects of omega-3 fatty acid in reducing the risk of hypertriglyceridemia have been investigated in pre-clinical and clinical studies, the mechanism of action remained unclear, which has hindered the development of treatments effective against conditions associated with elevated triglyceride levels.

In hepatocytes, for example, triglycerides are present as cytosolic lipid droplets (CLDs) distributed at the cell periphery. The development of methods, uses, and/or treatments for achieving reduction, turnover, or modulation (i.e. increase and/or decrease, as desired) of cellular lipid content, such as cellular lipid content present in the form of triglycerides contained in CLDs, has thus far proven difficult.

Herein, compounds, compositions, and methods for reduction, turnover, and/or modulation of cellular lipid or protein content are provided. By way of illustrative example, which is not meant to be limiting, results provided herein demonstrate that treatment of lipid-laden hepatic cells with eicosapentaenoic acid (EPA) leads to lipid degradation, which involves functional lysosomes. Therapeutically relevant targets for modulating (i.e. increasing and/or decreasing) lysosome-mediated lipid degradation are identified, and compounds, biomolecules, and/or compositions which may trigger lysosome-mediated lipid or protein degradation are described. Results indicate that the level of lysosome-mediated lipid or protein degradation may be modified, for example, but not limited to, by increasing or decreasing expression of particular genes (i.e. by overexpressing or silencing), by increasing or decreasing cellular levels of particular proteins, by inhibiting particular proteins or enzymes, or by the introduction of additional or mutant genes or proteins. Results also indicate that the extent of lysosomal interaction with CLDs in cells, or the extent of lysosomal motility (for example, lysosomal bidirectional motility), can be similarly modified (see, for example, FIG. 36).

In an embodiment, there is provided herein a method for increasing lysosome-mediated microautophagy of a lipid or protein substrate in a cell, said method comprising:

treating the cell with a microautophagy-enhancing agent which increases lysosomal association-dissociation events between lysosomes and the lipid or protein substrate;

thereby increasing lysosome-mediated microautophagy of the lipid or protein substrate.

In a further embodiment, there is provided herein a method for restoring or increasing lysosomal motility (for example, bidirectional motility) in a cell, said method comprising:

treating the cell with a microautophagy-enhancing agent which increases lysosomal association-dissociation events between lysosomes and the lipid or protein substrate;

thereby restoring or increasing lysosomal motility.

As will be understood, lysosome-mediated microautophagy refers to a cellular process in which a cellular lipid or protein substrate, or a portion thereof, is engulfed and degraded by a lysosome. In certain embodiments, without wishing to be bound by theory or considered limiting in any manner, lysosome-mediated microautophagy may refer to processes which are increased under elevated omega-3 fatty acid (or other natural lipid lowering supplement) conditions in a cell, for example. If the substrate is a lipid, the process may be considered as a microautolipophagy-type process involving direct and dynamic lysosomal association-and-dissociation with lipids, such as lipid droplets (LDs) or cytosolic lipid droplets (CLDs). Lysosome-mediated microautophagy of lipids is thought to involve lysosomal acquisition of small lipid fragments (which may occur via, for example, formation of a pore joining the lysosome and the CLD core during the "on" phase) without engaging complete fusion or engulfment of the entire CLD.

As described in further detail herein, and without wishing to be bound by theory, lysosome-mediated microautophagy of lipids appears to be governed by the rate of lysosomal dissociation from the substrate (i.e. lipid droplet) and/or the rate of lysosomal interaction with lipid droplets or substrates, a process which, as has been found herein, appears to depend upon numerous factors, for example but not limited to Arl8b-facilitated association/dissociation (i.e. "on" and "off" phases) between lysosomes and CLDs involving different subunits of the HOPS tethering complex.

It will be understood that references to increasing lysosome-mediated microautophagy refer to an increase in the rate, extent, capacity, or efficacy of the lysosome-mediated microautophagy process in a cell (such as, for example, a cell showing accumulation of lipid (as in non-alcoholic fatty liver disease, for example) or protein (as in Parkinson's disease, for example)) as compared to baseline levels of a corresponding treated or untreated control cell, or a cell treated with a different time course, or as compared to normal levels in a healthy subject or cell.

It will further be understood that references to restoring or increasing lysosomal motility or lysosomal bidirectional motility in a cell may refer to enhancing, increasing, activating, or otherwise restoring or rescuing lysosomal motility activity in a cell. Such restoration or rescue may result in an increase in autophagy (such as, for example, micro- and/or macro-autophagy) and/or lysosomal degradation capacity. As detailed herein, there are several diseases, conditions, and cellular states in which cellular lysosomal motility may be impaired, reduced, blocked, or suppressed. As lysosome-mediated microautophagy involves lysosomal motility and kiss-and-run events, microautophagy-enhancing agents may restore or increase lysosomal motility in a cell. Lysosomal motility may play an important role in several cellular functions, including lysosome-mediated microautophagy, lysosome-mediated macroautophagy, and lysosomal maturation processes. References to restoring lysosomal motility and/or lysosomal bidirectional motility may refer to modulating cellular lysosomal motility/bidirectional motility levels back to those of corresponding normal or healthy control cells having baseline levels of lysosomal motility/bidirectional motility. Such modulation may, in certain embodiments, also modulate degradation capacity (i.e. phagy) levels back to those of normal or healthy cells.

It will also be understood that impairment of lysosomes, lysosome-mediated microautophagy, macroautophagy, and/or lysosomal biogenesis in hepatic cells may lead to conditions under which a large amount of lipids may be accumulated as CLDs in cell cytoplasm, a condition commonly known as fatty liver. Impaired lysosomal movement (i.e. anterograde and retrograde lysosomal motility between the perinuclear regions and cell periphery, or between perinuclear region and target protein or lipid substrate) and/or impaired interaction with the target protein or lipid substrate, especially under fatty liver conditions, or hepatosteatosis, may result in either a persistent interaction of lysosomes with CLDs in cell periphery, or else a disturbed motility of lysosomes and/or a confined localization of lysosomes at the perinuclear regions of the cells. Thus, triggering lysosomal motility and its "on" and "off" interaction with lipid or protein substrates (i.e. in a "kiss-and-run" fashion) may facilitate lysosome-mediated microautophagy, and/or may increase levels of autophagy (i.e., lipophagy) flux.

Examples of suitable methods for determining whether lysosome-mediated microautophagy is increased in a cell, such as, for example, a steatoic liver cell, are outlined in detail in the examples provided below. By way of example, and without wishing to be limiting, an increase in lysosome-mediated microautophagy of lipid droplets may be identified using cell imaging, Western blotting of ADRP (an indirect quantitative measurement of cellular lipid contents), and/or direct CLD quantification techniques as described in, for example, Examples 1-3 below.

As will also be understood, a lipid or protein substrate of lysosome-mediated microautophagy may refer to any unnecessary, overabundant, or dysfunctional cellular component which is degraded within a cell through a lysosome-mediated microautophagy, or suitable general autophagy, process. By way of non-limiting examples, suitable substrates may include a lipid droplet or a cytosolic lipid droplet (as may be commonly present in, for example, hepatosteatosis), a hepatitis C virus (HCV) protein (as present in, for example, an HCV-infected liver), lipid droplets which interact with HCV proteins (including core and subunits), and/or alpha-synuclein (as present in, for example, Parkinson's disease brain cells) or other proteins which are increased and/or accumulated as part of disease development. Other substrates, such as protein aggregates in Alzheimer's disease (AD), are also contemplated.

The person of skill in the art having regard to this application will understand that a microautophagy-enhancing agent may be any suitable agent which increases or facilitates the rate, activity, extent, or efficacy of lysosome-mediated microautophagy in a cell, or that increases lysosomal motility or bidirectional motility. In a non-limiting embodiment, a suitable microautophagy-enhancing agent may comprise an omega-3 (such as, for example, eicosapentaenoic acid (EPA) or docosahexaenoic acid (DHA), or any combination thereof) fatty acid, such as an omega-3 fatty acid that can increase cellular levels of TG-rich CLDs, and/or increase TG-to-CE ratios in CLD; one or more gene silencing nucleic acids which decrease cellular levels of a putative GTP-bound form of Arl8b (e.g. $Arl8b^{Q75L}$), Vps41, or Vps11, or any combination thereof; or one or more expression vectors, mRNAs, or proteins which increase cellular levels of $Arl8b^{WT}$, a putative GDP-bound form of Arl8b (e.g. $Arl8b^{T34N}$), or Vps39, or regulation mechanisms leading to their overproduction, or any combination thereof; or any combination thereof.

In particular embodiments, a microautophagy-enhancing agent may be, or comprise, a GDP-bound form or Arl8b ($Arl8b^{GDP}$) such as, for example, $Arl8b^{T34N}$, or a functional equivalent thereof. Suitable GDP-bound forms of Arl8b may include any suitable Arl8b variant which is "dominant negative", or which preferentially binds GDP over GTP. Such $Arl8b^{GDP}$ variants may be identified using techniques known in the art (see, for example, Chan, C.-C. et al. Systematic Discovery of Rab GTPases with Synaptic Functions in *Drosophila*. Current Biology 21, 1704-1715 (2011); Tabancay, A. P. et al. Identification of dominant negative mutants of Rheb GTPase and their use to implicate the involvement of human Rheb in the activation of p70S6K. J. Biol. Chem. 278, 39921-39930 (2003); and Dumas, J. J., Zhu, Z., Connolly, J. L. & Lambright, D. G. Structural basis of activation and GTP hydrolysis in Rab proteins. Structure 7, 413-s2 (1999), each of which is herein incorporated by reference in its entirety), such as those used to identify $Arl8b^{T34N}$. By way of example, the $Arl8b^{GDP}$ may be $Arl8b^{T34N}$, or a functional equivalent thereof. Suitable functional equivalents of $Arl8b^{T34N}$ may include, for example, suitable Arl8b variants or mutants having at least 80% (or ≥85%, or ≥90%, or ≥95%, or ≥99%) sequence identity to $Arl8b^{WT}$ or $Arl8b^{T34N}$, and which preferentially bind GDP over GTP while also retaining the relevant cellular/biochemical functions of $Arl8b^{T34N}$ as described in detail herein. In further embodiments, it will further be understood that a microautophagy-enhancing agent may also be, or comprise, a nucleic acid/expression vector (i.e. vector, cassette, mRNA, modified mRNA, plasmid, for example) which encodes for/expresses a GDP-bound form of Arl8b ($Arl8b^{GDP}$) such as, for example, $Arl8b^{T34N}$, or a functional equivalent thereof.

It will be understood that, in certain embodiments, a microautophagy-enhancing agent may be any suitable agent which increases or facilitates the rate, activity, extent, or efficacy of lysosome-mediated microautophagy in a cell, or that increases lysosomal motility or bidirectional motility. Small molecule-based microautophagy-enhancing agents are contemplated herein, and may include, for example, those which inhibit or reduce cellular levels of a putative GTP-bound form of Arl8b (e.g. $Arl8b^{Q75L}$), Vps41, or Vps11, or any combination thereof; and/or those which increase activity or increase cellular levels of $Arl8b^{WT}$, a putative GDP-bound form of Arl8b (e.g. $Arl8b^{T34N}$), or Vps39, or any combination thereof. In an embodiment, a suitable small molecule-based microautophagy enhancing agent may be or comprise an omega-3 fatty acid or fish oil, for example EPA or DHA, or a suitable synthetic mimic, analogue, or derivative thereof.

Fish oil/omega-3 fatty acids and derivatives are discussed in, for example, Bronwell (2012), Groundbreaking study reveals new mechanism behind fish oil's health benefits, Life Extension Magazine (http://www.lifeextension.com/magazine/2012/9/fish-oils-health-benefits/page-01).

Microautophagy-enhancing agents may comprise one or more microautophagy-enhancing agents, such as those outlined above, in combination. In certain embodiments, suitable microautophagy-enhancing agents may include compositions comprising both an omega-3 fatty acid (such as, for example, EPA or DHA), and a protein as described herein, gene silencing nucleic acid such as a gene silencing nucleic acid as described herein, or an expression vector as described herein. By way of example, a suitable microautophagy-enhancing agent may comprise a microautophagy-enhancing agent as outlined herein, or any two, three, four, or more microautophagy-enhancing agents as outlined herein in combination.

In certain embodiments, microautophagy-enhancing agents may comprise compositions comprising both an omega-3 fatty acid (such as, for example, EPA or DHA) and one or more expression vectors, proteins, or mRNAs which increase cellular levels of $Arl8b^{WT}$, a putative GDP-bound form of Arl8b (e.g. $Arl8b^{T34N}$), or Vps39, or any combination thereof, as outlined herein.

In another embodiment, microautophagy-enhancing agents may comprise compositions comprising both an omega-3 fatty acid (such as, for example, EPA or DHA) and one or more gene silencing nucleic acid(s), such as a gene silencing nucleic acid which decreases cellular levels of a putative GTP-bound form of Arl8b (e.g. $Arl8b^{Q75L}$), Vps41, or Vps11, or any combination thereof, as outlined herein.

In an embodiment, a microautophagy-enhancing agent may comprise a microautophagy-enhancing agent as outlined herein, or any two, three, four, or more microautophagy-enhancing agents as outlined herein in combination.

It will be understood that in certain embodiments, microautophagy-enhancing agents may be used to correct a microautophagy deficiency in a cell, or a cellular condition in which microautophagy is decreased.

It will also be understood that microautophagy (i.e. lysosomal kiss-and-run with endosomes and CLDs) is an event involved with lysosomal biogenesis and/or maturation. Because lysosomes are involved also in macroautophagy, and because lysosomal maturation may be important for lysosomal function in this regard, an increase or improvement in microautophagy may also lead to improved macroautophagy activity in certain examples.

By way of example, and without wishing to be limiting, a cellular condition where microautophagy is compromised (for example, but not limited to, compromised or reduced lysosomal motility, bidirectional motility, and/or distribution, and/or reduced functional lysosome physiological pool) may occur in hepatosteatoic cells, in HCV-infected liver cells, and/or in alpha-synuclein accumulated Parkinson's disease brain cells. In certain embodiments, microautophagy-enhancing agents may be used to correct such microautophagy deficiencies and/or macroautophagy deficiencies.

It will be understood that lysosomal association-dissociation events between lysosomes and the lipid or protein substrate refer to events where a lysosome associates with a lipid or protein substrate (i.e. a lipid droplet or a protein aggregate, for example), acquires at least a portion of the lipid or protein substrate, and then dissociates from the lipid or protein substrate. Lysosomal association-dissociation (i.e. the "on" and "off") events between lysosomes and the lipid or protein substrate may be considered as "kiss-and-run" events as described in further detail below. As part of the association (or "kiss") event, at least a small piece of substrate (i.e. lipid) may be "grabbed" or engulfed by the lysosome from the substrate (i.e. CLD, for example). In the case of lipid droplet substrates, this may be achieved through the formation of a fusion pore between lysosome and the CLD. As part of the dissociation (or "run") event, dissociation of the lysosome from the substrate (i.e. CLD) may occur. An increase in lysosomal association-dissociation events may refer to an increase in the rate, extent, or efficacy of lysosomal association-dissociation events in a cell as compared to baseline levels of a corresponding treated or untreated control cell, for example an identical cell treated in identical conditions but without a microautophagy-modulating agent or with a compound or composition that is known not to affect the process.

In certain embodiments, the rate of the dissociation (or "run") event, in addition to the rate of the association (or "on") event, may be important factors in lysosome-dependent microautophagy of substrates such as lipids. Failure of lysosomal dissociation from CLD may interfere with lipid or protein degradation by blocking the engulfment process, even in the presence of an EPA microautophagy-enhancing agent. On the other hand, encouraging rapid disassociation of lysosomes from CLD (for example, by facilitating/accelerating the engulfment process) may accelerate lipid degradation in a manner which may involve the allowance of fast initiation of another round of kiss-and-run and/or may involve increasing the activity of microautophagy and/or macroautophagy and/or lysosomal degradation capacity.

The person of skill in the art will recognize that the expression of particular genes within a cell may be reduced, prevented, or "silenced" using any of a variety of well-known methods. By way of non-limiting example, a gene silencing nucleic acid may be used to reduce, prevent, or silence the expression of a target gene. Without wishing to be limiting, suitable gene silencing nucleic acids may include siRNAs, antisense oligonucleotides (AONs), short hairpin RNAs (shRNAs), microRNAs (miRNAs), or other RNA interference (RNAi) or antisense gene silencing triggers, among others. Given a particular gene sequence, the person of skill in the art will be able to design gene silencing oligonucleotides capable of targeting said gene, reducing expression (either transcription, translation, or both) of the gene. For example, an siRNA antisense strand, or an antisense oligonucleotide, which is fully or substantially complementary to a region of the gene-expressed mRNA sequence may be prepared, and used for targeted gene silencing by triggering RISC or RNase H-mediated mRNA degradation. Further detail is provided below.

Without wishing to be bound by theory, it will be recognized that Arl8b (ADP-ribosylation factor-like protein 8b, also known as Arl10c or Gie1) as referred to herein, or Arf-like protein, may be a putative small GTPase (based on sequence homology with other members of the Arl (Arf-like) family) involved in lysosome-mediated microautophagy. As such, based on sequence homology to other members of the Arl (Arf-like) family, wild-type Arl8b (Arl8b$^{WT}$) may alternate between two forms: GTP-bound Arl8b (Arl8b$^{GTP}$) and GDP-bound Arl8b (Arl8b$^{GDP}$). Arl8b$^{GTP}$ may refer to GTP-bound Arl8b$^{WT}$, or to mutant or dominant active ("DA") Arl8b variants that preferentially bind GTP over GDP (by way of example, Arl8b$^{Q75L}$, also referred to as "dominant-active" Arl8b, or Arl8b DA, for example, described in further detail below, is suspected to be a GTP-bound "DA" form based on sequence homology of amino acids involved in GTP/GDP binding in other GTPases such as the Rabs). Arl8b$^{GDP}$ may refer to GDP-bound Arl8b$^{WT}$, or to mutant or dominant negative ("DN") Arl8b variants that preferentially bind GDP over GTP (by way of example, Arl8b$^{T34N}$ (also referred to as "dominant-negative" or "DN" form), for example, described in further detail below, is suspected to be a GDP-bound "DN" form based on sequence homology of amino acids involved in GTP/GDP binding in other GTPases such as the Rabs). Arl8b$^{Q75L}$ is a mutant Arl8b which presumably binds only, or substantially only, GTP, whereas Arl8b$^{T34N}$ is a mutant Arl8b which presumably binds only, or substantially only, GDP. Arl8b$^{Q75L}$ has a Gln-to-Leu substitution at position 75, while Arl8b$^{T34N}$ has a Thr-to-Asn substitution at position 34 (see, for example, FIGS. 33-35 for further detail).

It will be understood that in an embodiment of a method for increasing lysosome-mediated microautophagy and/or macroautophagy by increasing the capacity of lysosomal degradation of a lipid or protein substrate in a cell, the cell may be a hepatic cell of a subject having hypertriglyceridemia, hepatosteatosis, fatty liver disease, non-alcoholic fatty liver disease (NAFLD), NASH, hyperglycemia, hepatic insulin insensitivity, or hepatitis C virus (HCV) infection, or a brain cell of a subject having Parkinson's disease, or a cell of a subject having obesity.

Accordingly, in an embodiment, there is provided herein an in vitro or in vivo method for increasing lysosome-mediated microautophagy of a lipid or protein substrate in a cell of a subject having hypertriglyceridemia, hepatosteatosis, fatty liver disease, non-alcoholic fatty liver disease (NAFLD), hyperglycemia, hepatic insulin insensitivity, hepatitis C virus (HCV) infection, Parkinson's disease, or obesity, said method comprising:

optionally, selecting a subject having hypertriglyceridemia, hepatosteatosis, fatty liver disease, non-alcoholic fatty liver disease (NAFLD), hyperglycemia, hepatic insulin insensitivity, hepatitis C virus (HCV) infection, Parkinson's disease, or obesity; and treating the cell of the subject with a microautophagy-enhancing agent which increases lysosomal association-dissociation events between lysosomes and the lipid or protein substrate;

thereby increasing lysosome-mediated microautophagy of the lipid or protein substrate.

In certain embodiments, selecting a subject may involve, for example, identifying subjects having hypertriglyceridemia, hepatosteatosis, fatty liver disease, non-alcoholic fatty liver disease (NAFLD), hyperglycemia, hepatic insulin insensitivity, hepatitis C virus (HCV) infection, Parkinson's disease, or obesity using suitable diagnostic techniques known in the art such as, for example, any suitable blood test, urine test, fluid test, genetic test, biopsy, surgical technique, physical examination, or other diagnostic procedure. Alternatively, or in addition, subjects may be selected by qualitatively or quantitatively assess the subject's baseline or normal levels of microautophagy in cells relevant to the disease being treated (such as hepatic cells, or neuron cells), and comparing these levels to those of a healthy subject, wherein a decreased microautophagy level may identify the subject as a subject whom may particularly benefit from treatment with a microautophagy-enhancing agent.

The skilled person will understand that, in certain embodiments, the microautophagy levels and/or diseases state of the subject may be monitored before, during, and/or after treatment with the microautophagy-enhancing agent, which may allow for determination of treatment efficacy, and for determination of whether increased or repeated treatments may be performed.

The skill person will further understand that, in certain embodiments, treatment of the subject with the microautophagy-enhancing agent may increase cellular levels of the microautophagy-enhancing agent within the subject beyond endogenous or otherwise naturally occurring levels for a period of time, or may restore cellular levels of the microautophagy-enhancing agent within the subject to endogenous or otherwise naturally occurring levels of a healthy subject for a period of time.

In certain non-limiting embodiments, increasing lysosome-mediated microautophagy of a lipid or protein substrate in a cell of a subject having, or at risk of getting, hypertriglyceridemia, hepatosteatosis, fatty liver disease, non-alcoholic fatty liver disease (NAFLD), hyperglycemia, hepatic insulin insensitivity, hepatitis C virus (HCV) infection, Parkinson's disease, or obesity may be of therapeutic interest. In an embodiment, increasing lysosome-mediated microautophagy of a lipid or protein substrate may be used as part of a treatment or preventative therapeutic approach for the treatment, prevention, or reduction of hypertriglyceridemia, hepatosteatosis, fatty liver disease, non-alcoholic fatty liver disease (NAFLD), hyperglycemia, hepatic insulin insensitivity, hepatitis C virus (HCV) infection, Parkinson's disease, or obesity. In certain embodiments, it is contemplated herein that methods for increasing lysosome-mediated microautophagy of a lipid or protein substrate may optionally be used in combination with known standard treatments (for example, any suitable lifestyle change, therapeutic treatment, or both), either prior to, concurrently, or afterwards.

By way of non-limiting example, methods for increasing lysosome-mediated microautophagy of a lipid or protein substrate may be used in combination with dietary modification, weight loss, exercise, and/or a fibrate- or statin-class drug in the treatment of hypertriglyceridemia; in combination with dietary changes, exercise, and/or medications that decrease insulin resistance in the treatment of hepatosteatosis, fatty liver disease, obesity, and/or non-alcoholic fatty liver disease; in combination with insulin or another diabetes treatment in the treatment of hyperglycemia; in combination with exercise, weight-loss, and/or metformin in the treatment of hepatic insulin insensitivity; in combination with interferon, ribavirin, boceprevir, telaprevir, sofosbuvir, and/or ledipasvir in the treatment of HCV; or in combination with levodopa, a dopamine agonist, and/or an MAO-B inhibitor in the treatment of Parkinson's disease.

In another embodiment, there is provided herein a method for decreasing lysosome-mediated microautophagy of a lipid or protein substrate in a cell, said method comprising:

treating the cell with a microautophagy-reducing agent which decreases lysosomal association-dissociation events between lysosomes and the lipid or protein substrate;

thereby decreasing lysosome-mediated microautophagy of the lipid or protein substrate.

It will be understood that references to decreasing lysosome-mediated microautophagy refer to decreases in the rate, extent of, or efficacy of the lysosome-mediated microautophagy process in a cell as compared to baseline levels of a corresponding treated or untreated control cell. Examples of suitable methods for determining whether lysosome-mediated microautophagy is decreased in a cell are outlined in detail in the examples provided below. By way of example, a decrease in lysosome-mediated microautophagy of lipid droplets may be identified using cell imaging, Western blotting of ADRP, and/or lipid droplet quantification techniques as described in Examples 1-3 below.

A person of skill in the art will understand that a microautophagy-reducing agent may be any suitable agent which decreases the rate, extent, activity, and/or efficacy of lysosome-mediated microautophagy in a cell, or that decreases lysosomal motility or bidirectional motility, or that impairs lysosomal distribution. In a non-limiting embodiment, a suitable microautophagy-reducing agent may comprise: one or more gene silencing nucleic acids which decrease cellular levels of $Arl8b^{WT}$, a putative GDP-bound form of Arl8b (i.e. $Arl8b^{T34N}$), Rab5, Rab7, Rab9, LAL (lysosomal acidic lipase), LAMP1 (lysosome-associated proteins), KIFbβ, FYCO1, RILP, or Vps39; or one or more expression vectors or mRNAs which increase cellular levels of a putative GTP-bound form of Arl8b (i.e. $Arl8b^{Q75L}$), Vps41, or Vps11, or regulation mechanisms leading to their overproduction.

In certain embodiments, a microautophagy-reducing agent may comprise oleate (OA). In certain embodiments, a microautophagy-reducing agent may comprise oleate (OA) and one or more suitable gene silencing nucleic acids that decreases cellular levels of $Arl8b^{WT}$, a putative GDP-bound form of Arl8b (i.e. $Arl8b^{T34N}$), Rab5, Rab7, Rab9, LAL (lysosomal acidic lipase), LAMP1 (lysosome-associated proteins), KIFbβ, FYCO1, RILP, or Vps39.

In certain embodiments, a microautophagy-reducing agent may comprise oleate (OA) and one or more suitable expression vectors or mRNAs which increase cellular levels of a putative GTP-bound form of Arl8b (i.e. Arl8b$^{Q75L}$), Vps41, or Vps11, or regulation mechanisms leading to their overproduction.

In particular embodiments, a microautophagy-reducing agent may be, or comprise, a GTP-bound form or Arl8b (Arl8b$^{GTP}$) such as, for example, Arl8b$^{Q75L}$, or a functional equivalent thereof. Suitable GTP-bound forms of Arl8b may include any suitable Arl8b variant which is "dominant active", or which preferentially binds GTP over GDP. Such Arl8b$^{GTP}$ variants may be identified using techniques known in the art (see, for example, Chan, C.-C. et al. Systematic Discovery of Rab GTPases with Synaptic Functions in *Drosophila*. Current Biology 21, 1704-1715 (2011); Tabancay, A. P. et al. Identification of dominant negative mutants of Rheb GTPase and their use to implicate the involvement of human Rheb in the activation of p70S6K. J. Biol. Chem. 278, 39921-39930 (2003); and Dumas, J. J., Zhu, Z., Connolly, J. L. & Lambright, D. G. Structural basis of activation and GTP hydrolysis in Rab proteins. Structure 7, 413-s2 (1999), each of which is herein incorporated by reference in its entirety), such as those used to identify Arl8b$^{Q75L}$. By way of example, the Arl8b$^{GTP}$ may be Arl8b$^{Q75L}$, or a functional equivalent thereof. Suitable functional equivalents of Arl8b$^{Q75L}$ may include, for example, suitable Arl8b variants or mutants having at least 80% (or ≥85%, or ≥90%, or ≥95%, or ≥99%) sequence identity to Arl8b$^{WT}$ or Arl8b$^{Q75L}$, and which preferentially bind GTP over GDP while also retaining the relevant cellular/biochemical functions of Arl8b$^{Q75L}$ as described in detail herein. In further embodiments, it will further be understood that a microautophagy-reducing agent may also be, or comprise, a nucleic acid/expression vector (i.e. vector, cassette, mRNA, modified mRNA, plasmid, for example) which encodes for/expresses a GTP-bound form of Arl8b (Arl8b$^{GTP}$) such as, for example, Arl8b$^{Q75L}$, or a functional equivalent thereof.

It will be recognized that expression vectors or mRNAs which increase cellular levels of a particular protein may be used in combination with, or substituted by, suitable agents which affect gene expression regulation mechanisms to produce increased expression of the particular protein, as will be known to the person of skill in the art.

It will be understood that, in certain embodiments, a microautophagy-reducing agent may be any suitable agent which decreases the rate, activity, extent, or efficacy of lysosome-mediated microautophagy in a cell, or that decreases lysosomal motility or bidirectional motility, or that impairs lysosomal distribution. Small molecule-based microautophagy-reducing agents are contemplated herein, and may include, for example, those which inhibit or reduce cellular levels of Arl8b$^{WT}$, a putative GDP-bound form of Arl8b (i.e. Arl8b$^{T34N}$), Rab5, Rab7, Rab9, LAL (lysosomal acidic lipase), LAMP1 (lysosome-associated proteins), KIFbβ, FYCO1, RILP, or Vps39; and/or those which increase activity or increase cellular levels of a putative GTP-bound form of Arl8b (i.e. Arl8b$^{Q75L}$), Vps41, or Vps11. In an embodiment, a suitable small molecule-based microautophagy reducing agent may be or comprise oleate, or a suitable synthetic mimic, analogue, or derivative thereof.

Microautophagy-reducing agents may comprise one or more microautophagy-reducing agents, such as those outlined above, in combination. In certain embodiments, suitable microautophagy-reducing agents may include compositions comprising both a gene silencing nucleic acid such as a gene silencing nucleic acid as described herein, or an expression vector or mRNA as described herein. By way of example, a suitable microautophagy-reducing agent may comprise a microautophagy-reducing agent as outlined herein, or any two, three, four, or more microautophagy-reducing agents as outlined herein in combination.

It will also be understood that decreases in lysosomal association-dissociation events between lysosomes and the lipid or protein substrate refers to a decrease in the rate, extent, activity, and/or efficacy of lysosomal association-dissociation events in a cell as compared to baseline levels of a corresponding treated or untreated control cell.

It will be understood that in an embodiment of a method for decreasing lysosome-mediated microautophagy of a lipid or protein substrate in a cell, the cell may be a hepatocellular carcinoma cell of a subject having liver cancer. It will be understood that, in certain embodiments, a decrease in lysosome-mediated microautophagy of a lipid substrate in a liver cancer cell may refer to a decrease in lysosome-mediated microautophagy of the lipid substrate as determined by the accumulation of lipid droplets in the cell. In the killing of cancer cells so as to prevent metastasis, lysosomal "sticking" to lipid droplets during the engulfment process may impair both microautophagy-mediated lipid degradation, and also macroautophagy processes, which may result in cell lethality.

Accordingly, in an embodiment, there is provided herein an in vitro or in vivo method for decreasing lysosome-mediated microautophagy of a lipid or protein substrate in a cell (as determined by, for example, lipid droplet accumulation in the cell) of a subject having liver cancer, said method comprising:

optionally, selecting a subject having liver cancer; and
treating the cell of the subject with a microautophagy-reducing agent which decreases lysosomal association-dissociation events between lysosomes and the lipid or protein substrate;

thereby decreasing lysosome-mediated microautophagy of the lipid or protein substrate.

In certain non-limiting embodiments, decreasing lysosome-mediated microautophagy of a lipid or protein substrate in a cell of a subject having, or at risk of getting, liver cancer may be of therapeutic interest. In an embodiment, decreasing lysosome-mediated microautophagy of a lipid or protein substrate, by lysosomes "sticking" to lipid droplets during the engulfment process, may be used as part of a treatment or preventative therapeutic approach for the treatment, prevention, or reduction of liver cancer. In certain embodiments, it is contemplated herein that methods for decreasing lysosome-mediated microautophagy of a lipid or protein substrate may optionally be used in combination with known standard treatments (for example, any suitable lifestyle change, therapeutic treatment, or both), either prior to, concurrently, or afterwards.

By way of non-limiting example, methods for decreasing lysosome-mediated microautophagy of a lipid or protein substrate may be used in combination with surgical resection, chemotherapeutics, or radiotherapy, in the treatment of liver cancer.

In a further embodiment, it is envisaged that increasing microautophagy activity, in contrast, may improve tissue recovery after liver surgery or liver transplant. It is known clinically that liver failure often occurs post-transplantation. In these cases, microautophagy activity may be compromised in the liver cells due to persistent association of lysosomes with cytosolic lipid droplets (i.e. impaired lysosomal motility or disruption of lysosomal lipid or protein engulfment processes). Thus, facilitation of microautophagy may, in certain embodiments, be used after liver surgery, or after liver transplantation, to provide therapeutic benefit in alleviating liver damage.

In a further embodiment, there is provided herein a method for modulating lysosome-mediated microautophagy of a lipid or protein substrate in a cell, said method comprising:

increasing lysosome-mediated microautophagy by treating the cell with a microautophagy-enhancing agent which increases lysosomal association-dissociation events between lysosomes and the cellular lipid or protein substrate; or decreasing lysosome-mediated microautophagy by treating the cell with a microautophagy-reducing agent which reduces lysosomal association-dissociation events between lysosomes and the cellular lipid or protein substrate;

thereby modulating lysosome-mediated microautophagy of the lipid or protein substrate.

It will be recognized that reference to modulating may refer to regulating, controlling, modifying, or otherwise adjusting. Modulation of lysosome-mediated microautophagy may refer to increasing or decreasing lysosome-mediated microautophagy as appropriate to reach, maintain, or stabilize lysosome-mediated microautophagy processes at a desired level or within a desired range. In certain embodiments, modulation of lysosome-mediated microautophagy may allow a desired level or a desired range of a lipid or protein substrate in a cell to be reached, maintained, or stabilized in the cell.

It will also be recognized that in an embodiment of a method for modulating lysosome-mediated microautophagy of a lipid or protein substrate in a cell, the method may be used to establish a cell culture or animal disease model having a hepatosteatosis level which may be controllable by modulating lysosome-mediated microautophagy of a lipid. In another embodiment, such a cell culture or animal disease model may be used for identifying biomarkers and/or microvesicle/exosome-based markers for hepatosteatosis-related diseases (or other diseases as described herein) and/or for screening and identifying therapeutic agents for the treatment of hepatosteatosis-related diseases (or other diseases as described herein). These embodiments are described in further detail below. By way of example, but not to be considered limiting in any manner, a hepatosteatosis-related disease may be fibrosis or non-alcoholic steatohepatitis (NASH).

In yet another embodiment, there is provided herein a method for identifying a microautophagy-enhancing agent, said method comprising:

treating a cell, such as a hepatic liver cell or a Parkinson's cell, with a candidate agent; and determining whether lysosome-mediated microautophagy of cytosolic lipid droplets is increased relative to a corresponding untreated control cell;

wherein determination of an increase in lysosome-mediated microautophagy of cytosolic lipid droplets indicates that the candidate agent is a microautophagy-enhancing agent.

In still another embodiment, there is provided herein a method for identifying a microautophagy-reducing agent, said method comprising:

treating a hepatic liver cell with a candidate agent;

determining whether lysosome-mediated microautophagy of cytosolic lipid droplets is decreased relative to an untreated control cell;

wherein determination of a decrease in lysosome-mediated microautophagy of cytosolic lipid droplets indicates that the candidate agent is a microautophagy-reducing agent.

In still a further embodiment, there is provided herein a method for facilitating, recovering, restoring, or modulating lysosome-mediated microautophagy in a cell, said method comprising:

treating the cell with a microautophagy-enhancing agent which increases lysosomal association-dissociation events between lysosomes and the cellular lipid or protein substrate.

In certain embodiments, such a method of facilitating, recovering, restoring, or modulating lysosome-mediated microautophagy in a cell may be used to restore or recover lysosomal function (microautophagy and/or macroautophagy), or balance activities between microautophagy and macroautophagy, in cells in which microautophagy and/or macroautophagy has been disturbed. By way of non-limiting example, in fatty liver, HCV, and Parkinson's conditions, lysosomes may be constantly engaged with CLDs, disturbing the balance or relative lysosomal function between microautophagy and macroautophagy.

In certain embodiments, there is provided herein a method for increasing lysosomal motility or bidirectional motility in a cell, said method comprising:

treating the cell with a microautophagy-enhancing agent which increases lysosomal association-dissociation events between lysosomes and the lipid or protein substrate;

thereby increasing lysosomal motility or bidirectional motility.

In a further embodiment of the method above, increasing lysosomal motility or bidirectional motility may increase lysosome-mediated microautophagy, lysosome-mediated macroautophagy, lysosomal maturation processes, or any combination thereof in the cell.

In another embodiment, there is provided herein a method for decreasing lysosomal motility or bidirectional motility in a cell, said method comprising:

treating the cell with a microautophagy-reducing agent which decreases lysosomal association-dissociation events between lysosomes and the lipid or protein substrate;

thereby decreasing lysosomal motility or bidirectional motility.

In a further embodiment of the method above, decreasing lysosomal motility or bidirectional motility may decrease lysosome-mediated microautophagy, lysosome-mediated macroautophagy, lysosomal maturation processes, or any combination thereof in the cell.

It will be understood that the functionality of lysosomes is involved in both microautophagy and macroautophagy processes. Functional lysosomes are regenerated through constant and dynamic interaction with endosomes and CLDs to acquire constituents (e.g. acidic enzymes) for lysosomal functions. Thus, the activity of microautophagy (i.e. lysosomal kiss-and-run with endosomes and CLDs) is not only related to lipid and protein degradation as described herein, but may also be related to lysosomal maturation/regeneration, and thus for lysosomal function. Therefore, microautophagy activities may be related to functional lysosomes, and macroautophagy activity. As described herein, macroautophagy has been shown to play a role in lipophagy under starvation conditions and in pathophysiology of Parkinson's disease. Compromised macroautophagy has been implicated in the pathology of hepatosteatosis, NASH, and Parkinson's disease.

It may be suggested, therefore, based on the discussions provided herein, that impaired lysosomal maturation/regeneration, as a consequence of a decrease in lysosomal motility or bidirectional motility (i.e. kiss-and-run), may give rise to diminished micro- and macro-autophagy, which may potentially lead to cell lethality.

When reviewing the various examples and/or embodiments outlined herein, and as previously mentioned herein, the person of skill in the art will recognize that the expression of particular genes within a cell may be reduced, prevented, or "silenced" using any of a variety of well-known methods. By way of non-limiting example, gene expression may be silenced using gene silencing nucleic acids such as siRNA (short interfering RNAs), antisense oligonucleotides (AONs), short hairpin RNAs (shRNAs), microRNAs (miRNAs), or other RNA interference (RNAi) or antisense gene silencing triggers, among others (see, for example, Gaynor et al., RNA interference: a chemist's perspective. Chem. Soc. Rev. (2010) 39: 4196-4184; Bennett et al., RNA Targeting Therapeutics: Molecular Mechanisms of Antisense Oligonucleotides as a Therapeutic Platform, Annual Review of Pharmacology and Toxicology, (2010) 50: 259-293). Gene expression may be decreased by other pre- or post-transcriptional gene silencing techniques known in the art. Given a particular gene sequence, the person of skill in the art will be able to design gene silencing oligonucleotides capable of targeting said gene sequence, reducing expression of the gene. Various software-based tools are available for designing siRNAs or AONs for targeting a particular gene, including those available from the Whitehead Institute (http://sirna.wi.mit.edu/) or those available from commercial providers of siRNAs. For example, an siRNA antisense strand, or an antisense oligonucleotide, which is fully or substantially complementary to a region of the gene-expressed mRNA sequence may be prepared, and used for targeted gene silencing by triggering RISC or RNase H-mediated mRNA degradation. Gene silencing nucleic acids may be prepared as described in, for example, Current Protocols in Nucleic Acids Chemistry, published by Wiley.

Gene silencing nucleotides may be introduced into cells using any of a number of well-known methods. Expression vectors (either viral, plasmid, or other) may be transfected, electroporated, or otherwise introduced into cells, which may then express the gene silencing nucleotide(s). Alternatively, gene silencing nucleotides themselves may be directly introduced into cells, for example via transfection or electroporation (i.e. using a transfection reagent such as but not limited to Lipofectamine™, Oligofectamine, or any other suitable delivery agent known in the art), or via targeted gene or nucleic acid delivery vehicles known in the art. Many delivery vehicles and/or agents are well-known in the art, several of which are commercially available. Delivery strategies for gene silencing nucleic acids are described in, for example, Yuan et al., Expert Opin. Drug Deliv. (2011) 8:521-536; Juliano et al., Acc. Chem. Res. (2012) 45: 1067-1076; and Rettig et al., Mol. Ther. (2012) 20:483-512. Examples of transfection methods are described in, for example, Ausubel et al., (1994) Current Protocols in Molecular Biology, John Wiley & Sons, New York. Expression vector examples are described in, for example, Cloning Vectors: A Laboratory Manual (Pouwels et al., 1985, Supp. 1987).

It will be understood that gene expression may refer to the production of a polypeptide from the nucleic acid sequence of a gene. Gene expression may include both transcription and translation processes, and so gene expression may refer to production of a nucleic acid sequence such as an mRNA (i.e. transcription), production of a protein (i.e. translation), or both. It will further be understood that overexpression of a particular gene in a cell may refer to increasing the expression of a particular gene within a cell as compared to wild-type, baseline, or untreated levels. Overexpression, or introduction of a mutant gene, into cells may be accomplished using any of several methods known in the art. By way of example, a vector (either viral, plasmid, or other) comprising one or more copies of the particular gene each driven by a suitable promoter sequence (for example, a constitutive or inducible promoter), or an mRNA or chemically modified version thereof may be introduced into cells via transfection, electroporation, or viral infection, or another suitable method know in the art. Suitable expression vector techniques for overexpressing or introducing a particular gene into a cell are known in the art (see, for example, Molecular Cloning: A Laboratory Manual ($4^{th}$ Ed.), 2012, Cold Spring Harbor Laboratory Press).

The skilled person will understand that antibodies, or antibody fragments, targeting one or more of the amino acids, nucleic acids, proteins, or enzymes described herein, such as monoclonal or polyclonal antibodies or $F_{ab}$ fragments thereof, may be generated for targeting a particular amino acid, nucleic acid, protein or enzyme target using standard laboratory techniques. By way of non-limiting example, monoclonal antibodies to a particular target may be prepared using a hybridoma technique (see, for example, Harlow et al., Antibodies: A Laboratory Manual, (Cold Spring Harbor Laboratory Press, 2nd ed. 1988); Hammerling, et al., in: Monoclonal Antibodies and T-Cell Hybridomas pp 563-681 (Elsevier, N.Y., 1981)). The person of skill in the art will be aware of methods and techniques for preparing antibodies for a particular amino acid, protein, nucleic acid, or enzyme target. Such antibodies may be used to bind an amino acid, protein, nucleic acid, or enzyme target, preventing it from performing its regular function, resulting in a similar outcome to that arising from gene silencing of the same amino acid, nucleic acid, protein or enzyme. Therefore, in certain embodiments, antibodies may be used in place of gene silencing nucleic acids for targeting or "silencing" a particular gene.

It will be understood that compounds and/or compositions comprising or consisting of one or more of the nucleic acid and/or polypeptides as described herein may be used. Compositions may additionally comprise one or more pharmaceutically acceptable diluents, carriers, excipients, or buffers. Compositions may be used for administering one or more nucleic acids and/or polypeptides to a cell in vitro or in vivo.

Introduction of a gene, in the context of inserting a nucleic acid sequence into a cell, refers to "transfection", "transformation", or "transduction", and includes the incorporation or introduction of a nucleic acid sequence into a eukaryotic cell where the nucleic acid sequence may optionally be incorporated into the genome of the cell, or transiently expressed (for example, transfected mRNA). A protein or enzyme may be introduced into a cell by delivering the protein or enzyme itself into the cell, or by expressing an mRNA encoding the protein or enzyme within the cell, leading to its translation.

As referenced herein, percent (%) identity or % sequence identity with respect to a particular sequence, or a specified portion thereof, may be defined as the percentage of nucleotides or amino acids in the candidate sequence identical with the nucleotides or amino acids in the subject sequence (or specified portion thereof), after aligning the sequences and introducing gaps, if necessary, to achieve the maximum percent sequence identity, as generated by the program WU-BLAST-2.0 with search parameters set to default values (Altschul et al., J. Mol. Biol. (1990) 215:403-410; website at blast.wustl.edu/blast/README.html).

By way of example, a % identity value may be determined by the number of matching identical nucleotides or amino acids divided by the sequence length for which the percent identity is being reported. Percent (%) amino acid sequence similarity may be determined by the same calculation as used for determining % amino acid sequence identity, but may, for example, include conservative amino acid substitutions in addition to identical amino acids in the computation.

Oligonucleotide alignment algorithms such as, for example, BLAST (GenBank; using default parameters) may be used to calculate sequence identity %.

An alternative indication that two nucleic acid sequences may be substantially identical is that the two sequences hybridize to each other under moderately stringent, or preferably stringent, conditions. Hybridization to filter-bound sequences under moderately stringent conditions may, for example, be performed according to Ausubel, et al. (eds), 1989, Current Protocols in Molecular Biology, Vol. 1, Green Publishing Associates, Inc., and John Wiley & Sons, Inc., New York, at p. 2.10.3. Alternatively, hybridization to filter-bound sequences under stringent conditions may, for example, be performed according to Ausubel, et al. (eds), 1989, supra. Hybridization conditions may be modified in accordance with known methods depending on the sequence of interest (see, for example, Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York. Generally, by way of non-limiting example, stringent conditions may be about 5° C. lower than the thermal melting point for the specific sequence at a defined ionic strength and pH.

It will be understood that the specific amino acid or nucleic acid sequence of a particular gene may vary from species to species. By way of example, according to the BLAST Tool provided by the NCBI, the human Arl8b amino acid sequence has homologs in other species having between about 85%-100% sequence identity. Arl8b is generally highly conserved in mammals, and thus the amino acid sequence of Arl8b has 100% sequence identity between human and rodent (e.g. rat and mouse) (see FIG. 44). An alignment of Arl8b amino acid sequences from examples of various animals (along with associated Uniprot identifier numbers) is shown in FIG. 44. Homologous sequences from different species may represent, or be considered as, variants of a particular gene. In some cases, although homologous sequences may vary between species, the general effect (for example, the phenotypic effect) of a homolog sequence may be substantially similar to the effect of the wild-type sequence in a given cell or subject.

As will be known to one of skill in the art, nucleotide sequences for expressing a particular gene may encode or include features as described in "Genes VII", Lewin, B. Oxford University Press (2000) or "Molecular Cloning: A Laboratory Manual", Sambrook et al., Cold Spring Harbor Laboratory, 3$^{rd}$ edition (2001). A nucleotide sequence encoding a polypeptide or protein may be incorporated into a suitable vector, such as a commercially available vector. Vectors may also be individually constructed or modified using standard molecular biology techniques, as outlined, for example, in Sambrook et al. (Cold Spring Harbor Laboratory, 3$^{rd}$ edition (2001)). The person of skill in the art will recognize that a vector may include nucleotide sequences encoding desired elements that may be operably linked to a nucleotide sequence encoding a polypeptide or protein. Such nucleotide sequences encoding desired elements may include transcriptional promoters, transcriptional enhancers, transcriptional terminators, translational initiators, translational terminators, ribosome binding sites, 5'-untranslated region, 3'-untranslated regions, cap structure, poly A tail, and/or an origin of replication. Selection of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

It will be understood that contemplated herein is a nucleic acid comprising a sequence:

a) encoding a protein as defined herein, or a fragment thereof;

b) that is the complement of a sequence encoding a protein as defined herein, or a fragment thereof;

c) that is capable of hybridizing to a nucleic acid encoding a protein as defined herein or fragment thereof under stringent hybridization conditions; or d) that exhibits greater than or equal to about 70%, or greater than or equal to about 85%, sequence identity with the nucleic acid defined in a) or b) or another nucleic acid sequence as described herein, for example, but not limited to, 86%, 87%, 88%, 89%, 90%, 91%, 92%, 93%, 94%, 95%, 96%, 97%, 98%, 99%, or 100%. The nucleic acid may also be characterized by a range of identities, for example any two of the percentages outlined above.

Derivative or variant nucleic acid molecules of a particular nucleic acid molecule may include sequences that hybridize to the nucleic acid sequence as discussed herein, or a sequence complementary to a nucleic acid sequence as discussed here. The stringency of hybridization may be controlled by temperature, ionic strength, pH, and the presence of denaturing agents such as formamide during hybridization and washing. Conditions routinely used would be well known to those in the art (see, for example, Current Protocol in Molecular Biology, Vol. I, Chap. 2.10, John Wiley & Sons, Publishers (1994)).

The person of skill in the art will understand that biomolecules and/or compounds described herein may be provided in pharmaceutical compositions together with a pharmaceutically acceptable diluent, carrier, or excipient, and/or together with one or more separate active agents or drugs as part of a pharmaceutical combination or pharmaceutical composition. In certain embodiments, the biomolecules, compounds, and/or pharmaceutical compositions may be administered in a treatment regimen simultaneously, sequentially, or in combination with other drugs or pharmaceutical compositions, either separately or as a combined formulation or combination.

Biomolecules, compounds, and/or compositions as described herein may include one or more pharmaceutically acceptable excipients, diluents, and/or carriers. A pharmaceutically acceptable carrier, diluent, or excipient may include any suitable carrier, diluent, or excipient known to the person of skill in the art. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, buffers, glidants, and disintegrants known in the art (see, for example, Remington: The Science and Practice of Pharmacy (2006)). Examples of pharmaceutically acceptable carriers, diluents, and excipients may be found in, for example, Remington's Pharmaceutical Sciences (2000—20$^{th}$ edition) and in the United States Pharmacopeia: The National Formulary (USP 24 NF19) published in 1999.

It will be understood that there is degeneracy in the genetic code, and that a particular amino acid sequence may be encoded by more than one nucleic acid sequence. Several exemplary nucleic acid sequences are provided herein, and it should be recognized that other nucleic acid sequences encoding the same amino acid sequence may also be possible, given that more than one nucleic acid codon may be used to encode for a particular amino acid.

It will also be understood that one or more conservative amino acid substitutions may be possible. As will be recognized, a conservative amino acid substitution may include one in which an amino acid is substituted for another amino acid having similar properties such that the folding, activity, or other functionality of the protein is not significantly affected. Examples of aromatic amino acids, which may be substitutable, may include phenylalanine, tryptophan, and tyrosine. Examples of interchangeable hydrophobic amino acids, which may be substitutable, may include leucine, isoleucine, methionine, and valine. Examples of interchangeable polar amino acids, which may be substitutable, may include glutamine and asparagine. Examples of interchangeable basic amino acids, which may be substitutable, may include arginine, lysine and histidine. Examples of interchangeable acidic amino acids, which may be substitutable, may include aspartic acid and glutamic acid. Finally, examples of interchangeable small amino acids, which may be substitutable, may include alanine, serine, threonine, cysteine, and glycine.

Cytosolic Lipid Droplet (CLD) Degradation

Herein, Arl8b-induced lysosome-mediated CLD degradation is investigated and described in detail. In certain examples, the effect of Arl8b on lipid metabolism in an in vitro cell culture system was studied. Treatment of cells with EPA at 0.4 mM markedly decreased cellular lipid content as compared with that in cells treated with equal amount of oleate (OA). The lowered cellular lipid content was not due to secretion of very low density lipoproteins (VLDL); in fact EPA treatment also reduced lipid secretion as VLDL. Further, lowered cellular lipid was not due to impaired fat synthesis. Rather, pulse-chase experiments showed that EPA stimulated lipid turnover.

Results described in O'Rourke, E. J., Kuballa, P., Xavier, R. & Ruvkun, G. ω-6 Polyunsaturated fatty acids extend life span through the activation of autophagy. Genes Dev. 27, 429-440 (2013) (herein incorporated by reference) may also be considered in this regard.

It is further demonstrated herein that EPA-induced CLD degradation is insensitive to inactivation of classical components of macroautophagy (i.e. Atg5 or Atg6), but can be inhibited by silencing Rab9 that is involved in Atg5-independent autophagy. Results obtained herein indicate that EPA-induced lipid degradation involves direct lysosomal interaction with CLD through a process resembling microautophagy, and is intimately associated with robust bidirectional motility (i.e. anterograde motility, via motor adapter FYCO1 which anchors lysosomes onto microtubules through linking Rab7 to kinesin; and retrograde motility, via motor adaptor RILP which links Rab7 to dynectin/dynein) of lysosomes along microtubules (see FIG. 13 models depicting the respective anterograde and retrograde lysosomal motility). Blocking lysosomal motility, by silencing Rab7-associated motor-adaptor proteins FYCO1 or RILP, effectively abolished lipid degradation.

It is further demonstrated herein that the EPA-induced lipid degradation involves Arl8b, a small GTPase that is present on both lysosomes and CLD. It is also demonstrated herein that Arl8b-induced lipid degradation may be accelerated by n-3 fatty acid. The nucleotide binding status of Arl8b appears to govern its organellar presentation and functionality; the putative GTP-bound form, Arl8b$^{Q75L}$, preferentially binds to lysosome, and the putative GDP-bound form, Arl8b$^{T34N}$, binds to CLD. Remarkably, it is found that overexpressing Arl8b$^{T34N}$ accelerates lipid droplet degradation with addition of EPA, whereas paradoxically overexpressing Arl8b$^{Q75L}$ blocks the process.

Without wishing to be bound by theory, mechanistically, Arl8b may facilitate lipid degradation through its dynamic recruitment of the tethering complex HOPS. As described in further detail below, silencing HOPS subunits Vps39, Vps41 or Vps11 blocked EPA-induced lipid degradation. The nucleotide binding status of Arl8b may be key to its differential interaction with individual HOPS subunits and for the rate of lipid degradation. Assembly of the lysosome-CLD tethering complex involves Arl8b$^{Q75L}$ binding to Vps41 and Vps11, whereas dissociation of the tethering complex involves Arl8b$^{T34N}$ binding to Vps39. These data indicate that unlike starvation-induced macroautophagy, EPA-induced lipid degradation may invoke an alternative and novel lysosomal motility-dependent mechanism and/or lysosomal degradation which is associated with direct interaction and engulfment of lipid droplets by lysosomes, which involves dynamic assembly and dissociation of Arl8b/HOPS-organized tethering complex between lysosomes and CLD.

Various examples and/or embodiments will now be discussed in detail, for illustrative purposes, to the person of skill in the art. It will be appreciated that embodiments and examples provided herein are for illustrative purposes, and are not meant to be limiting in any way. The skilled person will recognize that suitable variations, modifications, and/or substitutions may be possible.

Example 1—EPA Triggered Decrease in CLD

Figure 2:
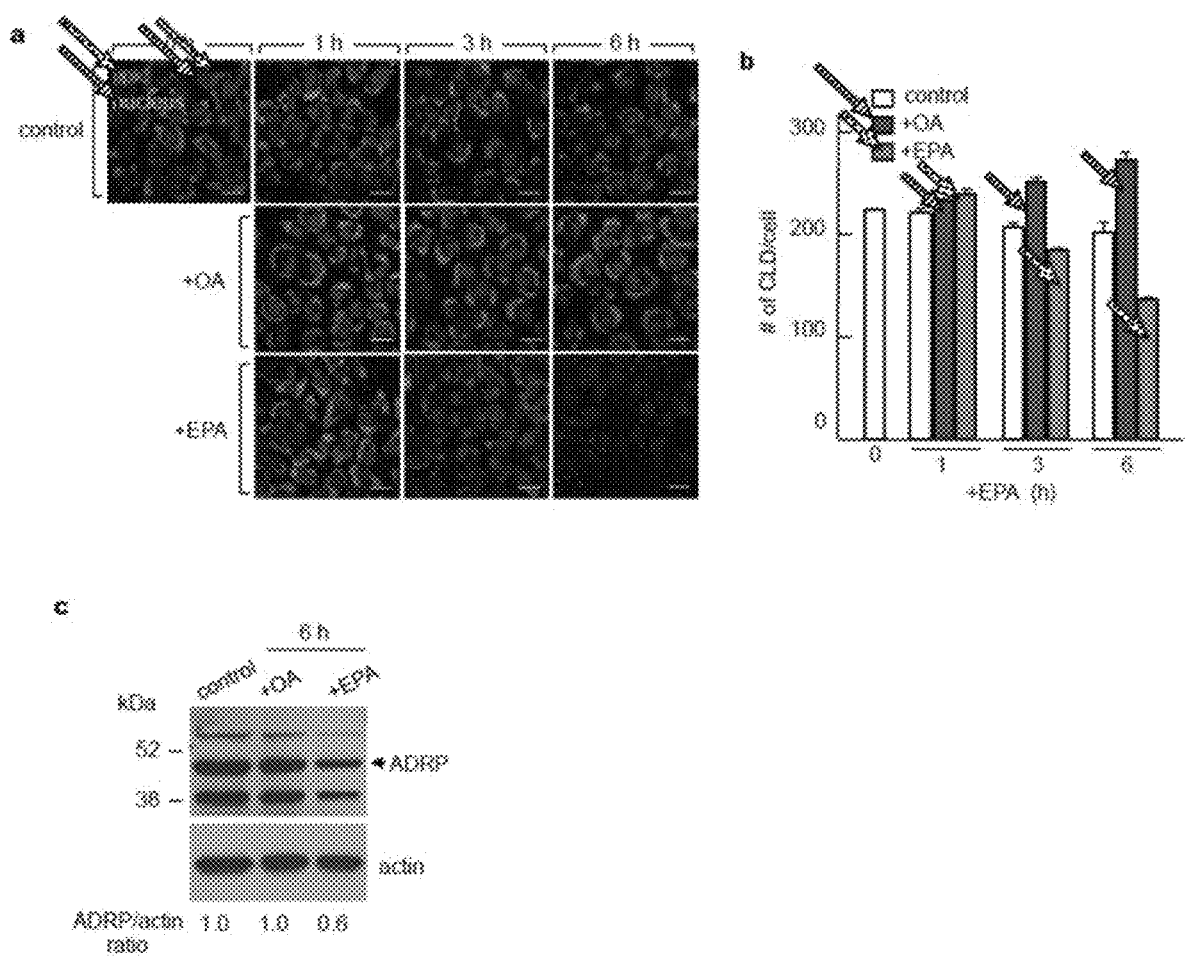
FIG. 2 illustrates that EPA treatment leads to lipid degradation. (a) Imaging analysis of CLD (stained with lipidTOX Red) in lipid-laden cells cultured in media ±OA or EPA. Scale bars, 22 μm. (b) Quantification of CLD. Control, baseline cells cultured in media without OA or EPA. (c) Western blots of adipose differentiation-related protein (ADRP)

Omega-3s are substrates of a variety of complex lipids, including TG, cholesteryl ester (CE) and phospholipids. The lipid-lowering effect of EPA in cultured hepatic cells is not attributable to deficiency in TG synthesis[1]. Treatment of hepatic cells with EPA at 0.4 mM, like that with OA (oleic acid), resulted in an initial accumulation of TG as cytosolic lipid droplets (CLD). The size of these CLD (0.1-50 μm in diameter) allows them to be readily detectable by light microscopy. Small lipid droplets (i.e. <100 nm in diameter) are not as detectable by light microscopy, and therefore their presence is detectable using electron microscopy (EM). Within several hours, the CLD-associated TG was hydrolyzed in cells treated with EPA (but not OA) through a process that may be demonstrated by pulse-chase experiments (FIGS. 1a and b, FIGS. 2a and b). The effect of EPA in reducing CLD could also be demonstrated by western blot analysis of perilipin 2 (ADRP) (FIG. 2c). The lowered cellular lipid content in EPA-treated cells is not due to increased secretion of VLDL, because secretion of VLDL-associated TG (FIG. 1c) and VLDL-associated apoB-100 (FIG. 1d) was suppressed under EPA treatment conditions as compared to that in OA-treated cells. Rather, the lowered CLD in EPA-treated cells was accompanied with enhanced β-oxidation (FIG. 1e)[9]. Amelioration of hepatic TG upon omega-3s supplementation was also observed in male Wistar rats fed with a high-fat high-sucrose diet (data not shown). Thus, EPA treatment of the lipid-laden cells lowered both cellular and secreted TG. Results indicate that EPA treatment may at least somewhat ameliorate hepatic steatosis and/or hypertriglyceridemia in vitro and/or in vivo.

Figure 3:
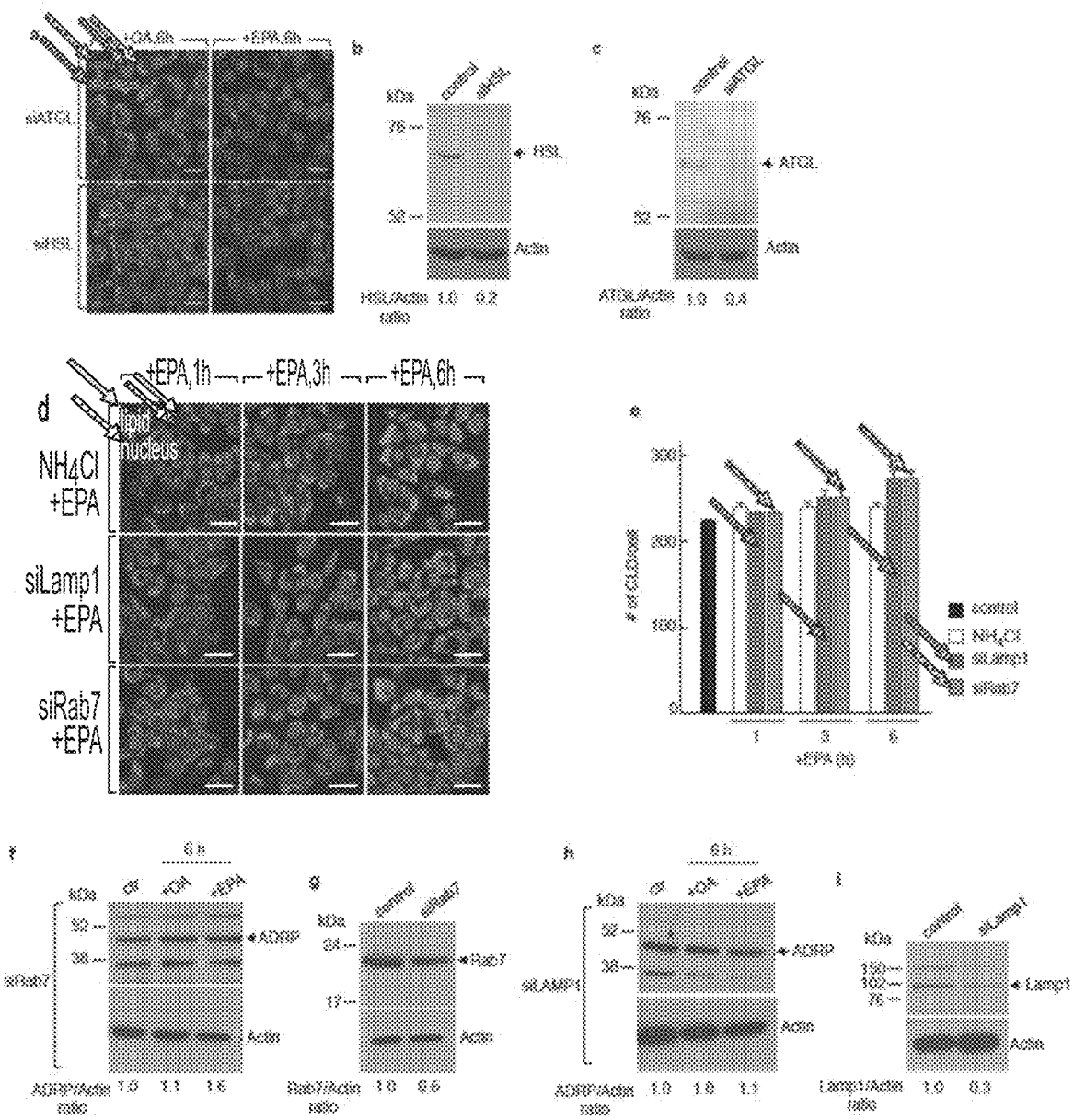
FIG. 3 illustrates that EPA-triggered lipid degradation does not require the cytosolic lipases ATGL or HSL, but requires lysosomal activity. (a) Images of CLD (stained with lipidTOX Red) 6 h post-OA or -EPA treatment in cells transfected with ATGL- or HSL-specific siRNA. Scale bars, 22 μm. (b) and (c) Western blots of HSL (b) or ATGL (c) showing the efficacy of silencing. Control, cells transfected with scrambled siRNA. (d) Images of CLD 1, 3, and 6 h post-EPA treatment in cells transfected with Lamp1- or Rab7-specific siRNA. Lysosomal inhibition is also achieved by alkalinisation of lysosomes using $NH_4Cl$. Scale bars, 22 μm. (e) Quantification of CLD as represented in (d). Control, baseline CLD content. (f) Western blots of ADRP in Rab7 silenced cells. (g) Western blots of Rab7 showing the efficacy of silencing. (h) Western blots of ADRP in Lamp1 silenced cells. (i) Western blots of Lamp1 showing the efficacy of silencing. Control, cells transfected with scrambled siRNA.
Figure 4:
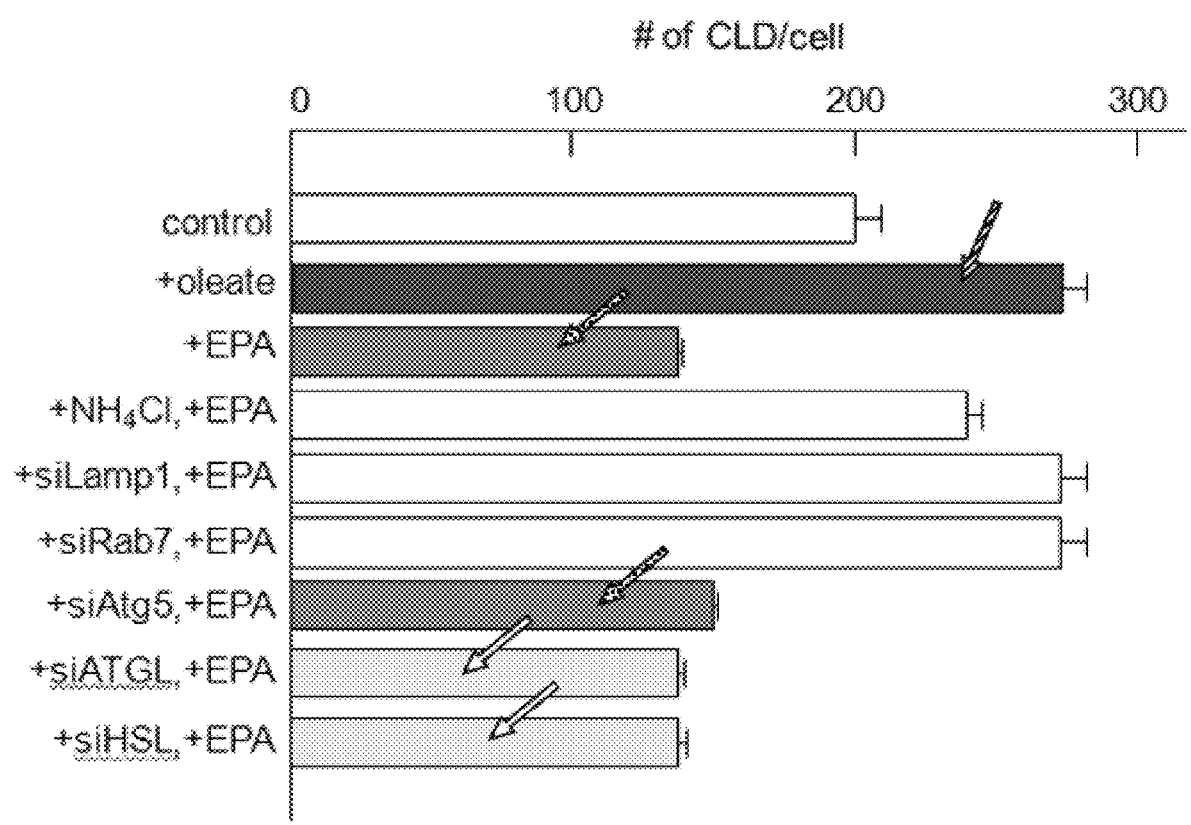
FIG. 4 illustrates additional gene silencing results showing observed effects on cellular lipid content as per Example 1.

To determine enzymatic mechanisms responsible for the EPA-induced CLD turnover, the involvement of cytosolic and lysosomal lipase activities was examined. Silencing cytosolic ATGL (adipocyte triglyceride lipase) or HSL (hormone sensitive lipase) had no effect on EPA-induced lipid degradation (FIG. 1f and FIG. 3a-c). However, inhibition of LAL (lysosomal acidic lipase) activity entirely blocked lipid turnover (FIG. 1f). The requirement of lysosomes in lipid turnover was confirmed by silencing LAMP1 (lysosome-associated proteins[10]) or Rab7[11] experiments, in which EPA-induced lipid degradation was completely abolished (FIG. 1g-h and FIG. 3d-e). Likewise, EPA-induced lipid turnover was inhibited by alkalinisation of lysosomes using $NH_4Cl$ (FIGS. 1g and h, and FIGS. 3d and e). These results suggest the EPA-induced lipid degradation requires functioning lysosomes. A summary of the gene silencing results showing these effects is provided in FIG. 4.

Figure 5:
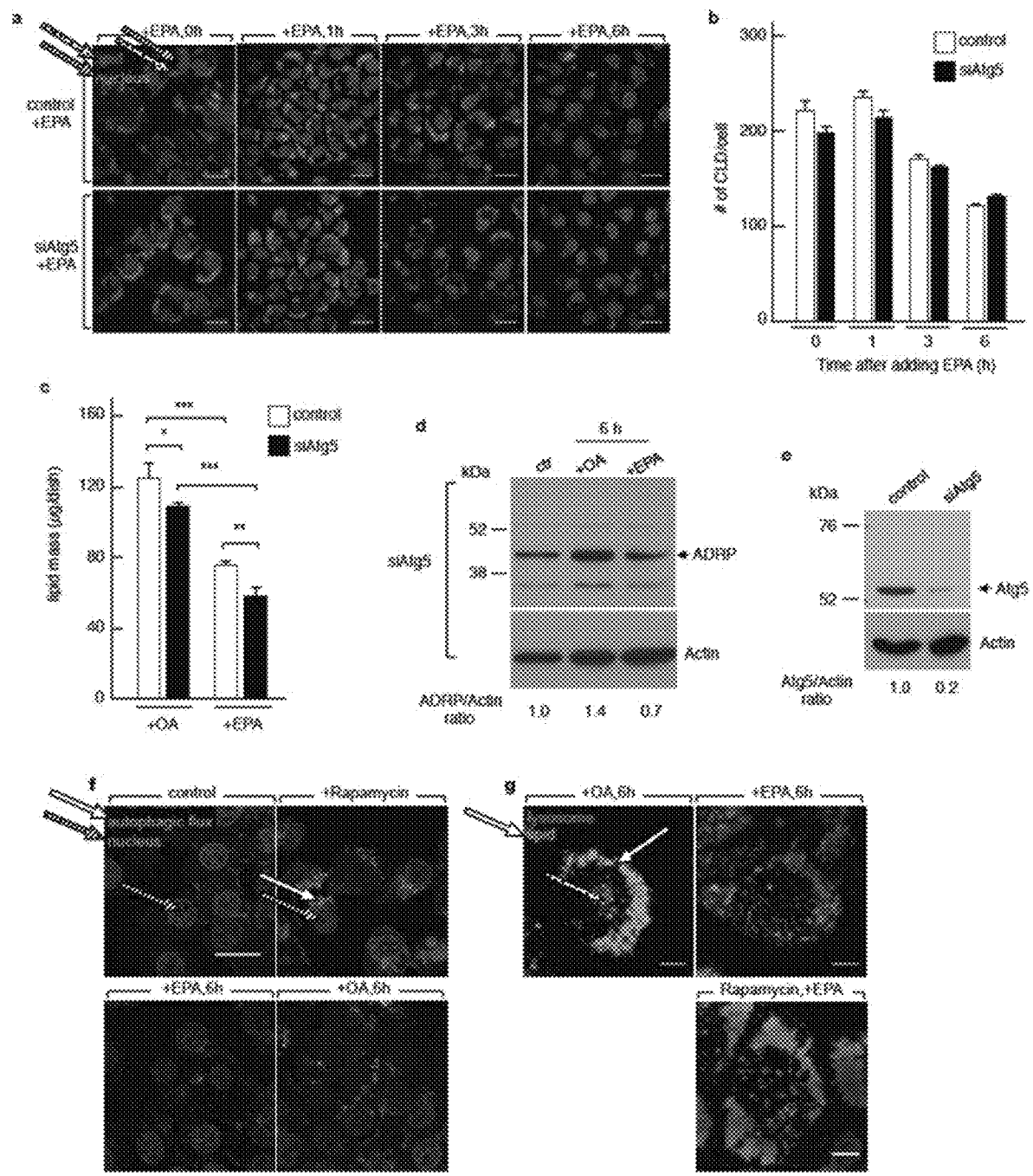
FIG. 5 illustrates that EPA-triggered lipid degradation is not affected by Atg5 silencing but is blocked by rapamycin treatment. (a) Images of CLD (stained with lipidTOX Red) in cells transfected with scramble (control) or Atg5-specific siRNA (siATG5). Scale bars, 22 μm. (b) and (c) Quantification of CLD as presented in (a) ((b)) or by lipid mass measurement (c). (d) Western blots of ADRP. (e) Western blots of Atg5 showing the efficacy of silencing. (f) rapamycin treatment resulted in enhanced autophagic flux. But EPA treatment, as compared to OA, did not induce autophagic flux. (g) Pretreatment of cells with rapamycin blocked EPA-triggered lysosomal motility, resulting in confined distribution of lysosomes at the perinuclear regions. The OA- or EPA-treated cells were stained with LipidTOX Red and LysoTracker. The bottom panel shows cells incubated with rapamycin for 15 min prior to EPA treatment. Lipid droplets are green, lysosomes are red.
Figure 6:
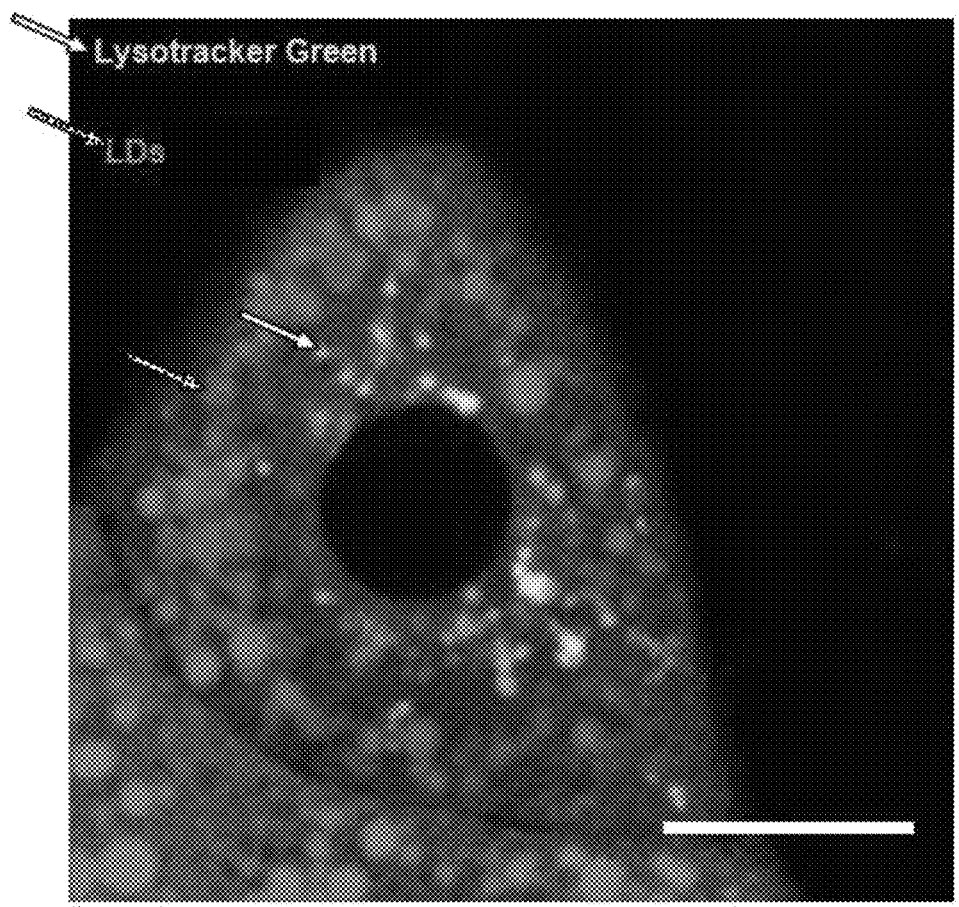
FIG. 6 illustrates that OA treatment did not show direct interaction between lysosomes and lipid droplets. Imaging of OA-treated cells stained with LipidTOX Red and LysoTracker. This figure shows that lysosomes did not redistribute toward the lipid droplets 1 hour after adding oleate.
Figure 11:
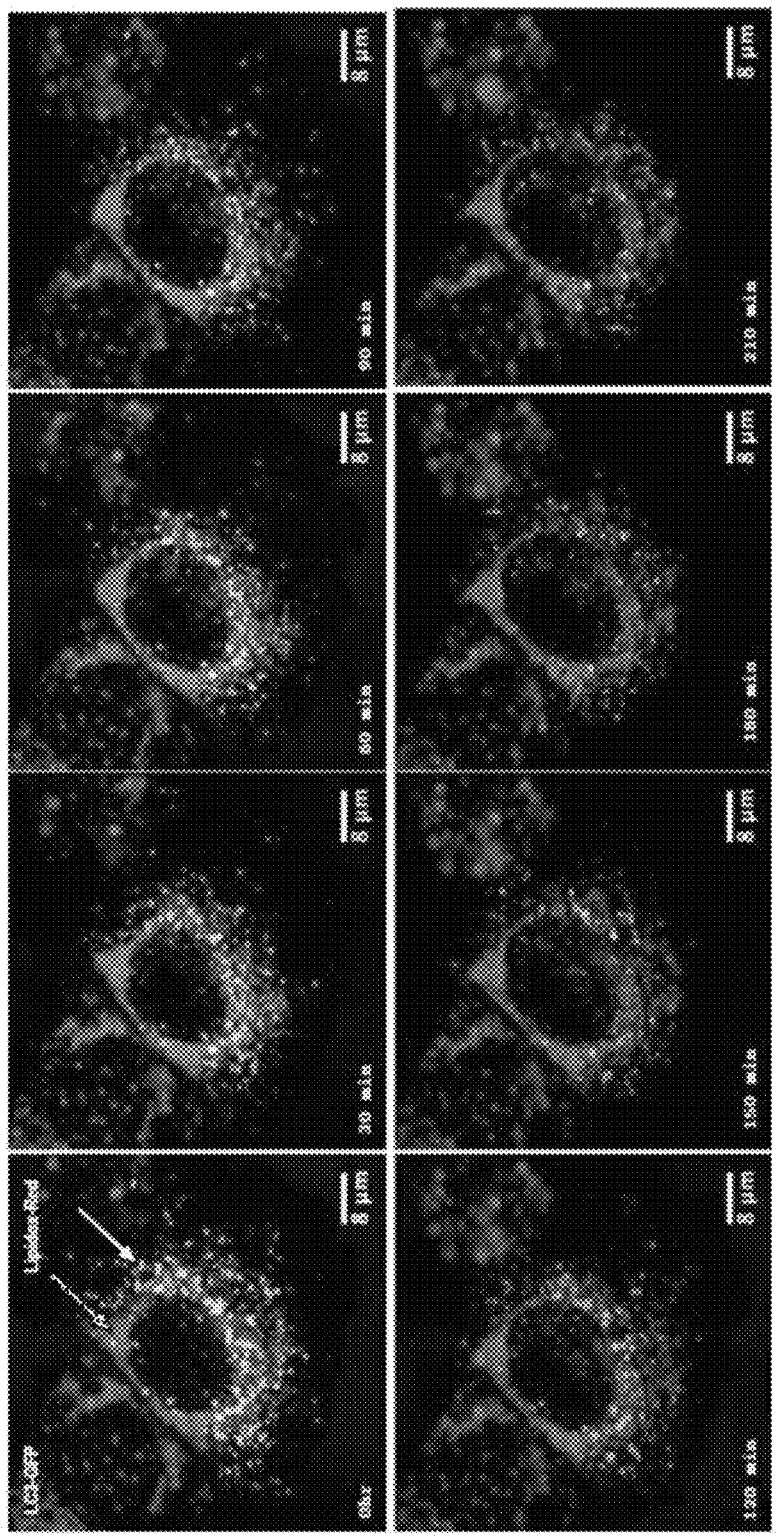
FIG. 11 illustrates that there is a lack of evidence for involvement of conventional macrolipophagy machinery in EPA-treated cells. Imaging of EPA-treated cells expressing $^{GFP}$LC3, an autophagosome marker. LC3 are green, lipid droplets red.

Lipid macroautophagy (or lipophagy) has been shown to play a role in hepatic CLD degradation under starvation conditions[12,13]. To determine whether or not EPA treatment has induced lipophagy, the involvement of the classical Atg5-dependent and Atg5-independent autophagic pathways[14] was determined. Silencing Atg5 had no effect on EPA-induced lipid degradation (FIG. 1i, FIG. 4, and FIG. 5a-e). Likewise, silencing another autophagy component (Atg6 or Beclin1) also exerted no impact on CLD degradation (FIG. 1i). Unlike increased macroautophagic flux induced by rapamycin treatment, macroautophagic flux in EPA treated cells was no higher than that in OA-treated cells (FIG. 5f). Noteworthy is that double-membrane structures resembling the typical LC3-containing autophagic isolation membranes (a hallmark of macroautophagy) surrounding CLD are not observed in cells treated with EPA (FIG. 11). Thus, these data indicate that the EPA-induced lipid degradation in hepatic cells is independent of the formation of Atg5-dependent autophagosomes.

A recent report has implicated Rab9 in an Atg5-independent autophagic pathway[15]. The Rab9 involvement in EPA-induced lipid degradation was thus tested, and it was found that depletion of Rab9 completely blocked the process (FIG. 1j). Live imaging of cells transfected with GFP::Rab9 (also referred to herein as $^{GFP}$Rab9) revealed its redistribution to CLD surface upon EPA treatment, and interestingly the lysosome-bound GFP::Rab9 was co-localized with lysosomes on the CLD surface during the "kiss" event/engulfment process (FIG. 1k). This direct lysosomal interaction with CLD is a Rab9-dependent process; depletion of Rab9 completely blocked such an interaction (movie not shown).

The above results suggest a unique direct lysosomal motility-dependent degradation process during EPA-induced lipid degradation. Indeed, live imaging of EPA-treated cells showed higher rate of lysosomal direct interaction with lipid droplets compared to controls and profound lysosomal dislocation from the perinuclear regions and redistribution towards cells periphery, as well as transient interactions between lysosomes and CLD (FIG. 5g top panels, 8, and 9). Robust lysosomal motility and direct interaction with CLDs is also observed in cells treated with docosahexaenoic acid (DHA), another omega-3 fatty acid (FIG. 4S). In contrast, lysosomes were confined to the perinuclear regions and reduced levels of interaction between lysosomes and lipid droplets were observed in OA-treated cells (FIG. 5g, top panels). The duration of lysosome-CLD interaction was approximately 10 seconds, resembling a phenomenon known as lysosomal kiss-and-run during endosome maturation[16]. Bidirectional (i.e. anterograde and retrograde) motility of lysosomes started approximately 15 min after EPA addition, and the peak intensity of the movement occurred around 1-2 h post EPA addition. Interaction between peroxisome and CLD has been observed previously[20]. However, EPA treatment does not alter the pattern of peroxisomal movement in cells (FIG. 10), indicating EPA specifically increased direct lysosomal interaction with CLD.

Figure 8:
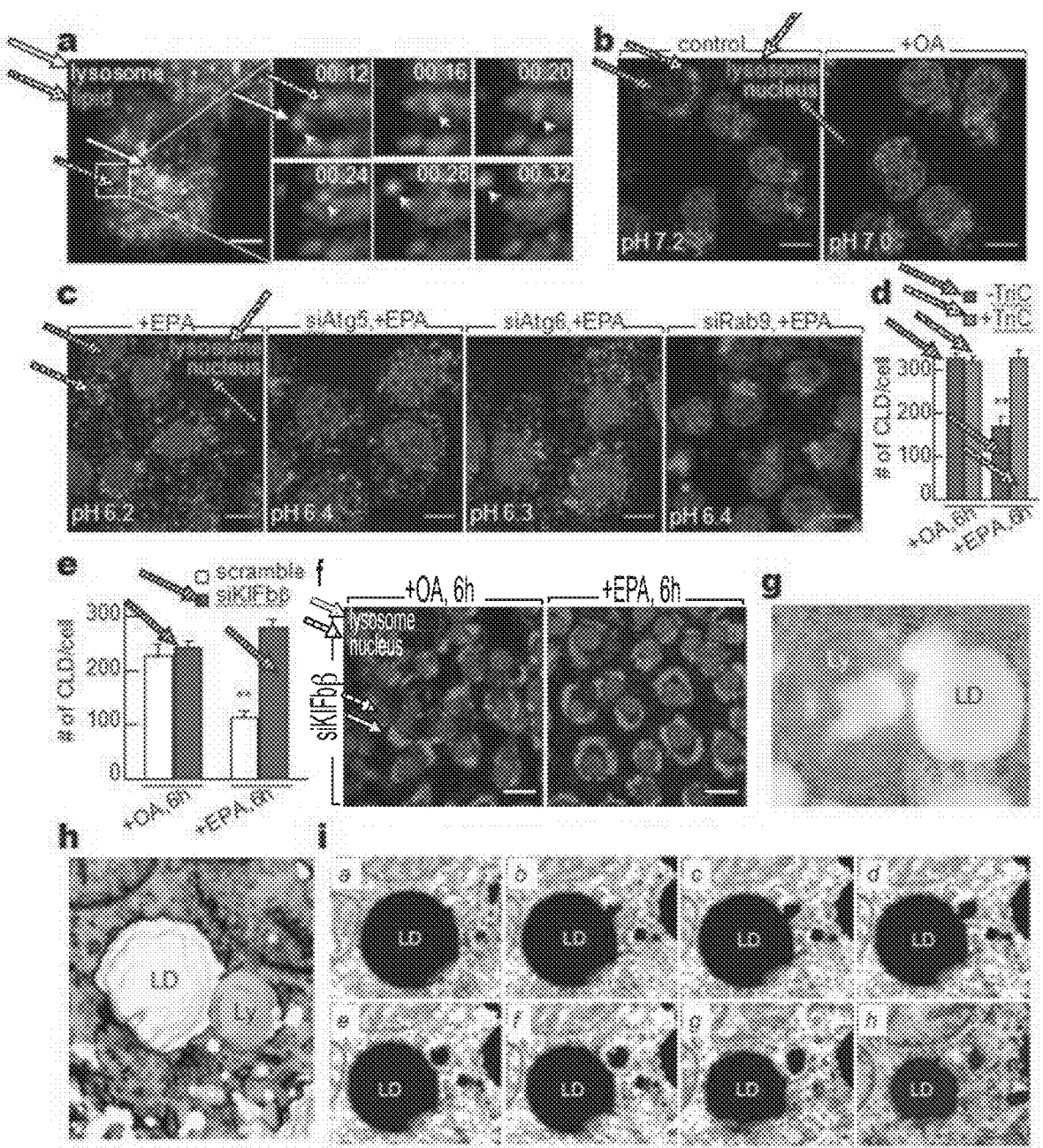
FIG. 8 illustrates that EPA increases interaction of lysosomes with CLDs, and triggers lysosomal bi-directional motility and direct interaction with CLD. (a) Time lapse imaging of transient lysosomal interaction with CLD (arrowhead) as further represented in FIG. 9. Scale bar, 8 μm. This shows clear interaction between lysosomes and lipid droplets after adding EPA, showing "kiss-and-run". (b) Cytoplasmic pH in baseline (control) and 6 h post-OA treatment. Scale bar, 22 μm. (c) Cytoplasmic pH 6 h post-EPA treatment in cells transfected with control (scramble) or Atg5-, Atg6- or Rab9-specific siRNA. (d) and (e) Quantification of CLD 6 h post-OA or EPA treatment in cells pre-treated with Triacsin C (TriC) (d) or transfected with KIFbβ-specific siRNA (e). (f) Representative images of CLD 6 h post-OA or -EPA treatment in cells transfected with KIFbβ-specific siRNA as used for quantification in (e). Scale bar, 22 μm. (g) Electron microscopy (EM) image of CLD in cells treated with EPA. Scale bar, 100 nm. (h) EM image of CLD in cells treated with EPA as represented in EM tomography. Scale bar, 100 nm. (i) Series of EM images represented in the computed 3D reconstruction movie. (g) and (i) show direct lysosomal interaction with lipid droplets.
Figure 9:
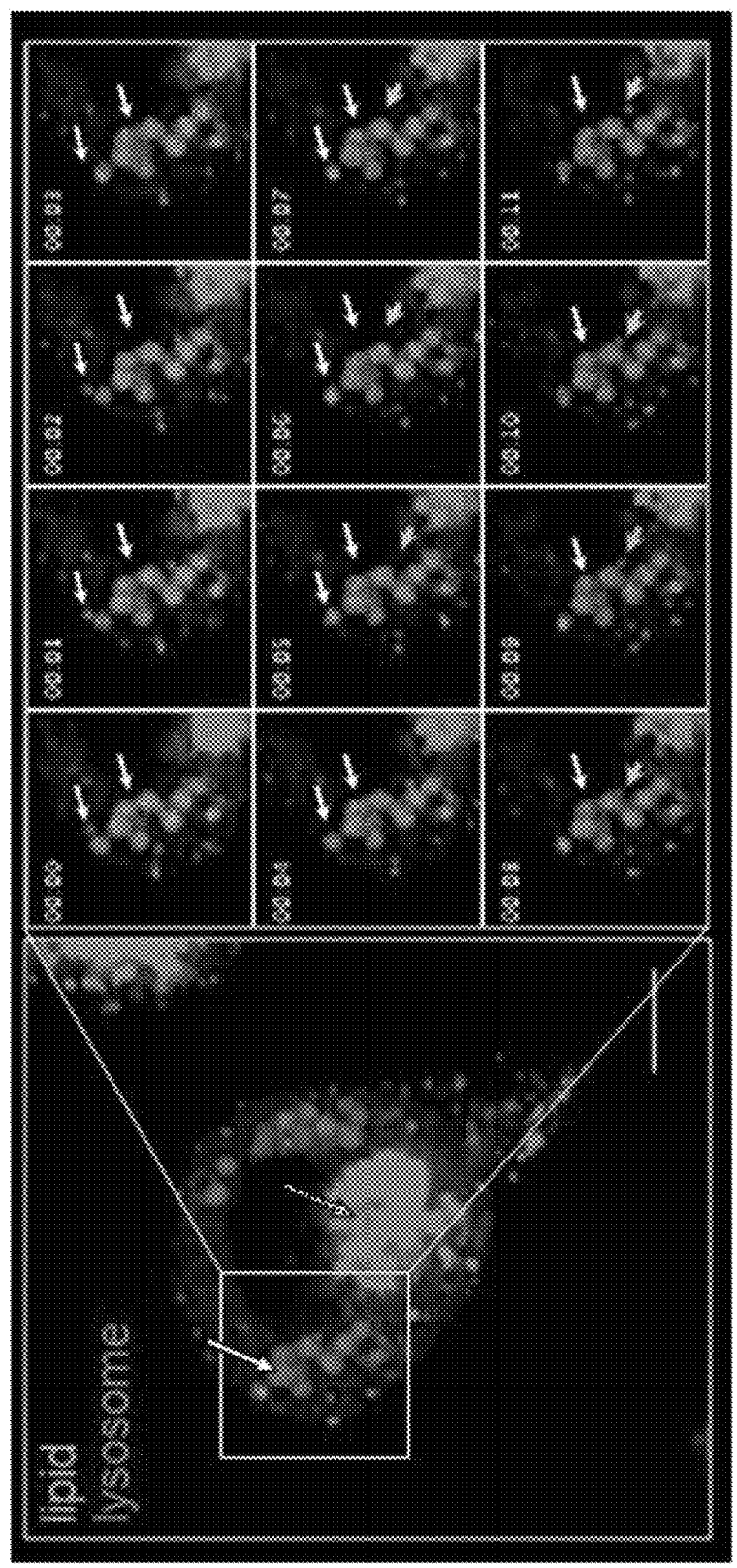
FIG. 9 illustrates that EPA-triggered lipid turnover is associated with lysosomal motility. Live imaging of cells treated with EPA show prominent movement from the perinuclear region towards lipids. Yellow arrows denote lysosomal interaction with lipid droplets, and cyan arrowheads show typical association/dissociation between lysosome and CLD.

It has been reported previously that cytoplasmic pH lowering can result in dislocation of lysosomes from the perinuclear regions towards cell periphery[17]. Lysosomal biogenesis and endosomal maturation processes are believed to be associated with change in pH toward an acidic environment. It was thus determined whether or not the EPA-triggered interaction between lysosomes and CLD, and lysosomal redistribution, is related to acidification of cytoplasm. Compared to cells treated with OA in which the cytoplasmic pH is neutral (FIG. 8b), EPA treatment resulted in acidification of cytoplasm, which is accompanied with decrease in number of cytosolic lipid droplets, and which is accompanied with lysosomal redistribution throughout the cytosol (FIG. 8c). Cytoplasmic acidification and lysosomal redistribution are also observed in cells where the autophagic component Atg5 or Atg6 was depleted (FIG. 8c). However, experiments with Rab9 depletion showed that lysosomal motility is not simply attributable to acidification of cytoplasm. Thus, although acidification of cytosol occurred in Rab9 silenced cells after addition of EPA, lysosomes remained in the perinuclear regions (FIG. 8c). The Rab9 silencing experiment, therefore, indicates that the EPA-triggered lysosomal redistribution is not merely attributable to cytoplasmic acidification.

Figure 7:
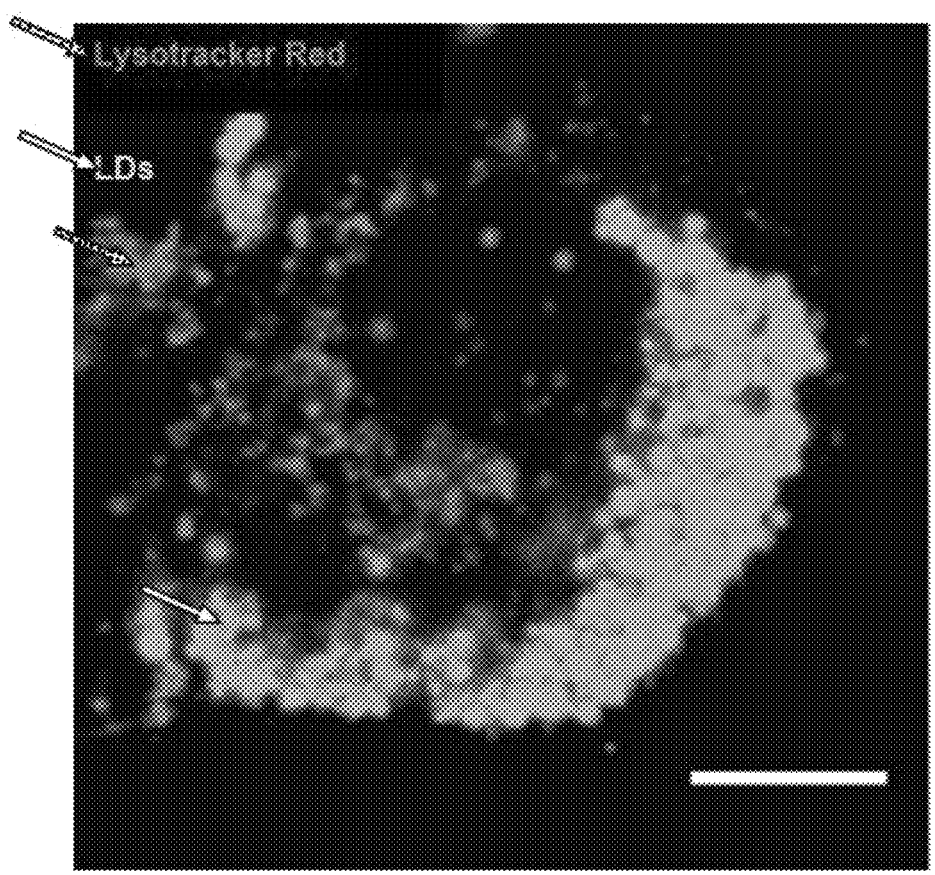
FIG. 7 illustrates that treatment with Triacsin C blocks EPA-induced lysosomal movement/lipid droplet degradation. Imaging of EPA-treated cells stained with LipidTOX Green and LysoTracker Red. Cells were incubated with Triacsin C for 15 min prior to EPA treatment. Lipid droplets are green, lysosomes red.

It is well established that inhibiting mTORC1 by rapamycin could induce macroautophagy. It is also known that during rapamycin-induced macroautophagy, lysosomes are clustered at the perinuclear regions rich in autophagosomes[23]. Under the present experimental conditions (i.e. EPA-triggered lysosomal motility and CLD degradation), we have observed that pretreatment of cells with rapamycin can effectively block EPA-triggered lysosomal motility and lipid droplet degradation (FIG. 5g). In addition, we have also observed that the EPA-triggered lysosomal motility can be blocked by the treatment of Triacsin C, a specific inhibitor of long-chain-fatty-acyl CoA synthetases (ACSL) (FIG. 7). Consequently, treatment of cells with Triacsin C inhibited EPA-induced lipid degradation (FIG. 8d). Thus, the EPA-triggered process occurred after acyl-CoA thioester formation. Moreover, depletion of KIFbβ, a member of kinesin superfamily proteins capable of promoting peripheral distribution of lysosomes[18], also blocked EPA-induced lipid turnover (FIG. 8e-f). These results indicate that the EPA-induced lipid degradation is closely associated with redistribution of lysosomes and direct interaction between lysosomes and CLDs, a process that is distinct from the classic autophagy or macroautophagy.

Ultrastructural analysis of EPA treated cells using transmission electron microscopy (EM) (FIG. 8g) and electron tomography (FIG. 8h-i), show lysosomal engulfment of a small piece of lipid at the contact sites between lysosome and CLD. In this regard, the EPA-induced lipid degradation process closely resembles microautophagy of lipids that occurs in yeast[19].

Figure 12:
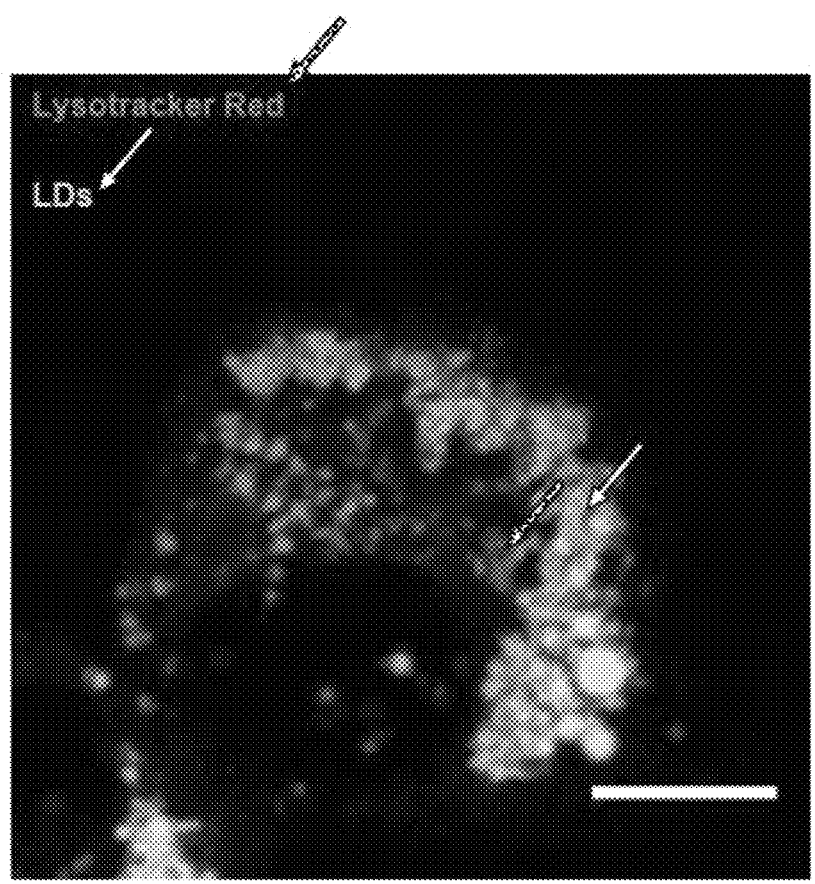
FIG. 12 illustrates that treatment with nocodazole blocks EPA-induced lysosomal movement and/or decreases the interaction between lysosomes and lipid droplets upon treatment with EPA. Imaging of EPA-treated cells stained with LipidTOX Red and LysoTracker. Cells were incubated with nocodazole for 15 min prior to EPA treatment. Lipid droplets are green, lysosomes red.
Figure 14:
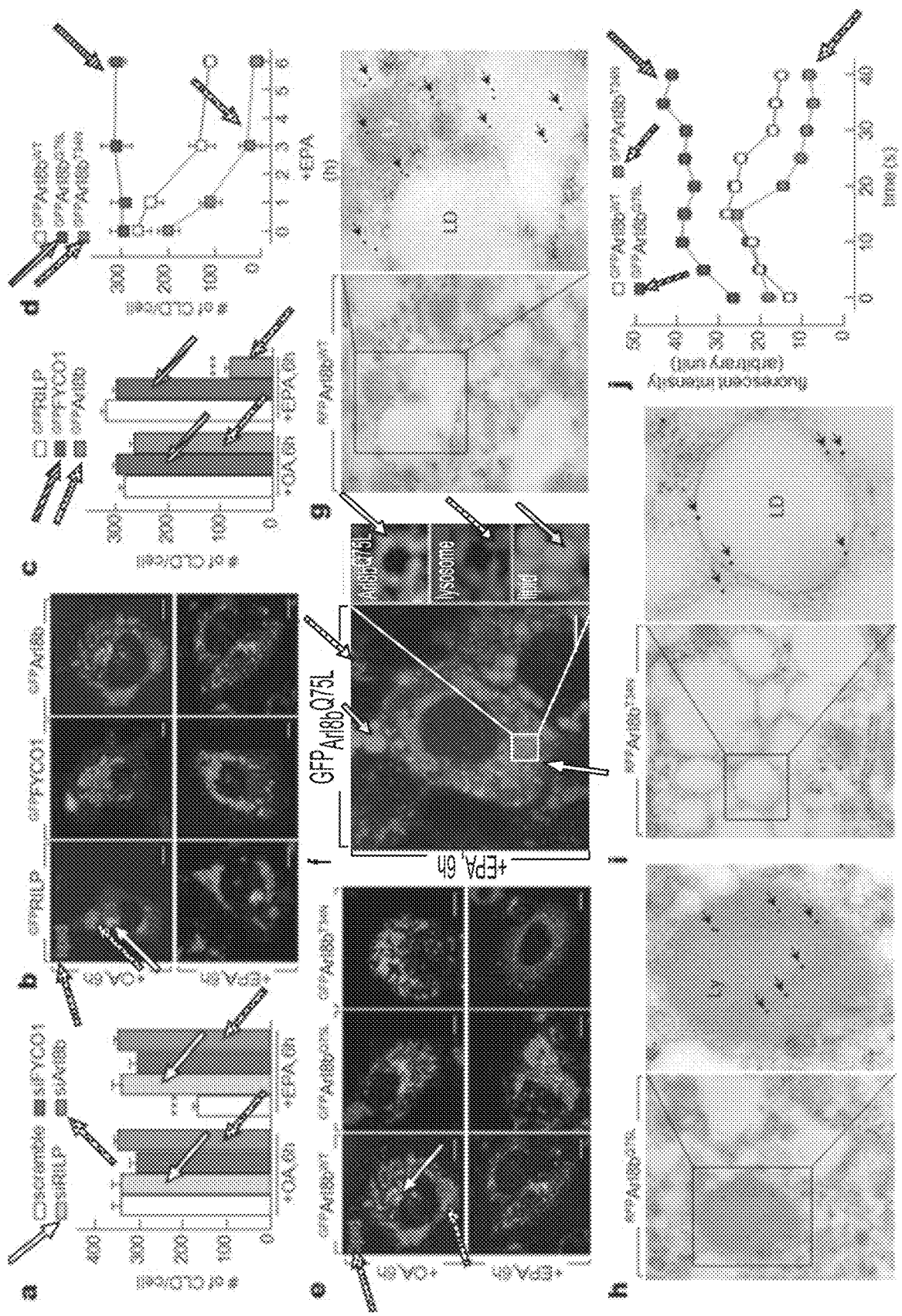
FIG. 14 illustrates that Arl8b, in association with lysosomes, plays an obligatory role in EPA-induced lipid degradation. (a) Quantification of CLD 6 h post-OA or EPA treatment in cells transfected with control (scramble), FYCO1-, RILP-, or Arl8b-specific siRNA as represented in FIG. 15a. (b) Images of cells transfected with GFP-tagged RILP, FYCO1 or Arl8b 6 h post-OA or EPA treatment. (c) Quantification of CLD as represented in (b). (d) Quantification of CLD 0, 1, 3 and 6 h post-EPA treatment in cells transfected with GFP-tagged Arl8b$^{WT}$, Arl8b$^{Q75L}$ or Arl8b$^{T34N}$ as represented in (e) and FIG. 19a. (f) Image of lysosomal interaction with CLD 6 h post-EPA treatment in cells transfected with Arl8b$^{Q75L}$. (g), (h), and (i) Immuno-EM of RFP-tagged Arl8$^{WT}$(g), Arl8b$^{Q75L}$ (h), or Arl8b$^{T34N}$ (i) expressed in transfected cells 1 h post-EPA treatment. Scale bar, 100 nm. (j) Quantification of lysosomal association with and disassociation from CLD in cells transfected with GFP-tagged Arl8b$^{WT}$, Arl8b$^{Q75L}$ or Arl8b$^{T34N}$ as represented in FIG. 24a-c. All scale bars are 8 µm.

Movement of lysosomes is important to their functions during the cell response to nutrient status[23]. The anterograde and retrograde lysosomal motility along microtubules is governed by Rab7 through its effector proteins FYCO1[21] and RILP[22], respectively (See FIG. 13a-b). Silencing FYCO1 or RILP completely abolished EPA-induced lipid degradation (FIG. 14a, FIG. 15a-e, and FIG. 16). Likewise, depolymerization of microtubules using nocodazole also blocked EPA-induced lipid degradation (FIG. 12). The blockage of lipid degradation upon FYCO1 or RILP depletion was accompanied with lysosomal immobility and retarded movement, indicating that these Rab7 effectors and microtubules are essential components for EPA-induced lipid degradation. However, merely overexpression of RILP or FYCO1 also adversely blocked EPA-induced lipid degradation (FIG. 14b-c). Live imaging shows that RILP or FYCO1 expression resulted in accumulation of lipid droplets and polarized distribution of lysosomes at the respective perinuclear regions and distal cell periphery (FIG. 14b and FIG. 17a-b), apparently due to hyper-activated centripetal and centrifugal motilities of lysosomes.

Figure 15:
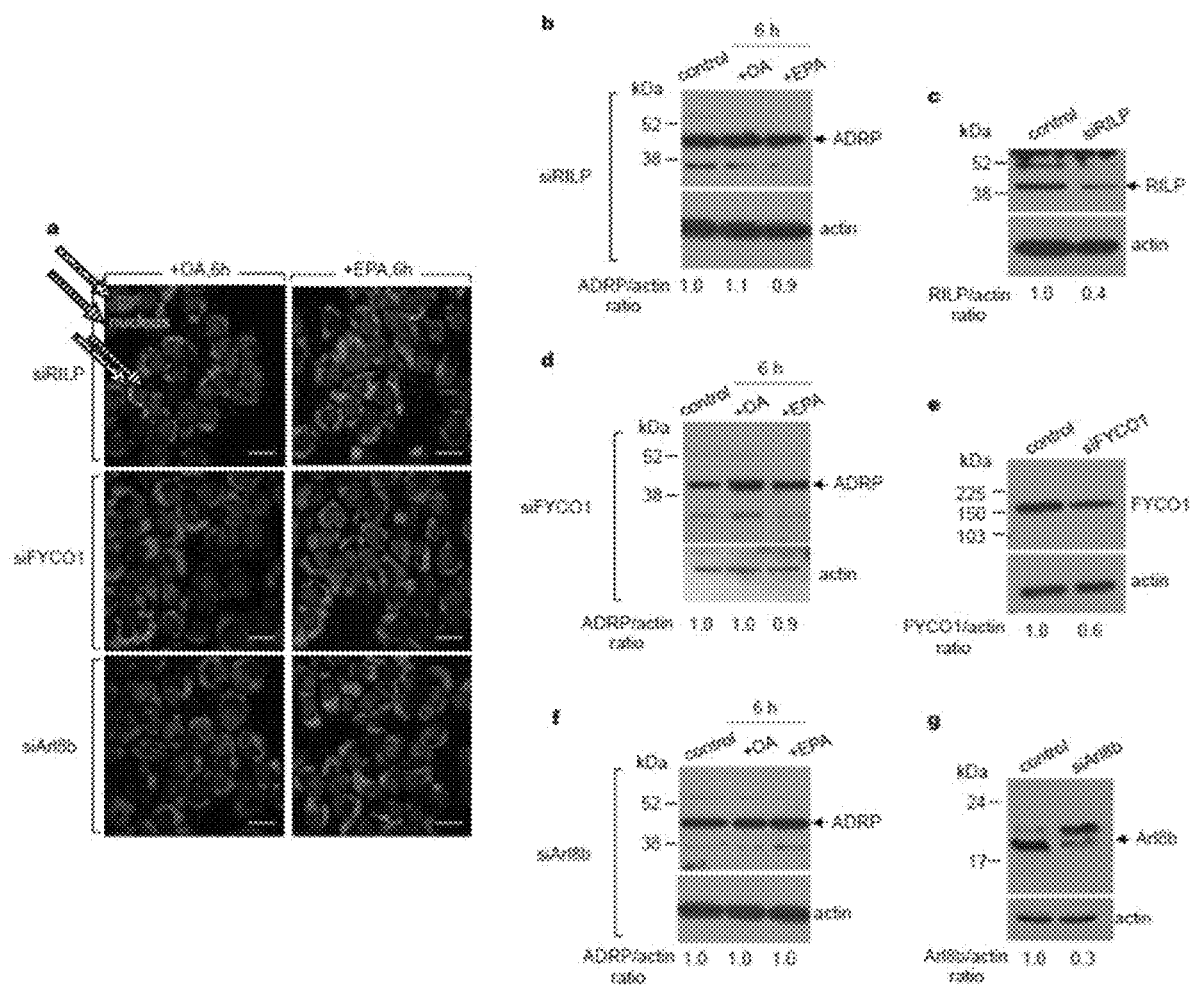
FIG. 15 illustrates that EPA-triggered microautophagy-like lipid degradation requires microtubule motor adaptor proteins RILP, FYCO1, and Arl8b. (a) Images of CLD (stained with lipidTOX Red) 6 h post-OA or -EPA treatment in cells transfected with RILP-, FYCO1-, or Arl8b-specific siRNA. Scale bars, 22 µm. (b) Western blots of ADRP in RILP silenced cells. (c) Western blots of RILP showing the efficacy of silencing. (d) Western blots of ADRP in FYCO1 silenced cells. (e) Western blots of FYCO1 showing the efficacy of silencing. (f) Western blots of ADRP in Arl8b silenced cells. (g) Western blots of Arl8b showing the efficacy of silencing. Control, cells transfected with scrambled siRNA.
Figure 18:
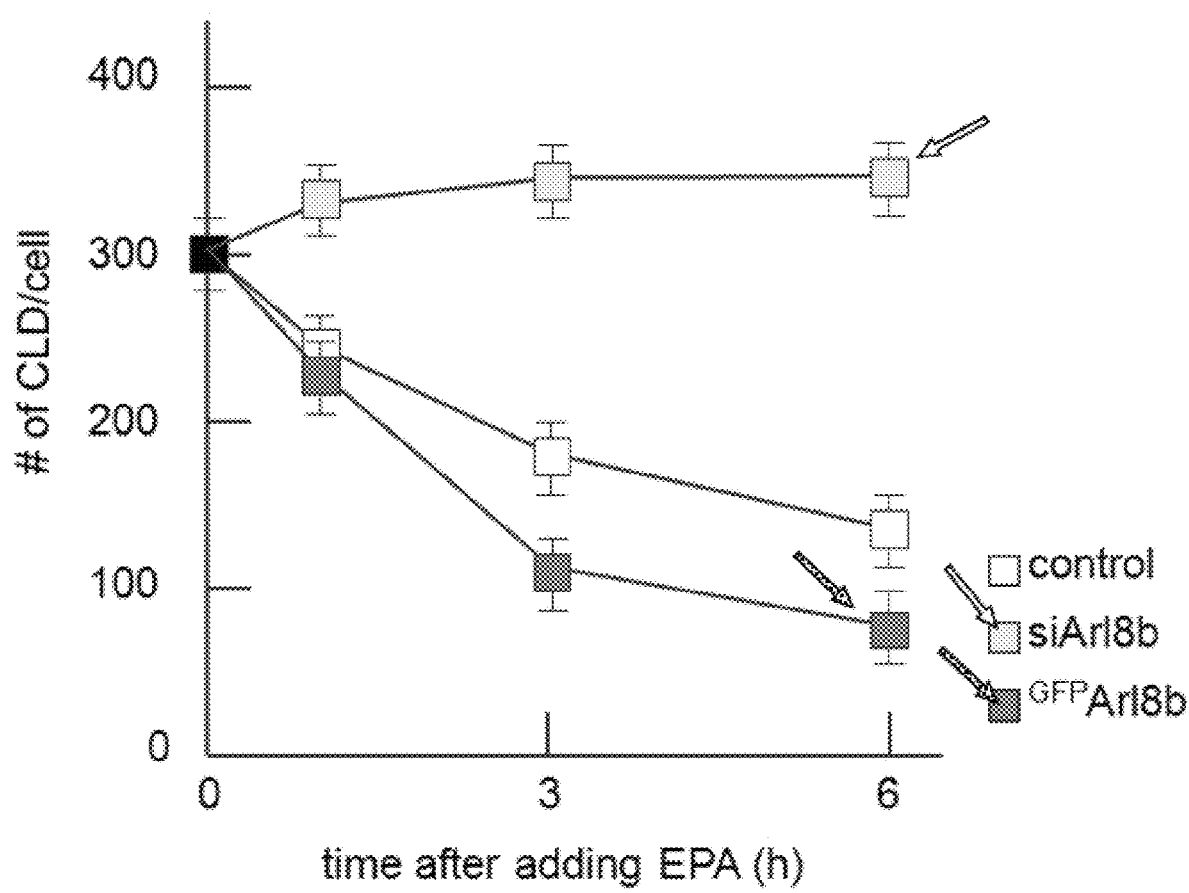
FIG. 18 illustrates that silencing Arl8b blocked EPA-induced lipid degradation, whereas transfection of cells with Arl8b accelerated lipid degradation.

Arl8b, a lysosome-associated protein, has been suggested to play a role in lysosomal anterograde motility[24]. However, live imaging experiments show that unlike that of FYCO1 or RILP, overexpression of Arl8b in hepatic cells does not affect lysosomal motility, nor does it have an apparent impact on lysosome-CLD interaction. An increase in lipid degradation upon EPA treatment is observed in cells overexpression of Arl8b (FIG. 14b-c). On the other hand, depletion of Arl8b, like that of FYCO1 or RILP, abolishes EPA-induced lipid degradation (FIG. 14a and FIG. 15a,f-g). These effects are further demonstrated in FIG. 18.

Figure 17:
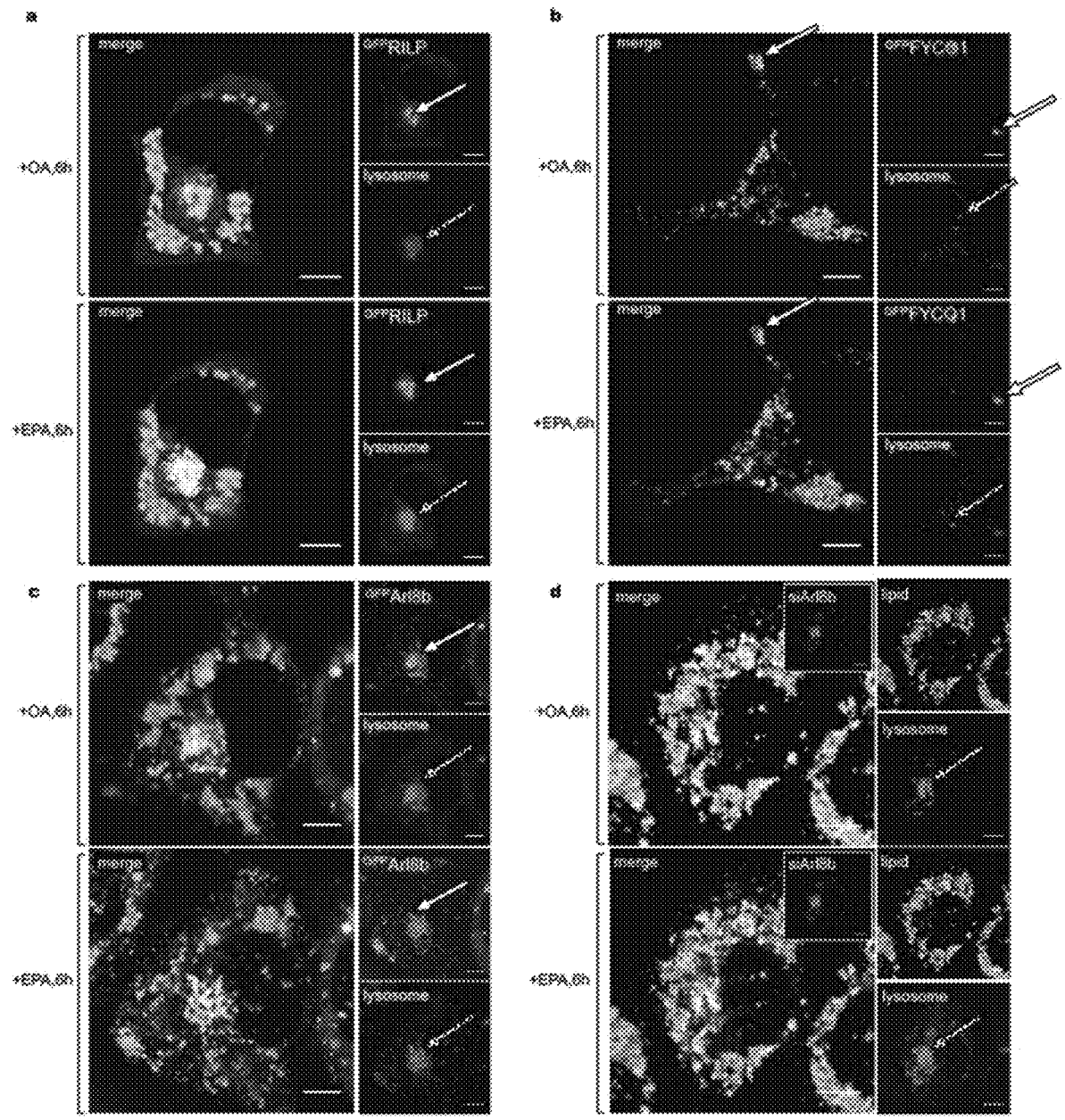
FIG. 17 illustrates the Effect of RILP, FYCO1, or Arl8b expression or Arl8b depletion, on lysosomal distribution. (a) and (b) EPA treatment in $^{GFP}$RILP- (a) or $^{GFP}$FYCO1-overexpressing cells (b) is unable to trigger lipid degradation due to polarized lysosomal distribution at cell periphery and the perinuclear regions, respectively. As seen in (a), overexpression of RILP results in lysosomal clustering in the perinuclear region and blocks EPA-triggered lysosomal interaction with LDs. As seen in (b), overexpression of FYCO1 displaces lysosomes towards the cell periphery and blocks EPA-triggered lysosomal interaction with LDs. (c) and (d) Expression (c) or depletion (d) of Arl8b does not interfere with lysosomal redistribution towards cell periphery, nor does it affect lysosomal interaction with CLD (pseudocolored cyan (c) or grey (d)). Lysosomes are visualized with LysoTracker (red). In (c), overexpression of Arl8b does not displace lysosomes to the cell periphery, nor does it interfere with lysosomal movement or interaction with lipid droplets. In Arl8b depletion experiments (d), cells transfected with Arl8b siRNA (siArl8b; Ambion (Invitrogen) #179124) were detected using iRNA Tracker (inset). Silencing Arl8b does not affect lysosomal interaction with lipid droplets but attenuates lipid degradation. Scale bars, 8 µm.

The abolished lipid degradation upon Arl8b depletion is not due to blockage of lysosomal motility or interaction with CLD. Rather, even under Arl8b siRNA treatment conditions, direct interaction between lysosomes and lipid droplets was observed. The EPA-triggered lysosomal motility and transient interaction with CLD appear normal in the absence of Arl8b (FIG. 17d). Thus, neither overexpression nor depletion of Arl8b in hepatic cells has a profound impact on lysosomal motility or lysosome-CLD interactions. In the absence of Arl8b, the anterograde and retrograde motility of lysosomes may still occur, as long as the Rab7, FYCO1, and RILP are present. However, FYCO1 or RILP cannot engage the interaction between lysosome and CLD, and thus does not facilitate lysosome-mediated lipid degradation.

The apparently normal interaction between lysosome and CLD, in the absence of Arl8b, indicates that there are other cellular factors (e.g. SNARE proteins) that may also mediate lysosome-CLD interactions. But these factors do not substitute Arl8b to promote lysosome-dependent lipid degradation, because as it will be further described in detail below, effective lipid degradation occurs with not only lysosomal interaction with CLD, but also with successful termination of the engulfment process (i.e. lysosomal dissociation from CLD). Therefore, the current data taken together suggest that the Arl8b-facilitated lipid degradation is achieved through a mechanism beyond merely promoting lysosomal motility or lysosomal direct interaction with CLD.

Example 2—Arl8b and EPA-Induced Lipid Degradation

Arl8b, or Arf-like protein, is a small GTPase which is highly conserved (i.e. 100% sequence identity between human and rodents). See, for example, FIG. 44.

To gain further insight into the Arl8b action in detail, the effect of expression of a putative GTP-bound (Arl8b$^{Q75L}$) or GDP-bound (Arl8b$^{T34N}$) form of Arl8b on lipid degradation and lysosomal motility was examined. Arl8b$^{Q75L}$ is a mutant Arl8b which presumably only binds GTP, whereas Arl8b$^{T34N}$ is a mutant Arl8b which presumably only binds GDP. Arl8b$^{Q75L}$ has a Gln-to-Leu substitution at position 75, while Arl8b$^{T34N}$ has a Thr to Asn substitution at position 34. Nucleic acid and amino acid sequences of Arl8b$^{WT}$, Arl8b$^{T34N}$, and Arl8b$^{Q75L}$ may be seen in FIGS. 32-35, 44, and 46.

Figure 19:
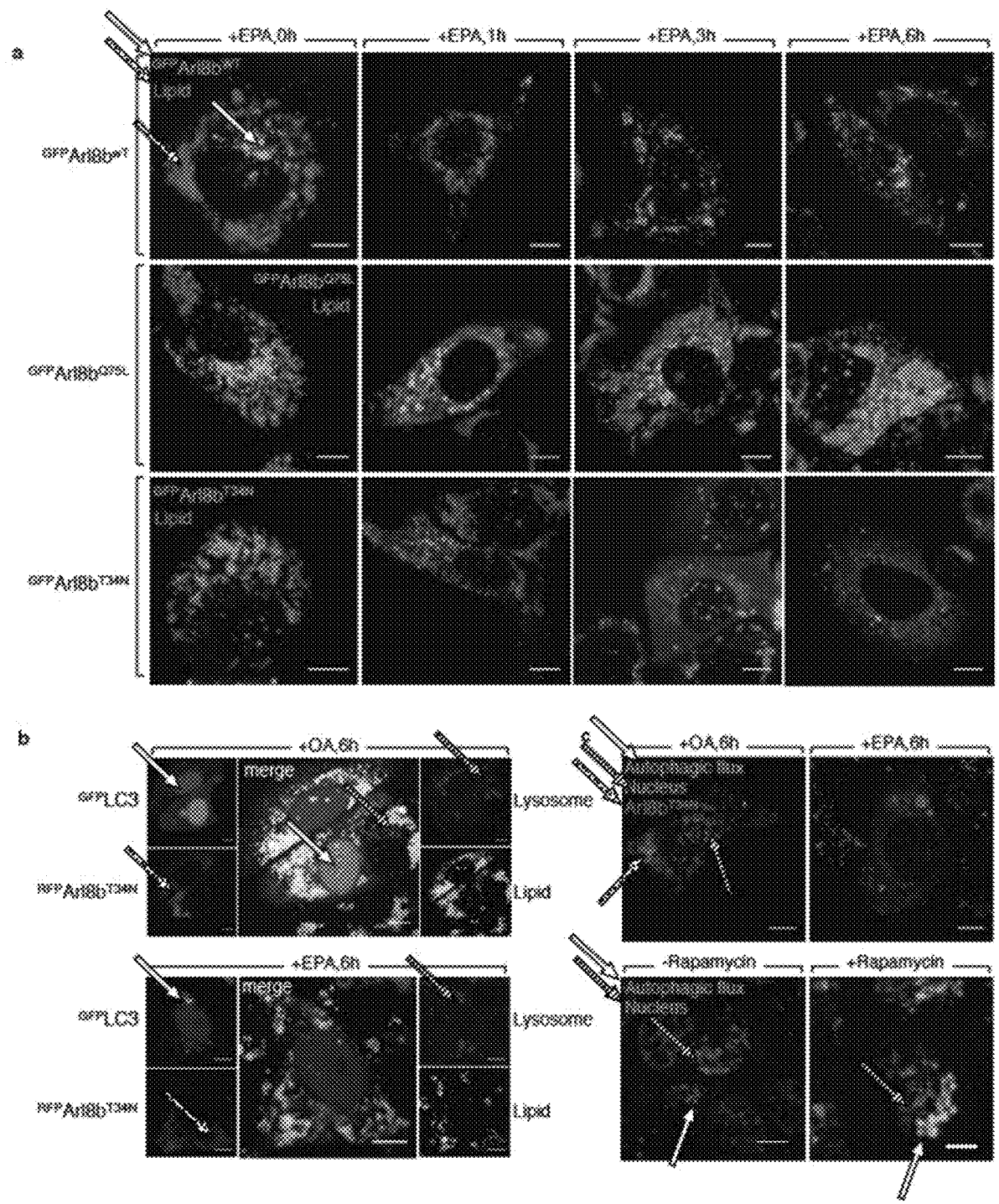
FIG. 19 illustrates that overexpressing Arl8b$^{Q75L}$ blocks, and overexpressing Arl8b$^{T34N}$ accelerates, EPA-induced lipid degradation. (a) Differential response to EPA treatment in cells expressing GFP-tagged Arl8b$^{WT}$ (top panels), Arl8b$^{Q75L}$ (middle panels), and Arl8b$^{T34N}$ (bottom panels), respectively. (b) Augmented lipid degradation in RFP-tagged Arl8b$^{T34N}$-expressing cells is unrelated to classical autophagy. No co-localization of GFP-tagged LC3 and CLD occurs in $^{RFP}$Arl8b$^{T34N}$-expressing cells, and EPA triggered lysosomal interaction with CLD does not coincide with LC3 clustering. (c) Cyto-ID assay shows that EPA treatment in $^{RFP}$Arl8b$^{T34N}$ expressing cells does not induce autophagic flux. Bottom panels show that autophagic flux can be induced using rapamycin. All scale bars are 8 µm.
Figure 24:
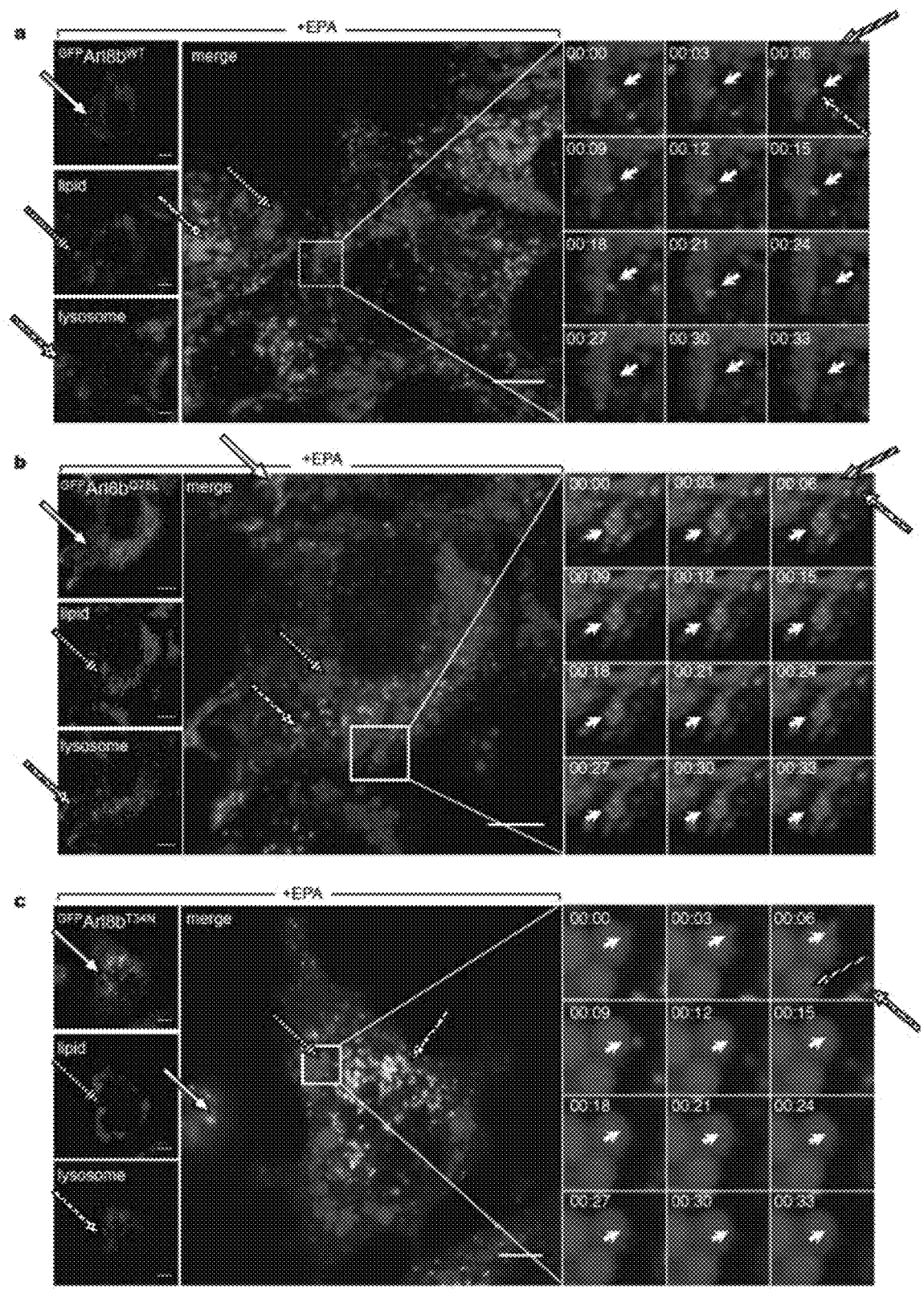
FIG. 24 illustrates the effect of Arl8b expression on EPA-triggered lysosomal interaction with CLD. (a) Arl8b$^{WT}$-expressing cells. Time lapse images of EPA-triggered lysosomal interaction with lipids (the "on" phase) and subsequent dissociation (the "off" phase) are shown. Arrows denote lysosomal interaction with lipid droplets. (b) Arl8b$^{Q75L}$-expressing cells. Time-lapse images are shown. As shown, overexpression of Arl8b$^{Q75L}$ confers hyper-activated lysosomal adherence with lipid droplets and paradoxically attenuates lipid degradation. (c) Arl8b$^{T34N}$-expressing cells. Time-lapse images are shown. As shown in (c), overexpression of Arl8b$^{T34N}$ accelerates lysosomal dissociation from lipid droplets, and shows less lysosomes interacting with CLDs. Scale bars, 8 μm.

Surprisingly, the EPA-induced lipid degradation was completely blocked by overexpression of Arl8b$^{Q75L}$, and yet was accelerated by overexpression of Arl8b$^{T34N}$ as compared with that in Arl8b$^{WT}$-expressing cells (FIG. 14d-e, FIG. 19a). These observations are unexpected because normally the GTP-bound GTPases are the active forms. As will be recognized below, and without wishing to be bound by theory, the blockage of lipid degradation by Arl8b$^{Q75L}$ overexpression may be due to "locked" interaction between lysosome and CLD, thus effectively preventing the dissociation of lysosome from CLD (i.e. "kiss" without "run") and preventing the termination of engulfment processes as seen by a number of lysosome-lipid droplet interactions (FIG. 24b). On the other hand, the accelerated lipid degradation by Arl8b$^{T34N}$ overexpression is attributable to rapid dissociation of lysosome from CLD after "kiss"/engulfment (FIG. 24c). The rate of lysosomal dissociation from CLD under EPA-treatment conditions is so fast that at any given moment, the majority of lysosomes is present in the perinuclear regions (FIG. 24c).

Figure 20:
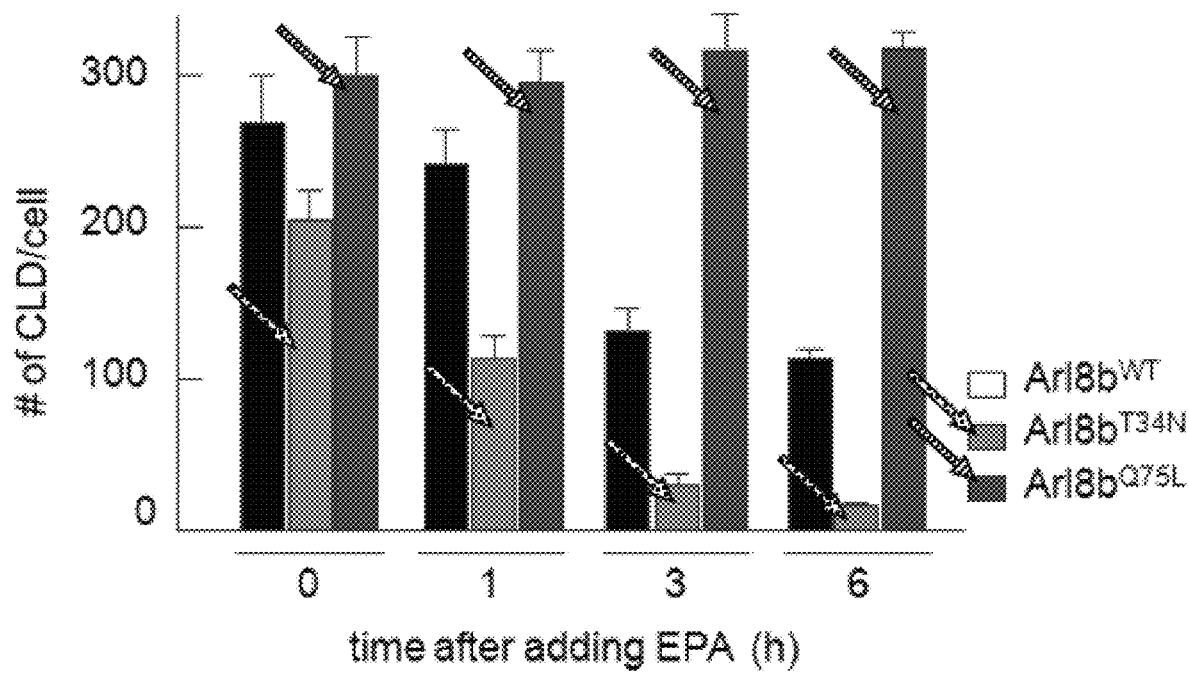
FIG. 20 illustrates that Arl8b$^{T34N}$ expression accelerated EPA-triggered lipid degradation, and lipid degradation was observed even without EPA treatment.
Figure 21:
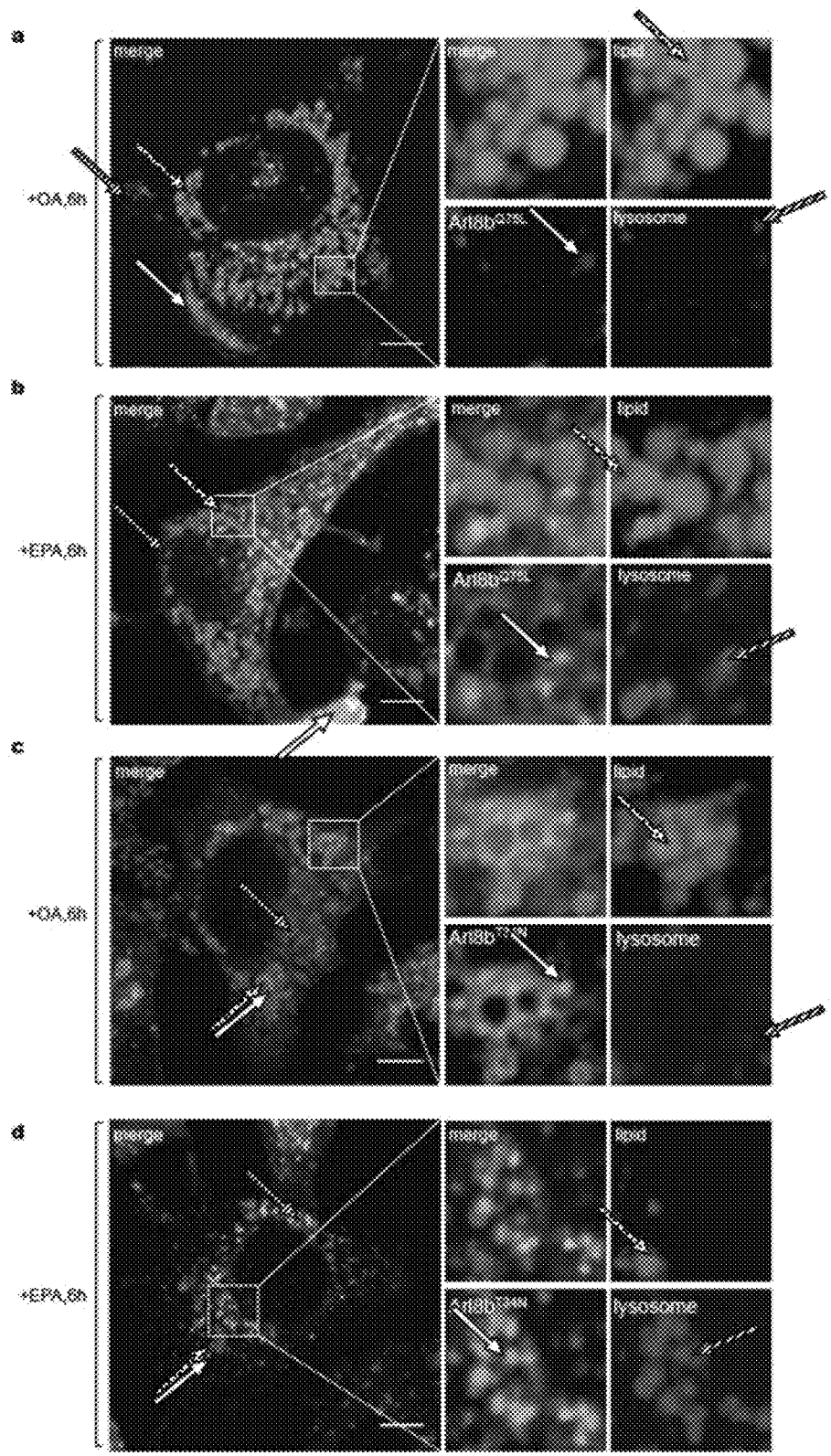
FIG. 21 illustrates that the nucleotide-binding status of Arl8b governs its association with lysosome or CLD. (a) and (b) Images of lysosome, CLD, and $^{GFP}$Arl8b$^{Q75L}$ distribution in cells 6 h post-OA (a) or -EPA (b) treatment. Note that $^{GFP}$Arl8b$^{Q75L}$ became lysosome associated only after EPA treatment. (c) and (d) Images of lysosome, CLD, and $^{GFP}$Arl8b$^{T34N}$ distribution in cells 6 h post-OA (c) or -EPA (d) Treatment. Note that $^{GFP}$Arl8b$^{T34N}$ was associated with CLD under both conditions. However, post-EPA treatment, lysosomes, together with most of the $^{GFP}$Arl8b$^{T34N}$, are colocalized with each other and returned to the perinuclear regions. All scale bars are 8 µm.

The expression of Arl8b$^{T34N}$ (the putative GDP-bound form) on lipid degradation is remarkable; the lipid content is lowered in the lipid-laden cells even without the addition of EPA (FIG. 14d-e and FIG. 20). Thus under OA-treatment conditions, cells expressing Arl8b$^{T34N}$ showed association of Arl8b$^{T34N}$ predominantly with cell peripheral CLD and little with lysosomes in the perinuclear regions (FIG. 21c-d). Addition of EPA to the Arl8b$^{T34N}$-transfected cells further accelerated lipid degradation (as compare to that in Arl8b$^{WT}$-transfected cells). Live imaging experiments show that after EPA-induced lipid degradation, Arl8b$^{T34N}$ returned to the perinuclear regions and became co-localized with lysosomes (FIG. 21c-d). Thus, expression of Arl8b$^{T34N}$ in hepatic cells, unlike Arl8b$^{Q75L}$, does not disturb lysosomal interaction and engulfment (i.e. microautophagy) of CLD (FIG. 24c).

Imaging analysis of cells expressing Arl8b$^{Q75L}$ shows higher incidence of direct lysosome-lipid droplet interaction, and redistribution of Arl8b$^{Q75L}$, together with lysosomes, from the perinuclear regions (under OA treatment) toward cell periphery after adding EPA. However, the interaction of lysosomes with CLD in the presence of Arl8b$^{Q75L}$ was so tight that no disassociation of lysosomes from CLD occurred, providing hybrid structure-like organelles between lysosomes and lipid droplets (FIG. 14f, FIG. 21a-b, and FIG. 24a). These data suggest that expression of Arl8b$^{Q75L}$, but not Arl8b$^{T34N}$, interferes with lysosomal engulfment processes and dissociation from CLD.

Figure 22:
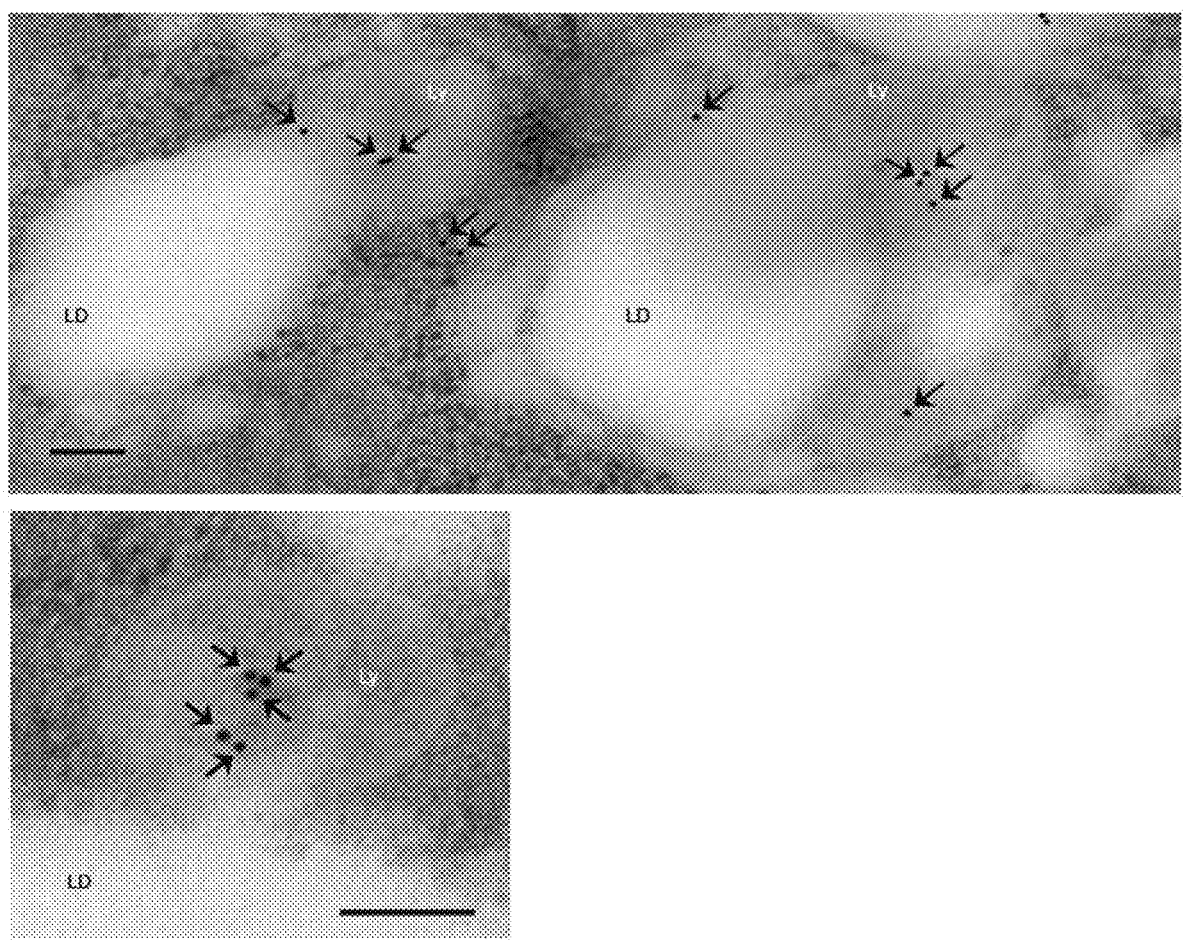
FIG. 22 illustrates organellar distribution of Arl8b. Immuno-EM of endogenous Arl8b. Cells were processed for immunogold staining 1 h post-EPA treatment using anti-Arl8b as the primary antibody. Scale bar, 100 nm. Arrows indicate positions of Arl8b molecules associated with lysosome (Ly) and cytosolic lipid droplets (LD)
Figure 23:
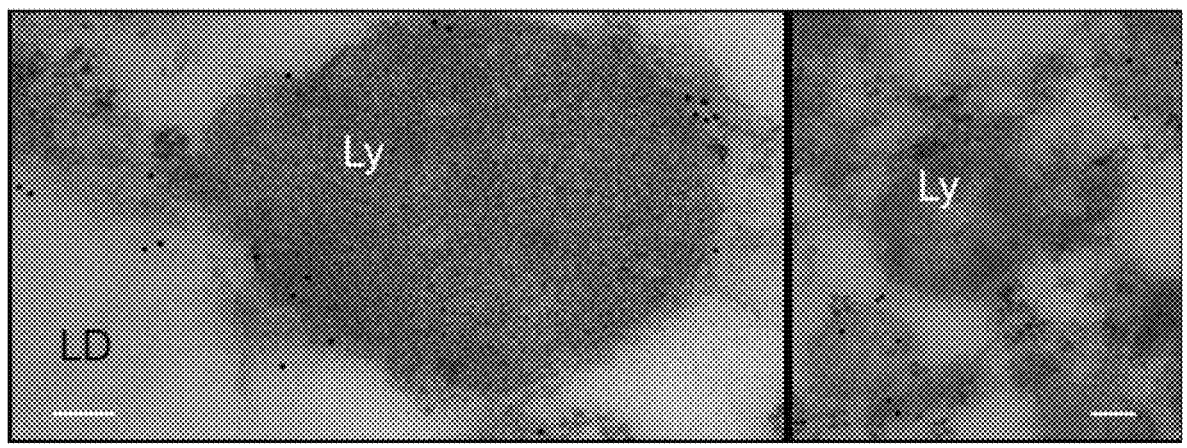
FIG. 23 illustrates organellar distribution of recombinant $^{RFP}$Arl8b$^{WT}$ in transfected cells. Immuno-EM was performed using an anti-RFP antibody to visualize the recombinant protein. Image shows that $^{RFP}$Arl8b$^{WT}$, like endogenous Arl8b, is also associated with both lysosomes (Ly) and cytosolic lipid droplets (LD). These data thus indicate that "tagging" Arl8b with a RFP moiety has little noticeable effect on the protein's ability to associate with lysosomes and/or CLDs. Scale bar, 100 nm.

Examination of Arl8b organellar association by immuno-EM shows that endogenous Arl8b (FIG. 22), as well as the recombinant Arl8b (FIG. 23), is associated with lysosomes and CLD in cells treated with EPA. Thus, similar to endogenous Arl8b, the recombinant RFP::Arl8b$^{WT}$ (also referred to herein as $^{RFP}$Arl8b$^{WT}$) in transfected cells also shows dual presentation between lysosomes and CLD (FIG. 14g). However, as being observed previously[24], RFP::Arl8b$^{Q75L}$ (also referred to herein as $^{RFP}$Arl8b$^{Q75L}$) is predominately associated with lysosomes (FIG. 14h), whereas RFP::Arl8b$^{T34N}$ (also referred to herein as $^{RFP}$Arl8b$^{T34N}$) is mainly CLD-borne (FIG. 14i). These observations suggest that alternating nucleotide-binding status of Arl8b (i.e. between GTP-binding and GDP-binding) may render its respective association between lysosomes and CLD.

Determination of association/dissociation kinetics between lysosomes and CLD reveals that nucleotide-binding status of Arl8b has a profound effect on lysosome-CLD interaction. A summary of lysosome-CLD interaction kinetics is shown in FIG. 14j, which is derived from live imaging experimental data shown in FIG. 24a-c. Comparison between Arl8b constructs showed higher levels of lysosomal interaction with lipid droplets with Arl8b$^{Q75L}$, which was accompanied by higher rate of lipid droplet accumulation, as compared to Arl8b$^{WT}$ and Arl8b$^{T34N}$. In GFP::Arl8b$^{WT}$-expressing cells, association between lysosomes and CLD (the "on" phase) persists for approximately 15 seconds, followed with gradual dissociation (the "off" phase) (FIG. 24a). In GFP::Arl8b$^{Q75L}$-expressing cells, prolonged lysosomal adherence to CLD ensued, thus virtually eliminating the "off" phase (FIG. 24b). On the contrary, in GFP::Arl8b$^{T34N}$-expressing cells, the rate of lysosomal dissociation from CLD (the "off" phase) was fastened (FIG. 24c). These data suggest that through its moderation of interaction/engulfment between lysosome and CLD, Arl8b can achieve a role in regulating association/dissociation between the two organelles which may affect the rate of microautophagy of lipid droplets as depicted in the previous Figures.

It is thus suggested that Arl8b may function at the stage when lysosomes are interacting with/engulfing CLD by facilitating tethering complex formation. Without wishing to be bound by theory, interaction and subsequent formation of a tethering complex between lysosomes and CLD may be controlled by Arl8b when it is in its GTP-bound form, whereas disassembly of the tethering complex and termination of the engulfment process is governed by Arl8b when it is in its GDP-bound form. In the absence of Arl8b-mediated lysosome-CLD tethering (e.g., in cells treated with Arl8b-silencing siRNA), although lysosomes appear to be able to move toward the cell periphery and interact with CLD, and they also appear to be able to dissociate from the CLD after the interaction, the lysosome-dependent lipid degradation (i.e. microautolipophagy) appears not to occur.

Example 3—Arl8b and HOPS in EPA-Induced Lipid Degradation

Without wishing to be limited by theory, the above data suggest that through its alternated nucleotide-binding status (i.e. GTP- or GDP-bound), Arl8b may play a role in microautophagy and lysosomal target engulfment processes by organizing interaction/dissociation between neighboring lysosome and CLD, through the assembly and disassembly of a tethering complex, during the EPA-induced microautophagic lipid degradation process.

Figure 25:
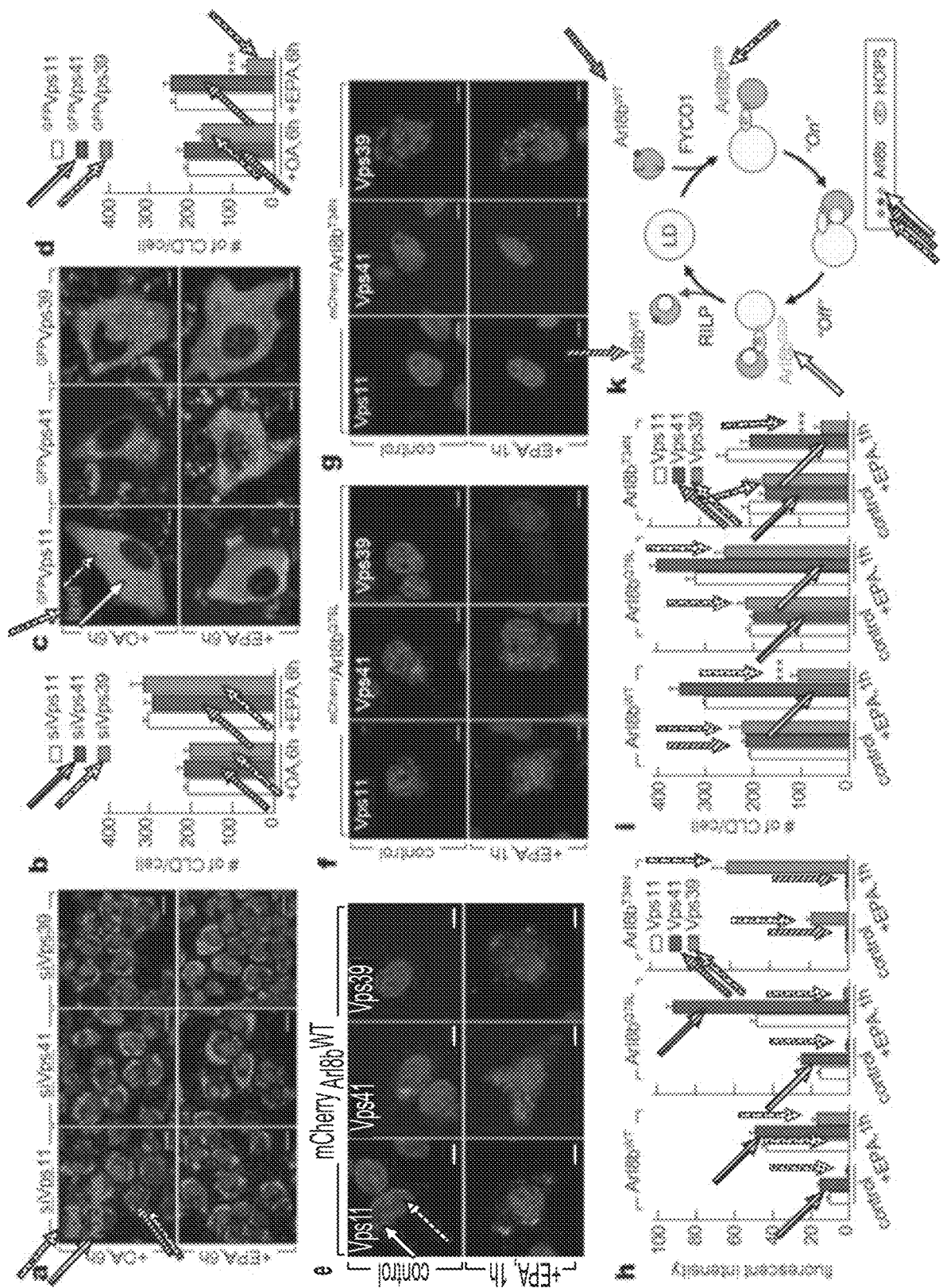
FIG. 25 illustrates that Arl8b organizes HOPS-dependent lysosomal tethering with CLD. (a) Images of cells transfected with Vps11-, Vps41- or Vps39-specific siRNA 6 h post-OA or -EPA treatment. Scale bar, 22 μm. (b) Quantification of CLD as represented in (a). (c) Images of cells transfected with GFP-tagged Vps11, Vps41 or Vps39. Scale bar, 8 μm. (d) Quantification of CLD as represented in (c). (e), (f), and (g) Proximity ligation assay (In situ co-IP) of protein-protein interactions between Arl8b and endogenous HOPS subunits in cells transfected with mCherry-tagged Arl8b$^{WT}$ (e), Arl8b$^{Q75L}$ (f), or Arl8b$^{T34N}$ (g) under baseline (control) and 1 h post-EPA treatment. Signals pseudocolored in Green indicate protein-protein interaction. Scale bar, 8 μm. (h) Quantification of protein-protein interactions as represented in (e)-(g). (h) Quantification of the intensity of fluorescence derived from Arl8b-Vps proximity ligation. (i) Quantification of CLD in cells co-transfected with Arl8b and HOPS subunits 6 h post-OA or -EPA treatment as represented in FIG. 27a-c. (k) A model depicting Arl8b action in EPA-induced lipid degradation (see below for further detail)
Figure 26:
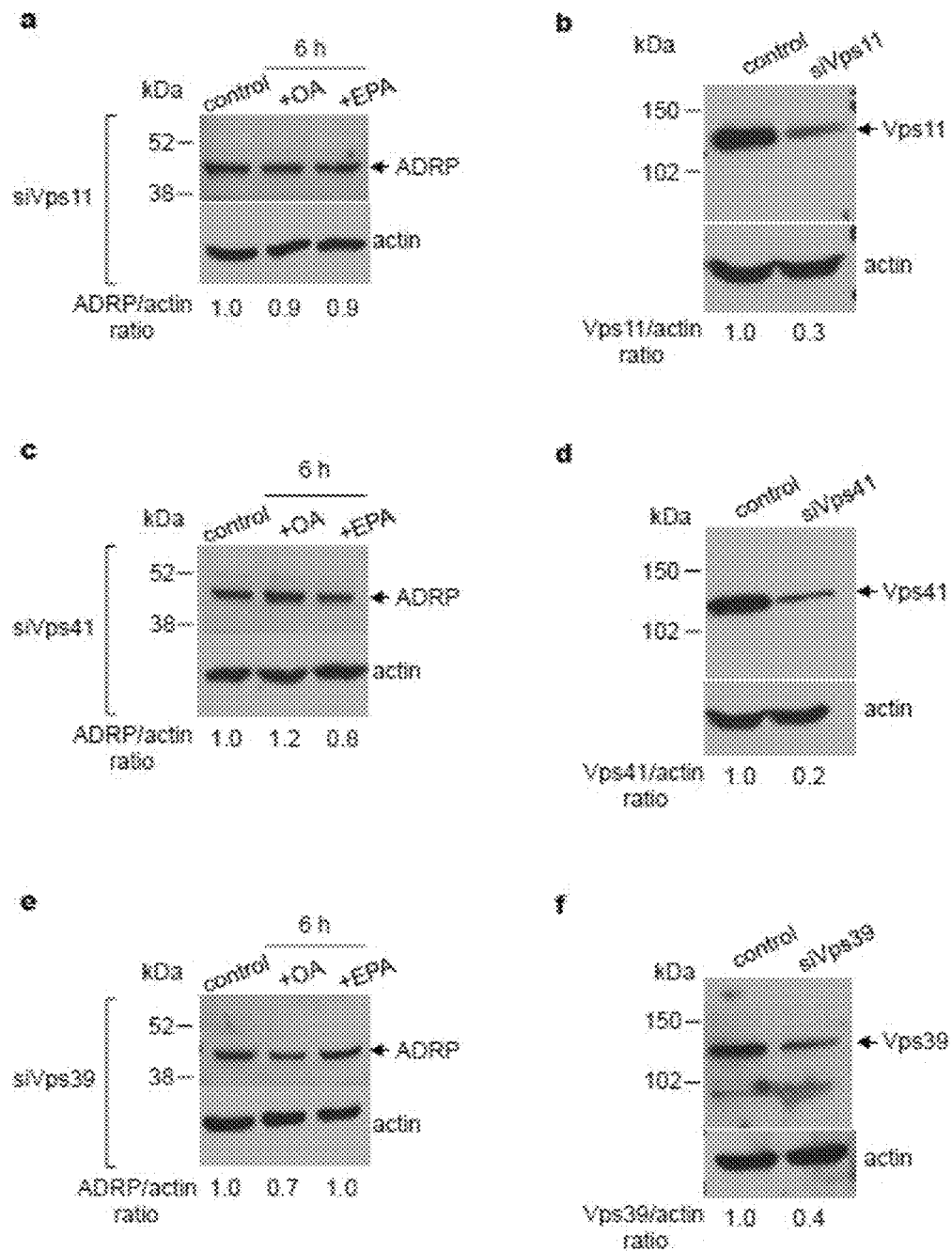
FIG. 26 illustrates that Silencing Vps11, Vps41, or Vps39 blocks EPA-triggered lipid degradation. Western blots of ADRP in the respective Vps11 (a), Vps41 (c), and Vps39 (e) silenced cells. Western blots of the respective Vps11 (b), Vps41 (d), and Vps39 (f) showing the efficacy of silencing. Control, cells transfected with scrambled siRNA.

Recent studies show that Arl8b can organize the HOPS tethering complex during lysosome-dependent microbial killing[25] and autophagosome-lysosome fusion[26]. As such, the involvement of HOPS complex in EPA-induced lipid degradation was examined. Depletion of HOPS subunit Vps41, Vps39, or Vps11 completely abolished EPA-induced lipid degradation (FIG. 25a-b, FIG. 26a-c). Overexpression of these Vps proteins exerts different effects; while GFP::Vps41 or GFP::Vps11 block lipid degradation, GFP::Vps39 promotes the process (FIG. 25c-d).

The amino acid sequences of human Vps39, human Vps41, and human Vps11 are shown in FIG. 46.

Human Vps39 (vacuolar protein sorting 39 homolog (S. cerevisiae) [Homo sapiens]) may be found on GenBank (AAH68559.1), and mouse (Mus musculus) and rat (Rattus norvegicus) may be found on NCBI as follows: vam6/Vps39-like protein isoform 1 [Mus musculus] NCBI Reference Sequence: NP_671495.1; vam6/Vps39-like protein isoform 2 [Mus musculus] NCBI Reference Sequence: NP_849182.1; and vam6/Vps39-like protein [Rattus norvegicus] NCBI Reference Sequence: NP_001012186.2.

Human Vps41 may include vacuolar protein sorting-associated protein 41 homolog isoform 1 [Homo sapiens] and/or vacuolar protein sorting-associated protein 41 homolog isoform 2 [Homo sapiens], both of which may be found on NCBI, Reference Sequence NP_055211.2 and NP_542198.2, respectively.

Human Vps11 may include vacuolar protein sorting-associated protein 11 homolog isoform 1 [Homo sapiens] and/or vacuolar protein sorting-associated protein 11 homolog isoform 2 [Homo sapiens], both of which may be found on NCBI, Reference Sequence NP_068375.3 and NP_001277114.1, respectively. Mouse (Mus musculus) and rat (Rattus norvegicus) may be found on NCBI as follows: vacuolar protein sorting-associated protein 11 homolog [Mus musculus] NCBI Reference Sequence: NP_082165.1; and vacuolar protein sorting-associated protein 11 homolog [Rattus norvegicus] NCBI Reference Sequence: NP_001101608.1.

Live imaging experiments show that expression of GFP::Vps41 or GFP::Vps11 resulted in enhanced lysosomal-CLD interaction, phenocopying what happened with Arl8b$^{Q75L}$ expression. However, expression of GFP::Vps39 does not interfere with termination of lysosomal lipid droplet engulfment process and dissociation from CLD, phenocopying the situation of Arl8b$^{T34N}$ expression.

Figure 27:
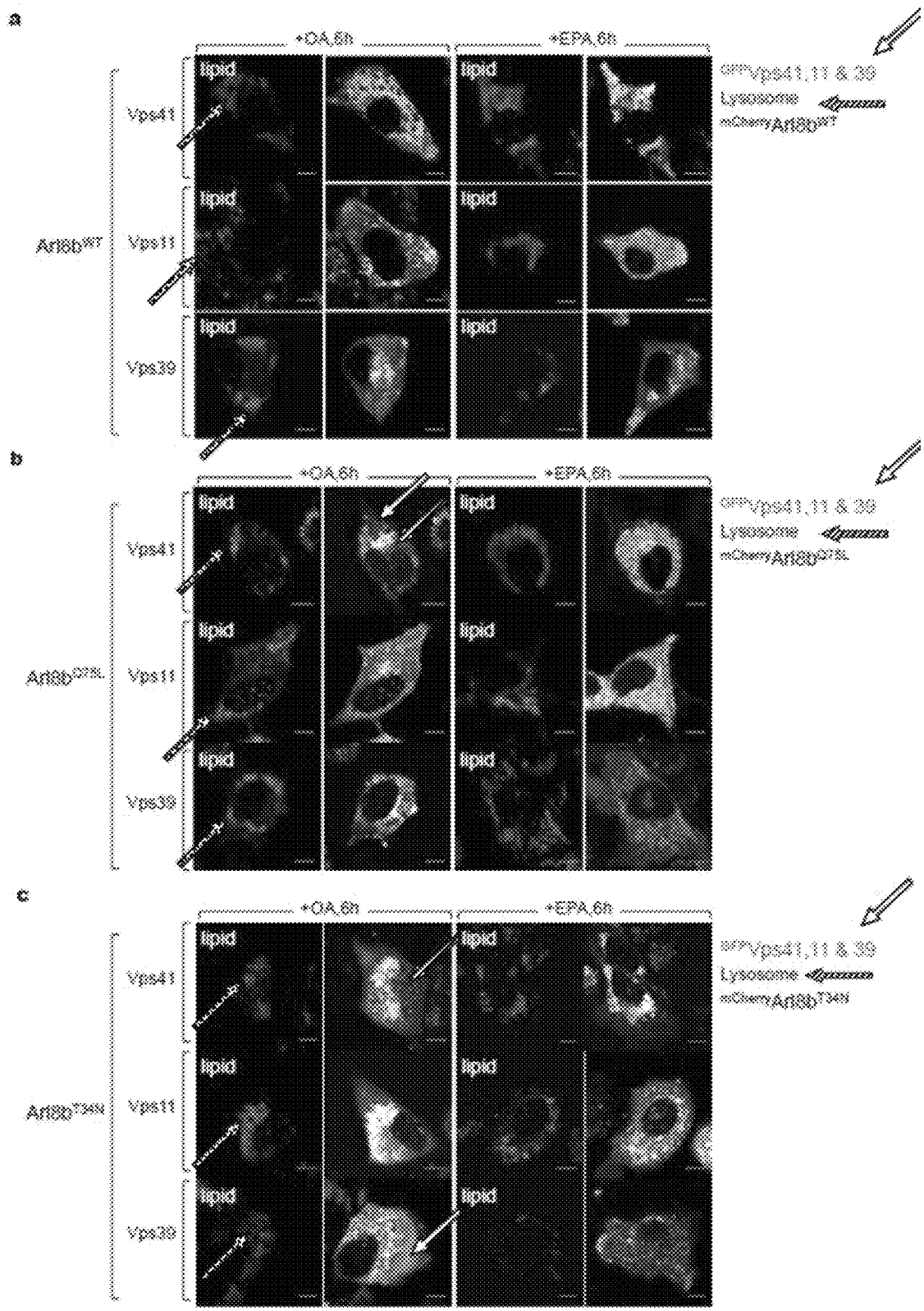
FIG. 27 illustrates that EPA treatment leads to lipid degradation in Vps39 transfected cells but not in Vps41 or Vps11 transfected cells. Cells were co-transfected with Vps41, Vps11, or Vps39 and the respective Arl8b$^{WT}$ (a), Arl8b$^{Q75L}$ (b), and Arl8b$^{T34N}$ (c). The transfected cells were cultured in media +OA or +EPA for 6 h. Images of CLD (stained with lipidTOX Red) in the co-transfected cells are shown, and images of the same cells showing expression of the respective Arl8 and Vps proteins are placed on the right of the lipid images. Scale bars, 22 μm. Imaging analysis of Vps (GFP) and Arl8b (mCherry; pseudocolored in grey) in the co-transfected cells is presented at the right side of the lipid images. Lysosome in these images is pseudocolored in blue.
Figure 28:
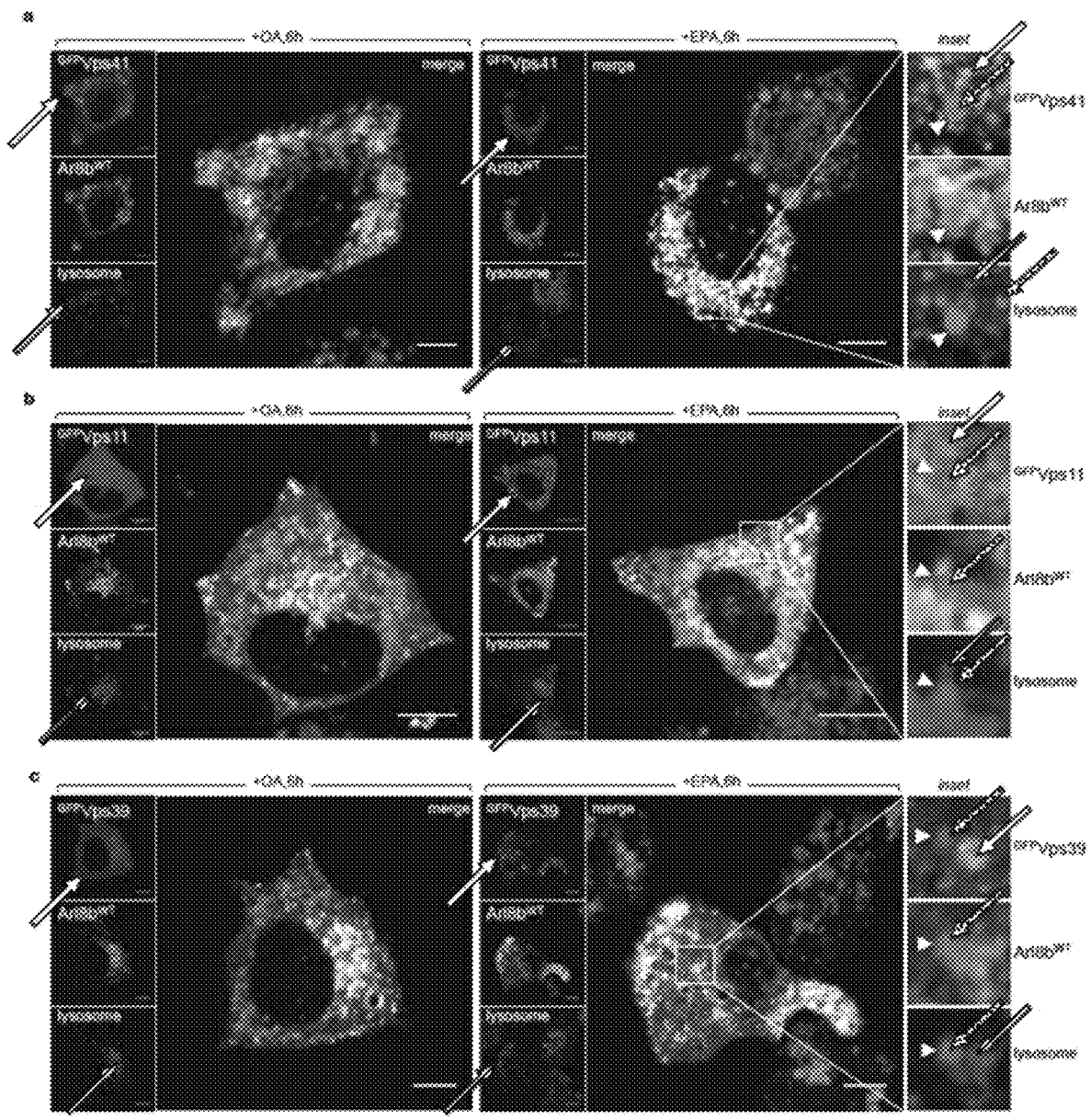
FIG. 28 illustrates that co-expression of Arl8b$^{WT}$ with Vps41 or Vps11, but not Vps39, resulted in increased Arl8b$^{WT}$ interaction with CLD in transfected cells. Cells were co-transfected with Arl8b$^{WT}$ together with Vps41 (a), Vps11 (b), or Vps39 (c). The transfected cells were cultured in media +OA or +EPA for 6 h. Lipid droplets were stained with lipidTOX Red). Lysosome in these images is shown in blue. Imaging analysis of Vps (GFP) and Arl8b (mCherry; pseudocolored in grey) in the co-transfected cells is presented at the left side of the merged images. Scale bars, 22 μm. Insets showing enhanced interaction of Arl8b$^{WT}$ with CLD (corona structures) in the presence of Vps41 or Vps11, but not Vps39, are present on the right. The presence of Vps41 and Vps11 on Arl8b$^{WT}$-positive lipid droplets can been seen.
Figure 29:
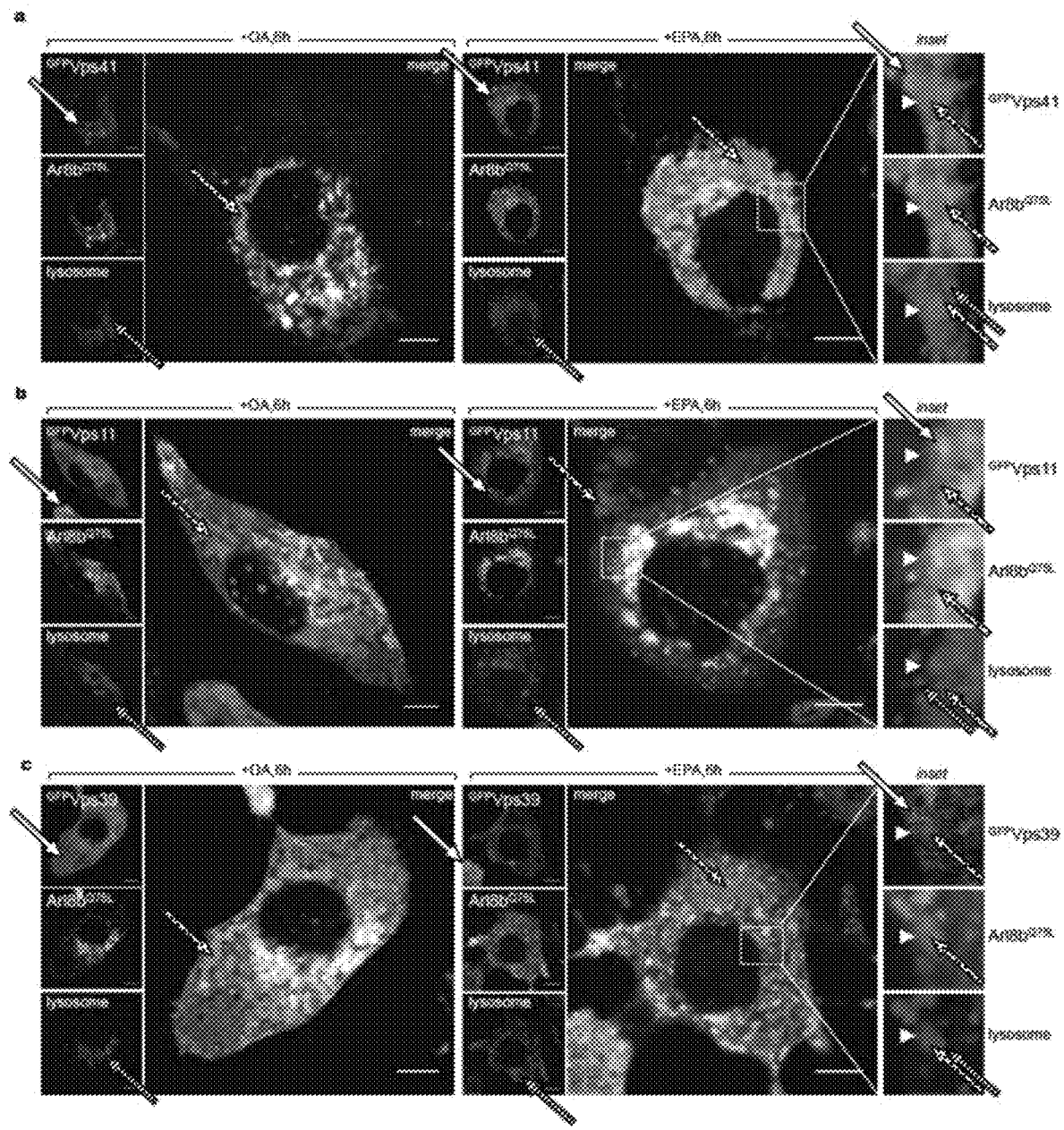
FIG. 29 illustrates that co-expression of Arl8b$^{Q75L}$ with Vps41 or Vps11, but not Vps39, resulted in intensified Arl8b$^{Q75L}$ interaction with lipid droplets in transfected cells. Cells were cotransfected with Arl8b$^{Q75L}$ together with Vps41 (a), Vps11 (b), or Vps39 (c). The transfected cells were cultured in media +OA or +EPA for 6 h. Lipid droplets were stained with lipidTOX Red). Lysosome in these images is shown in blue. Imaging analysis of Vps (GFP) and Arl8b (mCherry; pseudo-colored in grey) in the co-transfected cells is presented at the left side of the merged images. Scale bars, 22 μm. Insets showing enhanced interaction of Arl8b$^{Q75L}$ with lipid droplets (corona structures) in the presence of Vps41 or Vps11 are present on the right. Interaction of Arl8b$^{Q75L}$ with lipid droplets in the presence of Vps39 was less intense. These experiments show that Vps41 and Vps11, but not Vps39, may act as an effector for the GTP form of Arl8b.
Figure 30:
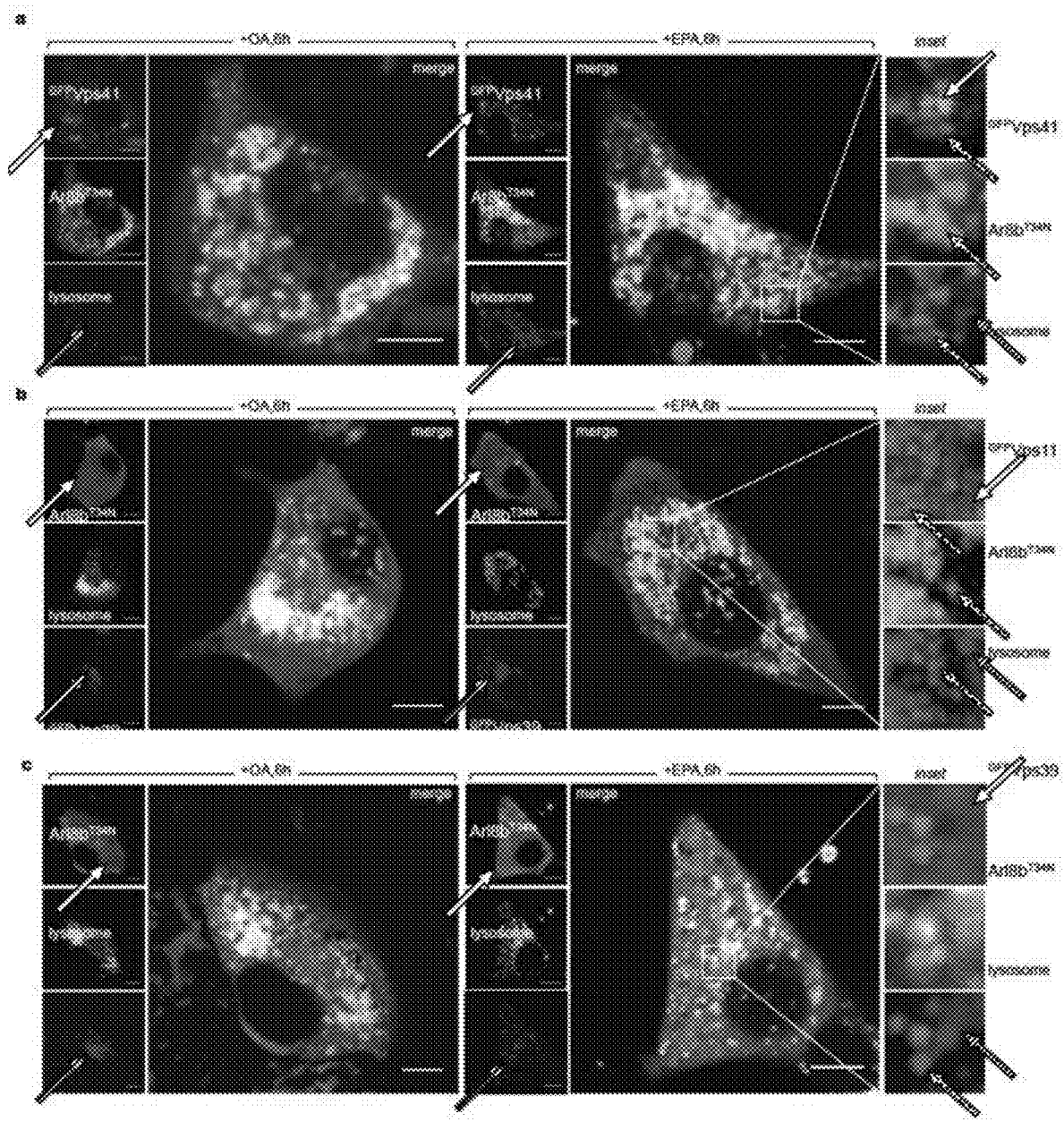
FIG. 30 illustrates that co-expression of Arl8b$^{T34N}$ resulted in attenuated interaction of Vps proteins with lipid droplets in transfected cells. Cells were co-transfected with Arl8b$^{Q75L}$ together with Vps41 (a), Vps11 (b), or Vps39 (c). The transfected cells were cultured in media +OA or +EPA for 6 h. Lipid droplets were stained with lipidTOX Red). Lysosome in these images is shown in blue. Imaging analysis of Vps (GFP) and Arl8b (mCherry; pseudocolored in grey) in the co-transfected cells is presented at the left side of the merged images. Scale bars, 22 μm. Insets showing attenuated interaction of the Vps proteins with lipid droplets are present on the right.

We further tested protein-protein interactions between mCherry-tagged Arl8b$^{WT}$, Arl8b$^{Q75L}$, or Arl8b$^{T34N}$ and endogenous HOPS subunits using proximity ligation assay[27]. In cells treated with OA, Arl8b$^{WT}$ binds predominately to endogenous Vps41 and to a lesser extent Vps11. Upon addition of EPA, Arl8b$^{WT}$ binds to all three Vps proteins examined (FIG. 25e). Arl8b$^{Q75L}$ binds to Vps41 and Vps11, but does not bind to Vps39 (FIG. 25f). On the other hand, Arl8b$^{T34N}$ only shows interaction with Vps39 (FIG. 25g-h). In additional experiments where Arl8b$^{WT}$, Arl8b$^{Q75L}$, or Arl8b$^{T34N}$ were co-expressed with the Vps proteins, we observed that expression of Vps41 or Vps11 invariably blocks lipid degradation, whereas expression of Vps39 promotes the process (FIG. 25i, FIGS. 27a and c). Live imaging shows that the blockage of lipid degradation in Vps41 or Vps11 co-transfected cells was invariably associated with intensified lysosomal attachment to CLD upon addition of EPA. In contrast, reduced levels of lysosome-CLD interactions, and rapid dissociation of lysosomes from CLD was observed in Vps39 co-transfected cells (FIG. 28, FIG. 29). Co-expression of any one of the HOPS subunits with Arl8b$^{Q75L}$ was unable to reverse the continued lysosomal interaction with CLD even after adding EPA (FIG. 30).

Figure 31:
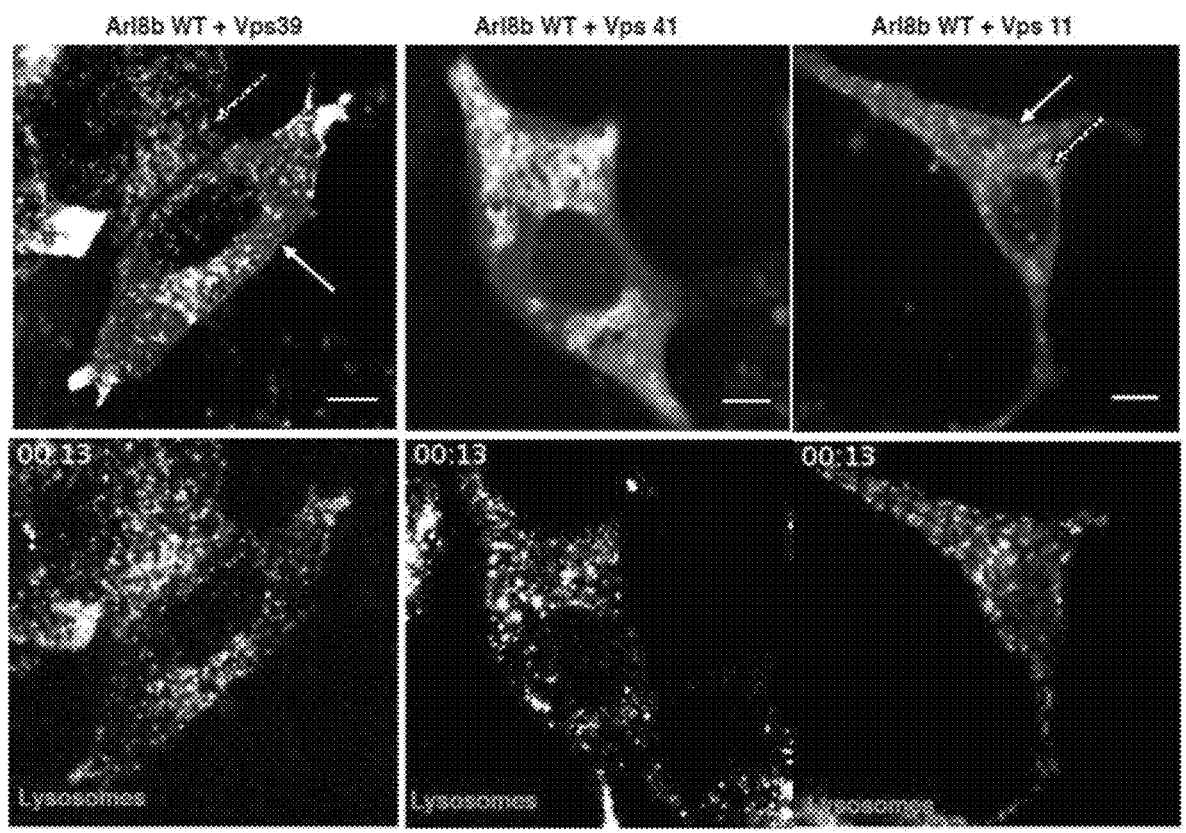
FIG. 31 illustrates co-transfection of HOPS subunits with Arl8b$^{WT}$. Vps39 facilitates Arl8b$^{WT}$ function regarding lysosomal movement and its bidirectional motility, and lysosomal degradation of lipid droplets. Note that lysosomes are mostly present around the perinuclear regions; this is because after degradation of intracellular LDs through macroautophagy, lysosomes move back to the perinuclear region. Overexpression of Vps41 and Vps11 interfered with lysosomal degradation of lipid droplets and lysosomal motility, particularly the retrograde movement of lysosomes towards the perinuclear regions. Thus, co-transfection of Vps41 or Vps11 with Arl8b$^{WT}$ resulted in lysosomal scattering throughout the cell cytoplasm. Live imaging experiments show that lysosomes are unable to return to perinuclear regions after interaction with LDs.

The effect of expression of various HOPS units on lysosomal lipid droplet interaction and distribution can be illustrated by co-expression experiments shown in FIG. 31. In these experiments, the HOPS subunits Vps39, Vps41, or Vps11 were co-transfected into cells with Arl8b$^{WT}$. In Vps39 and Arl8b co-expressing cells, lysosomes are not seen in interaction with lipid droplets, and are mostly present around the perinuclear regions upon EPA treatment. The low interaction and perinuclear localization of lysosomes with lipid droplets in these cells is likely due to degradation of intercellular LDs through microautophagy as shown by quantification of lipid droplets, and lysosomes becoming concentrated at the perinuclear regions through retrograde movement. However, co-transfection of Vps41 or Vps11 with Arl8b$^{WT}$ resulted in accumulation of lipid droplets and interruption of lysosomal engulfment processes as seen by high levels of lysosome-CLD interaction, and resulted in lysosomal scattering throughout the cell cytoplasm. This is because Vps41 and Vps11 interfered with lysosomal motility, particularly the retrograde movement of lysosomes. Live imaging experiments show that lysosomes are unable to return to perinuclear regions after interaction with LDs.

Example 4—Arl8b-Mediated, Lysosome-Dependent Degradation of CLD Under EPA Treatment Conditions Without wishing to be limited by theory, the above-described results together put forward a model for Arl8b-mediated, lysosome-dependent lipid degradation (FIG. 25k), and indicate methods and uses relating to the reduction, turnover, or modulation of cellular lipid content, as well as methods and uses relating to the treatment or prevention of diseases or conditions relating to lysosomal function and/or cellular lipid accumulation.

In this model, which is not bound by theory or limiting in any manner, lysosomal bi-directional motility requires FYCO1 and RILP, and lysosomal tethering with CLD depends upon Arl8b and the HOPS complex. The GTP-bound Arl8b (e.g. Arl8b$^{Q75L}$) interacts with Vps41 (as well as Vps11) and promotes the "on" phase or engulfment process, whereas the GDP-bound Arl8b (e.g. Arl8b$^{T34N}$) interacts with Vps39 promotes the "off" or termination of engulfment pore formation phase.

These studies, by using a candidate gene approach, have revealed a unique lysosome motility-dependent and direct lipid degradation mechanism, resembling the conserved microlipophagy process, and provided a mechanistic explanation for the beneficial effect of omega-3 fatty acids in hepatic lipid lowering. Recent work has shown the involvement of macroautophagy in hepatic lipid turnover under starvation[13]. In cholesterol-laden macrophages, Atg-dependent autophagic degradation of cholesteryl esters by lysosomes dictates the rate of cholesterol efflux[12]. Contrary to the current paradigm, it is established here that lysosome-mediated lipid turnover induced by omega-3 fatty acid does not involve macroautophagocytosis. In macroautophagy, lysosomes are positioned in the perinuclear regions to enhance lysosome-autophagosome fusion near the MTOC[19]. Data provided herein suggests that microautolipophagy is achieved through dislocation of lysosomes from perinuclear region and direct and dynamic lysosomal association-and-dissociation with CLD. Observations herein suggest a mechanism for lysosomal acquisition of small lipid fragments (which may occur via, for example, formation of a pore joining the lysosome and the CLD core during the "on" phase) without engaging complete fusion or engulfment of the entire CLD. One possible advantage of such a mechanism may be to prevent neutralization of the lysosomal acidity by large lipid droplets.

Surprisingly, the EPA-induced microautophagy lipid degradation appears to be governed by the rate of lysosomal dissociation from lipids, a process which has been found herein to depend upon Arl8b. Arl8b, a member of the Arf family and Ras superfamily of GTPases, is ubiquitously expressed and its expression in mouse brain has been shown to decrease upon feeding with a high-fat diet[28]. As a small GTPase, Arl8b can interact with various effectors involved in endo-lysosome membrane traffic[25]. The effectors involved in Arl8b-facilitated association/dissociation between lysosomes and CLD under omega-3 fatty acid treatment include, at least partly, the HOPS complex. Such an understanding may be key to understanding the potential utility of Arl8b and the HOPS machinery in the treatment of lipid metabolism disorders, such as nonalcoholic fatty liver disease.

Figure 36:
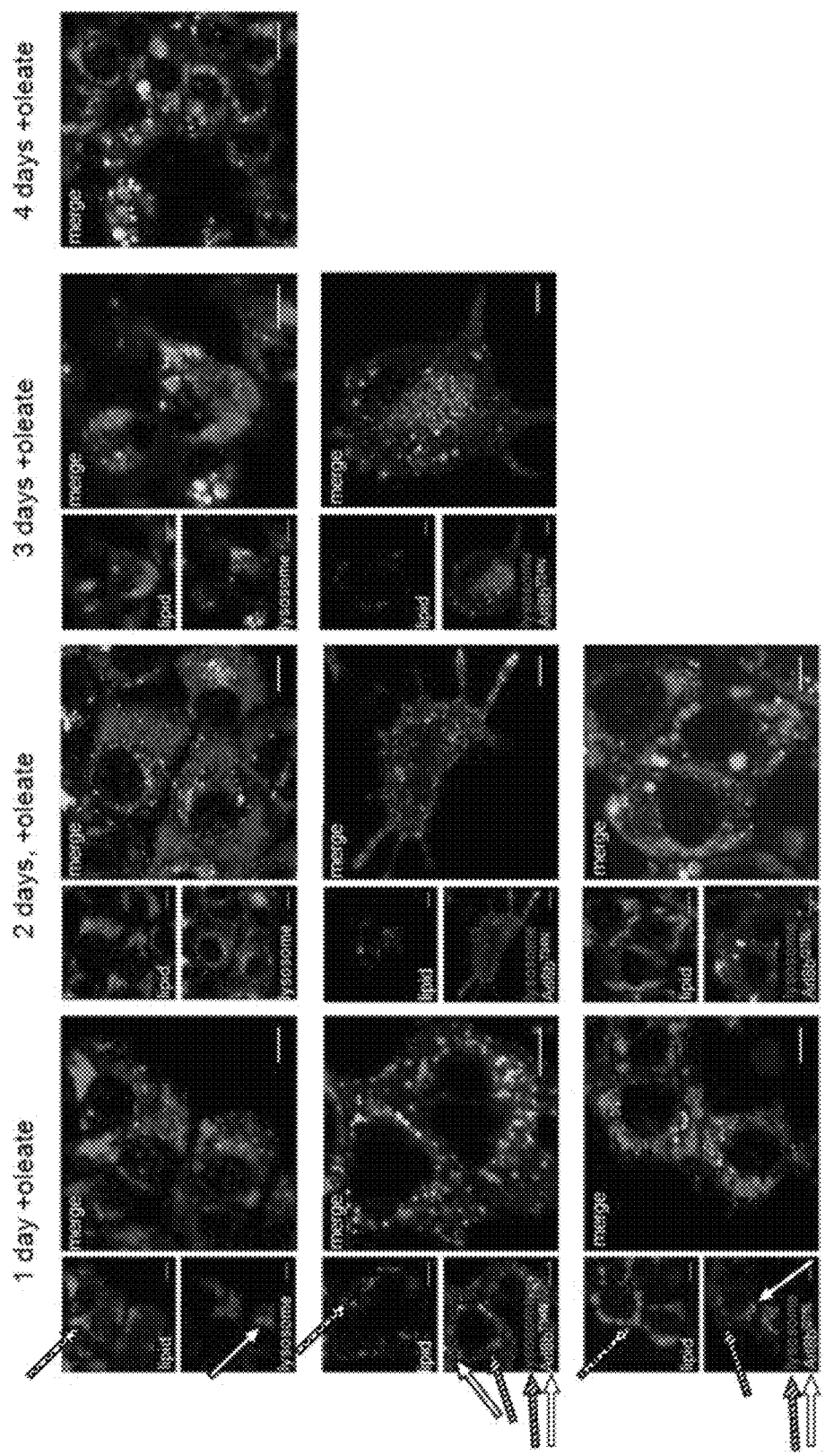
FIG. 36 illustrates that the LD content in cells cultured under lipid-rich conditions may be manipulated by expression of different forms of Arl8b. Images in the top row show position of lysosomes in cells cultured in a lipid-rich medium (i.e. supplemented with oleate) for up to 4 days. After 1-day treatment with oleate, lysosomes (stained with LysoTracker, green) were accumulated in the perinuclear regions of cells. However after 2-day oleate treatment, lysosomes were relocated towards the LDs at cell periphery. The relocation of lysosomes from the perinuclear region toward cell periphery indicates perturbed lysosomal motility under oleate-treatment conditions, which leads to prolonged association of lysosomes with LDs. Accumulation/higher interaction of lysosomes on LDs became more pronounced after 3- and 4-day treatment with oleate, with clear rings of lysosomes around LDs. Expression of the GDP-bound form of Arl8b, or Arl8b$^{T34N}$ (or Arl8b "DN", dominant negative), protects hepatocytes from accumulation of LDs upon long-term treatment with oleate. Note that even after 3 days, cells expressing Arl8b "DN" were healthy and accumulated low numbers of LDs (middle row). In contrast, expression of the GTP-bound form of Arl8b, or Arl8b$^{Q75L}$ (or Arl8b "DA", dominant active), exacerbated accumulation of LDs in cells (images in the bottom row). In fact, the cells could not tolerate long-term treatment and started to die after day 2. This situation may be similar to that in advanced levels of fatty liver, which causes hepatocyte apoptosis.

Example 5—Expression of Arl8b$^{T34N}$ Prevents Hepatosteatosis in Cells Undergoing Prolonged Treatment with Oleate As shown in FIG. 36, hepatic cells treated with oleate (OA, 0.4 mM) for up to 3 days developed severe steatosis (images in the top row). In these cells, lysosomes were continuously in contact with CLD, indicative of stalled lysosomal motility. This persistent lysosomal interaction with CLDs (i.e. "kiss" without "run") clearly indicates the interfered process of microautophagy and lack of a mechanism in the cells, after prolonged OA treatment, that facilitates dissociation of lysosomes from CLDs, blocking the engulfment process. Thus, phenotypically, accumulation of CLD in cells cultured in lipid-rich media (e.g. supplementation with 0.4 mM OA) is invariably associated with a compromised lysosomal motility (i.e. kiss-and-run).

In contrast, cells expressing Arl8b$^{T34N}$ (a putative GDP-bound form, or dominant negative form of Arl8b) exhibited a protective role under the OA-induced steatosis conditions (images in the middle row). Thus, transfection of Arl8b$^{T34N}$ into hepatic cells rendered them resistance to oleate treatment at least for up to 3 days, without indication of steatosis. These data indicate that increasing cellular levels of Arl8b$^{T34N}$, either before or during the treatment with oleate, may effectively promote lipid clearance through continued microautophagy (i.e. effective lysosomal engulfment processes, increased microautophagy capacity, and/or effective lysosomal kiss-and-run).

It is shown herein that preventing or reducing the accumulation of CLD in hepatic cells may be achieved by overexpressing Arl8b$^{T34N}$ alone, without the need of omega-3 fatty acids.

These results suggest that increasing cellular levels of Arl8b$^{T34N}$ may facilitate healthy function of hepatocytes under stress conditions (e.g. high level of fatty acids), through a mechanism that maintains proper functionality of the cellular microautophagy process.

On the other hand, cells expressing Arl8b$^{Q75L}$ (the putative GTP-bound form or the dominant active form of Arl8b) developed severe steatosis, which is accompanied with high degree of lysosomal interaction with lipid droplets and with loss of lysosomal motility (images in the bottom row). Moreover, cells expressing Arl8b$^{Q75L}$ became extremely sensitive to OA treatment, and most of the cells died after 2-day of incubation in a medium supplemented with 0.4 mM OA.

These results suggest that overexpression of Arl8b$^{Q75L}$ may effectively block cellular microautophagy and induce cell death.

Figure 37:
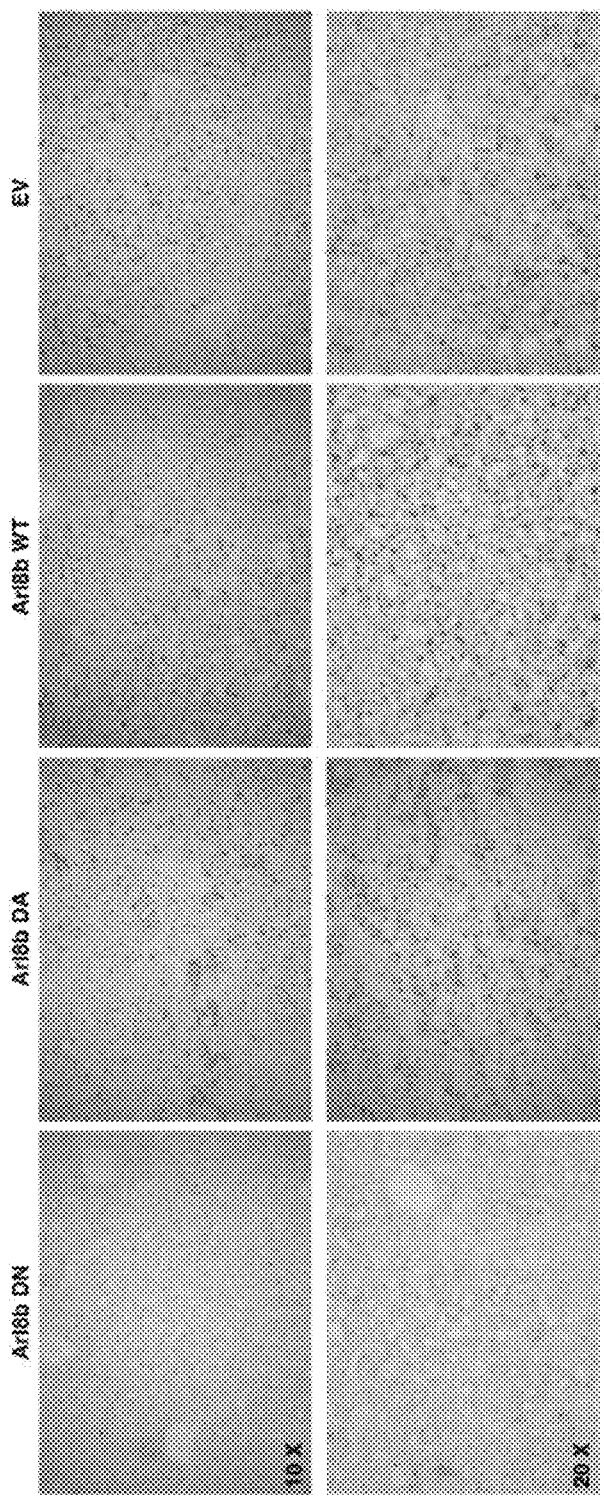
FIG. 37 provides in vivo data demonstrating that Arl8b$^{T34N}$ (Arl8b "DN") successfully prevents steatosis (accumulation of cytosolic lipid droplets) in the liver of mice fed with a high fat diet. The respective Arl8b$^{T34N}$ (DN), Arl8b$^{Q75L}$ (DA), and Arl8b$^{WT}$ constructs, along with empty virus (EV; control treatment) were injected into mice 1 day prior to feeding with a high fat diet for up to 4 days. The livers were stained with Oil Red O to determine the lipid contents, under the expression of various forms of Arl8b. Note that in agreement with cell culture studies, Arl8b$^{T34N}$ (Arl8b "DN", the GDP-bound form) significantly reduced intercellular fat in the liver, which contrasts with the other three treatment conditions that were unable to prevent steatosis in the liver. These data suggest that Arl8b$^{T34N}$ (Arl8b "DN") may be used as a therapeutic means in the prevention and treatment of fatty liver diseases.

The protective role of overexpressing Arl8b$^{T34N}$ under stress conditions has been demonstrated in experiments using a diet-induced fatty liver mouse model (FIG. 37). In these experiments, C57BL/6 mice were injected with adenovirus encoding different variants, namely Arl8b$^{T34N}$, Arl8b$^{Q75L}$, and Arl8b$^{WT}$. In these mice, expression of Arl8b proteins encoded by the adenoviral vectors lasts at least a few weeks. Thus, 1-day after viral injection, the mice were placed on a high-fat-high-sucrose (HFHS) diet for up to 4 days. In mice that were injected with an "empty" vector (i.e. containing no Arl8b cDNA sequences) or vector encoding Arl8b$^{WT}$, steatosis became apparent in the livers after 4-day HFHS diet feeding (images in the right two columns). Mice injected with the vector encoding Arl8b$^{Q75L}$ (a putative GTP-bound and dominant active form of Arl8b) developed pronounced steatosis as compared to mice injected with empty vector or Arl8b$^{WT}$ (images in the second column from left). In contrast, mice injected with Arl8b$^{T34N}$ were resistant to HFHS diet-induced steatosis; thus the liver in Arl8b$^{T34N}$ expressing mice showed nearly absent lipid accumulation (images in the first column from left).

These in vivo experimental data are in excellent agreement with the cell culture results, further indicating that increasing cellular levels of Arl8b$^{T34N}$ may prevent and/or reduce intercellular lipid droplets under metabolic stress conditions (i.e. overabundance of fatty acids often present in, for example, diabetic dyslipidemia). It is thus suggested that promoting/elevating cellular microautophagy processes, through overexpressing Arl8b$^{T34N}$, may offer a protective and/or a corrective action for ameliorating the development of diet-induced fatty liver diseases.

Modulating Lipid Degradation

The results described herein detail the functions of lysosomes, Arl8b, and the HOPS machinery in omega-3 fatty acid induced lysosome-mediated lipid degradation. Without wishing to be bound by theory, we have identified Arl8b$^{T34N}$ as a protein factor that, in combination with Vps39, can effectively promote lysosome-dependent degradation of intracellular lipids, a process resembling microautophagy. On the other hand, Arl8b$^{Q75L}$, in combination with Vps41 or Vps11, interferes with the microautophagy process by preventing lysosomal dissociation from CLD. The driving force behind these events may be Arl8b, and the HOPS components (the Vps proteins) may merely act as tethering components recruited by the Arl8b proteins. Thus, simple overexpression of the HOPS components alone does not exert a significant effect on microautophagy of lipids.

Methods and uses relating to the reduction, turnover, or modulation of cellular lipid content or protein, as well as methods and uses relating to the treatment or prevention of diseases or conditions relating to lysosomal function and/or cellular lipid or protein accumulation are described herein, such as but not limited to methods which may be useful in the treatment of lipid storage and/or metabolism conditions or disorders which may include nonalcoholic fatty liver disease and/or hypertriglyceridemia.

In certain non-limiting embodiments, there is provided herein a method for modulating cellular cytosolic lipid droplet (CLD) content, comprising:

decreasing cellular CLD content by increasing omega-3 fatty acid-induced lysosome-mediated microautophagy, whereby cellular CLD content is decreased by increasing cellular levels of Arl8b$^{T34N}$ (a putative GDP-bound form of Arl8b), Vps39, or any combination thereof, or by increasing cellular levels of Arl8b$^{T34N}$, Vps39, or any combination thereof, in combination with treatment with an omega-3 fatty acid (for example, EPA or DHA); or by decreasing cellular levels of a GTP-bound form of Arl8b (e.g. Arl8b$^{Q75L}$), Vps41, or Vps11, or any combination thereof; or any combination thereof; or increasing cellular CLD content by decreasing omega-3 fatty acid-induced lysosome-mediated microautophagy, whereby cellular CLD content is increased by increasing cellular levels of Arl8b$^{Q75L}$ (a putative GTP-bound form of Arl8b), Vps41, Vps11, oleate (OA) or any combination thereof, or any combination thereof in combination with oleate (OA); or by decreasing cellular levels of Rab9, Arl8b$^{WT}$, a GDP-bound form of Arl8b (e.g. Arl8b$^{T34N}$), LAL (lysosomal acidic lipase), LAMP1 (lysosome-associated proteins), Rab7, KIFbβ, FYCO1, RILP, Vps39, or any combination thereof; or any combination thereof; or any combination thereof in combination with oleate (OA).

It will be understood that, in certain embodiments, cellular CLD content may be increased or decreased using a combination of two or more suitable options as outlined above. By way of example, in certain embodiments cellular CLD content may be decreased by treatment with an omega-3 fatty acid before, during, or after treatment with Arl8b$^{T34N}$, the putative GDP-bound form of Arl8b, or Vps39. In an embodiment, treatments may involve simultaneous, combined, or sequential administration or treatment with two or more suitable options as outlined above.

The person of skill in the art will recognize that cellular levels of a particular gene product, for example Arl8b$^{WT}$, a putative GDP-bound form of Arl8b (e.g. Arl8b$^{T34N}$), Vps39, a putative GTP-bound form of Arl8b (e.g. Arl8b$^{Q75L}$), Vps41, Rab9, LAL, LAMP1, Rab7, KIFbβ, FYCO1, RILP, or Vps11 may be increased using any of a variety of approaches known in the art. For example, an expression vector (for example, a retrovirus-delivered expression vector), such as a gene expression vector as previously described herein, comprising the particular gene and having suitable sequence elements to allow the gene product to be expressed within a cell may be introduced into the cell. Another example may be an mRNA encoding the particular gene product. Such an mRNA may, in an embodiment, comprise a modified 5'-untranslated region and/or 3'-untranslated region, or other chemical modifications, which increases mRNA stability before, during, and/or after introduction into the cells. Cellular expression of the introduced gene produces increased cellular levels of the particular gene products relative to wild-type cells.

Cellular levels of a particular gene may also be increased by treating cells directly with the amino acid encoded by the gene. For example, cells may be treated with a protein (or a peptide derived therefrom) or enzyme such as Arl8b$^{WT}$, a putative GDP-bound form of Arl8b (e.g. Arl8b$^{T34N}$), Vps39, a putative GTP-bound form of Arl8b (e.g. Arl8b$^{Q75L}$), Vps41, or Vps11, or other genes as identified herein, increasing cellular levels of the protein or enzyme.

The person of skill in the art will also recognize that cellular levels of a particular gene, for example Arl8b, a putative GDP-bound form of Arl8b (e.g. Arl8b$^{T34N}$), Vps41, Vps11, Rab9, or another gene as identified herein, may be decreased using any of a variety of approaches known in the art. For example, gene silencing nucleic acids, previously described above in further detail, may be used to reduce cellular levels of a particular gene. By way of example, gene silencing nucleic acids, such as siRNA or antisense oligonucleotides, may be prepared which specifically target mRNA transcribed from a target gene, and transfected or otherwise administered to, delivered to, or introduced into cells. Silencing of the gene (i.e. degradation of the mRNA transcribed from the gene) decreases cellular levels of that gene.

It will also be understood that inhibition of a particular protein or enzyme, using either a small-molecule, or a biomolecule such as an antibody, may have substantially the same phenotypic effect as a decrease in cellular levels of that protein or enzyme. As such, inhibitors or antibodies targeting proteins or enzymes such as Arl8b, a GTP-bound form of Arl8b (e.g. Arl8b$^{Q75L}$), Vps41, Vps11, Rab9, or another gene or gene product as described herein are also contemplated herein. Such an antibody may, for example, either be a polyclonal antibody raised against the protein, or a monoclonal antibody that recognizes a particular epitope of the protein.

In accordance with the descriptions provided herein, plasmids or vectors encoding genes as described herein are contemplated. Gene silencing nucleic acids, such as siRNAs or antisense oligonucleotides, targeting genes as described herein are also contemplated. Antibodies, such as monoclonal or polyclonal antibodies, targeting gene products (i.e. proteins or enzymes) as described herein are also contemplated. Purified proteins (or peptides derived therefrom) or enzymes (or peptides derived therefrom), such as proteins or enzymes prepared through recombinant expression or solid phase synthesis, corresponding to gene products as described herein are also contemplated. Compositions comprising any of these nucleic acids or proteins (or peptides derived therefrom), and a pharmaceutically acceptable carrier or excipient are also contemplated herein.

Degradation of Cytosolic Lipid Droplets (CLDs) and Proteins Through Microautolipophagy Without wishing to be bound by theory or to be limiting in any way, lysosome-dependent degradation of cytosolic lipid droplets (CLD), or "microautolipophagy," as elucidated and described herein, represents a novel discovery of such a mechanism occurring in mammalian cells such as hepatocytes. This microautolipophagy process does not occur at substantial levels under basal conditions; the intensity and level of flux are low (close to or almost zero). Moreover, when cellular lipid (especially cholesteryl esters) contents are high, this process is virtually blocked. When cellular lipid contents are high, degradation of lipids by lysosomes is achieved through an alternative process termed "macroautolipophagy," or commonly known as "lipophagy."

As described herein, microautolipophagy in hepatocytes may be augmented by treatment of omega-3 fatty acids such as EPA, which may be accompanied by enhanced degradation of intracellular CLD. As discussed, a key protein factor during the process of EPA-induced lipid degradation is a small GTPase, Arl8b. Silencing Arl8b in hepatocytes blocked the EPA-induced lipid degradation, whereas overexpression of Arl8b could accelerate the process. Importantly, when Arl8b was expressed in a GDP-bound form (known as the "dominant-negative" form, or DN form, e.g. Arl8b$^{T34N}$), lipid degradation is markedly accelerated even without the treatment of EPA.

As such, in certain embodiments, there is provided herein a method for increasing lysosome-mediated microautophagy of a lipid or protein substrate in a cell, comprising increasing cellular levels of a GDP-bound form of Arl8b. The cellular levels of the GDP-bound forms of Arl8b may be increased by, for example, treating the cells with Arl8b$^{T34N}$ proteins or mRNA, or by using an expression vector encoding and expressing the recombinant Arl8b$^{T34N}$ to transfect the cells. In certain embodiments, an omega-3 fatty acid, such as EPA, may be used in combination with increasing cellular levels of Arl8b$^{T34N}$. In certain non-limiting embodiments, the lipid or protein substrate may be a cytosolic lipid droplet (CLD), a hepatitis C virus protein, or alpha-synuclein. In still further embodiments, the cell may be a cell of a patient having or at risk of getting hypertriglyceridemia, hepatosteatosis, fatty liver disease, non-alcoholic fatty liver disease (NAFLD), hepatitis C virus (HCV) infection, Parkinson's disease, obesity, hyperglycemia, or hepatic insulin insensitivity.

In another embodiment, there is provided herein the use of Arl8b$^{T34N}$, or an expression vector thereof which increases cellular levels of Arl8b$^{T34N}$, for increasing lysosome-mediated microautophagy of a lipid or protein substrate in a cell. In certain embodiments, an omega-3 fatty acid, such as EPA or DHA, may be used in combination with Arl8b$^{T34N}$, or an expression vector thereof which increases cellular levels of Arl8b$^{T34N}$. In certain non-limiting embodiments, the lipid or protein substrate may be a cytosolic lipid droplet (CLD), a hepatitis C virus protein, or alpha-synuclein. In still further non-limiting embodiments, the cell may be a cell of a patient having or at risk of getting hypertriglyceridemia, hepatosteatosis, fatty liver disease, non-alcoholic fatty liver disease (NAFLD), hepatitis C virus (HCV) infection, Parkinson's disease, obesity, hyperglycemia, or hepatic insulin insensitivity.

The amino acid sequence of Arl8b$^{T34N}$, a non-limiting example of a nucleic acid sequence encoding Arl8b$^{T34N}$, and an example of an expression vector for expressing Arl8b$^{T34N}$ (which, in this non-limiting example, also includes an optional mCherry tag on Arl8b$^{T34N}$) are provided in FIG. 35.

Expression of Arl8b$^{T34N}$ (or Arl8b-DN, the putative dominant negative form of Arl8b), in the absence of EPA, results in drastic lysosomal redistribution toward the LDs and rapid degradation of lipids. Without wishing to be limited by theory, the stimulatory effect of Arl8b$^{T34N}$ on lysosome-dependent lipid degradation may be attributable to altered protein coating (and perhaps lipid composition) of CLD, allowing efficient lipid degradation by lysosomes.

Figure 42:
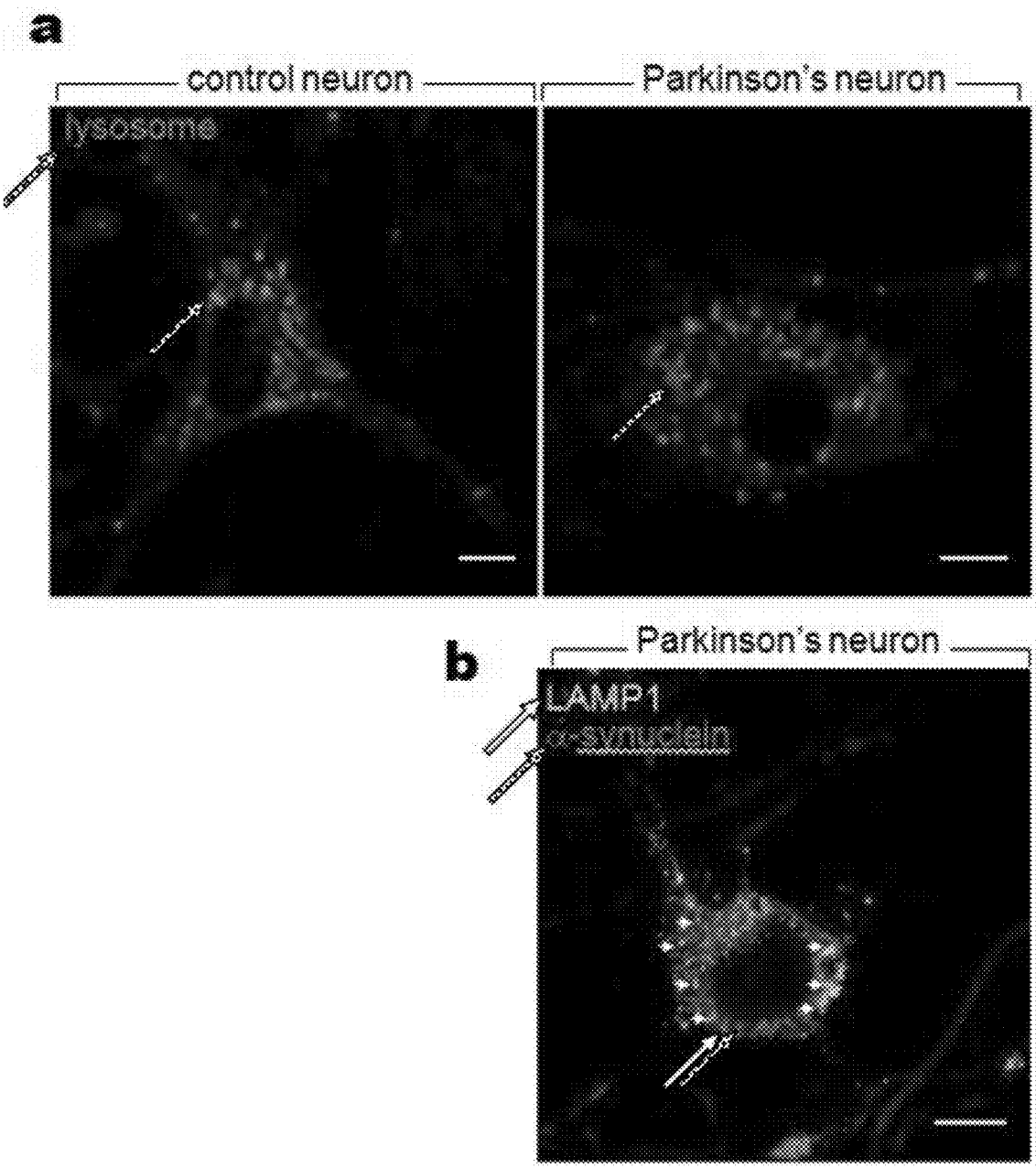
FIG. 42 provides data demonstrating high levels of interaction between lysosomes and alpha-synuclein in brain cells of a Parkinson's disease mouse model, suggesting that compromised lysosomal motility has occurred. (a) Images showing that in Parkinson's neurons (right panel), lysosomes (stained with LysoTracker; red) are scattered throughout the cell cytoplasm, which is in sharp contrast to that in normal neurons (left panel), where lysosomes are concentrated in the perinuclear regions. (b) Abnormal accumulation of alpha-synuclein occurs in cell periphery in Parkinson's neurons, which is colocalized with the lysosomal marker LAMP1 (pseudocolored in green). Arrows indicate lysosome and alpha-synuclein colocalization. These data demonstrate that lysosomes may be "stuck" on alpha-synuclein aggregates in Parkinson's neurons, thus resulting in impaired lysosomal kiss-and-run (i.e. a hallmark of microautophagy) and/or microautophagy processes.

It has further been envisaged that the lysosome-dependent microautophagy not only can effectively degrade intracellular lipids, but also may remove other intracellular substrates such as proteins. For instance in brain cells of Parkinson's disease, accumulation of alpha-synuclein (a hallmark of the disease) is accompanied with scattered distribution of lysosomes in the cytoplasm (FIG. 42, top right panel), rather than perinuclear localization as seen in normal brain cells (FIG. 42, top left panel). The abnormal lysosomal distribution is indicative of compromised microautophagy in Parkinson's cells. Thus, activating microautophagy may remove alpha-synuclein aggregates in Parkinson's neurons and therefore may reverse the process of disease development.

Therefore, in certain embodiments, there is provided herein a method for increasing lysosome-mediated microautophagy of a lipid or protein substrate in a cell, said method comprising: treating the cell with a microautophagy-enhancing agent which increases lysosomal association-dissociation events (i.e. kiss-and-run) between lysosomes and the lipid or protein substrate; thereby increasing lysosome-mediated microautophagy of the lipid or protein substrate.

Inducing Microautolipophagy by Modifying the Lipid Composition (i.e. the CE/TG Ratio) of CLD.

In certain embodiments, there is provided herein a method for inducing microautophagy, said method comprising: increasing TG (triglyceride) contents of CLDs, or equivalently decreasing CE (cholesteryl ester) contents of CLDs.

In a further embodiment, there is provided herein a method for decreasing microautophagy, said method comprising: increased cellular (cholesteryl ester) content.

A prevailing feature of mammalian microautophagy is the robust motility of lysosomes along the microtubules. When microautophagy is activated, lysosomes are actively "searching" for substrates (lipids and proteins) through a "kiss-and-run" process.

Research described herein indicates that the lysosome-dependent microautolipophagy is not entirely specific to EPA treatment. Indeed, microautolipophagy can be activated also by oleate treatment, although the activation is transient and is of low magnitude. Upon adding oleate, lysosomes are able to interact with a small number of CLDs. However, compared to that in EPA-treated cells, the extent of interaction between lysosomes and CLDs is low. After this brief activation (approximately 10-15 min), the cells returned to basal condition where lysosomes are clustered in the perinuclear region of the cells. As mentioned above, under the basal conditions, macrolipophagy (not microautophagy) is the main mechanism responsible for lipid degradation.

The question of why oleate only transiently activates microautolipophagy has been studied herein. Obtained experimental evidence suggests that the active interaction between lysosomes and CLDs may be dependent on the cholesteryl ester (CE) and triglyceride (TG) contents within the cells. Thus, TG-rich CLDs are good substrate for lysosomal degradation, whereas CE-rich CLDs are more resistant to lysosomal degradation. (see FIG. 43 for details). Thus, in cells having elevated cellular CE content, microautophagy is apparently inhibited. As EPA treatment can trigger microautophagy, it was hypothesized that EPA-triggered lysosomal motility may be associated with increased cellular TG contents (i.e. enrichment of TG-containing LDs). It is known that EPA is a good substrate for TG synthesis, but a poor substrate for CE synthesis. Thus, addition of EPA to the cells may effectively increase cellular TG content, which may lead to effective activation of microautophagy.

Figure 43:
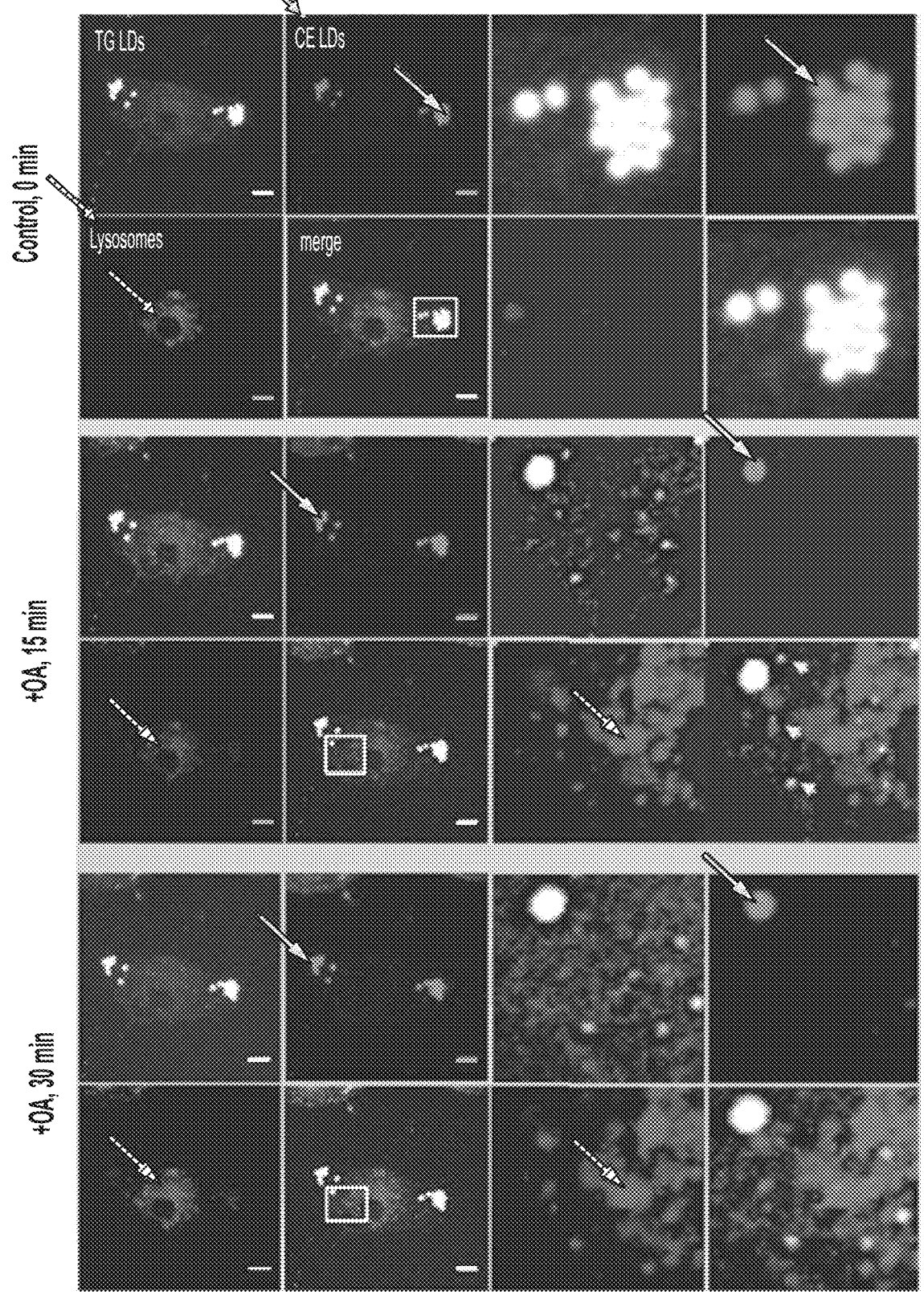
FIG. 43 provides data demonstrating that the composition of LD has a major impact on lysosome-mediated lipid degradation through microautophagy (i.e. via kiss-and-run). In these experiments, TG- and CE- (cholesteryl ester)-rich LDs are stained with different dyes in live cells. Thus, TG-rich LDs are pseudo-colored in white, CE-rich LDs are pseudo-colored in red, and lysosomes are blue (LysoTracker). The top panel (total of 8 images) shows distribution of TG- and CE-rich LDs and lysosomes under basal conditions (i.e. cells have been cultured under normal media for overnight). Under these conditions, TG and CE coexisted in the same LDs (as shown by a red ring on the LD surface), and there was no lysosomal "attack" to these LDs. The four images on the right are high magnifications of the region demarcated by the white box (inset). The middle panel (total of eight images) shows cells that had been treated with OA for 5 min. Under these conditions, some of the newly synthesized TG had not fused with CE, and lysosomes apparently started to "attack" these TG-rich LDs (depicted by arrows). The bottom panel (total of 8 images) shows cells that had been treated with OA for 15 min. Under these conditions, TG-LDs started to gain CE (apparently through lipid droplet fusion), and lysosomes were no longer "attacking" these LDs. These observations, through live imaging, clearly demonstrate that the lipid composition of LDs, at least the TG-to-CE ratio, may play an important role in governing the lysosome-dependent lipid degradation through the "kiss-and-run" mechanism.

Unlike EPA, oleate is a good substrate for both CE and TG synthesis. Thus, addition of oleate to cells results in formation of both TG and CE. Because CE and TG are synthesized in separate locales in the cells (CE is synthesized in the ER and TG can be synthesized in the Golgi apparatus), at the early stage of OA treatment (e.g. <5 min), the TG-rich LDs have not fused with CE-rich LDs. Under this condition, lysosomes may "attack" these TG-rich CLDs (but not CE-rich CLDs) through microautophagy (FIG. 43, bottom panel). Thus, the transient activation of microautolipophagy in oleate-treated cells may occur before TG-rich and CE-rich CLDs are fused together. Once these two populations of CLDs are mixed, lysosomes may no longer be able to interact with (or may reduce interaction with) CLDs, and the microautophagy process is stalled (FIG. 43, bottom panel).

Because under most cell culture conditions (i.e. basal conditions), OA is included in the culture media and hence the cellular CLDs are a mixture of TG and CE, the lysosome-mediated microautophagy and kiss-and-run becomes silent. Thus, in the so-called "basal conditions", hepatic microautophagy is seldom observed, and lysosomes may be confined to the perinuclear regions with little or no motility.

It is noted that accumulation of CE-rich CLDs commonly occurs in late stage of hepatic steatosis. Under these conditions, lysosome-mediated microautolipophagy is markedly inhibited. Similarly, it is also noted that CE-rich CLDs accumulate in HCV infected hepatocytes. Thus, increasing TG contents of CLDs, or equivalently decreasing CE contents of CLDs, may effectively trigger lysosome-mediated lipid degradation, as in the case of EPA treatment. This may be because, as mentioned above, EPA is mainly used for the formation of TG, so robust lysosome-mediated lipid degradation ensues.

Although some factors triggering microautophagy in mammalian cells remain unclear, experimental evidence indicates that microautophagy can be induced by increased cellular TG content, and inhibited by increased cellular CE content. As such, treatments that increase TG or decrease CE (i.e., using CE synthesis inhibitors) may represent a means for inducing microautophagy in cells.

EPA-Induced Lipid Degradation

Results provided herein suggest a requirement of lysosomal motility during EPA-induced lipid degradation. Lysosomal bi-directional movement (i.e. forward and backward) has been found to be important for EPA-induced lipid degradation. Results provided herein suggest that direct interaction of lysosomes and LDs is presented in a kiss-and-run fashion, and interfering either "kiss" or "run" may effectively block lipid degradation.

As discussed, the process of kiss-and-run between lysosomes and LDs is regulated by the small GTPase termed Arl8b. Without wishing to be bound by theory, the GTP-bound form of Arl8b is responsible for the engulfment or "kiss" event, through which a small piece of lipids is "grabbed" by lysosome from the neighboring LD. This may be achieved through the formation of a fusion pore between lysosome and LD, a process mediated by the GTP-bound forms of Arl8b (e.g. Arl8b$^{Q75L}$) and its recruitment of tethering molecules termed HOPS subunits, including Vps41 and Vps11.

Also without wishing to be bound by theory, the putative GDP-bound form of Arl8b$^{T34N}$ may be responsible for facilitating the termination of the engulfment process, the "run" event, where Arl8b$^{T34N}$ recruits another HOPS subunit, Vps39. Interaction of Arl8b$^{T34N}$ and Vps39 apparently triggers lysosomal dissociation from CLD, and this disassembly event is equally important for lysosome-dependent lipid degradation. Failure of termination of lysosomal engulfment/lysosomal dissociation from CLD, such as in the case of over-expression of a putative GTP-bound form of Arl8b, Arl8b$^{Q75L}$, may result in abolished lipid degradation even in the presence of EPA. On the other hand, expression of Arl8b$^{T34N}$ vastly accelerated lipid degradation, apparently due to facilitating the engulfment process and rapid disassociation of lysosomes from LDs, ensuring fast initiation of another round of kiss-and-run. The effect of Arl8b$^{T34N}$ on lipid degradation can be phenocopied, to some extent, by overexpression of Vps39. Thus, expression of Vps39, in combination with Arl8b$^{T34N}$, resulted in rapid degradation of LDs.

Based on the results described herein, the development of hepatic steatosis is most likely due to the impairment in lysosomal microautophagy as well as microautophagy functions. Such an impairment in lysosomal function may be manifested by either (i) blockage of bidirectional lysosomal motility, (ii) compromised kiss-and-run events between lysosomes and LDs, or (iii) constant attachment (i.e. "kiss") of lysosomes to lipid droplets or protein. Without wishing to be bound by theory, these events appear to require a functioning Arl8b, and the conversion from the GTP-bound form (that associated with lysosome) to the GDP-bound form (that associated with CLD) may be of particular significance in efficient lipid degradation.

From a therapeutic perspective, delivery of Arl8b$^{T34N}$ (for example, a plasmid or expression vector encoding Arl8b$^{T34N}$ cDNA, or Arl8b$^{T34N}$ mRNA, or Arl8b$^{T34N}$ protein) into the liver may represent an option in treating non-alcoholic hepatosteatosis under various medical and/or clinical conditions, such as diabetic dyslipidemia and hypertriglyceridemia of metabolic syndromes, post-transplantation of liver, fatty liver, and liver failure induced by total parenteral nutrition (TPN; see Burrin et al., (2014) Advances in Nutrition, 5:82-91), and/or fatty liver associated with intravenous nutrition.

Thus, in an embodiment, there is provided herein a method for treatment of hepatosteatosis comprising increasing microautophagy in cells using a microautophagy-enhancing agent as described herein.

Treatment of Lipid or Protein Accumulation/Storage-Related Conditions or Diseases The results provided herein indicate methods through which cellular cytosolic lipid droplet (CLD) content, and/or cellular levels of a cellular protein, may be modulated, altered, or controlled through microautophagy.

By way of non-limiting example, the results provided herein indicate that microautophagy may be increased by increasing cellular levels of an omega-3 fatty acid (such as, for example, EPA or DHA), Arl8b, a GDP-bound form of Arl8b (e.g. Arl8b$^{T34N}$), Vps39, or any combination thereof; or decreasing cellular levels of a GTP-bound form of Arl8b (e.g Arl8b$^{Q75L}$), Vps41, Vps11, or any combination thereof; or any combination thereof; or any combination thereof in combination with one or more omega-3 fatty acids.

In addition, and also by way of non-limiting example, the results provided herein indicate that microautophagy may be decreased by increasing cellular levels of a GTP-bound form of Arl8b (e.g Arl8b$^{Q75L}$), Vps41, Vps11, oleate (OA) or any combination thereof, or any combination thereof in combination with oleate (OA); or by decreasing cellular levels of Rab9, Arl8b, a GDP-bound form of Arl8b (e.g. Arl8b$^{T34N}$), LAL (lysosomal acidic lipase), LAMP1 (lysosome-associated proteins), Rab7, KIFbβ, FYCO1, RILP, Vps39, or any combination thereof, or any combination thereof in combination with oleate (OA); or any combination thereof.

These results indicate that cellular CLD or protein content may be either increased or decreased as desired by increasing or decreasing omega-3 fatty acid-triggered lysosome dependent CLD degradation through a microautophagy (i.e. kiss-and-run) process.

Conditions or diseases involving cellular lipid accumulation or storage dysfunction may include cellular lipotoxicity and/or hypertriglyceridemia, where reduction of cellular CLD content may be beneficial (see, for example, Perry, R. J. et al. (2013) Cell Metabolism, 18:740-748 and Pejic, R. N. and Lee, D. T. (2006) J Am Board Fam Med, 19:310-316). As described in further detail below, conditions or diseases involving cellular protein accumulation or storage dysfunction may include Parkinson's disease, or hepatitis C infection, where reduction of aberrant, viral, or accumulated cellular protein content may be beneficial.

Accordingly, there is provided herein a method for treating hypertriglyceridemia, hepatosteatosis, fatty liver disease, non-alcoholic fatty liver disease (NAFLD), or hepatitis C virus (HCV) infection comprising inducing microautophagy in cells using a microautophagy-enhancing agent as described herein. By way of non-limiting example, inducing microautophagy of LDs may be used in the treatment of hypertriglyceridemia, hepatosteatosis, fatty liver disease, or non-alcoholic fatty liver disease (NAFLD). As another example, inducing microautophagy may be used in the prevention of fatty liver and/or liver failure induced by total parenteral nutrition or intravenous nutrition. As yet another example, inducing microautophagy of a hepatitis C (HCV) protein may be used in the treatment of HCV infection.

Other examples of possible HCV treatment options are described in further detail below. As yet another example, inducing microautophagy of alpha-synuclein may be used in the treatment of Parkinson's disease.

Prevention and/or Treatment of Non-Alcoholic Fatty Liver Disease and/or Obesity

As described above in Example 5 provided herein, in vivo data in C57BL mice expressing either a putative GTP-bound form of Arl8b (Arl8b$^{Q75L}$) or a putative GTP-bound form of Arl8b (i.e. Arl8b$^{T34N}$) show that the development of hepatosteatosis may be exacerbated or attenuated under high-fat-high-sucrose diet feeding (FIG. 37). Increasing cellular levels of Arl8b$^{T34N}$, in this example through adenovirus-mediated gene transfer, effectively reduced the development of steatosis. In contrast, increasing cellular levels of Arl8b$^{Q75L}$ markedly exacerbated steatosis. These data indicate that increasing cellular lysosome-mediated microautophagy (using, for example, a microautophagy-enhancing agent as provided herein) may allow for the prevention, treatment, or alleviation of non-alcoholic fatty liver disease in a subject.

Figure 48:
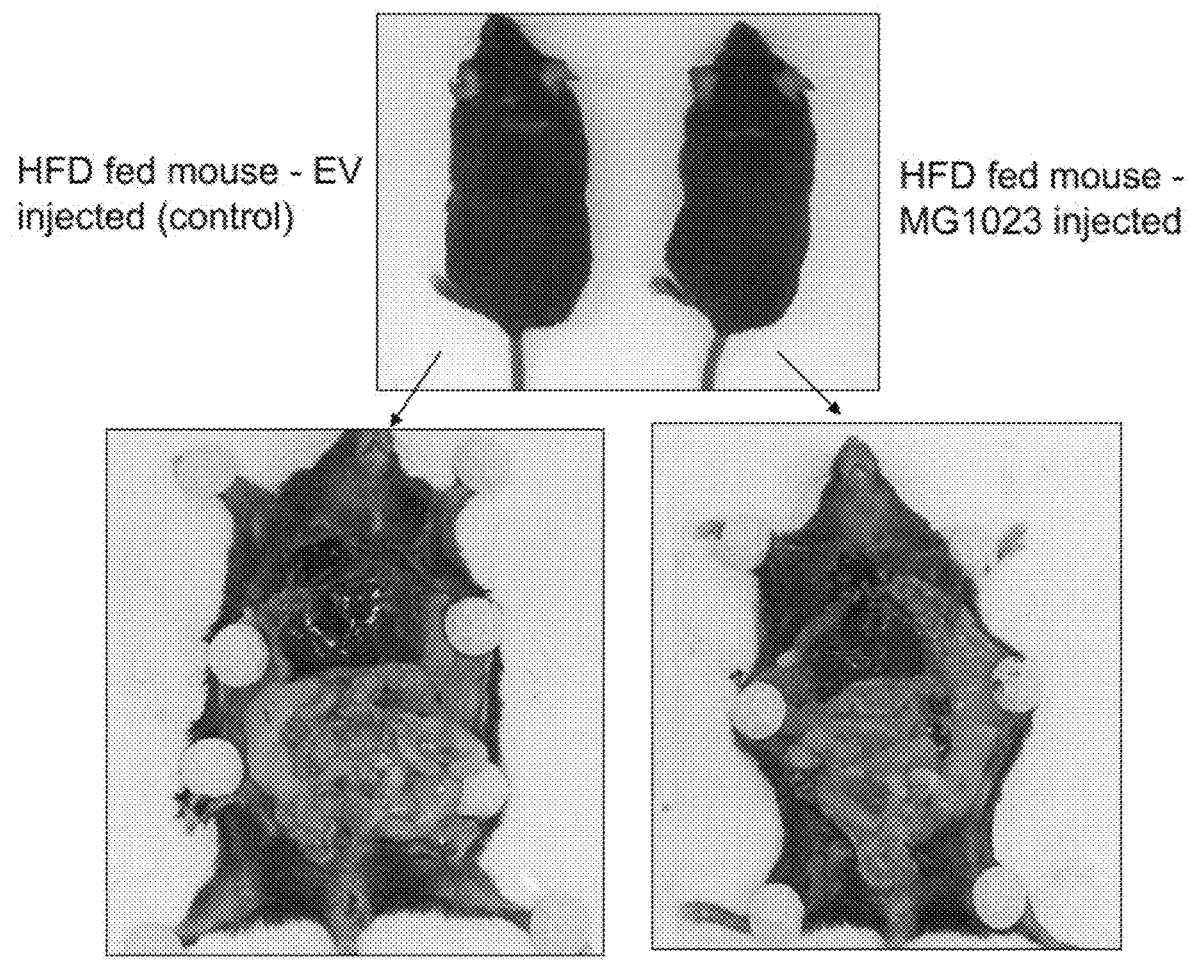
FIG. 48 shows in vivo data demonstrating improved resistance to obesity, abdominal fat accumulation, and fatty liver disease in mice treated with Arl8b$^{T34N}$. Mice were fed with a high fat diet (HFD) for 30 days, and injected with Adv-empty vector (EV) or Adv-MG1023 expressing Arl8b$^{T34N}$ via the tail vein ($10^9$ pfu/mouse). Forty eight hours after virus injection, mice were euthanized and dissected to collect liver tissue samples. Liver tissues were frozen fresh in Cryomatrix (ThermoScientific), and then sectioned and processed for oil red o staining. Intrahepatic liver lipid droplets in the liver sections were observed under bright field microscope (Zeiss AxioImager M2). (A) Comparison of the dissected control (EV) HFD mouse with the dissected Arl8b$^{T34N}$ treated HFD mouse (MG1023) indicates that Arl8b$^{T34N}$-treated mice are less obese and notably accumulate less abdominal fat than control mice under HFD conditions. (B) Representative photomicrographs of liver pathology sections stained with Oil Red O. Stained liver sections indicate that the Arl8b$^{T34N}$-treated mice are more resistant to fatty liver arising from HFD conditions than control mice.
Figure 49:
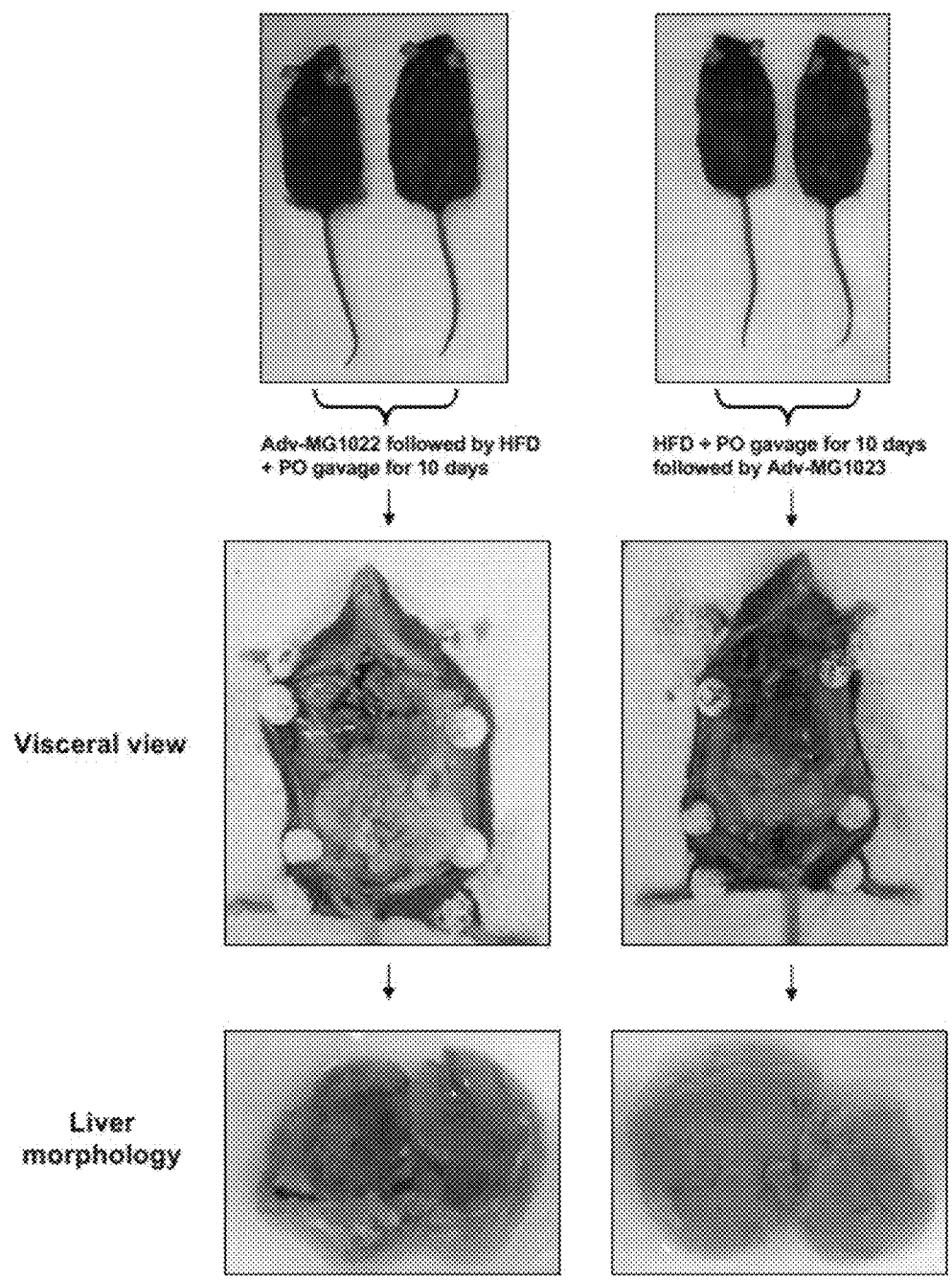
FIG. 49 shows in vivo data in which mice were subjected to a high fat diet and PO gavage for 10 days, followed by treatment with Adv-MG1023 vector expressing Arl8b$^{T34N}$. For comparison, control mice were treated with Adv-MG1022 (a vector expressing Arl8b$^{Q75L}$) and then subjected to HFD and PO gavage for 10 days. (A) provides visceral views, and liver morphology views, of Arl8b$^{Q75L}$ and Arl8b$^{T34N}$-treated mice, showing enhanced resistance to fatty liver and fat accumulation in Arl8b$^{T34N}$-treated mice. (B) provides images of liver sections stained with Oil Red O from mice subjected to a high fat diet and PO gavage for 10 days followed by treatment with Adv-MG1023 vector expressing Arl8b$^{T34N}$. For comparison, images of liver sections stained with Oil Red O obtained from mice treated with Adv-MG1022 (a vector expressing Arl8b$^{Q75L}$) and then subjected to HFD and PO gavage for 10 days are also provided. These results indicate that Arl8b$^{T34N}$-treated mice have enhanced resistance to fatty liver disease arising from HFD in comparison with Arl8b$^{Q75L}$-treated mice under the conditions tested.
Figure 49:
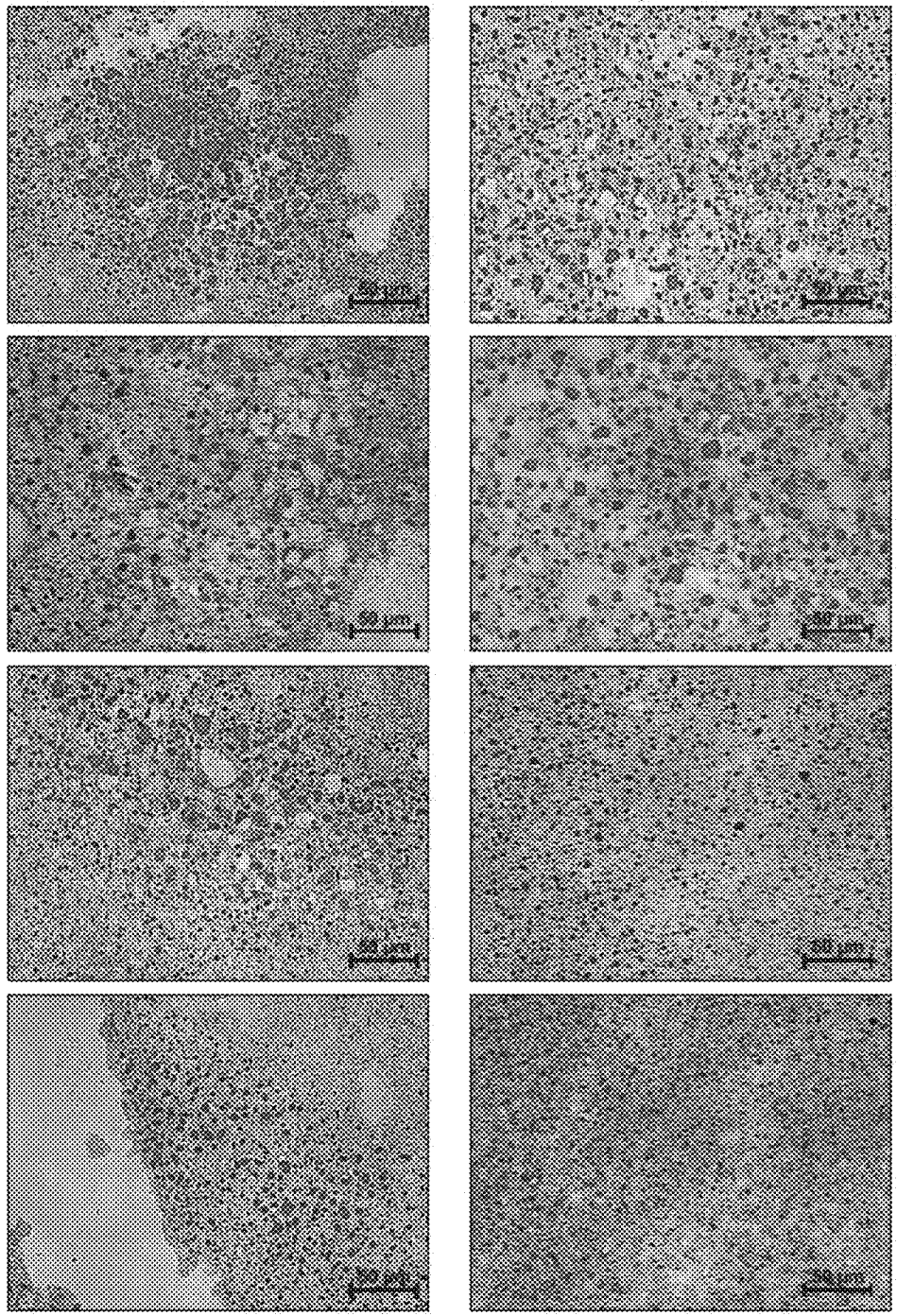

FIGS. 48 and 49 provide further in vivo data demonstrating improved resistance to obesity, abdominal fat accumulation, and fatty liver disease in mice treated with Arl8b$^{T34N}$. In FIG. 48, mice were fed with a high fat diet (HFD) for 30 days, and injected with Adv-empty vector (EV) or Adv-MG1023 vector (FIG. 46) expressing Arl8b$^{T34N}$ via the tail vein ($10^9$ pfu/mouse). Forty eight hours after virus injection, mice were euthanized and dissected to collect liver tissues. Liver tissues were frozen fresh in Cryomatrix (ThermoScientific), and then sectioned and processed for oil red o staining. Intrahepatic liver lipid droplets in the liver sections were observed under bright field microscope (Zeiss Axio-Imager M2). Comparison of the dissected control (EV) HFD mouse with the dissected Arl8b$^{T34N}$ treated HFD mouse (MG1023) shown in FIG. 48A indicates that Arl8b$^{T34N}$-treated mice are less obese and accumulate less abdominal fat than control mice under HFD conditions. As shown in the stained liver sections depicted in FIG. 48B, the Arl8b$^{T34N}$-treated mice are also more resistant to fatty liver arising from HFD conditions than control mice.

In FIG. 49, mice were subjected to a high fat diet and PO gavage for 10 days, followed by treatment with Adv-MG1023 vector expressing Arl8b$^{T34N}$. For comparison, mice were treated with Adv-MG1022 (a vector expressing Arl8b$^{Q75L}$; FIG. 46) and then subjected to HFD and PO gavage for 10 days. These experiments may be considered as palm oil-induced NASH mouse models. FIG. 49A provides visceral views, and liver morphology views, of Arl8b$^{Q75L}$ and Arl8b$^{T34N}$-treated mice, showing enhanced resistance to fatty liver and fat accumulation in Arl8b$^{T34N}$-treated mice. FIG. 49B provides images of liver sections stained with Oil Red O from mice subjected to a high fat diet and PO gavage for 10 days followed by treatment with Adv-MG1023 vector expressing Arl8b$^{T34N}$. For comparison, images of liver sections stained with Oil Red O obtained from mice treated with Adv-MG1022 (a vector expressing Arl8b$^{Q75L}$; FIG. 46) and then subjected to HFD and PO gavage for 10 days are also provided. These results indicate that Arl8b$^{T34N}$-treated mice have enhanced resistance to fatty liver disease arising from HFD in comparison with Arl8b$^{Q75L}$-treated mice under the conditions tested.

Alleviating Diabetes or Other Diseases Involving Hepatic Insulin Insensitivity and/or Improving Hepatic Glucose Uptake The activity of microautolipophagy in hepatocytes decreases as the amount of CLDs increases. Without wishing to be bound by theory, the decreased microautolipophagy activity upon hepatic lipid accumulation appears to be attributable to disregulated Arl8b expression, and/or more specifically, may be due to lack of conversion from the GTP-bound form to the GDP-bound form. As a consequence, lysosomes become "locked" on the CLD during the engulfment process and are unable to dissociate from CLD. The persisted lysosomal attachment to CLD not only effectively blocks lysosome-dependent lipid degradation, but also results in continued mTORC1 activation. It is known that constant mTORC1 activation could lead to ER stress and activation of the JNK pathway, both of which are implicated in insulin insensitivity. The beneficial effects of omega-3 fatty acids in improving insulin sensitivity and alleviating hyperglycemia have been reported in several human studies. These effects may stem from accelerating lysosomal disassociation from CLD, and thus triggering the microautolipophagy process.

The resumed microautolipophagy activity, for example through delivering a putative GDP-bound form of Arl8b (e.g. Arl8b$^{T34N}$), into hepatocytes, may provide two important metabolic consequences. One, it may effectively prevent hepatic accumulation of lipids thus alleviating steatosis. Two, it may bring back normal mTORC1 function. The activity of mTORC1 oscillates between "on" and "off" stages, which are closely correlated with lysosomal bidirectional movement. The plus-end movement of lysosomes correlates with mTORC1 "on" stage, whereas the minus-end movement of lysosomes correlates with mTORC1 "off" stage. Normal mTORC1 function alleviates ER stress and prevents activation of JNK signalling pathway.

Figure 38:
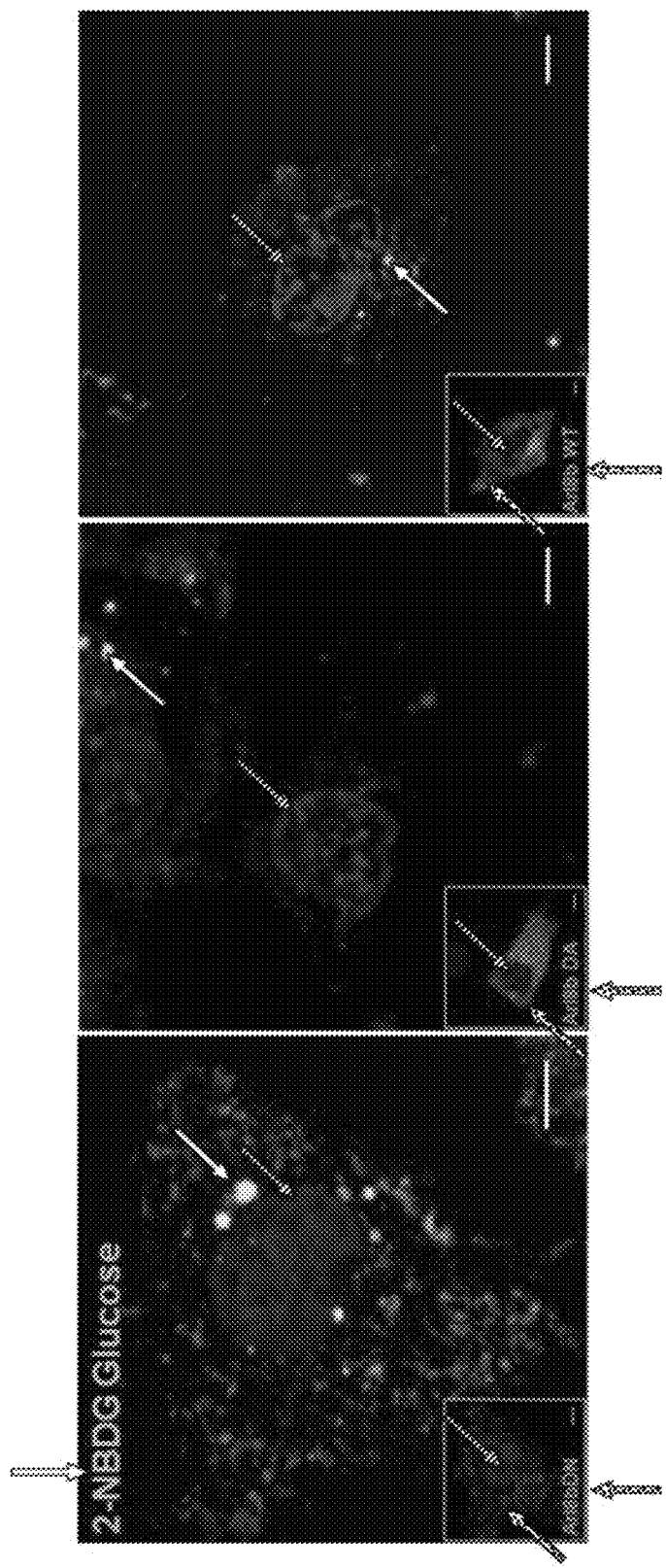
FIG. 38 provides data demonstrating an interrelationship between microautophagy and hepatic glucose uptake. In these experiments, cells were transfected with Arl8b$^{T34N}$ (Arl8b DN), Arl8b$^{Q75L}$ (Arl8b DA), and Arl8b$^{WT}$ constructs, respectively. The transfected cells were treated with EPA, and the amount of glucose uptake was measured (using a fluorescent 2-NBDG assay; glucose are labeled green). In cells expressing Arl8b "DN" (left panel), where microautophagy (i.e. lysosome and LD kiss-and-run) was promoted, the level of glucose uptake was markedly increased. In cells expressing Arl8b "DA" (middle panel), where microautophagy was attenuated (due to the accumulation of a large amount of cytosolic lipid droplets and the lack of efficient dissociation between lysosomes and LDs), the level of glucose uptake was virtually absent. Low level of glucose uptake was observed in cells expressing Arl8bWT (right panel). Insets, showing expression of the respective Arl8b DN, Arl8b DA, and Arl8bWT (pseudo-colored in red). Cell nucleus is stained with DAPI (pseudo-colored in blue)
Figure 39:
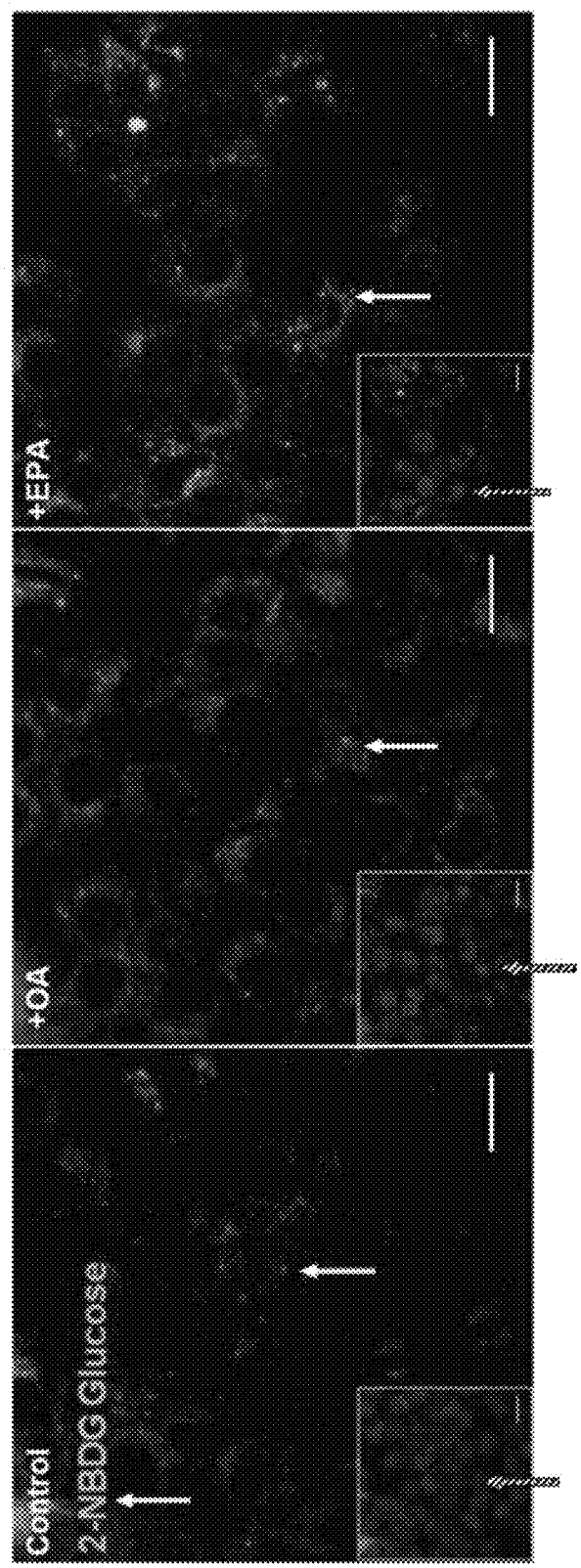
FIG. 39 provides additional data demonstrating the relationship between functional microautophagy and hepatic glucose uptake. In these experiments, microautophagy was induced by omega-3 fatty acids alone (without overexpression of Arl8b). Cells were cultured under basal conditions (Control, media containing no fatty acids; left panel), or cultured in media supplemented with oleate (+OA; middle panel) or omega-3 fatty acids (+EPA; right panel), and the amount of glucose uptake was measured (using a fluorescent 2-NBDG assay). Insets, showing cells stained by DAPI for cell nucleus (pseudo-colored in blue). These data indicate that the level of hepatic glucose uptake is intimately correlated with function microautophagy. Thus, microautophagy may not only relate to lysosome-mediated degradation, it may also encompass the full process of lysosomal bidirectional motility. The anterograde motility allows lysosomes to interact with entities (e.g. lipids and endosomes) at the cell periphery, and the retrograde motility allows lysosomes to return to the perinuclear region. This process of lysosomal motility includes three steps: Go>Interact>Back, which may be described graphically as "kiss-and-run"
Figure 40:
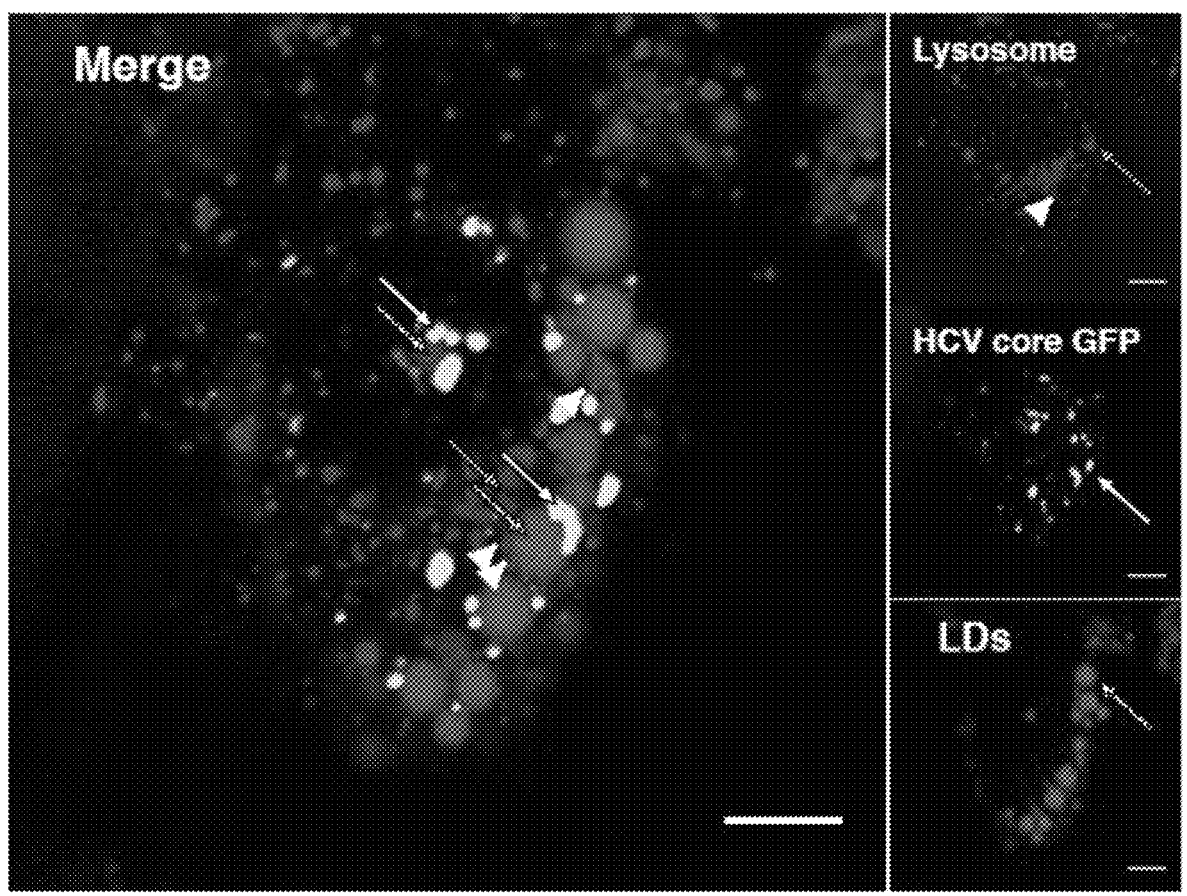
FIG. 40 provides data demonstrating the potential use of Arl8b$^{T34N}$ (Arl8b DN) in attenuating HCV production. The image (merge, left panel) shows that in cells transfected with HCV core proteins, a high number of lysosomes are constantly in association with LDs in cell periphery, indicating compromised microautophagy (i.e. "kiss" without "run"). This may be because the presence of HCV core protein may "lock" lysosomes onto the LD surface during the lysosomal engulfment process, resulting in scattered distribution of lysosomes throughout the cell cytoplasm. This situation is similar to that observed in cells after prolonged treatment with oleate (see FIG. 36, top row). White arrows indicate HCV core protein (pseudo-colored in green) and lysosomes (LysoTracker; blue) in association with LDs.

Normal mTORC1 function is closely associated with cell uptake of nutrients, such as amino acids and glucose. We have discovered that hepatic glucose uptake is intimately associated with microautophagy. Thus, in cells where microautophagy is induced by EPA treatment, hepatic uptake of glucose is also increased (FIG. 39). In another set of experiments in which cell microautophagy was either inhibited (by overexpression of a putative GTP-bound form of Arl8b, Arl8b$^{Q75L}$) or activated (by overexpression of a putative GDP-bound form of Arl8b, Arl8b$^{T34N}$), hepatic glucose was markedly attenuated or enhanced accordingly (FIG. 38). Thus, overexpression of Arl8b$^{T34N}$ (FIG. 38, left panel), results in increased rate of glucose uptake as compared to that of Arl8b$^{WT}$ (FIG. 38, right panel), whereas overexpression of Arl8b$^{Q75L}$ (FIG. 38, middle panel) virtually abolished glucose uptake.

The above data suggest strongly that the activity of hepatic microautophagy may play an important role in total body glucose metabolism, though augmenting hepatic glucose uptake and glucose utilization under stress conditions (e.g. diabetic dyslipidemia and hyperglyceridemia). It is hypothesized that the close relationship between hepatic glucose uptake, hepatic insulin sensitivity/resistance, and the extent of hepatic lipid accumulation reported to date in the literature may be interpreted by the function of cellular microautophagy (i.e. lysosome kiss-and-run). Factors (such as abnormal accumulation of a large amount of CLDs) that negatively impact lysosomal function would inevitably disturb the balance between microautophagy and macroautophagy, and eventually impair lysosomal functions.

As such, increasing cellular levels or Arl8b$^{T34N}$ in liver cells, or otherwise delivering Arl8b$^{T34N}$ into liver cells, may alleviate and/or improve therapeutic insulin sensitivity through augmenting the hepatic lipid degradation process mediated by lysosome-dependent microautolipophagy.

Treatment or Attenuation of Hepatitis C Virus Production

Intracellular pathogens may take advantage of autophagy processes (mainly macroautophagy, since microautophagy, and specifically microautolipophagy, was not elucidated in mammalian systems) for their survival and propagation. In the case of Hepatitis C virus, propagation of viral particles originates on the cellular lipid droplet surface, where the viral proteins and viral RNAs are assembled. Hence, it appears that expression of the HCV proteins can somehow "stabilize" the CLDs for the purpose of propagation. It is observed that in HCV infected cells, lysosomes are no longer able to degrade CLDs through microautophagy processes. It is also observed that the HCV core proteins may effectively "sabotage" lysosome-dependent microautolipophagy, resulting in disengaging lysosomes from their function (such as, for example, micro- and macro-autophagy) and stabilization of CLD that are the platform for viral assembly and secretion.

Figure 41:
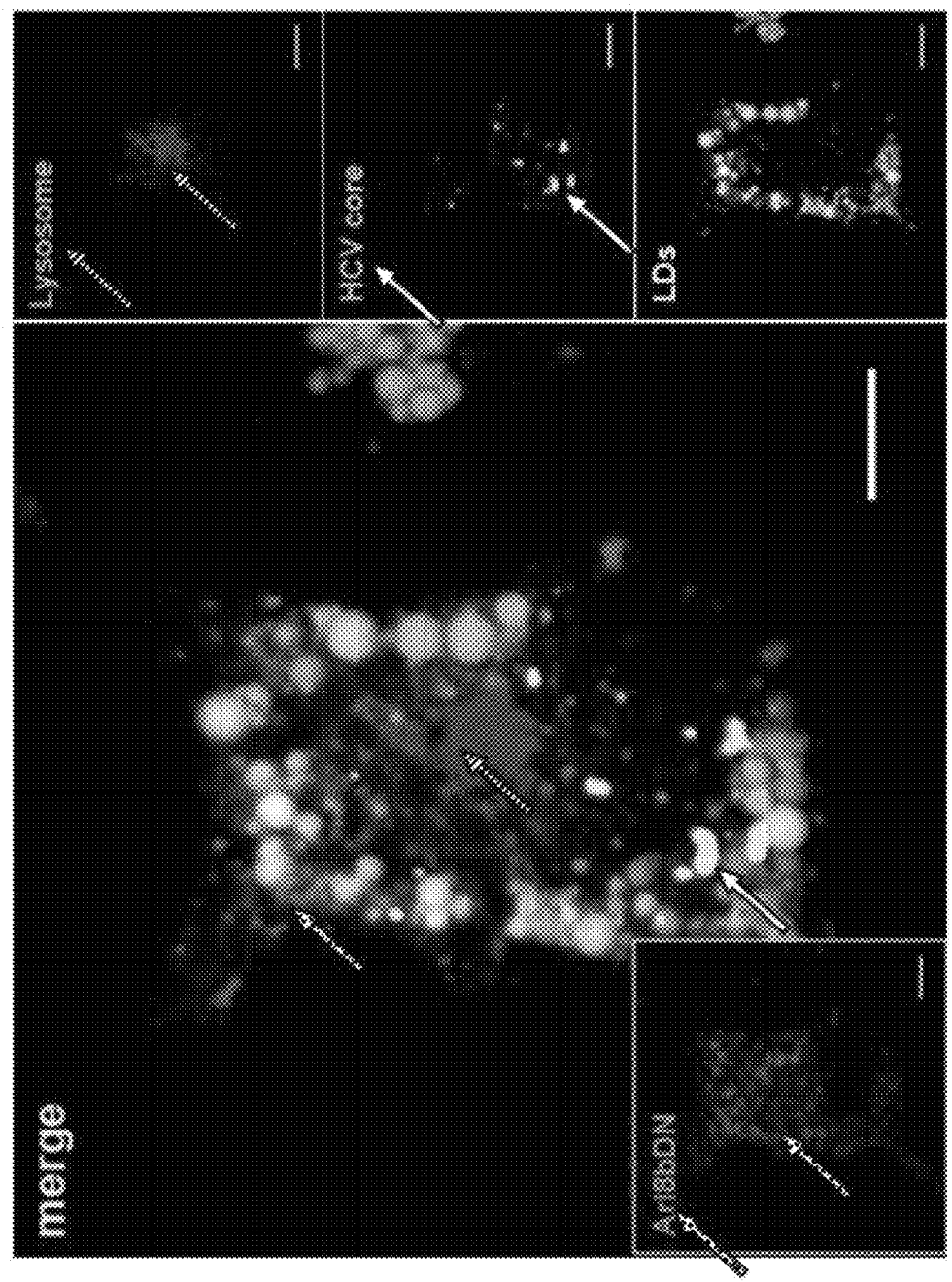
FIG. 41 provides data illustrating the effect of Arl8b "DN" on HCV core distribution and interaction between lysosomes and lipid droplets. The image (merge, left panel) shows that expression of Arl8b-DN could effectively displace lysosomes from LD surface, thus lysosomes returned to the perinuclear regions in cells under basal conditions (i.e. no HCV core protein expression). These data suggest that HCV-infected cells can regain normal microautophagy through overexpression of Arl8b-DN.

As shown in HCV core protein expressing cells (FIG. 41, left panel), the HCV core proteins (GFP-tagged) are bound to CLDs. The core protein binding to the CLDs apparently renders persistent lysosomal interaction with CLDs (i.e. kiss without run) and thus impaired microautophagy. As explained with reference to FIG. 39, functional microautophagy includes proper lysosomal engulfment (Kiss) and termination of this process, via lysosomal "go", "interact", and "back" events. As detailed herein, by introducing a putative GDP-bound form or Arl8b (Arl8b$^{T34N}$) into the HCV core protein-expressing cells, microautophagy functionality may be restored (FIG. 41, right panel). It is observed that expression of Arl8b$^{T34N}$ displaced HCV core protein from the CLD surface, thus "unlocking" lysosomes from CLDs, allowing lysosomes to return to the perinuclear regions. Under these conditions, the displaced HCV core proteins appeared in cell cytoplasm (FIG. 41, right panel), and were no longer able to sabotage the lysosomal microautophagy process.

As such, activating microautophagy through overexpression of Arl8b$^{T34N}$ may be a therapeutic anti-HCV option. This approach differs from the current direct-anti-virus approaches, because activating microautophagy aims at improving host degradative mechanisms/machinery (i.e. lysosomal kiss-and-run), rather than targeting the HCV proteins. It is hypothesized, without wishing to be bound by theory, that through activation of lysosomal microautophagy, the lipid platform for HCV survival/propagation may be effectively removed. It is also hypothesized that the approach of activating microautophagy may have reduced side effects, which may be advantageous over direct-anti-virus approaches that may have associated undesirable immunological responses in the host.

The results provided herein indicate methods through which HCV survival and propagation may be attenuated through "unlocking" lysosomes from CLDs and allowing for functional microautophagy to take place. Locking lysosomes onto CLDs upon HCV core expression may be detrimental to cell functions for at least two reasons: (i) it may prevent lysosomal regenerations, and the decrease the functioning lysosomal pool; and (ii) it may inhibit lipid degradation owing to a blockage of lysosomal microautophagy. Without wishing to be bound by theory, the HCV core may achieve these inhibitory effects on cellular microautophagy through locking Arl8b in the GTP-bound form and upregulation of Vps41. The inhibitory effect of a putative GTP-bound form of Arl8b, Arl8b$^{Q75L}$ and Vps41 expression on microautolipophagy is described in detail herein. It is noteworthy that increased Vps41 expression/ dysregulation during HCV infection has been reported previously through proteomic analysis (Sherman, et al. (2014) Sci Transl Med 6:246). However, the functional significance of Vps41 overexpression has never been previously elucidated.

As such, delivering Arl8b$^{T34N}$ into HCV-infected hepatocytes may counter the action of HCV core, and activate microautolipophagy. Cell culture studies have shown that expression of a putative GDP-bound form of Arl8b, Arl8b$^{T34N}$, can override the inhibitory effect of Vps41 and a GTP-bound form of Arl8b on microautolipophagy. Therefore, there is provided herein a method for treating HCV comprising activating microlipoautophagy using a microautophagy-enhancing agent as described herein.

Disease Models and Diagnostic Kits—Liver-Specific Secretory Biomarkers, Identification of Therapeutic Treatments for Hepatosteatosis-Related Diseases, or Identification of Delivery Agents for Hepatosteatosis Therapeutics Liver biopsy has been considered the most reliable clinic diagnostic tool for the assessment of NAFLD (non-alcoholic fatty liver disease) related NASH (Non-alcoholic steatohepatitis) and fibrosis. Development of a non-invasive diagnostic tool may be desirable for routine screening and early identification of the pathology. Microvesicles, exosomes, and ectosomes (ME) have the potential to serve as a biomarker for the liver diseases (as well as drug delivery for a target organelle).

The descriptions herein provide, in certain embodiments, a cell culture model or animal model in which the hepatosteatosis process may be "tuned" (i.e. increased or decreased) as desired. In this manner, cell culture or animal models for exploration of the hepatosteatosis spectrum may be generated. The cell culture models described herein, which could either accelerate the hepatosteatosis process (using, for example, expression of a putative GTP-bound form of Arl8b, Arl8b$^{Q75L}$) or reducing or eliminating almost entirely steatosis (using, for example, expression of a putative GDP-bound form of Arl8b, Arl8b$^{T34N}$), provide a "tunable" system which may be useful diseases models, and/or may allow identification of specific biomarkers associated with ME. Establishment of this tunable system in animals (i.e., adenovirus-mediated expression of Arl8b$^{Q75L}$ and/or Arl8b$^{T34N}$ in mice) may allow for the development of specific blood-based diagnostic kits that may, in some cases, circumvent or reduce the need of liver biopsy.

Current methodology of isolating ME relies on separation according to the size of these vesicles. A practical issue of liver-derived ME is the contamination by lipoproteins such as HDLs that are of similar size and/or buoyancy. Another limitation of the current method using ME as a biomarker is the lack of diagnostic power relating to different stages of liver pathology. This limitation is largely due to a lack of knowledge on health/disease stages of the liver at cellular or molecular levels, and a lack of knowledge on the conditions under which the liver can handle lipid homeostasis properly. The current hepatosteatosis categorizing criteria that is done based on the amount of CLD within hepatocytes may be inadequate and somewhat misleading because it fails to determine the capacity of hepatocytes in metabolizing these lipids.

In certain embodiments, a model system in which the hepatosteatosis process may be "tuned" as provided herein may be used to identify biomarkers related to hepatocyte lipid droplet accumulation. Secreted microvesicles/exosomes from normal (control) and high lipid-droplet accumulation conditions, or intermediate lipid droplet accumulation conditions therebetween, may be analyzed to identify biomarker candidates. The tunable model system may allow access to suitable control condition samples, and suitable disease/lipid droplet accumulation condition samples, facilitating the identification of biomarkers associated with intermediate and/or high lipid droplet accumulation states. Some biomarkers relating to lipid droplet accumulation have been previously identified (see for example Adams et al. (2011) J Gastroenterol Hepatol 26:802-809; and Molleken et al. (2009) Hepatology 49:1257-1266), however these systems do not provide the tunable characteristics as provided herein and therefore lack the range of control samples and disease progression state samples provided herein.

Figure 47:
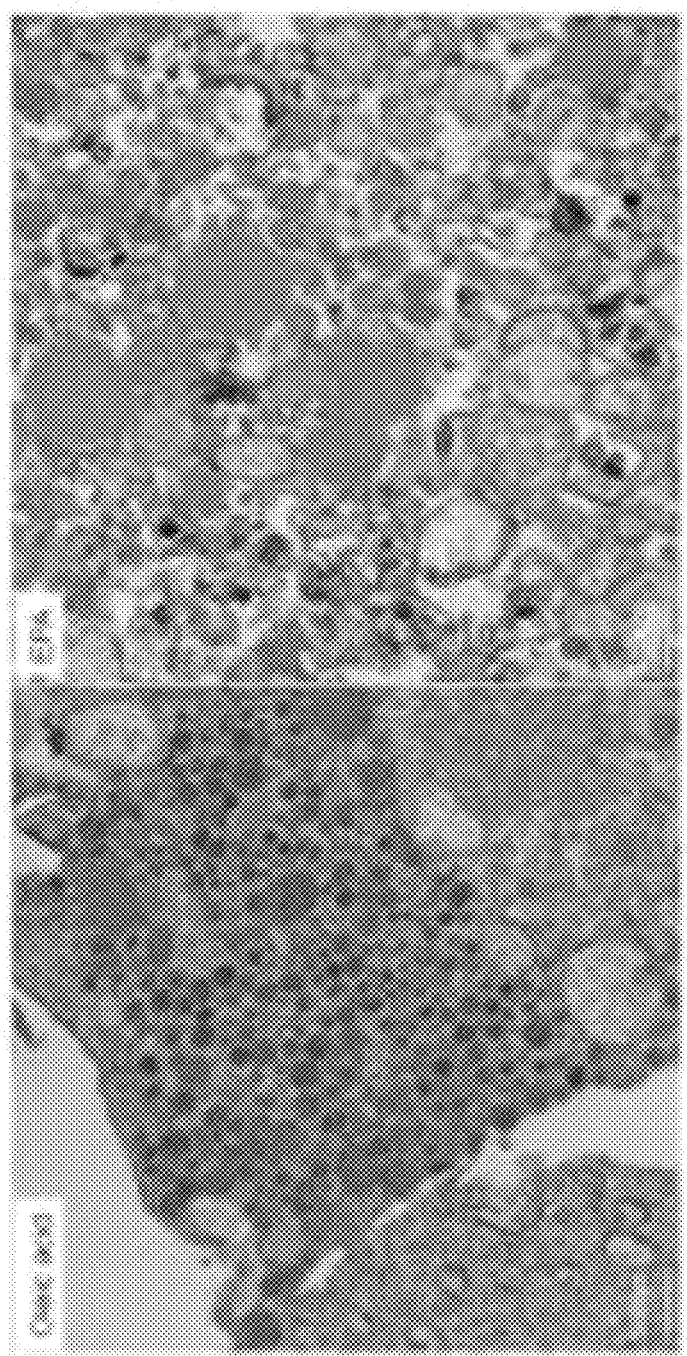
FIG. 47 shows electron microscopic images of microvesicles/endosomes (MEs) isolated from cells that had been treated with either OA (to suppress microautophagy) or with EPA (to promote microautophagy). Note the substantial size difference in MEs released from cells cultured under different conditions. Scale bar, 500 nm.

It is described herein that hepatocytes may function properly even under nutrient overloaded conditions (i.e. high-fat and high-glucose), as long as a GDP-bound form of Arl8b (e.g. Arl8b$^{T34N}$), is properly expressed. Further, the development of hepatosteatosis under nutrient overloaded conditions can be exacerbated in a cell culture system simply by overexpression of a GTP-bound form of Arl8b (Arl8b$^{Q75L}$)(for example, see FIG. 36). A dramatic difference in the quantity and size of MEs released between hepatocytes treated with oleate or EPA has been observed (FIG. 47).

As such, using knowledge of Arl8b actions described herein, there is provided herein a tunable system in which the two extreme conditions, i.e. either accelerated or eliminated hepatosteatosis, or optionally an intermediate state therebetween, may be established.

It is thus envisaged that through proteomic analysis of respective MEs, exosomes, ectosomes, or proteins that are released from hepatocytes expressing the respective Arl8b$^{Q75L}$ or Arl8b$^{T34N}$, biomarkers relevant to NAFLD and/or NASH may be identified.

Further, an in vivo animal model (for, by way of example, liver and/or metabolic disease) in which Arl8b$^{Q75L}$ and/or Arl8b$^{T34N}$ are respectively expressed in the liver may also be of use. Comparative analysis of proteomes associated with ME isolated from the blood samples of these mice may be performed to further identify biomarkers relevant to NAFLD and/or NASH.

It is further contemplated that in vitro cell models and/or in vivo animal models as described herein in which Arl8b$^{Q75L}$ and/or Arl8b$^{T34N}$, or the like, are expressed (and/or other microautophagy-enhancing and/or microautophagy-reducing agents are used) may also be useful in screening for/identifying therapeutic treatments for hepatosteatosis-related diseases (and/or other diseases as described herein) (such as, for example, small molecules, antibodies, DNA, RNA, or modified nucleic acids, or proteins), or delivery agents for hepatosteatosis (and/or other diseases as described herein) therapeutics (such as, for example, microvesicles, exosomes, ectosomes). By way of example, such models as described herein may be useful for screening for/selecting/identifying microautophagy-enhancing agents, microautophagy-reducing agents, and/or therapeutics candidates for the treatment of hypertriglyceridemia, hepatosteatosis, fatty liver disease, non-alcoholic fatty liver disease (NAFLD), non-alcoholic steatosis (NASH), hepatitis C virus (HCV) infection, obesity, Parkinson's disease, or liver cancer, for example.

Microautophagy Kits

In certain embodiments, there is provided herein kits for studying, monitoring, and/or manipulating microautophagy processes in cells, or lysosomal motility in cells. In an embodiment, a suitable kit for studying, monitoring, or manipulating microautophagy processes in cells may, by way of non-limiting example, comprise one or more microautophagy-enhancing agent(s) and/or one or more microautophagy-reducing agent(s) as described herein. Optionally, kits for studying, monitoring, and/or manipulating microautophagy processes in cells may additionally comprise one or more components which may include, but are not limited to, buffers, EPA, DHA, oleate, and/or instructions for use.

In certain embodiments, there is provided herein a kit for measuring Arl8b GTPase activity and/or the ratio of GTP/GDP forms of Arl8b. Specific kits for measuring the activities of GTPases (e.g. Arf1) have been previously developed (for example, those available from BioCat—see http://www.biocat.com/cell-biology/small-gtpase-gtp-binding-proteins-activity/gtpase-activity-assay-kits). Measurements of Arl8b activity may be used as an indicator of cellular lysosomal activity and/or microautophagy and/or macroautophagy levels (for example, comparison between normal and diseased liver samples in subjects). By way of non-limiting example, a high level of the GTP-bound form of Arl8b may be indicative of lysosomal dysfunction as a result of lysosomal "immobilization" onto CLD surface and stalled cellular microautophagy (a situation common in NAFLD liver). Conversely, a high level of the GDP-bound forms of Arl8b may be indicative of healthy lysosomal function.

In certain embodiments, determination of relative GTP and GDP forms of Arl8b may be useful for monitoring or quick evaluation of intracellular lysosomal activity, either in terms of microautophagy or macroautophagy. Determination of relative GTP and GDP forms of Arl8b may be useful for monitoring lysosomal motility, lysosomal position, and/or lysosomal functionality as described herein. High levels of Arl8b in GTP-bound form in comparison to GDP-bound form may serve as a biomarker for impaired and/or damaged lysosomal functionality. Such determinations may allow for high-throughput screening in certain embodiments.

As such, by measuring the GTPase activity of Arl8b and its GTP/GDP bound ratio, the activity of cellular micro- and macro-autophagy status may be deduced and/or the functionality of lysosomes may be assessed.

Targeting Hepatocellular Carcinoma Cells to Reduce Metastasis

ER stress and mTORC1-inducing agents have been used for targeting/treatment of tumor cells (by eliminating these cells before metastasis), and preventing their advancing and induction of malignancy. As described herein, persistent mTORC1 activation occurs in cells overexpressing a GTP-bound form of Arl8b (e.g. Arl8b$^{Q75L}$), apparently due to "locked" lysosomal interaction with LDs (i.e. prolonged lysosomal engulfment process during microautophagy). Persistent mTORC1 activation may lead to the ER stress. This property may be used to specifically reduce or eliminate cirrhotic cells in the liver and prevent or reduce metastasis.

Overexpression of Arl8b$^{Q75L}$ results in accelerated CLD accumulation, which eventually leads to cell death. Thus, cells overexpressing Arl8b$^{Q75L}$ may exhibit phenotypes resembling rapid development of fatty liver, advanced liver cirrhosis, and eventual hepatocellular carcinoma. As such, delivery of Arl8b$^{Q75L}$ to liver tumor cells (or otherwise accelerating CLD accumulation) may be used to induce cell death in some cases.

Indeed, the results provided herein indicate that cellular lipid degradation through the lysosome-dependent microautophagy process may be decreased by increasing cellular levels of a putative GTP-bound form of Arl8b (e.g. Arl8b$^{Q75L}$), Vps41, Vps11, or any combination thereof; or by decreasing cellular levels of a putative GDP-bound form of Arl8b (e.g. Arl8b$^{T34N}$), Vps39, or any combination thereof.

In certain embodiments, it may be envisaged that a microautophagy-reducing agent may attenuate lysosomal motility (i.e. kiss-and-run), and therefore interfere with lysosomal maturation/regeneration, which may lead to accelerated cell lethality. Accordingly, there is provided herein a method for treating hepatocellular carcinoma (i.e. killing the cell before tumorigenesis and/or metastasis), said method comprising interfering with or decreasing lysosomal motility/bidirectional motility using a microautophagy-reducing agent as described herein.

Treatment of Parkinson's Disease and Other Neurological Diseases

Omega-3 fatty acids may improve and help to manage Parkinson's patients. Diet supplementation with omega-3 fatty acids protects against the development of Parkinson's as well (Bousquet, M. et al. (2008) FASEB J. 22:1213-1225; Bousquet, M., Calon, F., & Cicchetti, F. (2011) Ageing Research Reviews, 10:453-463; Seidl, S. E. et al., (2014) Front Aging Neurosci. 6: DOI: 10.3389/fnagi.2014.00036), albeit with limited effectiveness (Juliano, L. et al. (2012) J. Alzheimer's Disease and Parkinsonism. 2:e119, doi: 10.4172/2161-0460.1000e119). It has been shown that macroautophagy plays an important role in protecting Parkinson's disease. Thus, accumulation of alpha-synuclein, the hallmark of developing Parkinson's disease, may be linked to the lack of proper macroautophagy in the brain. However, how compromised macroautophagy results in accumulation of alpha-synuclein has not been explained.

The omega-3 fatty acid such as DHA may be used as the fatty acid fuel in brain cells (Schonfeld, P. & Reiser, G. (2013) J. Cerebral Blood Flow & Metabolism, 33:1493-1499; Bazinet, R. P. & Lave, S. (2014) Nature Reviews Neuroscience, 15:771-785). Thus, microautophagy presumably will be constantly active due to the high levels of DHA in the brain, even though diet supplementation with DHA is considered to improve the brain function. On the other hand, high level of cholesterol has been established to promote the development of Parkinson's disease. Cholesterol lowering drugs have been shown to improve life expectancy of Parkinson's patients.

Interestingly, it has been reported in one study that Arl8b mRNA in the brain of mice is decreased under high fat, mainly cholesterol, diet (Haraguchi, T. et al. (2006) Biosci. Biotechnol. Biochem. 70:1798-1802), which may be correlated with development of Parkinson's disease. In addition, aging may decrease the functionality of microautophagy due to diminished activity of Arl8b.

Figure 45:
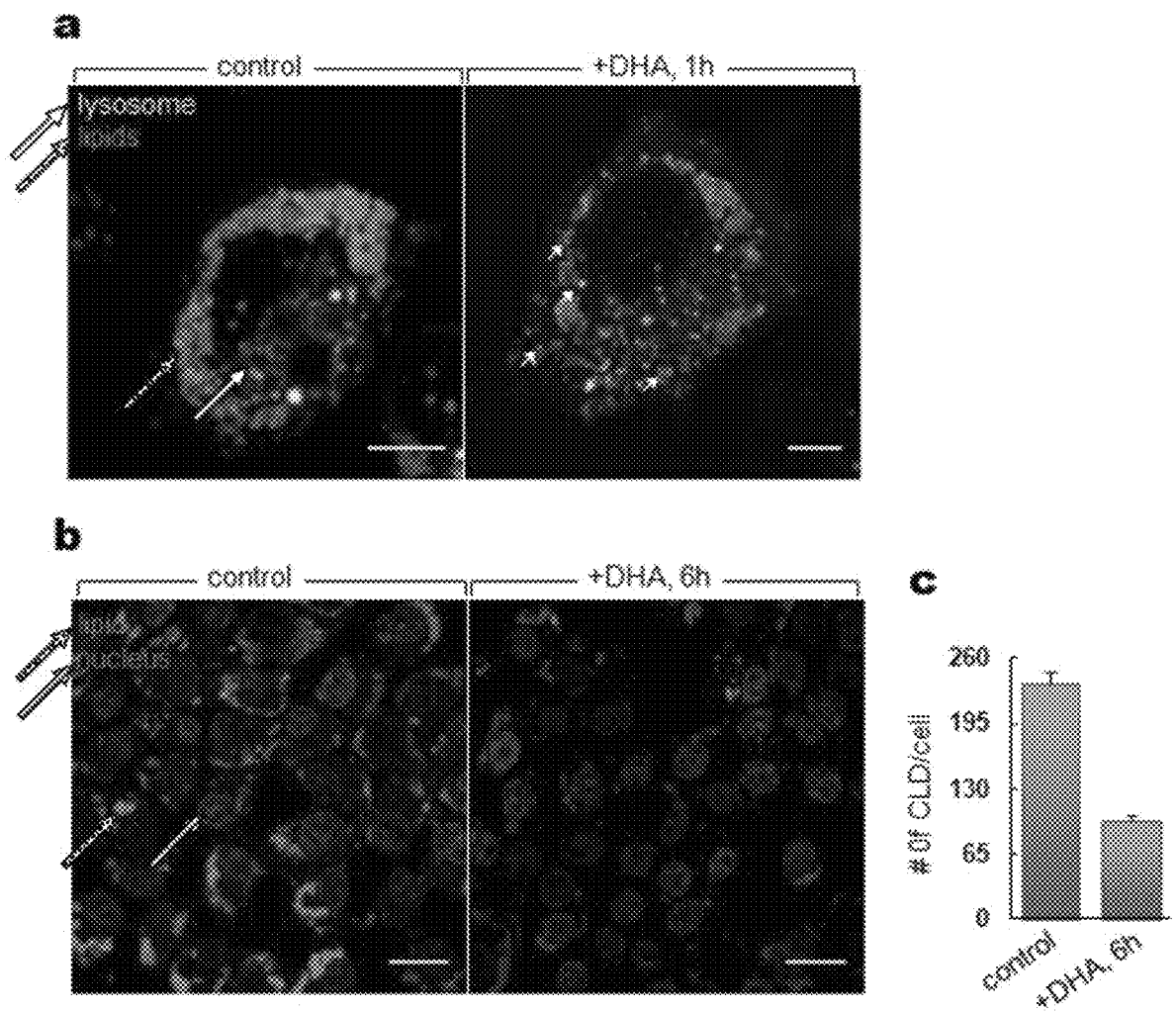
FIG. 45 shows that increased lysosomal motility/lysosomal interaction with lipid droplets can be triggered by the omega-3 fatty acid DHA, resulting in increased lipid degradation. (a) Images of cells treated with OA overnight (control) and then switched to media containing DHA for 1 h (+DHA, 1 h). Note marked redistribution of lysosomes (pseudocolored in green) towards lipid droplets (red) triggered by DHA. Arrows indicate interaction between lysosomes and CLD. Scale bar, 22 μm. (b) Images of cells in baseline (control) and 6 h post DHA-treatment. Scale bar, 22 μm. (c) Quantification of CLD as represented in (b)

It is observed herein that the omega-3 fatty acid DHA, similar to EPA, stimulates microautolipophagy in hepatocytes and can induce lysosome-dependent lipid degradation (FIG. 45 (b)). It is thus envisaged that restoration of normal microautophagy (i.e. lysosomal kiss-and-run) by treatment with omega-3 fatty acids may lead to degradation of the alpha-synuclein aggregates in Parkinson's neurons (see FIG. 42 for an example of blockage of microautophagy as a consequence of persistent lysosomal interaction with alpha-synuclein aggregates).

By way of non-limiting example, delivery of Arl8b$^{T34N}$ (i.e. a plasmid or expression vector encoding Arl8b$^{T34N}$, Arl8b$^{T34N}$ cDNA, or Arl8b$^{T34N}$ mRNA, or Arl8b$^{T34N}$ protein, or a peptide derived therefrom) Vps39, or any combination thereof, into brain cells may restore normal function of lysosomes and microautophagy, thus enhancing the neuron's capability of preventing accumulation of alpha-synuclein and/or the ability of degradation of alpha-synuclein aggregates in Parkinson's disease. By way of another non-limiting example, the neuron's capacity of preventing alpha-synuclein accumulation and degradation of alpha-synuclein aggregates may be increased by delivery of Arl8b$^{T34N}$ and/or Vps39 in combination with an omega-3 fatty acid (i.e. EPA or DHA). Thus, Arl8b$^{T34N}$ (a plasmid or expression vector encoding Arl8b$^{T34N}$, Arl8b$^{T34N}$ cDNA, or Arl8b$^{T34N}$ mRNA, or Arl8b$^{T34N}$ protein (or a peptide derived therefrom)) may represent a biologics drug candidate targeting against Parkinson's disease.

Figure 50:
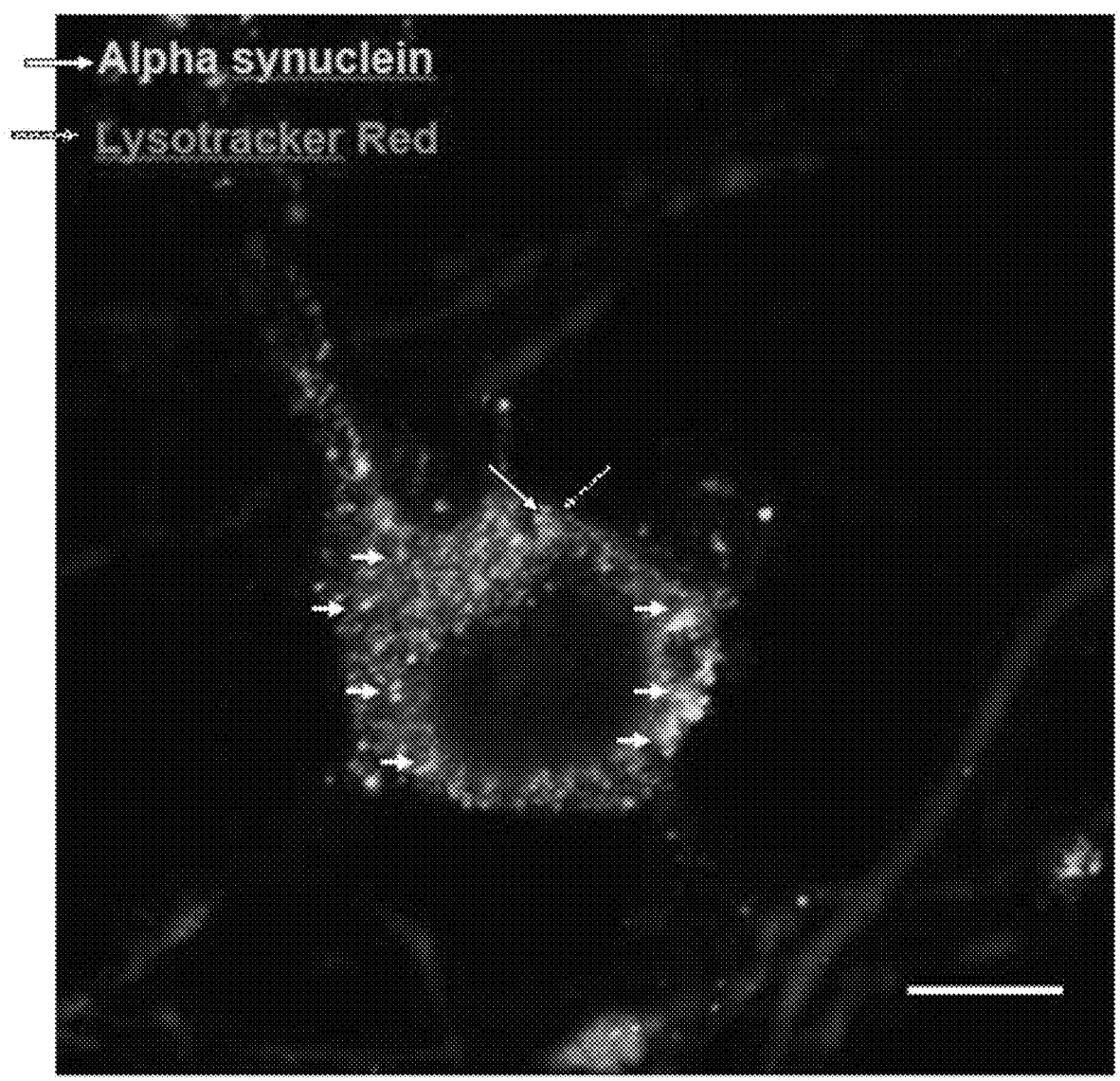
FIG. 50 shows data in which Arl8b$^{T34N}$ treatment is observed to reduce Parkinson's disease (PD) phenotype in neurons, whereas Arl8b$^{Q75L}$ is observed to trigger PD phenotype. (A) provides experimental evidence indicating a colocalization of LAMP1 and alpha-syncline in cells derived from Parkinson's mice (arrows indicate interaction of these two proteins). These results may indicate the possibility of microautophagy defects. (B) provides experimental evidence indicating that Arl8b$^{T34N}$ treatment is able to restore a normal lysosomal phenotype in Parkinson's primary neurons under the conditions tested. In the depicted Parkinson's disease (PD) primary neurons, lysosomes are observed as having a ring-shape structure (left image). Arrows indicate lysosomes. Transfection of PD primary neurons with Arl8b$^{T34N}$ cleared the ring shape structure of lysosomes. The observed ring shape lysosome structure may indicate a defect in microautophagy processes. (C) provides experimental evidence indicating that Arl8b$^{T34N}$ treatment restored axonal swelling and degeneration present in PD neurons. PD neurons show severe axonal swelling (as indicated by arrows in left image). Transfection of PD primary neurons with Arl8b$^{T34N}$ was able to restore axons in primary PD neurons under the conditions tested. Arrows in the right image indicate the regeneration of axons and normal structure. (D) provides experimental evidence indicating that Arl8b$^{Q75L}$ converts normal neuronal lysosomes to PD primary neuron phenotype. Lysosomes in normal primary neurons are observed as having ring shape structure after transfection with Arl8b$^{Q75L}$, and resemble lysosome structure in PD primary neurons. Arrows indicate lysosomal ring shape structure which may indicate disturbed microautophagy processes (left image). The right image indicates the ring shape structure of lysosomes in PD primary neurons, for comparison.
Figure 50:
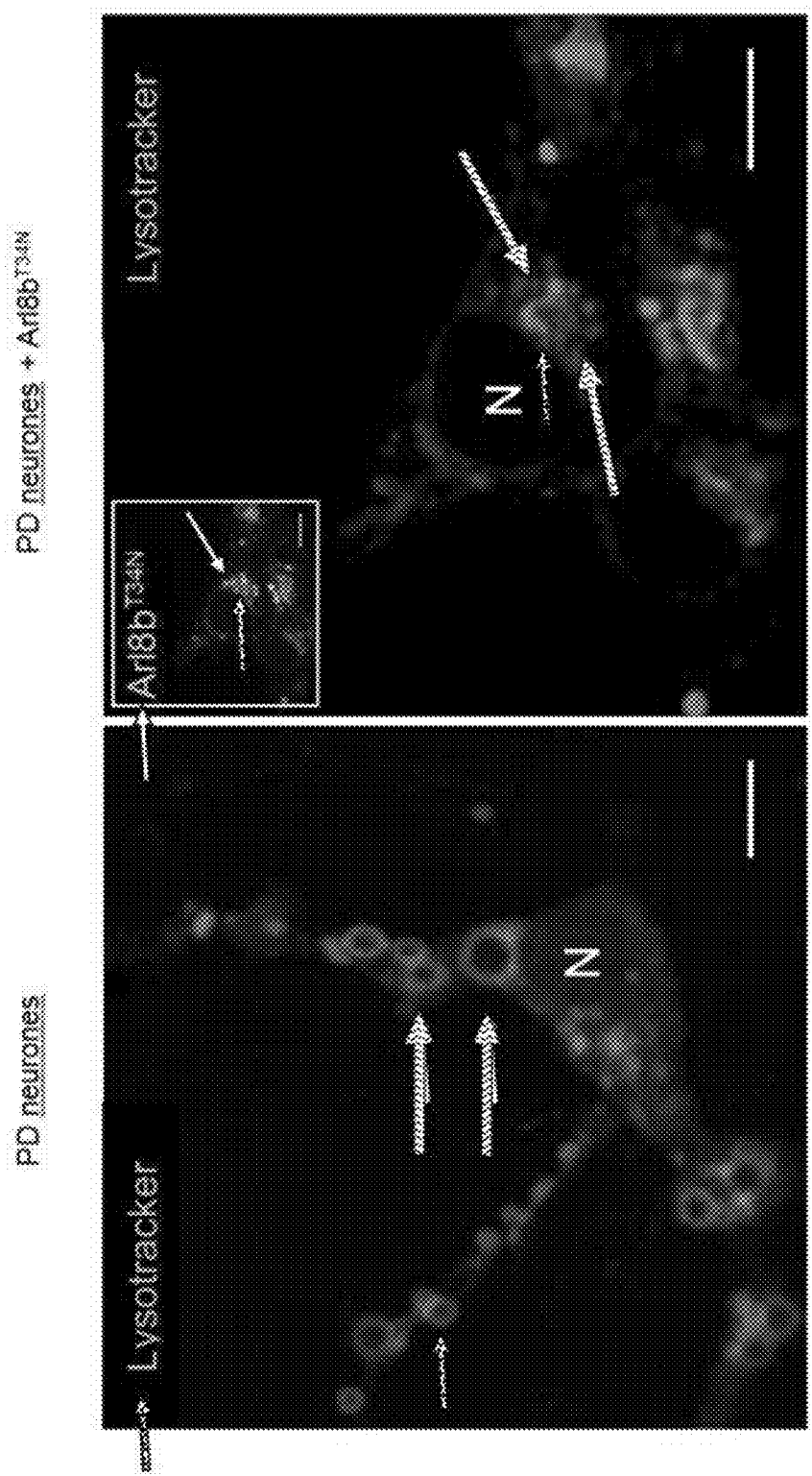
Figure 50:
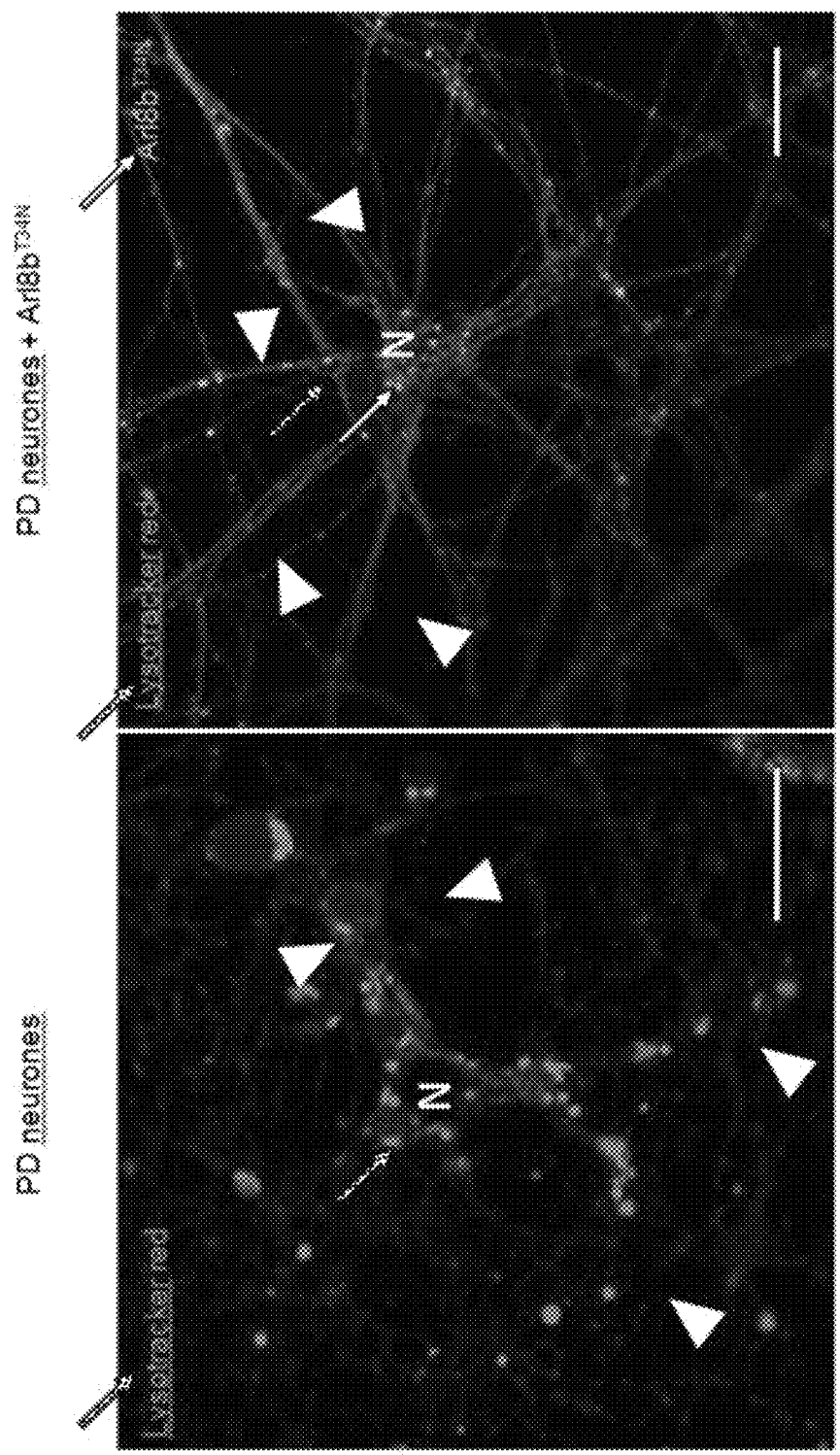
Figure 50:
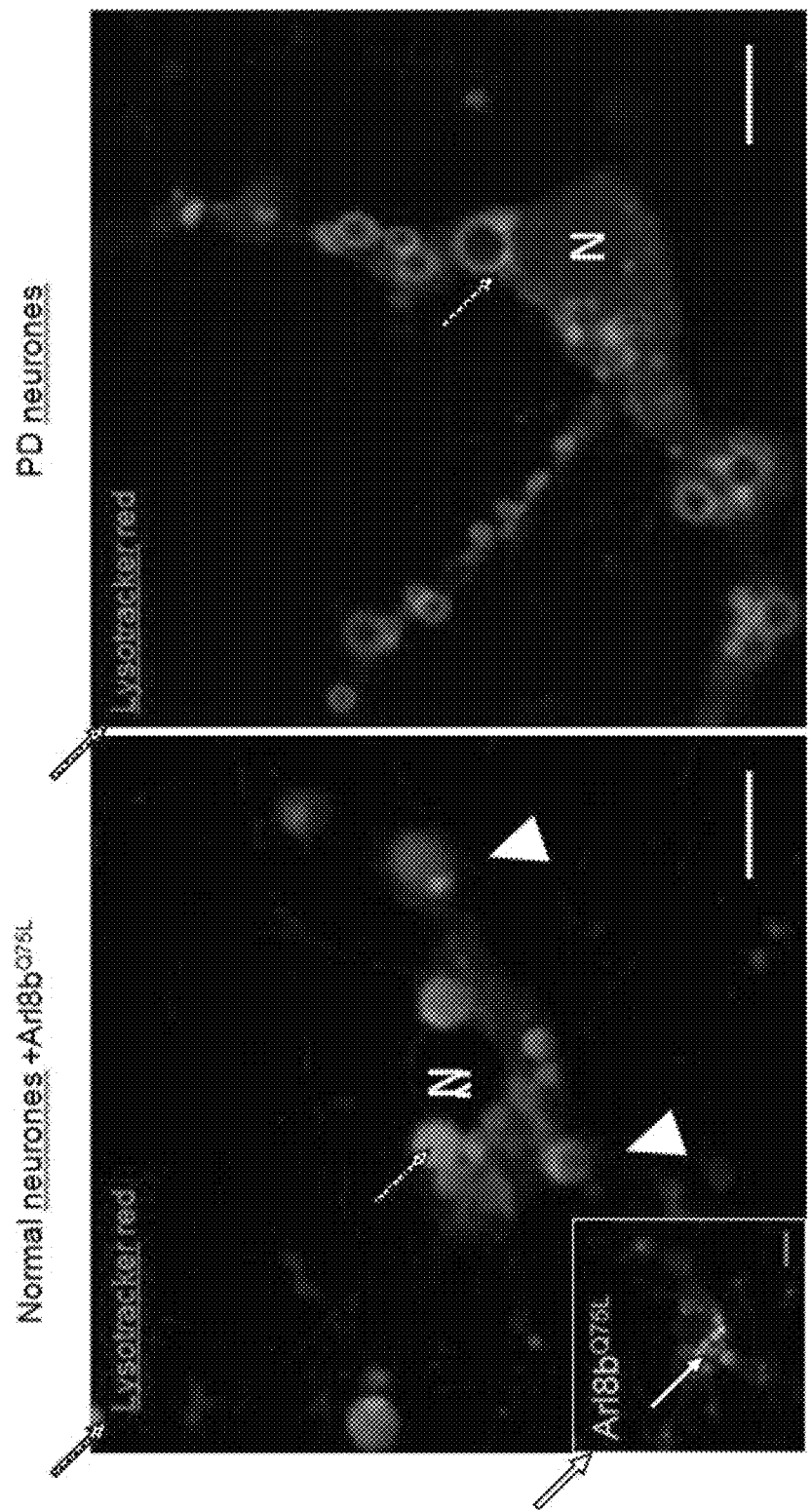

Experimental evidence indicates a colocalization of LAMP1 and alpha syncline in cells derived from Parkinson's mice (FIG. 50A; arrows indicate interaction of these two proteins). These results may indicate the possibility of microautophagy defects. As shown in FIG. 50B, Arl8b$^{T34N}$ treatment is able to restore a normal lysosomal phenotype in Parkinson's primary neurons under the conditions tested. In the depicted Parkinson's disease (PD) primary neurons, lysosomes are observed as having a ring-shape structure (left image). Arrows indicate lysosomes. Transfection of PD primary neurons with Arl8b$^{T34N}$ cleared the ring shape structure of lysosomes. The observed ring shape lysosome structure may indicate a defect in microautophagy processes.

As shown in FIG. 50C, Arl8b$^{T34N}$ treatment restored axonal swelling and degeneration present in PD neurons. PD neurons show severe axonal swelling (as indicated by arrows in left image).

Transfection of PD primary neurons with Arl8b$^{T34N}$ was able to restore axons in primary PD neurons. Arrows in the right image indicate the regeneration of axons and normal structure. As shown in FIG. 50D, Arl8b$^{Q75L}$ converts normal neuronal lysosomes to PD primary neuron phenotype. Lysosomes in normal primary neurons are observed as having ring shape structure after transfection with Arl8b$^{Q75L}$, and resemble lysosome structure in PD primary neurons. Arrows indicate lysosomal ring shape structure which may indicate disturbed microautophagy processes (left image). The right image indicates the ring shape structure of lysosomes in PD primary neurons, for comparison.

In FIG. 50A, primary neuronal cells from parkinsonian mice were fixed with paraformaldehyde and labeled with primary (LAMP1 and alpha synuclein) antibody, followed by proper secondary antibody accordingly. In FIGS. 50B, C, and D, primary neurons from parkinsonian mice were transfected with Arl8b$^{T34N}$ and Arl8b$^{Q75L}$ GFP virus, and labeled with lysotracker red. Lysosome and cell morphology were monitored using confocal scanning microscopy.

Accordingly, there is provided herein a method for treating, preventing, or slowing the development of Parkinson's disease, said method comprising increasing or restoring normal functionality of microautophagy (i.e. lysosomal kiss-and-run) using a microautophagy-enhancing agent as described herein, which may be regarded as a lysosomal motility-enhancing agent.

Lysosome-Mediated Degradation—Microautophagy

Lysosomes are an important subcellular organelle that normally is present in perinuclear regions in mammalian cells. Lysosomes are responsible for degradation of a variety of biomolecules of either extracellular or intracellular origins through various membrane trafficking events, including endocytosis, phagocytosis, and autophagy. The commonly known lysosomal storage diseases are mainly due to defects in lysosomal enzymes responsible for catalyzing degradation of lipids or glycoproteins. However, the vast majority of metabolic disorders associated with abnormal accumulation of lipids (e.g. hepatosteatosis in non-alcoholic fatty liver diseases, or NAFLD) and proteins (e.g. alpha-synuclein in Parkinson's diseases) cannot be explained by deficiency in lysosomal enzymes.

As discussed, the data provided herein suggest that failure of lysosomal degradation of unwanted lipids or proteins is not attributable to enzymatic dysfunction of lysosomes, and rather may be due to impairments in lysosome motility. Live imaging experimental evidence indicates that stalled or disturbed lysosomal motility/microautophagy indeed occurred in severe lipid-laden hepatocytes either caused by nutrient overload (FIG. 36) or HCV infection (FIG. 41), as well as in neurons of Parkinson's disease that abnormally accumulated alpha-synuclein (FIG. 42).

Briefly, unique lysosome-dependent process in mammalian cells believed to be responsible for degradation of unwanted lipid and/or protein substrates is described in detail herein. This process, termed microphagy, microautophagy or microlipoautophagy, appears to be distinct from the well-characterized Atg-dependent-macroautophagy that requires the formation of rather elaborate autophagolysosomes and formation of a bilayer on the target membrane (the autophagic membrane). Instead, microautophagy comprises three steps, namely (i) signaling for activation of microautophagy (mTORC1) and activation of bi-directional (i.e. anterograde and retrograde) motility of lysosomes, (ii) tethering of lysosomes directly onto lipid or protein substrates, and (iii) kiss-and-run between lysosome and the substrates (i.e. engulfment of lipid or protein substrate via a piecemeal eating process), resulting in effective degradation. Thus, rather than autophagosome formation during macroautophagy, and rather than "sitting" passively in the perinuclear regions and "waiting" for substrates to be delivered to them through endosomes or autophagosomes, lysosomes in the microautophagy process are actively "seeking" substrates throughout the cytoplasm. Factors that govern the aforementioned lysosomal motility, lysosome/substrate interaction, and robust engulfment process/kiss-and-run are described in detail herein. A number of protein factors that are essential and sufficient for microautophagy of lipid and/or proteins are provided herein. Interestingly, in certain embodiments, the microautophagy process in mammalian cells may be activated transiently by increased cellular TG-rich LDs, or upstream events and/or downstream events associated therewith, apparently as a consequence of the treatment with omega-3 fatty acids, as demonstrated by results provided herein.

Results provided herein indicate, in certain non-limiting embodiments, that the microautophagy process can be activated or inactivated through manipulating Arl8b expression. Activating microautophagy, or increasing/facilitating lysosomal motility, in hepatocytes may lead to ameliorated steatosis (anti-NAFLD), improved hepatic glucose uptake (anti-hyperglycemia), and/or alleviation of hepatic insulin insensitivity, as well as attenuated HCV viral assembly. Likewise, activating microautophagy, or increasing lysosomal motility, in brain cells may lead to effective clearance and/or secretion of accumulated alpha-synuclein in Parkinson's disease. On the other hand, inactivating microautophagy (for example, as determined by increasing lipid droplet content in cells due to lysosomal constant interaction with LDs during engulfment (i.e. "sticking" to lipid droplets), using, for example, Arl8b$^{GTP}$, leading to cell death, may target cancer cells (e.g. hepatocellular carcinoma) to prevent metastasis. Utilizing lysosome-mediated microautophagy to clear unwanted lipid/protein in disease cells (including aging) may represent an effective therapeutic means.

Experimental Methods Summary

Below, the experimental methods used in the Examples outlined above are summarized. It will be understood by the person of skill in the art that these methods are provided for illustrative purposes, and are not intended to be limiting in any way. The person of skill in the art will be aware that substitutions and/or modifications of the outlined methods may be possible.

In certain non-limiting examples described herein, McA-RH7777 cells stably expressing human apoB-100 and human apoC-III (designated A18-C3) were used for the studies. The A18-C3 cells possess the ability to synthesize and secrete authentic TG-rich $VLDL_1$ ($S_f>100$) under lipid-rich conditions, thus representing a suitable cell culture model for studies of hepatic glucose, lipid, and lipoprotein metabolism. In addition, these studies, particularly those concerning EPA- or DHA-triggered lysosomal motility and CLD degradation, were also performed using primary rat hepatocytes. Transfection of plasmids encoding proteins of interest, or transfection of siRNA specific for silencing target gene expression, was achieved using the FuGENE HP Extreme reagent (Roche). Representative gene silencing siRNA sequences, which are not meant to be limiting, are described in Table 1, and plasmids encoding proteins of interest are described in Table 2. The effectiveness of siRNA silencing was verified by Western-blotting of cellular content of the target proteins, and by intracellular localization assay using siRNA-Tracker (Mirus Bioscience). Twenty-four h after plasmid transfection, or 48 h after siRNA transfection, the cells were cultured in lipid-rich media containing fetal bovine serum (20%) and OA (0.4 mM). The lipid-laden cells were switched to fresh media supplemented with OA or EPA (0.4 mM). In live imaging experiments, LipidTOX Red (Life Technologies) and LysoTracker (Life Technologies) were added to media prior to EPA treatment, to visualize lipid droplets and lysosomes, respectively. For visualizing peroxisomes, Peroxisome-GFP (Invitrogen) was introduced to the cells 24 h prior to experiments. Quantification of cell lipid contents was achieved either by direct mass measurement (HPTLC) and counting the number of lipid droplets using Image J Lipid Droplet Counter Plug-In, or indirectly by Western blot analysis of cellular content of ADRP. Secretion of apoB and TG-rich lipoprotein was determined by Western blot analysis and metabolic labeling. Mitochondrial β-oxidation was measured using MitoSOX Red (Life Technologies) in situ. Autophagic flux was determined by using Cyto-ID assay (Enzo Life Science) and by monitoring GFP-LC3 clustering in situ. Interaction of Arl8b and subunits of the HOPS complex was determined in situ by the proximity ligation assay (Olink Biosience). Cytoplasmic pH was measured using the cytosolic pHrodo indicator reagent (Invitrogen). Live imaging of fluorescent-tagged proteins was performed 1 h post-EPA treatment. Cells were also collected at the time of EPA treatment for transmission EM and tomography, as well as immuno-EM. For movies, cells were imaged at 60 sec intervals every 5 min, for a total of 30 min.

TABLE 1

Gene Silencing siRNA Sequences

| siRNA Target | Sequence of Human Gene | Ambion (Invitrogen) siRNA ID No. (siRNAs target rat genes in McA-RH7777 cell line) |
|---|---|---|
| ATGL | Gene ID: 57104 | 79210 |
| HSL | Gene ID: 3991 | 197144 |
| LAL | Gene ID: 3988 | s128900 (note: siRNA caused cell death; a chemical inhibitor of LAL was used instead) |
| LAMP1 | Gene ID: 3916 | 197138 |
| Rab7 | Gene ID: 7879 (Rab7A) Gene ID: 338382 (Rab7B) | 150453 |
| Atg5 | Gene ID: 9474 | 256088 |
| Atg6 | Gene ID: 8678 | s137745 |
| Rab9 | Gene ID: 9367 | s136762 |
| FYCO1 | NCBI number NM_024513.3 | RSS313149 |
| RILP | NCBI number NM_031430.2 | RSS304923 |
| Arl8b | Uniprot ID: 9606 | 257174 |
| Vps41 | Human Vps41 Isoform 1: NP_055211.2; and Human Vps41 Isoform 2: NP_542198.2 | RSS316512 |
| Vps11 | Human Vps11 Isoform 1: NP_068375.3; and Human Vps11 Isoform 2: NP_001277114.1 | s221247 |
| Vps39 | Human Vps39: GenBank AAH68559.1 | 255016 |
| KIFbβ | Gene ID: 23095 | s138816 |

TABLE 2

Gene-Encoding Plasmid Sequences

| Expressed Gene | Gene Sequence (sequences may be available online at the NCBI databases, where available) |
|---|---|
| $^{GFP}$Rab9 | GenBank number U44103.1 |
| ORPL1 (ORP1) | GenBank number AF323726.2 |
| Arl8b | NCBI number: NM_018184.2 |
| Arl8b$^{Q75L}$ | — |
| Arl8b$^{T34N}$ | — |
| $^{GFP}$Arl8b$^{WT}$ | — |
| $^{GFP}$Arl8b$^{Q75L}$ | — |
| $^{GFP}$Arl8b$^{T34N}$ | — |
| Vps41 | NCBI number NM_014396.3 |
| Vps11 | GenBank number AF308800.1 |
| Vps39 | GenBank number AF281052.1 |
| FYCO1 | NCBI number NM_024513.3 |
| RILP | NCBI number NM_031430.2 |
| $^{GFP}$Vps41 | — |
| $^{GFP}$Vps39 | — |
| $^{GFP}$Vps11 | — |
| $^{mCherry}$Arl8b$^{WT}$ | (see FIG. 33 for an example of the gene sequence and an encoding plasmid) |
| $^{mCherry}$Arl8b$^{Q75L}$ | (see FIG. 34 for an example of the gene sequence and an encoding plasmid) |
| $^{mCherry}$Arl8b$^{T34N}$ | (see FIG. 35 for an example of the gene sequence and an encoding plasmid) |

Detailed Experimental Methods:

Cell Culture and Transfection.

The A18-C3 cells were cultured in DMEM (Invitrogen) supplemented with fetal bovine serum (20%), penicillin (50 U/mL), streptomycin (50 µg/mL, Invitrogen) and Geneticin/G418 (500 µg/mL, Gibco) at 37° C. in 5% $CO_2$. Transfection was conducted when cells were 60-70% confluence. Appropriate plasmids were mixed with FuGENE HP extreme reagent (Roche Diagnostic), according to manufacturer's protocol, and incubated for 30 min. Twenty-four h after transfection, cells were switched to lipid-rich media containing OA (0.4 mM) for additional 16 h prior to imaging and biochemical analysis. In silencing experiments, appropriate siRNAs were transfected into cells using the X-treme GENE siRNA regent (Roche Diagnostic). Localization of siRNA in transfected cells in situ was carried out using the Cy5 Label IT-siRNA Tracker (Minis Bioscience #7213) according to manufacturer's protocol. Forty-eight h after transfection, cells were switched to lipid-rich media containing OA (0.4 mM) for additional 16 h prior to imaging and biochemical analysis.

Plasmids and Antibodies.

Plasmids encoding the GFP-tagged or RFP-tagged $Arl8b^{WT}$, $Arl8b^{T34N}$, and $Arl8b^{Q75L}$, and GFP-tagged FYCO1 and RILP, are gifts of Roberto Botelho (Ryerson University, Canada), Sean Munro (MRC Laboratory of Molecular Biology, UK), and Tuanlao Wang (Xiamen University, China). The following primary antibodies were used in this study: actin (Sigma #SAB4200248), ADRP (Abcam #52355), Arl8b (Fitzgerald #70R-3486), Atg5 (Abeam #108327), ATGL (Santa Cruz #365278), FYCO1 (Abeam #126603), HSL (Santa Cruz #25843), LAMP1 (Sigma #SAB3500285), Rab7 (Santa Cruz #10767), RFP (Abeam #62341), RILP (Santa Cruz #98331), Vps11 (Abeam #170869), Vps41 (Abeam #181078), and Vps39 (Abcam #107570). Anti-human apoB monoclonal antibody 1D1 is a gift of Ross Milne (University of Ottawa Heart Institute). Secondary antibodies were goat (sigma #A5420), mouse (GE Healthcare #NA931V), and rabbit (GE Healthcare #NA934V).

siRNA.

All siRNAs were purchased from Ambion (Invitrogen): Arl8b (#179124), Atg5 (#172246), ATGL (#167782), FYCO1 (#236103), HSL (#129501), Lamp1 (#129497), Rab7 (#131442), RILP (#142632), Vps39 (#168690), Vps41 (#157874), Vps11 (s221247), Atg6 (137745), Rab9 (136762), and K1Fbβ (138816).

Live Cell Imaging.

Cells were grown on 35-mm glass bottom dishes (Ibidi GmbH München, Germany) for 16 h in DMEM supplemented with FBS (20%) and OA (0.4 mM). Cells were imaged using a Zeiss 510 META laser scanning confocal microscope with a heated $CO_2$-controlled stage (5% $CO_2$ at 37° C.). Images were captured at a frame-rate of 30 frame/sec using a 63×. N.A.1.4 objective. Recommended laser lines and filter combinations were used for each dye. For visualization of lipid droplets, lysosomes, mitochondria, and mitochondrial β-oxidation, the respective reagents Lipid-TOX Red (Invitrogen), LysoTracker (Life Technology), MitoTracker (Life Technology), MitoSox Red (Invitrogen), and Peroxisome-GFP BacMam2.0 (Invitrogen) were introduced into the cells, according to manufacturers' recommendations, prior to EPA treatment.

Autophagic Flux Measurement.

Cells were cultured with lipid-rich media containing OA (0.4 mM) for 16 h. The lipid-laden cells were incubated with the Cyto-ID green autophagy detection regent and Hoechst 33342 (Enzo Life Science) for 30 min. The cells were switched to fresh media containing OA or EPA (0.4 mM) and cultured for 1 h. Cells were washed and re-suspended with 1× assay buffer (Enzo Life Science) according to manufacturer's instructions. A control group of cells were treated with rapamycin (500 nm) to induce autophagy.

Quantification of Cellular Lipid Droplet Numbers.

Quantification of lipid droplets was carried out using confocal and differential interface contrast (DIC) microscopy. Lipid droplets were stained with LipidTOX Red (Invitrogen) before adding OA or EPA. All images were visualized using a 63× oil immersion objective lens. Z-series stacks were acquired with 0.2 μm steps. Before quantification of the number of lipid droplets, 3D images were reconstructed using the 3D Image Reconstruction Plug-In[29]. Lipid droplets were then counted using an unbiased watershed algorithm for segmentation (Image J Lipid Droplet Counter Plug-In[30] in 50 randomly selected cells for each condition.

Measurement of Lysosomal Residence Time on the Lipid Droplet Surface.

Cells were cultured with lipid-rich media containing OA (0.4 mM) for 16 h. The lipid-laden cells were switched to fresh media containing EPA (0.4 mM) for 1 h, and the lysosomal movement towards lipid droplets was recorded by time-lapse microscopy. Fluorescent intensity of lysosomal signals at the periphery of selected individual lipid droplet was measured using Image J Live Intensity Profiler Plug-in[31-33] over a period of 40 sec. Quantification for each condition was carried out for 60 individual lipid droplets from three independent experiments. Constant threshold was applied to all of the images in each experiment.

Metabolic Labeling of Lipids.

Cells were metabolically labeled with [$^3$H]glycerol (5 μCi/ml) for 1 and 2 h in DMEM supplemented with 20% FBS and 0.4 mM OA or 0.4 mM EPA. At indicated time, media were collected and subjected to cumulative rate floatation ultracentrifugation as previously described[34] to separate $VLDL_1$, $VLDL_2$ and IDL/LDL fractions. Lipids were extracted from the fractionated lipoproteins as described previously[35] and separated by TLC. The bands containing $^3$H-TG were scrapped from TLC plate and radioactivity was quantified by liquid scintillation counting.

Lipid Mass Quantification.

Lipids were extracted from cells using the Bligh/Dyer method[36], separated by HPTLC in a solvent of hexane:diethylether:acetic acid (105:45:1.5; v/v/v). TG and CE were stained with Commassie G-250[37] and quantified relative to known amount of standards spotted on the same HPTLC plates.

Proximity Ligation Assay (In Situ co-IP).

Cells were transfected with plasmids encoding RFP-tagged $Arl8b^{WT}$, $Arl8b^{Q75L}$, or $Arl8b^{T34N}$. The cells were treated with OA for 16 h (baseline condition as control). One h post-EPA treatment, the cells were fixed, permeabilized and incubated with an anti-RFP antibody together with proper anti-Vps11, -Vps39, and -Vps41 antibodies. The proximity ligation was achieved using the Duolink secondary PLA probes (Olink AB) that detects substrate formation between the two antibodies as described previously[38]. Quantification of signals was done in a total of 50 cells under each condition from 3 independent experiments.

Measurement of Cytosolic pH.

Cells were cultured with lipid-rich media containing OA (0.4 mM) for 16 h. The lipid-laden cells were switched to fresh media containing 10 μM pHrodo green (Invitrogen) for 30 min before adding 0.4 mM OA or 0.4 mM EPA. One h post-OA or -EPA treatment, the intensity of pHrodo green was measured using a proper EX/EM filter, and the intercellular pH was calibrated against the standard curve in the range of pH 4.5, 5.5, 6.5, and 7.5. Nigericin and Valinomycin (Invitrogen) were used for standard curve generation. The pH measurement was done in a total of 50 cells under each condition from 3 independent experiments.

Transmission EM.

Cells were cultured in media containing 0.4 mM OA or 0.4 mM EPA for 30-60 min and harvested for morphological investigation. After two washes with ice-cold, 0.2 M sodium cacodylate buffer containing 0.1% calcium chloride, pH 7.4, samples were fixed overnight at 4° C. in 2.5% glutaraldehyde and washed three times. Pellets were post-fixed with 1% aqueous OsO4+1.5% aqueous potassium ferrocyanide for 1 h, and washed three times. Cells were dehydrated in a graded alcohol series, infiltrated with graded epon:alcohol and embedded in epon. Sections were polymerized at 58° C. for 48 h. Ultrathin sections (90-100 nm) were prepared with a diamond knife using Reichert Ultracut E Ultramicrotome, placed on 200 mesh copper grids, and stained with 2% uranyl acetate for 6 min and Reynold's lead for 5 min. The grids were examined with a 120 kV TEM (Tecnai 12) equipped with a Gatan 792 Bioscan CCD Camera (Gatan Inc.).

Immuno-EM.

For immunogold labeling, pellets of cells cultured in media containing OA or EPA (0.4 mM) were fixed with 0.5% glutaraldehyde and 4% paraformaldehyde in 0.1 M phosphate buffer (pH 7.4) and dehydrated through a series of graded ethanol dilutions, and embedded in LR White acrylic resin (London Resin Company). Ultrathin sections (80 nm) were placed on Formvar-coated nickel grids. For post-embedding immunolabeling, the sections were incubated with an anti-Arl8b antibody (Fitzgerald) for 1 h. For $^{RFP}$Arl8b-transfected cells, that primary antibody used was anti-RFP (Abcam). After washing with 0.2 M sodium cacodylate buffer containing 0.1% calcium chloride, pH 7.4, the samples were incubated with the secondary antibody conjugated with 10-nm gold particles. To increase contrast, the ultrathin sections were stained with 2% uranyl acetate for 6 min and Reynold's lead for 5 min. The grids were examined with a Tecnai 12 120 kV TEM as described above.

Electron Tomography.

Samples were prepared as described above, except thick sections (~250 nm) were cut and transferred onto carbon coated copper grids. Images were collected on a Titan Krios microscope operated at 300 kV using an UltraScan 4 k×4 k CCD camera (Gatan Inc.). Data were collected at an electron dose of approximately 1500 electrons/Å$^2$ per tomogram. Focusing was done on an adjacent area to minimize electron dose exposure. A total of >30 tomograms were collected at different magnifications (ranging from 20 to 50 k). Tilt series were taken using the FEI software in the angular range between −64° and +64° with 2° increments to obtain resolution of 2 nm following the Crowther formula[39]. Reconstruction of 3D volumes was done using the IMOD software suite[40]. The final tomograms were binned 3 times in order to increase the signal to noise ratio. To determine location of the metal particles in relation to the carbon substrate, we searched the volumes for high intensity voxels in the reconstructed volume using SPARX. Three-dimensional rendering was done using Chimera[41].

Statistical Analysis.

Results of lipid quantification are reported as means±standard deviation. Significance of difference was analyzed using Student's t-test.

One or more illustrative embodiments have been described by way of example. It will be understood to persons skilled in the art that a number of variations and modifications can be made without departing from the scope of the invention as defined in the claims.

It will also be understood that mechanisms and pathways discussed herein are provided for illustrative purposes for the person of skill in the art. The mechanisms and pathways discussed herein are based on the data and hypotheses currently available, and may evolve. It will be understood that mechanisms and pathways described herein are not intended to be limiting in any way.

All documents cited herein are hereby incorporated by reference in their entirety.

REFERENCES

1. Tran, K. et al. Attenuated secretion of very low density lipoproteins from McA-RH7777 cells treated with eicosapentaenoic acid is associated with impaired utilization of triacylglycerol synthesized via phospholipid remodeling. Biochim. Biophys. Acta 1761, 463-473 (2006).
2. Pan, M. et al. Lipid peroxidation and oxidant stress regulate hepatic apolipoprotein B degradation and VLDL production. J Clin Invest 113, 1277-1287 (2004).
3. Pan, M. et al. Presecretory oxidation, aggregation, and autophagic destruction of apoprotein-B: a pathway for late-stage quality control. Proc. Natl. Acad. Sci. U.S.A 105, 5862-5867 (2008).
4. Masterton, G. S., Plevris, J. N. & Hayes, P. C. Review article: omega-3 fatty acids—a promising novel therapy for non-alcoholic fatty liver disease. Aliment. Pharmacol. Ther. 31, 679-692 (2010).
5. Ishii, H. et al. Eicosapentaenoic acid ameliorates steatohepatitis and hepatocellular carcinoma in hepatocyte-specific Pten-deficient mice. J Hepatol. 50, 562-571 (2009).
6. Depner, C. M., Philbrick, K. A. & Jump, D. B. Docosahexaenoic acid attenuates hepatic inflammation, oxidative stress, and fibrosis without decreasing hepatosteatosis in a Ldlr(−/−) mouse model of western diet-induced nonalcoholic steatohepatitis. J Nutr. 143, 315-323 (2013).
7. Oh, D. Y. et al. GPR120 is an omega-3 fatty acid receptor mediating potent anti-inflammatory and insulin-sensitizing effects. Cell 142, 687-698 (2010).
8. Serhan, C. N. Novel eicosanoid and docosanoid mediators: resolvins, docosatrienes, and neuroprotectins. Curr. Opin. Clin Nutr. Metab Care 8, 115-121 (2005).
9. Brown, A. M., Baker, P. W. & Gibbons, G. F. Changes in fatty acid metabolism in rat hepatocytes in response to dietary n-3 fatty acids are associated with changes in the intracellular metabolism and secretion of apolipoprotein B-48. J Lipid Res. 38, 469-481 (1997).
10. Huynh, K. K. et al. LAMP proteins are required for fusion of lysosomes with phagosomes. EMBO J. 26, 313-324 (2007).
11. Bucci, C., Thomsen, P., Nicoziani, P., McCarthy, J. & van, D. B. Rab7: a key to lysosome biogenesis. Mol. Biol. Cell 11, 467-480 (2000).
12. Ouimet, M. et al. Autophagy regulates cholesterol efflux from macrophage foam cells via lysosomal acid lipase. Cell Metab 13, 655-667 (2011).
13. Singh, R. et al. Autophagy regulates lipid metabolism. Nature 458, 1131-1135 (2009).
14. Mizushima, N. et al. Dissection of autophagosome formation using Apg5-deficient mouse embryonic stem cells. J Cell Biol. 152, 657-668 (2001).
15. Nishida, Y. et al. Discovery of Atg5/Atg7-independent alternative macroautophagy. Nature 461, 654-658 (2009).
16. Storrie, B. & Desjardins, M. The biogenesis of lysosomes: is it a kiss and run, continuous fusion and fission process? Bioessays 18, 895-903 (1996).

17. Heuser, J. Changes in lysosome shape and distribution correlated with changes in cytoplasmic pH. J Cell Biol. 108, 855-864 (1989).
18. Swanson, J. A., Locke, A., Ansel, P. & Hollenbeck, P. J. Radial movement of lysosomes along microtubules in permeabilized macrophages. J Cell Sci. 103 (Pt 1), 201-209 (1992).
19. van Zutphen, T. et al. Lipid droplet autophagy in the yeast *Saccharomyces cerevisiae*. Mol. Biol. Cell 25, 290-301 (2014).
20. Binns, D. et al. An intimate collaboration between peroxisomes and lipid bodies. J Cell Biol. 173, 719-731 (2006).
21. Pankiv, S. et al. FYCO1 is a Rab7 effector that binds to LC3 and PI3P to mediate microtubule plus end-directed vesicle transport. J Cell Biol. 188, 253-269 (2010).
22. Jordens, I. et al. The Rab7 effector protein RILP controls lysosomal transport by inducing the recruitment of dynein-dynactin motors. Curr. Biol. 11, 1680-1685 (2001).
23. Korolchuk, V. I. et al. Lysosomal positioning coordinates cellular nutrient responses. Nat. Cell Biol. 13, 453-460 (2011).
24. Hofmann, I. & Munro, S. An N-terminally acetylated Arf-like GTPase is localised to lysosomes and affects their motility. J Cell Sci. 119, 1494-1503 (2006).
25. Garg, S. et al. Lysosomal trafficking, antigen presentation, and microbial killing are controlled by the Arf-like GTPase Arl8b. Immunity. 35, 182-193 (2011).
26. Jiang, P. et al. The HOPS complex mediates autophagosome-lysosome fusion through interaction with syntaxin 17. Mol. Biol. Cell 25, 1327-1337 (2014).
27. Soderberg, O. et al. Direct observation of individual endogenous protein complexes in situ by proximity ligation. Nat. Methods 3, 995-1000 (2006).
28. Haraguchi, T. et al. Expression of ADP-ribosylation factor-like protein 8B mRNA in the brain is down-regulated in mice fed a high-fat diet. Biosci. Biotechnol. Biochem. 70, 1798-1802 (2006).
29. Schmid, B. et al. A high-level 3D visualization API for Java and ImageJ. BMC Bioinformatics 11, 274 (2010).
30. McDonough, P. M. et al. Quantification of lipid droplets and associated proteins in cellular models of obesity via high-content/high-throughput microscopy and automated image analysis. Assay Drug Dev Technol 7, 440-460 (2009).
31. Waters, J. C. Accuracy and precision in quantitative fluorescence microscopy. J. Cell Biol. 185, 1135-1148 (2009).
32. Burgess A. et al. Loss of human Greatwall results in G2 arrest and multiple mitotic defects due to deregulation of the cyclin B-Cdc2/PP2A balance. Proc. Natl. Acad. Sci. U.S.A. 107, 12564-12569 (2010).
33. Potapova T. A. et al. Mitotic progression becomes irreversible in prometaphase and collapses when Wee1 and Cdc25 are inhibited. Mol. Biol. Cell 22, 1191-1206 (2011).
34. Redgrave, T. G. & Carlson, L. A. Changes in plasma very low density and low density lipoprotein content, composition, and size after a fatty meal in normo- and hypertriglyceridemic man. J. Lipid Res. 20, 217-229 (1979).
35. Tran, K. et al. Attenuated secretion of very low density lipoproteins from McA-RH7777 cells treated with eicosapentaenoic acid is associated with impaired utilization of triacylglycerol synthesized via phospholipid remodeling. Biochim. Biophys. Acta 1761, 463-473 (2006).
36. Bligh, E. G. & Dyer, W. J. A rapid method of total lipid extraction and purification. Can. J Biochem. Physiol 37, 911-917 (1959).
37. Nakamura, K. & Handa, S. Coomassie brilliant blue staining of lipids on thin-layer plates. Anal. Biochem. 142, 406-410 (1984).
38. Soderberg, O. et al. Direct observation of individual endogenous protein complexes in situ by proximity ligation. Nat. Methods 3, 995-1000 (2006).
39. Crowther, R. A., DeRosier, D. J., & Klug, A. The reconstruction of a three-dimensional structure from projections and its application to electron microscopy. Proc. Royal Society London A. 317, 319-340 (1970).
40. Kremer, J. R., Mastronarde, D. N. & McIntosh, J. R. Computer visualization of three-dimensional image data using IMOD. J. Struct. Biol. 116, 71-76 (1996).
41. Pettersen, E. F. et al. UCSF Chimera—a visualization system for exploratory research and analysis. J. Comput. Chem. 25, 1605-1612 (2004).

All cited documents are herein incorporated by reference in their entirety.

SEQUENCE LISTING

```
<160> NUMBER OF SEQ ID NOS: 20

<210> SEQ ID NO 1
<211> LENGTH: 186
<212> TYPE: PRT
<213> ORGANISM: Homo Sapiens

<400> SEQUENCE: 1

Met Leu Ala Leu Ile Ser Arg Leu Leu Asp Trp Phe Arg Ser Leu Phe
1               5                   10                  15

Trp Lys Glu Glu Met Glu Leu Thr Leu Val Gly Leu Gln Tyr Ser Gly
            20                  25                  30

Lys Thr Thr Phe Val Asn Val Ile Ala Ser Gly Gln Phe Ser Glu Asp
        35                  40                  45

Met Ile Pro Thr Val Gly Phe Asn Met Arg Lys Val Thr Lys Gly Asn
    50                  55                  60
```

```
Val Thr Ile Lys Ile Trp Asp Ile Gly Gly Gln Pro Arg Phe Arg Ser
 65                  70                  75                  80

Met Trp Glu Arg Tyr Cys Arg Gly Val Asn Ala Ile Val Tyr Met Ile
                 85                  90                  95

Asp Ala Asp Arg Glu Lys Ile Glu Ala Ser Arg Asn Glu Leu His
            100                 105                 110

Asn Leu Leu Asp Lys Pro Gln Leu Gln Gly Ile Pro Val Leu Val Leu
            115                 120                 125

Gly Asn Lys Arg Asp Leu Pro Asn Ala Leu Asp Glu Lys Gln Leu Ile
130                 135                 140

Glu Lys Met Asn Leu Ser Ala Ile Gln Asp Arg Glu Ile Cys Cys Tyr
145                 150                 155                 160

Ser Ile Ser Cys Lys Glu Lys Asp Asn Ile Asp Ile Thr Leu Gln Trp
                165                 170                 175

Leu Ile Gln His Ser Lys Ser Arg Arg Ser
            180                 185
```

<210> SEQ ID NO 2
<211> LENGTH: 875
<212> TYPE: PRT
<213> ORGANISM: Homo Sapiens

<400> SEQUENCE: 2

```
Met His Asp Ala Phe Glu Pro Val Pro Ile Leu Glu Lys Leu Pro Leu
  1               5                  10                  15

Gln Ile Asp Cys Leu Ala Ala Trp Glu Glu Trp Leu Leu Val Gly Thr
             20                  25                  30

Lys Gln Gly His Leu Leu Leu Tyr Arg Ile Arg Lys Asp Val Gly Cys
         35                  40                  45

Asn Arg Phe Glu Val Thr Leu Glu Lys Ser Asn Lys Asn Phe Ser Lys
 50                  55                  60

Lys Ile Gln Gln Ile His Val Val Ser Gln Phe Lys Ile Leu Val Ser
 65                  70                  75                  80

Leu Leu Glu Asn Asn Ile Tyr Val His Asp Leu Leu Thr Phe Gln Gln
                 85                  90                  95

Ile Thr Thr Val Ser Lys Ala Lys Gly Ala Ser Leu Phe Thr Cys Asp
            100                 105                 110

Leu Gln His Thr Glu Thr Gly Glu Glu Val Leu Arg Met Cys Val Ala
            115                 120                 125

Val Lys Lys Lys Leu Gln Leu Tyr Phe Trp Lys Asp Arg Glu Phe His
130                 135                 140

Glu Leu Gln Gly Asp Phe Ser Val Pro Asp Val Pro Lys Ser Met Ala
145                 150                 155                 160

Trp Cys Glu Asn Ser Ile Cys Val Gly Phe Lys Arg Asp Tyr Tyr Leu
                165                 170                 175

Ile Arg Val Asp Gly Lys Gly Ser Ile Lys Glu Leu Phe Pro Thr Gly
            180                 185                 190

Lys Gln Leu Glu Pro Leu Val Ala Pro Leu Ala Asp Gly Lys Val Ala
            195                 200                 205

Val Gly Gln Asp Asp Leu Thr Val Val Leu Asn Glu Glu Gly Ile Cys
210                 215                 220

Thr Gln Lys Cys Ala Leu Asn Trp Thr Asp Ile Pro Val Ala Met Glu
225                 230                 235                 240
```

```
His Gln Pro Pro Tyr Ile Ile Ala Val Leu Pro Arg Tyr Val Glu Ile
                245                 250                 255

Arg Thr Phe Glu Pro Arg Leu Leu Val Gln Ser Ile Glu Leu Gln Arg
                260                 265                 270

Pro Arg Phe Ile Thr Ser Gly Gly Ser Asn Ile Ile Tyr Val Ala Ser
                275                 280                 285

Asn His Phe Val Trp Arg Leu Ile Pro Val Pro Met Ala Thr Gln Ile
                290                 295                 300

Gln Gln Leu Leu Gln Asp Lys Gln Phe Glu Leu Ala Leu Gln Leu Ala
305                 310                 315                 320

Glu Met Lys Asp Asp Ser Asp Ser Glu Lys Gln Gln Ile His His
                325                 330                 335

Ile Lys Asn Leu Tyr Ala Phe Asn Leu Phe Cys Gln Lys Arg Phe Asp
                340                 345                 350

Glu Ser Met Gln Val Phe Ala Lys Leu Gly Thr Asp Pro Thr His Val
                355                 360                 365

Met Gly Leu Tyr Pro Asp Leu Leu Pro Thr Asp Tyr Arg Lys Gln Leu
                370                 375                 380

Gln Tyr Pro Asn Pro Leu Pro Val Leu Ser Gly Ala Glu Leu Glu Lys
385                 390                 395                 400

Ala His Leu Ala Leu Ile Asp Tyr Leu Thr Gln Lys Arg Ser Gln Leu
                405                 410                 415

Val Lys Lys Leu Asn Asp Ser Asp His Gln Ser Ser Thr Ser Pro Leu
                420                 425                 430

Met Glu Gly Thr Pro Thr Ile Lys Ser Lys Lys Leu Leu Gln Ile
                435                 440                 445

Ile Asp Thr Thr Leu Leu Lys Cys Tyr Leu His Thr Asn Val Ala Leu
                450                 455                 460

Val Ala Pro Leu Leu Arg Leu Glu Asn Asn His Cys His Ile Glu Glu
465                 470                 475                 480

Ser Glu His Val Leu Lys Lys Ala His Lys Tyr Ser Glu Leu Ile Ile
                485                 490                 495

Leu Tyr Glu Lys Lys Gly Leu His Glu Lys Ala Leu Gln Val Leu Val
                500                 505                 510

Asp Gln Ser Lys Lys Ala Asn Ser Pro Leu Lys Gly His Glu Arg Thr
                515                 520                 525

Val Gln Tyr Leu Gln His Leu Gly Thr Glu Asn Leu His Leu Ile Phe
                530                 535                 540

Ser Tyr Ser Val Trp Val Leu Arg Asp Phe Pro Glu Asp Gly Leu Lys
545                 550                 555                 560

Ile Phe Thr Glu Asp Leu Pro Glu Val Glu Ser Leu Pro Arg Asp Arg
                565                 570                 575

Val Leu Gly Phe Leu Ile Glu Asn Phe Lys Gly Leu Ala Ile Pro Tyr
                580                 585                 590

Leu Glu His Ile Ile His Val Trp Glu Glu Thr Gly Ser Arg Phe His
                595                 600                 605

Asn Cys Leu Ile Gln Leu Tyr Cys Glu Lys Val Gln Gly Leu Met Lys
                610                 615                 620

Glu Tyr Leu Leu Ser Phe Pro Ala Gly Lys Thr Pro Val Pro Ala Gly
625                 630                 635                 640

Glu Glu Glu Gly Glu Leu Gly Glu Tyr Arg Gln Lys Leu Leu Met Phe
                645                 650                 655
```

-continued

```
Leu Glu Ile Ser Ser Tyr Tyr Asp Pro Gly Arg Leu Ile Cys Asp Phe
            660                 665                 670

Pro Phe Asp Gly Leu Leu Glu Glu Arg Ala Leu Leu Leu Gly Arg Met
        675                 680                 685

Gly Lys His Glu Gln Ala Leu Phe Ile Tyr Val His Ile Leu Lys Asp
    690                 695                 700

Thr Arg Met Ala Glu Glu Tyr Cys His Lys His Tyr Asp Arg Asn Lys
705                 710                 715                 720

Asp Gly Asn Lys Asp Val Tyr Leu Ser Leu Arg Met Tyr Leu Ser
                725                 730                 735

Pro Pro Ser Ile His Cys Leu Gly Pro Ile Lys Leu Glu Leu Glu
            740                 745                 750

Pro Lys Ala Asn Leu Gln Ala Ala Leu Gln Val Leu Glu Leu His His
        755                 760                 765

Ser Lys Leu Asp Thr Thr Lys Ala Leu Asn Leu Leu Pro Ala Asn Thr
    770                 775                 780

Gln Ile Asn Asp Ile Arg Ile Phe Leu Glu Lys Val Leu Glu Glu Asn
785                 790                 795                 800

Ala Gln Lys Lys Arg Phe Asn Gln Val Leu Lys Asn Leu Leu His Ala
                805                 810                 815

Glu Phe Leu Arg Val Gln Glu Arg Ile Leu His Gln Gln Val Lys
            820                 825                 830

Cys Ile Ile Thr Glu Glu Lys Val Cys Met Val Cys Lys Lys Ile
        835                 840                 845

Gly Asn Ser Ala Phe Ala Arg Tyr Pro Asn Gly Val Val His Tyr
    850                 855                 860

Phe Cys Ser Lys Glu Val Asn Pro Ala Asp Thr
865                 870                 875

<210> SEQ ID NO 3
<211> LENGTH: 854
<212> TYPE: PRT
<213> ORGANISM: Homo Sapiens

<400> SEQUENCE: 3

Met Ala Glu Ala Glu Glu Gln Glu Thr Gly Ser Leu Glu Glu Ser Thr
1               5                   10                  15

Asp Glu Ser Glu Glu Glu Ser Glu Glu Pro Lys Leu Lys Tyr
                20                  25                  30

Glu Arg Leu Ser Asn Gly Val Thr Glu Ile Leu Gln Lys Asp Ala Ala
            35                  40                  45

Ser Cys Met Thr Val His Asp Lys Phe Leu Ala Leu Gly Thr His Tyr
    50                  55                  60

Gly Lys Val Tyr Leu Leu Asp Val Gln Gly Asn Ile Thr Gln Lys Phe
65                  70                  75                  80

Asp Val Ser Pro Val Lys Ile Asn Gln Ile Ser Leu Asp Glu Ser Gly
                85                  90                  95

Glu His Met Gly Val Cys Ser Glu Asp Gly Lys Val Gln Val Phe Gly
            100                 105                 110

Leu Tyr Ser Gly Glu Glu Phe His Glu Thr Phe Asp Cys Pro Ile Lys
        115                 120                 125

Ile Ile Ala Val His Pro His Phe Val Arg Ser Ser Cys Lys Gln Phe
    130                 135                 140

Val Thr Gly Gly Lys Lys Leu Leu Leu Phe Glu Arg Ser Trp Met Asn
145                 150                 155                 160
```

```
Arg Trp Lys Ser Ala Val Leu His Glu Gly Glu Asn Ile Arg Ser
            165                 170                 175

Val Lys Trp Arg Gly His Leu Ile Ala Trp Ala Asn Asn Met Gly Val
            180                 185                 190

Lys Ile Phe Asp Ile Ile Ser Lys Gln Arg Ile Thr Asn Val Pro Arg
            195                 200                 205

Asp Asp Ile Ser Leu Arg Pro Asp Met Tyr Pro Cys Ser Leu Cys Trp
            210                 215                 220

Lys Asp Asn Val Thr Leu Ile Ile Gly Trp Gly Thr Ser Val Lys Val
225                 230                 235                 240

Cys Ser Val Lys Glu Arg His Ala Ser Glu Met Arg Asp Leu Pro Ser
            245                 250                 255

Arg Tyr Val Glu Ile Val Ser Gln Phe Glu Thr Glu Phe Tyr Ile Ser
            260                 265                 270

Gly Leu Ala Pro Leu Cys Asp Gln Leu Val Val Leu Ser Tyr Val Lys
            275                 280                 285

Glu Ile Ser Glu Lys Thr Glu Arg Glu Tyr Cys Ala Arg Pro Arg Leu
            290                 295                 300

Asp Ile Ile Gln Pro Leu Ser Glu Thr Cys Glu Glu Ile Ser Ser Asp
305                 310                 315                 320

Ala Leu Thr Val Arg Gly Phe Gln Glu Asn Glu Cys Arg Asp Tyr His
            325                 330                 335

Leu Glu Tyr Ser Glu Gly Glu Ser Leu Phe Tyr Ile Val Ser Pro Arg
            340                 345                 350

Asp Val Val Ala Lys Glu Arg Asp Gln Asp His Ile Asp Trp
            355                 360                 365

Leu Leu Glu Lys Lys Lys Tyr Glu Glu Ala Leu Met Ala Ala Glu Ile
            370                 375                 380

Ser Gln Lys Asn Ile Lys Arg His Lys Ile Leu Asp Ile Gly Leu Ala
385                 390                 395                 400

Tyr Ile Asn His Leu Val Glu Arg Gly Asp Tyr Asp Ile Ala Ala Arg
            405                 410                 415

Lys Cys Gln Lys Ile Leu Gly Lys Asn Ala Ala Leu Trp Glu Tyr Glu
            420                 425                 430

Val Tyr Lys Phe Lys Glu Ile Gly Gln Leu Lys Ala Ile Ser Pro Tyr
            435                 440                 445

Leu Pro Arg Gly Asp Pro Val Leu Lys Pro Leu Ile Tyr Glu Met Ile
            450                 455                 460

Leu His Glu Phe Leu Glu Ser Asp Tyr Glu Gly Phe Ala Thr Leu Ile
465                 470                 475                 480

Arg Glu Trp Pro Gly Asp Leu Tyr Asn Asn Ser Val Ile Val Gln Ala
            485                 490                 495

Val Arg Asp His Leu Lys Lys Asp Ser Gln Asn Lys Thr Leu Leu Lys
            500                 505                 510

Thr Leu Ala Glu Leu Tyr Thr Tyr Asp Lys Asn Tyr Gly Asn Ala Leu
            515                 520                 525

Glu Ile Tyr Leu Thr Leu Arg His Lys Asp Val Phe Gln Leu Ile His
            530                 535                 540

Lys His Asn Leu Phe Ser Ser Ile Lys Asp Lys Ile Val Leu Leu Met
545                 550                 555                 560

Asp Phe Asp Ser Glu Lys Ala Val Asp Met Leu Leu Asp Asn Glu Asp
            565                 570                 575
```

-continued

Lys Ile Ser Ile Lys Lys Val Val Glu Leu Glu Asp Arg Pro Glu
            580                 585                 590

Leu Gln His Val Tyr Leu His Lys Leu Phe Lys Arg Asp His His Lys
            595                 600                 605

Gly Gln Arg Tyr His Glu Lys Gln Ile Ser Leu Tyr Ala Glu Tyr Asp
        610                 615                 620

Arg Pro Asn Leu Leu Pro Phe Leu Arg Asp Ser Thr His Cys Pro Leu
625                 630                 635                 640

Glu Lys Ala Leu Glu Ile Cys Gln Gln Arg Asn Phe Val Glu Glu Thr
                645                 650                 655

Val Tyr Leu Leu Ser Arg Met Gly Asn Ser Arg Ser Ala Leu Lys Met
            660                 665                 670

Ile Met Glu Glu Leu His Asp Val Asp Lys Ala Ile Glu Phe Ala Lys
            675                 680                 685

Glu Gln Asp Asp Gly Glu Leu Trp Glu Asp Leu Ile Leu Tyr Ser Ile
        690                 695                 700

Asp Lys Pro Pro Phe Ile Thr Gly Leu Leu Asn Asn Ile Gly Thr His
705                 710                 715                 720

Val Asp Pro Ile Leu Leu Ile His Arg Ile Lys Glu Gly Met Glu Ile
                725                 730                 735

Pro Asn Leu Arg Asp Ser Leu Val Lys Ile Leu Gln Asp Tyr Asn Leu
            740                 745                 750

Gln Ile Leu Leu Arg Glu Gly Cys Lys Lys Ile Leu Val Ala Asp Ser
        755                 760                 765

Leu Ser Leu Leu Lys Lys Met His Arg Thr Gln Met Lys Gly Val Leu
770                 775                 780

Val Asp Glu Glu Asn Ile Cys Glu Ser Cys Leu Ser Pro Ile Leu Pro
785                 790                 795                 800

Ser Asp Ala Ala Lys Pro Phe Ser Val Val Phe His Cys Arg His
                805                 810                 815

Met Phe His Lys Glu Cys Leu Pro Met Pro Ser Met Asn Ser Ala Ala
            820                 825                 830

Gln Phe Cys Asn Ile Cys Ser Ala Lys Asn Arg Gly Pro Gly Ser Ala
        835                 840                 845

Ile Leu Glu Met Lys Lys
    850

<210> SEQ ID NO 4
<211> LENGTH: 829
<212> TYPE: PRT
<213> ORGANISM: Homo Sapiens

<400> SEQUENCE: 4

Met Ala Glu Ala Glu Gln Glu Thr Gly Ser Leu Glu Glu Ser Thr
1               5                   10                  15

Asp Glu Ser Glu Glu Glu Ser Glu Glu Pro Lys Leu Lys Tyr
            20                  25                  30

Glu Arg Leu Ser Asn Gly Val Thr Glu Ile Leu Gln Lys Asp Ala Ala
        35                  40                  45

Ser Cys Met Thr Val His Asp Lys Phe Leu Ala Leu Gly Thr His Tyr
    50                  55                  60

Gly Lys Val Tyr Leu Leu Asp Val Gln Gly Asn Ile Thr Gln Lys Phe
65                  70                  75                  80

Asp Val Val Gln Val Phe Gly Leu Tyr Ser Gly Glu Glu Phe His Glu
                85                  90                  95

-continued

Thr Phe Asp Cys Pro Ile Lys Ile Ile Ala Val His Pro His Phe Val
            100                 105                 110

Arg Ser Ser Cys Lys Gln Phe Val Thr Gly Gly Lys Lys Leu Leu Leu
            115                 120                 125

Phe Glu Arg Ser Trp Met Asn Arg Trp Lys Ser Ala Val Leu His Glu
        130                 135                 140

Gly Glu Gly Asn Ile Arg Ser Val Lys Trp Arg Gly His Leu Ile Ala
145                 150                 155                 160

Trp Ala Asn Asn Met Gly Val Lys Ile Phe Asp Ile Ser Lys Gln
                165                 170                 175

Arg Ile Thr Asn Val Pro Arg Asp Asp Ile Ser Leu Arg Pro Asp Met
            180                 185                 190

Tyr Pro Cys Ser Leu Cys Trp Lys Asp Asn Val Thr Leu Ile Ile Gly
            195                 200                 205

Trp Gly Thr Ser Val Lys Val Cys Ser Val Lys Glu Arg His Ala Ser
        210                 215                 220

Glu Met Arg Asp Leu Pro Ser Arg Tyr Val Glu Ile Val Ser Gln Phe
225                 230                 235                 240

Glu Thr Glu Phe Tyr Ile Ser Gly Leu Ala Pro Leu Cys Asp Gln Leu
            245                 250                 255

Val Val Leu Ser Tyr Val Lys Glu Ile Ser Glu Lys Thr Glu Arg Glu
            260                 265                 270

Tyr Cys Ala Arg Pro Arg Leu Asp Ile Ile Gln Pro Leu Ser Glu Thr
            275                 280                 285

Cys Glu Glu Ile Ser Ser Asp Ala Leu Thr Val Arg Gly Phe Gln Glu
            290                 295                 300

Asn Glu Cys Arg Asp Tyr His Leu Glu Tyr Ser Glu Gly Glu Ser Leu
305                 310                 315                 320

Phe Tyr Ile Val Ser Pro Arg Asp Val Val Ala Lys Glu Arg Asp
                325                 330                 335

Gln Asp Asp His Ile Asp Trp Leu Leu Glu Lys Lys Lys Tyr Glu Glu
            340                 345                 350

Ala Leu Met Ala Ala Glu Ile Ser Gln Lys Asn Ile Lys Arg His Lys
            355                 360                 365

Ile Leu Asp Ile Gly Leu Ala Tyr Ile Asn His Leu Val Glu Arg Gly
            370                 375                 380

Asp Tyr Asp Ile Ala Ala Arg Lys Cys Gln Lys Ile Leu Gly Lys Asn
385                 390                 395                 400

Ala Ala Leu Trp Glu Tyr Glu Val Tyr Lys Phe Lys Glu Ile Gly Gln
                405                 410                 415

Leu Lys Ala Ile Ser Pro Tyr Leu Pro Arg Gly Asp Pro Val Leu Lys
            420                 425                 430

Pro Leu Ile Tyr Glu Met Ile Leu His Glu Phe Leu Glu Ser Asp Tyr
            435                 440                 445

Glu Gly Phe Ala Thr Leu Ile Arg Glu Trp Pro Gly Asp Leu Tyr Asn
            450                 455                 460

Asn Ser Val Ile Val Gln Ala Val Arg Asp His Leu Lys Lys Asp Ser
465                 470                 475                 480

Gln Asn Lys Thr Leu Leu Lys Thr Leu Ala Glu Leu Tyr Thr Tyr Asp
                485                 490                 495

Lys Asn Tyr Gly Asn Ala Leu Glu Ile Tyr Leu Thr Leu Arg His Lys
            500                 505                 510

-continued

Asp Val Phe Gln Leu Ile His Lys His Asn Leu Phe Ser Ser Ile Lys
            515                 520                 525

Asp Lys Ile Val Leu Leu Met Asp Phe Asp Ser Glu Lys Ala Val Asp
        530                 535                 540

Met Leu Leu Asp Asn Glu Asp Lys Ile Ser Ile Lys Lys Val Val Glu
545                 550                 555                 560

Glu Leu Glu Asp Arg Pro Glu Leu Gln His Val Tyr Leu His Lys Leu
                565                 570                 575

Phe Lys Arg Asp His His Lys Gly Gln Arg Tyr His Glu Lys Gln Ile
            580                 585                 590

Ser Leu Tyr Ala Glu Tyr Asp Arg Pro Asn Leu Leu Pro Phe Leu Arg
        595                 600                 605

Asp Ser Thr His Cys Pro Leu Glu Lys Ala Leu Glu Ile Cys Gln Gln
    610                 615                 620

Arg Asn Phe Val Glu Glu Thr Val Tyr Leu Leu Ser Arg Met Gly Asn
625                 630                 635                 640

Ser Arg Ser Ala Leu Lys Met Ile Met Glu Glu Leu His Asp Val Asp
                645                 650                 655

Lys Ala Ile Glu Phe Ala Lys Glu Gln Asp Asp Gly Glu Leu Trp Glu
            660                 665                 670

Asp Leu Ile Leu Tyr Ser Ile Asp Lys Pro Pro Phe Ile Thr Gly Leu
        675                 680                 685

Leu Asn Asn Ile Gly Thr His Val Asp Pro Ile Leu Leu Ile His Arg
    690                 695                 700

Ile Lys Glu Gly Met Glu Ile Pro Asn Leu Arg Asp Ser Leu Val Lys
705                 710                 715                 720

Ile Leu Gln Asp Tyr Asn Leu Gln Ile Leu Leu Arg Glu Gly Cys Lys
                725                 730                 735

Lys Ile Leu Val Ala Asp Ser Leu Ser Leu Leu Lys Lys Met His Arg
            740                 745                 750

Thr Gln Met Lys Gly Val Leu Val Asp Glu Glu Asn Ile Cys Glu Ser
        755                 760                 765

Cys Leu Ser Pro Ile Leu Pro Ser Asp Ala Ala Lys Pro Phe Ser Val
    770                 775                 780

Val Val Phe His Cys Arg His Met Phe His Lys Glu Cys Leu Pro Met
785                 790                 795                 800

Pro Ser Met Asn Ser Ala Ala Gln Phe Cys Asn Ile Cys Ser Ala Lys
                805                 810                 815

Asn Arg Gly Pro Gly Ser Ala Ile Leu Glu Met Lys Lys
            820                 825

<210> SEQ ID NO 5
<211> LENGTH: 941
<212> TYPE: PRT
<213> ORGANISM: Homo Sapiens

<400> SEQUENCE: 5

Met Ala Ala Tyr Leu Gln Trp Arg Arg Phe Val Phe Asp Lys Glu
1               5                   10                  15

Leu Val Lys Glu Pro Leu Ser Asn Asp Gly Ala Ala Pro Gly Ala Thr
            20                  25                  30

Pro Ala Ser Gly Ser Ala Ala Ser Lys Phe Leu Cys Leu Pro Pro Gly
        35                  40                  45

Ile Thr Val Cys Asp Ser Gly Arg Gly Ser Leu Val Phe Gly Asp Met
    50                  55                  60

```
Glu Gly Gln Ile Trp Phe Leu Pro Arg Ser Leu Gln Leu Thr Gly Phe
 65                  70                  75                  80

Gln Ala Tyr Lys Leu Arg Val Thr His Leu Tyr Gln Leu Lys Gln His
                 85                  90                  95

Asn Ile Leu Ala Ser Val Gly Glu Asp Glu Gly Ile Asn Pro Leu
                100                 105                 110

Val Lys Ile Trp Asn Leu Glu Lys Arg Asp Gly Gly Asn Pro Leu Cys
            115                 120                 125

Thr Arg Ile Phe Pro Ala Ile Pro Gly Thr Glu Pro Thr Val Val Ser
130                 135                 140

Cys Leu Thr Val His Glu Asn Leu Asn Phe Met Ala Ile Gly Phe Thr
145                 150                 155                 160

Asp Gly Ser Val Thr Leu Asn Lys Gly Asp Ile Thr Arg Asp Arg His
                165                 170                 175

Ser Lys Thr Gln Ile Leu His Lys Gly Asn Tyr Pro Val Thr Gly Leu
                180                 185                 190

Ala Phe Arg Gln Ala Gly Lys Thr Thr His Leu Phe Val Val Thr Thr
            195                 200                 205

Glu Asn Val Gln Ser Tyr Ile Val Ser Gly Lys Asp Tyr Pro Arg Val
210                 215                 220

Glu Leu Asp Thr His Gly Cys Gly Leu Arg Cys Ser Ala Leu Ser Asp
225                 230                 235                 240

Pro Ser Gln Asp Leu Gln Phe Ile Val Ala Gly Asp Glu Cys Val Tyr
                245                 250                 255

Leu Tyr Gln Pro Asp Glu Arg Gly Pro Cys Phe Ala Phe Glu Gly His
                260                 265                 270

Lys Leu Ile Ala His Trp Phe Arg Gly Tyr Leu Ile Ile Val Ser Arg
            275                 280                 285

Asp Arg Lys Val Ser Pro Lys Ser Glu Phe Thr Ser Arg Asp Ser Gln
290                 295                 300

Ser Ser Asp Lys Gln Ile Leu Asn Ile Tyr Asp Leu Cys Asn Lys Phe
305                 310                 315                 320

Ile Ala Tyr Ser Thr Val Phe Glu Asp Val Asp Val Leu Ala Glu
                325                 330                 335

Trp Gly Ser Leu Tyr Val Leu Thr Arg Asp Gly Arg Val His Ala Leu
                340                 345                 350

Gln Glu Lys Asp Thr Gln Thr Lys Leu Glu Met Leu Phe Lys Lys Asn
            355                 360                 365

Leu Phe Glu Met Ala Ile Asn Leu Ala Lys Ser Gln His Leu Asp Ser
370                 375                 380

Asp Gly Leu Ala Gln Ile Phe Met Gln Tyr Gly Asp His Leu Tyr Ser
385                 390                 395                 400

Lys Gly Asn His Asp Gly Ala Val Gln Gln Tyr Ile Arg Thr Ile Gly
                405                 410                 415

Lys Leu Glu Pro Ser Tyr Val Ile Arg Lys Phe Leu Asp Ala Gln Arg
            420                 425                 430

Ile His Asn Leu Thr Ala Tyr Leu Gln Thr Leu His Arg Gln Ser Leu
                435                 440                 445

Ala Asn Ala Asp His Thr Thr Leu Leu Leu Asn Cys Tyr Thr Lys Leu
            450                 455                 460

Lys Asp Ser Ser Lys Leu Glu Glu Phe Ile Lys Lys Ser Glu Ser
465                 470                 475                 480
```

```
Glu Val His Phe Asp Val Glu Thr Ala Ile Lys Val Leu Arg Gln Ala
                485                 490                 495

Gly Tyr Tyr Ser His Ala Leu Tyr Leu Ala Glu Asn His Ala His His
            500                 505                 510

Glu Trp Tyr Leu Lys Ile Gln Leu Glu Asp Ile Lys Asn Tyr Gln Glu
            515                 520                 525

Ala Leu Arg Tyr Ile Gly Lys Leu Pro Phe Glu Gln Ala Glu Ser Asn
    530                 535                 540

Met Lys Arg Tyr Gly Lys Ile Leu Met His His Ile Pro Glu Gln Thr
545                 550                 555                 560

Thr Gln Leu Leu Lys Gly Leu Cys Thr Asp Tyr Arg Pro Ser Leu Glu
                565                 570                 575

Gly Arg Ser Asp Arg Glu Ala Pro Gly Cys Arg Ala Asn Ser Glu Glu
            580                 585                 590

Phe Ile Pro Ile Phe Ala Asn Asn Pro Arg Glu Leu Lys Ala Phe Leu
            595                 600                 605

Glu His Met Ser Glu Val Gln Pro Asp Ser Pro Gln Gly Ile Tyr Asp
    610                 615                 620

Thr Leu Leu Glu Leu Arg Leu Gln Asn Trp Ala His Glu Lys Asp Pro
625                 630                 635                 640

Gln Val Lys Glu Lys Leu His Ala Glu Ala Ile Ser Leu Leu Lys Ser
                645                 650                 655

Gly Arg Phe Cys Asp Val Phe Asp Lys Ala Leu Val Leu Cys Gln Met
            660                 665                 670

His Asp Phe Gln Asp Gly Val Leu Tyr Leu Tyr Glu Gln Gly Lys Leu
            675                 680                 685

Phe Gln Gln Ile Met His Tyr His Met Gln His Glu Gln Tyr Arg Gln
    690                 695                 700

Val Ile Ser Val Cys Glu Arg His Gly Glu Gln Asp Pro Ser Leu Trp
705                 710                 715                 720

Glu Gln Ala Leu Ser Tyr Phe Ala Arg Lys Glu Glu Asp Cys Lys Glu
                725                 730                 735

Tyr Val Ala Ala Val Leu Lys His Ile Glu Asn Lys Asn Leu Met Pro
            740                 745                 750

Pro Leu Leu Val Val Gln Thr Leu Ala His Asn Ser Thr Ala Thr Leu
            755                 760                 765

Ser Val Ile Arg Asp Tyr Leu Val Gln Lys Leu Gln Lys Gln Ser Gln
    770                 775                 780

Gln Ile Ala Gln Asp Glu Leu Arg Val Arg Arg Tyr Arg Glu Glu Thr
785                 790                 795                 800

Thr Arg Ile Arg Gln Glu Ile Gln Glu Leu Lys Ala Ser Pro Lys Ile
                805                 810                 815

Phe Gln Lys Thr Lys Cys Ser Ile Cys Asn Ser Ala Leu Glu Leu Pro
            820                 825                 830

Ser Val His Phe Leu Cys Gly His Ser Phe His Gln His Cys Phe Glu
            835                 840                 845

Ser Tyr Ser Glu Ser Asp Ala Asp Cys Pro Thr Cys Leu Pro Glu Asn
    850                 855                 860

Arg Lys Val Met Asp Met Ile Arg Ala Gln Glu Gln Lys Arg Asp Leu
865                 870                 875                 880

His Asp Gln Phe Gln His Gln Leu Lys Cys Ser Asn Asp Ser Phe Ser
                885                 890                 895
```

-continued

Val Ile Ala Asp Tyr Phe Gly Arg Gly Val Phe Asn Lys Leu Thr Leu
            900                 905                 910

Leu Thr Asp Pro Pro Thr Ala Arg Leu Thr Ser Ser Leu Glu Ala Gly
            915                 920                 925

Leu Gln Arg Asp Leu Leu Met His Ser Arg Arg Gly Thr
            930                 935                 940

<210> SEQ ID NO 6
<211> LENGTH: 931
<212> TYPE: PRT
<213> ORGANISM: Homo Sapiens

<400> SEQUENCE: 6

Met Lys Ser Val Cys Arg Arg Gly Pro Cys Arg Ala Pro Leu Trp Phe
1               5                   10                  15

Ser Trp Ser Ser Arg Val Val Leu Trp Ser Thr Gly Arg Lys Lys Glu
            20                  25                  30

Val His Leu Leu Thr Cys Tyr Gln Leu Ser Asn Pro Gly Arg Leu Leu
        35                  40                  45

Asp Tyr Pro Ala His Met Glu Gly Gln Ile Trp Phe Leu Pro Arg Ser
    50                  55                  60

Leu Gln Leu Thr Gly Phe Gln Ala Tyr Lys Leu Arg Val Thr His Leu
65                  70                  75                  80

Tyr Gln Leu Lys Gln His Asn Ile Leu Ala Ser Val Gly Glu Asp Glu
                85                  90                  95

Glu Gly Ile Asn Pro Leu Val Lys Ile Trp Asn Leu Glu Lys Arg Asp
            100                 105                 110

Gly Gly Asn Pro Leu Cys Thr Arg Ile Phe Pro Ala Ile Pro Gly Thr
        115                 120                 125

Glu Pro Thr Val Val Ser Cys Leu Thr Val His Glu Asn Leu Asn Phe
    130                 135                 140

Met Ala Ile Gly Phe Thr Asp Gly Ser Val Thr Leu Asn Lys Gly Asp
145                 150                 155                 160

Ile Thr Arg Asp Arg His Ser Lys Thr Gln Ile Leu His Lys Gly Asn
                165                 170                 175

Tyr Pro Val Thr Gly Leu Ala Phe Arg Gln Ala Gly Lys Thr Thr His
            180                 185                 190

Leu Phe Val Val Thr Thr Glu Asn Val Gln Ser Tyr Ile Val Ser Gly
        195                 200                 205

Lys Asp Tyr Pro Arg Val Glu Leu Asp Thr His Gly Cys Gly Leu Arg
    210                 215                 220

Cys Ser Ala Leu Ser Asp Pro Ser Gln Asp Leu Gln Phe Ile Val Ala
225                 230                 235                 240

Gly Asp Glu Cys Val Tyr Leu Tyr Gln Pro Asp Glu Arg Gly Pro Cys
                245                 250                 255

Phe Ala Phe Glu Gly His Lys Leu Ile Ala His Trp Phe Arg Gly Tyr
            260                 265                 270

Leu Ile Ile Val Ser Arg Asp Arg Lys Val Ser Pro Lys Ser Glu Phe
        275                 280                 285

Thr Ser Arg Asp Ser Gln Ser Ser Asp Lys Gln Ile Leu Asn Ile Tyr
    290                 295                 300

Asp Leu Cys Asn Lys Phe Ile Ala Tyr Ser Thr Val Phe Glu Asp Val
305                 310                 315                 320

```
Val Asp Val Leu Ala Glu Trp Gly Ser Leu Tyr Val Leu Thr Arg Asp
                325                 330                 335

Gly Arg Val His Ala Leu Gln Glu Lys Asp Thr Gln Thr Lys Leu Glu
                340                 345                 350

Met Leu Phe Lys Lys Asn Leu Phe Glu Met Ala Ile Asn Leu Ala Lys
                355                 360                 365

Ser Gln His Leu Asp Ser Asp Gly Leu Ala Gln Ile Phe Met Gln Tyr
            370                 375                 380

Gly Asp His Leu Tyr Ser Lys Gly Asn His Asp Gly Ala Val Gln Gln
385                 390                 395                 400

Tyr Ile Arg Thr Ile Gly Lys Leu Glu Pro Ser Tyr Val Ile Arg Lys
                405                 410                 415

Phe Leu Asp Ala Gln Arg Ile His Asn Leu Thr Ala Tyr Leu Gln Thr
            420                 425                 430

Leu His Arg Gln Ser Leu Ala Asn Ala Asp His Thr Thr Leu Leu Leu
            435                 440                 445

Asn Cys Tyr Thr Lys Leu Lys Asp Ser Ser Lys Leu Glu Glu Phe Ile
            450                 455                 460

Lys Lys Lys Ser Glu Ser Glu Val His Phe Asp Val Glu Thr Ala Ile
465                 470                 475                 480

Lys Val Leu Arg Gln Ala Gly Tyr Tyr Ser His Ala Leu Tyr Leu Ala
                485                 490                 495

Glu Asn His Ala His His Glu Trp Tyr Leu Lys Ile Gln Leu Glu Asp
            500                 505                 510

Ile Lys Asn Tyr Gln Glu Ala Leu Arg Tyr Ile Gly Lys Leu Pro Phe
            515                 520                 525

Glu Gln Ala Glu Ser Asn Met Lys Arg Tyr Gly Lys Ile Leu Met His
            530                 535                 540

His Ile Pro Glu Gln Thr Thr Gln Leu Leu Lys Gly Leu Cys Thr Asp
545                 550                 555                 560

Tyr Arg Pro Ser Leu Glu Gly Arg Ser Asp Arg Glu Ala Pro Gly Cys
                565                 570                 575

Arg Ala Asn Ser Glu Glu Phe Ile Pro Ile Phe Ala Asn Asn Pro Arg
            580                 585                 590

Glu Leu Lys Ala Phe Leu Glu His Met Ser Glu Val Gln Pro Asp Ser
            595                 600                 605

Pro Gln Gly Ile Tyr Asp Thr Leu Leu Glu Leu Arg Leu Gln Asn Trp
            610                 615                 620

Ala His Glu Lys Asp Pro Gln Val Lys Glu Lys Leu His Ala Glu Ala
625                 630                 635                 640

Ile Ser Leu Leu Lys Ser Gly Arg Phe Cys Asp Val Phe Asp Lys Ala
                645                 650                 655

Leu Val Leu Cys Gln Met His Asp Phe Gln Asp Gly Val Leu Tyr Leu
            660                 665                 670

Tyr Glu Gln Gly Lys Leu Phe Gln Gln Ile Met His Tyr His Met Gln
            675                 680                 685

His Glu Gln Tyr Arg Gln Val Ile Ser Val Cys Glu Arg His Gly Glu
            690                 695                 700

Gln Asp Pro Ser Leu Trp Glu Gln Ala Leu Ser Tyr Phe Ala Arg Lys
705                 710                 715                 720

Glu Glu Asp Cys Lys Glu Tyr Val Ala Ala Val Leu Lys His Ile Glu
                725                 730                 735
```

```
Asn Lys Asn Leu Met Pro Pro Leu Val Val Gln Thr Leu Ala His
            740                 745                 750

Asn Ser Thr Ala Thr Leu Ser Val Ile Arg Asp Tyr Leu Val Gln Lys
        755                 760                 765

Leu Gln Lys Gln Ser Gln Gln Ile Ala Gln Asp Glu Leu Arg Val Arg
    770                 775                 780

Arg Tyr Arg Glu Glu Thr Thr Arg Ile Arg Gln Glu Ile Gln Glu Leu
785                 790                 795                 800

Lys Ala Ser Pro Lys Ile Phe Gln Lys Thr Lys Cys Ser Ile Cys Asn
                805                 810                 815

Ser Ala Leu Glu Leu Pro Ser Val His Phe Leu Cys Gly His Ser Phe
        820                 825                 830

His Gln His Cys Phe Glu Ser Tyr Ser Glu Ser Asp Ala Asp Cys Pro
    835                 840                 845

Thr Cys Leu Pro Glu Asn Arg Lys Val Met Asp Met Ile Arg Ala Gln
    850                 855                 860

Glu Gln Lys Arg Asp Leu His Asp Gln Phe Gln His Gln Leu Lys Cys
865                 870                 875                 880

Ser Asn Asp Ser Phe Ser Val Ile Ala Asp Tyr Phe Gly Arg Gly Val
                885                 890                 895

Phe Asn Lys Leu Thr Leu Leu Thr Asp Pro Pro Thr Ala Arg Leu Thr
        900                 905                 910

Ser Ser Leu Glu Ala Gly Leu Gln Arg Asp Leu Leu Met His Ser Arg
    915                 920                 925

Arg Gly Thr
    930

<210> SEQ ID NO 7
<211> LENGTH: 854
<212> TYPE: PRT
<213> ORGANISM: Homo Sapiens

<400> SEQUENCE: 7

Met Ala Glu Ala Glu Glu Gln Glu Thr Gly Ser Leu Glu Glu Ser Thr
1               5                   10                  15

Asp Glu Ser Glu Glu Glu Ser Glu Glu Pro Lys Leu Lys Tyr
                20                  25                  30

Glu Arg Leu Ser Asn Gly Val Thr Glu Ile Leu Gln Lys Asp Ala Ala
            35                  40                  45

Ser Cys Met Thr Val His Asp Lys Phe Leu Ala Leu Gly Thr His Tyr
        50                  55                  60

Gly Lys Val Tyr Leu Leu Asp Val Gln Gly Asn Ile Thr Gln Lys Phe
65                  70                  75                  80

Asp Val Ser Pro Val Lys Ile Asn Gln Ile Ser Leu Asp Glu Ser Gly
                85                  90                  95

Glu His Met Gly Val Cys Ser Glu Asp Gly Lys Val Gln Val Phe Gly
                100                 105                 110

Leu Tyr Ser Gly Glu Glu Phe His Glu Thr Phe Asp Cys Pro Ile Lys
            115                 120                 125

Ile Ile Ala Val His Pro His Phe Val Arg Ser Cys Lys Gln Phe
        130                 135                 140

Val Thr Gly Gly Lys Lys Leu Leu Phe Glu Arg Ser Trp Met Asn
145                 150                 155                 160

Arg Trp Lys Ser Ala Val Leu His Glu Gly Glu Gly Asn Ile Arg Ser
                165                 170                 175
```

```
Val Lys Trp Arg Gly His Leu Ile Ala Trp Ala Asn Asn Met Gly Val
            180                 185                 190

Lys Ile Phe Asp Ile Ile Ser Lys Gln Arg Ile Thr Asn Val Pro Arg
        195                 200                 205

Asp Asp Ile Ser Leu Arg Pro Asp Met Tyr Pro Cys Ser Leu Cys Trp
210                 215                 220

Lys Asp Asn Val Thr Leu Ile Ile Gly Trp Gly Thr Ser Val Lys Val
225                 230                 235                 240

Cys Ser Val Lys Glu Arg His Ala Ser Glu Met Arg Asp Leu Pro Ser
                245                 250                 255

Arg Tyr Val Glu Ile Val Ser Gln Phe Glu Thr Glu Phe Tyr Ile Ser
            260                 265                 270

Gly Leu Ala Pro Leu Cys Asp Gln Leu Val Val Leu Ser Tyr Val Lys
        275                 280                 285

Glu Ile Ser Glu Lys Thr Glu Arg Glu Tyr Cys Ala Arg Pro Arg Leu
    290                 295                 300

Asp Ile Ile Gln Pro Leu Ser Glu Thr Cys Glu Glu Ile Ser Ser Asp
305                 310                 315                 320

Ala Leu Thr Val Arg Gly Phe Gln Glu Asn Gly Cys Arg Asp Tyr His
                325                 330                 335

Leu Glu Tyr Ser Glu Gly Glu Ser Leu Phe Tyr Ile Val Ser Pro Arg
            340                 345                 350

Asp Val Val Ala Lys Glu Arg Asp Gln Asp His Ile Asp Trp
        355                 360                 365

Leu Leu Glu Lys Lys Tyr Glu Glu Ala Leu Met Ala Ala Glu Ile
    370                 375                 380

Ser Gln Lys Asn Ile Lys Arg His Lys Ile Leu Asp Ile Gly Leu Ala
385                 390                 395                 400

Tyr Ile Asn His Leu Val Glu Arg Gly Asp Tyr Asp Ile Ala Ala Arg
                405                 410                 415

Lys Cys Gln Lys Ile Leu Gly Lys Asn Ala Ala Leu Trp Glu Tyr Glu
            420                 425                 430

Val Tyr Lys Phe Lys Glu Ile Gly Gln Leu Lys Ala Ile Ser Pro Tyr
        435                 440                 445

Leu Pro Arg Gly Asp Pro Val Leu Lys Pro Leu Ile Tyr Glu Met Ile
    450                 455                 460

Leu His Glu Phe Leu Glu Ser Asp Tyr Glu Gly Phe Ala Thr Leu Ile
465                 470                 475                 480

Arg Glu Trp Pro Gly Asp Leu Tyr Asn Asn Ser Val Ile Val Gln Ala
                485                 490                 495

Val Arg Asp His Leu Lys Lys Asp Ser Gln Asn Lys Thr Leu Leu Lys
            500                 505                 510

Thr Leu Ala Glu Leu Tyr Thr Tyr Asp Lys Asn Tyr Gly Asn Ala Leu
        515                 520                 525

Glu Ile Tyr Leu Thr Leu Arg His Lys Asp Val Phe Gln Leu Ile His
    530                 535                 540

Lys His Asn Leu Phe Ser Ser Ile Lys Asp Lys Ile Val Leu Leu Met
545                 550                 555                 560

Asp Phe Asp Ser Glu Lys Ala Val Asp Met Leu Leu Asp Asn Glu Asp
                565                 570                 575

Lys Ile Ser Ile Lys Lys Val Val Glu Glu Leu Glu Asp Arg Pro Glu
            580                 585                 590
```

```
Leu Gln His Val Tyr Leu His Lys Leu Phe Lys Arg Asp His His Lys
            595                 600                 605

Gly Gln Arg Tyr His Glu Lys Gln Ile Ser Leu Tyr Ala Glu Tyr Asp
610                 615                 620

Arg Pro Asn Leu Leu Pro Phe Leu Arg Asp Ser Thr His Cys Pro Leu
625                 630                 635                 640

Glu Lys Ala Leu Glu Ile Cys Gln Gln Arg Asn Phe Val Glu Glu Thr
                645                 650                 655

Val Tyr Leu Leu Ser Arg Met Gly Asn Ser Arg Ser Ala Leu Lys Met
                660                 665                 670

Ile Met Glu Glu Leu His Asp Val Asp Lys Ala Ile Glu Phe Ala Lys
            675                 680                 685

Glu Gln Asp Asp Gly Glu Leu Trp Glu Asp Leu Ile Leu Tyr Ser Ile
690                 695                 700

Asp Lys Pro Pro Phe Ile Thr Gly Leu Leu Asn Asn Ile Gly Thr His
705                 710                 715                 720

Val Asp Pro Ile Leu Leu Ile His Arg Ile Lys Glu Gly Met Glu Ile
                725                 730                 735

Pro Asn Leu Arg Asp Ser Leu Val Lys Ile Leu Gln Asp Tyr Asn Leu
            740                 745                 750

Gln Ile Leu Leu Arg Glu Gly Cys Lys Lys Ile Leu Val Ala Asp Ser
            755                 760                 765

Leu Ser Leu Leu Lys Lys Met His Arg Thr Gln Met Lys Gly Val Leu
770                 775                 780

Val Asp Glu Glu Asn Ile Cys Glu Ser Cys Leu Ser Pro Ile Leu Pro
785                 790                 795                 800

Ser Asp Ala Ala Lys Pro Phe Ser Val Val Phe His Cys Arg His
                805                 810                 815

Met Phe His Lys Glu Cys Leu Pro Met Pro Ser Met Asn Ser Ala Ala
                820                 825                 830

Gln Phe Cys Asn Ile Cys Ser Ala Lys Asn Arg Gly Pro Gly Ser Ala
            835                 840                 845

Ile Leu Glu Met Lys Lys
        850

<210> SEQ ID NO 8
<211> LENGTH: 829
<212> TYPE: PRT
<213> ORGANISM: Homo Sapiens

<400> SEQUENCE: 8

Met Ala Glu Ala Glu Glu Gln Glu Thr Gly Ser Leu Glu Glu Ser Thr
1               5                   10                  15

Asp Glu Ser Glu Glu Glu Ser Glu Glu Pro Lys Leu Lys Tyr
                20                  25                  30

Glu Arg Leu Ser Asn Gly Val Thr Glu Ile Leu Gln Lys Asp Ala Ala
                35                  40                  45

Ser Cys Met Thr Val His Asp Lys Phe Leu Ala Leu Gly Thr His Tyr
            50                  55                  60

Gly Lys Val Tyr Leu Leu Asp Val Gln Gly Asn Ile Thr Gln Lys Phe
65                  70                  75                  80

Asp Val Val Gln Val Phe Gly Leu Tyr Ser Gly Glu Glu Phe His Glu
                85                  90                  95

Thr Phe Asp Cys Pro Ile Lys Ile Ile Ala Val His Pro His Phe Val
                100                 105                 110
```

```
Arg Ser Ser Cys Lys Gln Phe Val Thr Gly Lys Lys Leu Leu Leu
        115                 120                 125
Phe Glu Arg Ser Trp Met Asn Arg Trp Lys Ser Ala Val Leu His Glu
130                 135                 140
Gly Glu Gly Asn Ile Arg Ser Val Lys Trp Arg Gly His Leu Ile Ala
145                 150                 155                 160
Trp Ala Asn Asn Met Gly Val Lys Ile Phe Asp Ile Ile Ser Lys Gln
                165                 170                 175
Arg Ile Thr Asn Val Pro Arg Asp Asp Ile Ser Leu Arg Pro Asp Met
                180                 185                 190
Tyr Pro Cys Ser Leu Cys Trp Lys Asp Asn Val Thr Leu Ile Ile Gly
            195                 200                 205
Trp Gly Thr Ser Val Lys Val Cys Ser Val Lys Glu Arg His Ala Ser
            210                 215                 220
Glu Met Arg Asp Leu Pro Ser Arg Tyr Val Glu Ile Val Ser Gln Phe
225                 230                 235                 240
Glu Thr Glu Phe Tyr Ile Ser Gly Leu Ala Pro Leu Cys Asp Gln Leu
                245                 250                 255
Val Val Leu Ser Tyr Val Lys Glu Ile Ser Lys Thr Glu Arg Glu
                260                 265                 270
Tyr Cys Ala Arg Pro Arg Leu Asp Ile Ile Gln Pro Leu Ser Glu Thr
            275                 280                 285
Cys Glu Glu Ile Ser Ser Asp Ala Leu Thr Val Arg Gly Phe Gln Glu
            290                 295                 300
Asn Glu Cys Arg Asp Tyr His Leu Glu Tyr Glu Gly Glu Ser Leu
305                 310                 315                 320
Phe Tyr Ile Val Ser Pro Arg Asp Val Val Ala Lys Glu Arg Asp
                325                 330                 335
Gln Asp Asp His Ile Asp Trp Leu Leu Glu Lys Lys Tyr Glu Glu
                340                 345                 350
Ala Leu Met Ala Ala Glu Ile Ser Gln Lys Asn Ile Lys Arg His Lys
            355                 360                 365
Ile Leu Asp Ile Gly Leu Ala Tyr Ile Asn His Leu Val Glu Arg Gly
            370                 375                 380
Asp Tyr Asp Ile Ala Ala Arg Lys Cys Gln Lys Ile Leu Gly Lys Asn
385                 390                 395                 400
Ala Ala Leu Trp Glu Tyr Glu Val Tyr Lys Phe Lys Glu Ile Gly Gln
                405                 410                 415
Leu Lys Ala Ile Ser Pro Tyr Leu Pro Arg Gly Asp Pro Val Leu Lys
            420                 425                 430
Pro Leu Ile Tyr Glu Met Ile Leu His Glu Phe Leu Gly Ser Asp Tyr
            435                 440                 445
Glu Gly Phe Ala Thr Leu Ile Arg Glu Trp Pro Gly Asp Leu Tyr Asn
450                 455                 460
Asn Ser Val Ile Val Gln Ala Val Arg Asp His Leu Lys Lys Asp Ser
465                 470                 475                 480
Gln Asn Lys Thr Leu Leu Lys Thr Leu Ala Glu Leu Tyr Thr Tyr Asp
                485                 490                 495
Lys Asn Tyr Gly Asn Ala Leu Glu Ile Tyr Leu Thr Leu Arg His Lys
                500                 505                 510
Asp Val Phe Gln Leu Ile His Lys His Asn Leu Phe Ser Ser Ile Lys
            515                 520                 525
```

```
Asp Lys Ile Val Leu Leu Met Asp Phe Asp Ser Glu Lys Ala Val Asp
    530                 535                 540

Met Leu Leu Asp Asn Glu Asp Lys Ile Ser Ile Lys Lys Val Val Glu
545                 550                 555                 560

Glu Leu Glu Asp Arg Pro Glu Leu Gln His Val Tyr Leu His Lys Leu
                565                 570                 575

Phe Lys Arg Asp His His Lys Gly Gln Arg Tyr His Glu Lys Gln Ile
            580                 585                 590

Ser Leu Tyr Ala Glu Tyr Asp Arg Pro Asn Leu Pro Phe Leu Arg
        595                 600                 605

Asp Ser Thr His Cys Pro Leu Glu Lys Ala Leu Glu Ile Cys Gln Gln
    610                 615                 620

Arg Asn Phe Val Glu Glu Thr Val Tyr Leu Leu Ser Arg Met Gly Asn
625                 630                 635                 640

Ser Arg Ser Ala Leu Lys Met Ile Met Glu Glu Leu His Asp Val Asp
                645                 650                 655

Lys Ala Ile Glu Phe Ala Lys Gly Gln Asp Asp Gly Glu Leu Trp Glu
            660                 665                 670

Asp Leu Ile Leu Tyr Ser Ile Asp Lys Pro Pro Phe Ile Thr Gly Leu
        675                 680                 685

Leu Asn Asn Ile Gly Thr His Val Asp Pro Ile Leu Leu Ile His Arg
    690                 695                 700

Ile Lys Glu Gly Met Glu Ile Pro Asn Leu Arg Asp Ser Leu Val Lys
705                 710                 715                 720

Ile Leu Gln Asp Tyr Asn Leu Gln Ile Leu Arg Glu Gly Cys Lys
                725                 730                 735

Lys Ile Leu Val Ala Asp Ser Leu Ser Leu Leu Lys Lys Met His Arg
            740                 745                 750

Thr Gln Met Lys Gly Val Leu Val Asp Glu Glu Asn Ile Cys Glu Ser
        755                 760                 765

Cys Leu Ser Pro Ile Leu Pro Ser Asp Ala Ala Lys Pro Phe Ser Val
    770                 775                 780

Val Val Phe His Cys Arg His Met Phe His Lys Glu Cys Leu Pro Met
785                 790                 795                 800

Pro Ser Met Asn Ser Ala Ala Gln Phe Cys Asn Ile Cys Ser Ala Lys
                805                 810                 815

Asn Arg Gly Pro Gly Ser Ala Ile Leu Glu Met Lys Lys
            820                 825

<210> SEQ ID NO 9
<211> LENGTH: 941
<212> TYPE: PRT
<213> ORGANISM: Homo Sapiens

<400> SEQUENCE: 9

Met Ala Ala Tyr Leu Gln Trp Arg Arg Phe Val Phe Phe Asp Lys Glu
1               5                   10                  15

Leu Val Lys Glu Pro Leu Ser Asn Asp Gly Ala Ala Pro Gly Ala Thr
            20                  25                  30

Pro Ala Ser Gly Ser Ala Ala Ser Lys Phe Leu Cys Leu Pro Pro Gly
        35                  40                  45

Ile Thr Val Cys Asp Ser Gly Arg Gly Ser Leu Val Phe Gly Asp Met
    50                  55                  60

Glu Gly Gln Ile Trp Phe Leu Pro Arg Ser Leu Gln Leu Thr Gly Phe
65                  70                  75                  80
```

```
Gln Ala Tyr Lys Leu Arg Val Thr His Leu Tyr Gln Leu Lys Gln His
            85                  90                  95

Asn Ile Leu Ala Ser Val Gly Glu Asp Glu Glu Gly Ile Asn Pro Leu
            100                 105                 110

Val Lys Ile Trp Asn Leu Glu Lys Arg Asp Gly Gly Asn Pro Leu Cys
            115                 120                 125

Thr Arg Ile Phe Pro Ala Ile Pro Gly Thr Glu Pro Thr Val Val Ser
130                 135                 140

Cys Leu Thr Val His Glu Asn Leu Asn Phe Met Ala Ile Gly Phe Thr
145                 150                 155                 160

Asp Gly Ser Val Thr Leu Asn Lys Gly Asp Ile Thr Arg Asp Arg His
            165                 170                 175

Ser Lys Thr Gln Ile Leu His Lys Gly Asn Tyr Pro Val Thr Gly Leu
            180                 185                 190

Ala Phe Arg Gln Ala Gly Lys Thr Thr His Leu Phe Val Val Thr Thr
            195                 200                 205

Glu Asn Val Gln Ser Tyr Ile Val Ser Gly Lys Asp Tyr Pro Arg Val
210                 215                 220

Glu Leu Asp Thr His Gly Cys Gly Leu Arg Cys Ser Ala Leu Ser Asp
225                 230                 235                 240

Pro Ser Gln Asp Leu Gln Phe Ile Val Ala Gly Asp Glu Cys Val Tyr
            245                 250                 255

Leu Tyr Gln Pro Asp Glu Arg Gly Pro Cys Phe Ala Phe Glu Gly His
            260                 265                 270

Lys Leu Ile Ala His Trp Phe Arg Gly Tyr Leu Ile Ile Val Ser Arg
            275                 280                 285

Asp Arg Lys Val Ser Pro Lys Ser Glu Phe Thr Ser Arg Asp Ser Gln
290                 295                 300

Ser Ser Asp Lys Gln Ile Leu Asn Ile Tyr Asp Leu Cys Asn Lys Phe
305                 310                 315                 320

Ile Ala Tyr Ser Thr Val Phe Glu Asp Val Val Asp Val Leu Ala Glu
            325                 330                 335

Trp Gly Ser Leu Tyr Val Leu Thr Arg Asp Gly Arg Val His Ala Leu
            340                 345                 350

Gln Glu Lys Asp Thr Gln Thr Lys Leu Glu Met Leu Phe Lys Lys Asn
            355                 360                 365

Leu Phe Glu Met Ala Ile Asn Leu Ala Lys Ser Gln His Leu Asp Ser
370                 375                 380

Asp Gly Leu Ala Gln Ile Phe Met Gln Tyr Gly Asp His Leu Tyr Ser
385                 390                 395                 400

Lys Gly Asn His Asp Gly Ala Val Gln Gln Tyr Ile Arg Thr Ile Gly
            405                 410                 415

Lys Leu Glu Pro Ser Tyr Val Ile Arg Lys Phe Leu Asp Ala Gln Arg
            420                 425                 430

Ile His Asn Leu Thr Ala Tyr Leu Gln Thr Leu His Arg Gln Ser Leu
            435                 440                 445

Ala Asn Ala Asp His Thr Thr Leu Leu Leu Asn Cys Tyr Thr Lys Leu
450                 455                 460

Lys Asp Ser Ser Lys Leu Glu Glu Phe Ile Lys Lys Ser Glu Ser
465                 470                 475                 480

Glu Val His Phe Asp Val Glu Thr Ala Ile Lys Val Leu Arg Gln Ala
            485                 490                 495
```

```
Gly Tyr Tyr Ser His Ala Leu Tyr Leu Ala Glu Asn His Ala His His
                500                 505                 510
Glu Trp Tyr Leu Lys Ile Gln Leu Glu Asp Ile Lys Asn Tyr Gln Glu
    515                 520                 525
Ala Leu Arg Tyr Ile Gly Lys Leu Pro Phe Glu Gln Ala Glu Ser Asn
530                 535                 540
Met Lys Arg Tyr Gly Lys Ile Leu Met His His Ile Pro Glu Gln Thr
545                 550                 555                 560
Thr Gln Leu Leu Lys Gly Leu Cys Thr Asp Tyr Arg Pro Ser Leu Glu
                565                 570                 575
Gly Arg Ser Asp Arg Glu Ala Pro Gly Cys Arg Ala Asn Ser Glu Glu
            580                 585                 590
Phe Ile Pro Ile Phe Ala Asn Asn Pro Arg Glu Leu Lys Ala Phe Leu
        595                 600                 605
Glu His Met Ser Glu Val Gln Pro Asp Ser Pro Gln Gly Ile Tyr Asp
    610                 615                 620
Thr Leu Leu Glu Leu Arg Leu Gln Asn Trp Ala His Glu Lys Asp Pro
625                 630                 635                 640
Gln Val Lys Glu Lys Leu His Ala Glu Ala Ile Ser Leu Leu Lys Ser
                645                 650                 655
Gly Arg Phe Cys Asp Val Phe Asp Lys Ala Leu Val Leu Cys Gln Met
            660                 665                 670
His Asp Phe Gln Asp Gly Val Leu Tyr Leu Tyr Glu Gln Gly Lys Leu
        675                 680                 685
Phe Gln Gln Ile Met His Tyr His Met Gln His Glu Gln Tyr Arg Gln
    690                 695                 700
Val Ile Ser Val Cys Glu Arg His Gly Glu Gln Asp Pro Ser Leu Trp
705                 710                 715                 720
Glu Gln Ala Leu Ser Tyr Phe Ala Arg Lys Glu Glu Asp Cys Lys Glu
                725                 730                 735
Tyr Val Ala Ala Val Leu Lys His Ile Glu Asn Lys Asn Leu Met Pro
            740                 745                 750
Pro Leu Leu Val Val Gln Thr Leu Ala His Asn Ser Thr Ala Thr Leu
        755                 760                 765
Ser Val Ile Arg Asp Tyr Leu Val Gln Lys Leu Gln Lys Gln Ser Gln
    770                 775                 780
Gln Ile Ala Gln Asp Glu Leu Arg Val Arg Arg Tyr Arg Glu Glu Thr
785                 790                 795                 800
Thr Arg Ile Arg Gln Glu Ile Gln Glu Leu Lys Ala Ser Pro Lys Ile
                805                 810                 815
Phe Gln Lys Thr Lys Cys Ser Ile Cys Asn Ser Ala Leu Glu Leu Pro
            820                 825                 830
Ser Val His Phe Leu Cys Gly His Ser Phe His Gln His Cys Phe Glu
        835                 840                 845
Ser Tyr Ser Glu Ser Asp Ala Asp Cys Pro Thr Cys Leu Pro Glu Asn
    850                 855                 860
Arg Lys Val Met Asp Met Ile Arg Ala Gln Glu Gln Lys Arg Asp Leu
865                 870                 875                 880
His Asp Gln Phe Gln His Gln Leu Lys Cys Ser Asn Asp Ser Phe Ser
                885                 890                 895
Val Ile Ala Asp Tyr Phe Gly Arg Gly Val Phe Asn Lys Leu Thr Leu
            900                 905                 910
```

-continued

Leu Thr Asp Pro Pro Thr Ala Arg Leu Thr Ser Ser Leu Glu Ala Gly
            915                 920                 925

Leu Gln Arg Asp Leu Leu Met His Ser Arg Arg Gly Thr
    930                 935                 940

<210> SEQ ID NO 10
<211> LENGTH: 931
<212> TYPE: PRT
<213> ORGANISM: Homo Sapiens

<400> SEQUENCE: 10

Met Lys Ser Val Cys Arg Arg Gly Pro Cys Arg Ala Pro Leu Trp Phe
1               5                   10                  15

Ser Trp Ser Ser Arg Val Val Leu Trp Ser Thr Gly Arg Lys Lys Glu
            20                  25                  30

Val His Leu Leu Thr Cys Tyr Gln Leu Ser Asn Pro Gly Arg Leu Leu
        35                  40                  45

Asp Tyr Pro Ala His Met Glu Gly Gln Ile Trp Phe Leu Pro Arg Ser
    50                  55                  60

Leu Gln Leu Thr Gly Phe Gln Ala Tyr Lys Leu Arg Val Thr His Leu
65                  70                  75                  80

Tyr Gln Leu Lys Gln His Asn Ile Leu Ala Ser Val Gly Glu Asp Glu
                85                  90                  95

Glu Gly Ile Asn Pro Leu Val Lys Ile Trp Asn Leu Glu Lys Arg Asp
            100                 105                 110

Gly Gly Asn Pro Leu Cys Thr Arg Ile Phe Pro Ala Ile Pro Gly Thr
        115                 120                 125

Glu Pro Thr Val Val Ser Cys Leu Thr Val His Glu Asn Leu Asn Phe
    130                 135                 140

Met Ala Ile Gly Phe Thr Asp Gly Ser Val Thr Leu Asn Lys Gly Asp
145                 150                 155                 160

Ile Thr Arg Asp Arg His Ser Lys Thr Gln Ile Leu His Lys Gly Asn
                165                 170                 175

Tyr Pro Val Thr Gly Leu Ala Phe Arg Gln Ala Gly Lys Thr Thr His
            180                 185                 190

Leu Phe Val Val Thr Thr Glu Asn Val Gln Ser Tyr Ile Val Ser Gly
        195                 200                 205

Lys Asp Tyr Pro Arg Val Glu Leu Asp Thr His Gly Cys Gly Leu Arg
    210                 215                 220

Cys Ser Ala Leu Ser Asp Pro Ser Gln Asp Leu Gln Phe Ile Val Ala
225                 230                 235                 240

Gly Asp Glu Cys Val Tyr Leu Tyr Gln Pro Asp Glu Arg Gly Pro Cys
                245                 250                 255

Phe Ala Phe Glu Gly His Lys Leu Ile Ala His Trp Phe Arg Gly Tyr
            260                 265                 270

Leu Ile Ile Val Ser Arg Asp Arg Lys Val Ser Pro Lys Ser Glu Phe
        275                 280                 285

Thr Ser Arg Asp Ser Gln Ser Ser Asp Lys Gln Ile Leu Asn Ile Tyr
    290                 295                 300

Asp Leu Cys Asn Lys Phe Ile Ala Tyr Ser Thr Val Phe Glu Asp Val
305                 310                 315                 320

Val Asp Val Leu Ala Glu Trp Gly Ser Leu Tyr Val Leu Thr Arg Asp
                325                 330                 335

```
Gly Arg Val His Ala Leu Gln Glu Lys Asp Thr Gln Thr Lys Leu Glu
            340                 345                 350

Met Leu Phe Lys Lys Asn Leu Phe Glu Met Ala Ile Asn Leu Ala Lys
            355                 360                 365

Ser Gln His Leu Asp Ser Asp Gly Leu Ala Gln Ile Phe Met Gln Tyr
            370                 375                 380

Gly Asp His Leu Tyr Ser Lys Gly Asn His Asp Gly Ala Val Gln Gln
385                 390                 395                 400

Tyr Ile Arg Thr Ile Gly Lys Leu Glu Pro Ser Tyr Val Ile Arg Lys
                405                 410                 415

Phe Leu Asp Ala Gln Arg Ile His Asn Leu Thr Ala Tyr Leu Gln Thr
            420                 425                 430

Leu His Arg Gln Ser Leu Ala Asn Ala Asp His Thr Thr Leu Leu Leu
            435                 440                 445

Asn Cys Tyr Thr Lys Leu Lys Asp Ser Ser Lys Leu Glu Glu Phe Ile
            450                 455                 460

Lys Lys Lys Ser Glu Ser Glu Val His Phe Asp Val Glu Thr Ala Ile
465                 470                 475                 480

Lys Val Leu Arg Gln Ala Gly Tyr Tyr Ser His Ala Leu Tyr Leu Ala
                485                 490                 495

Glu Asn His Ala His His Glu Trp Tyr Leu Lys Ile Gln Leu Glu Asp
            500                 505                 510

Ile Lys Asn Tyr Gln Glu Ala Leu Arg Tyr Ile Gly Lys Leu Pro Phe
            515                 520                 525

Glu Gln Ala Glu Ser Asn Met Lys Arg Tyr Gly Lys Ile Leu Met His
            530                 535                 540

His Ile Pro Glu Gln Thr Thr Gln Leu Leu Lys Gly Leu Cys Thr Asp
545                 550                 555                 560

Tyr Arg Pro Ser Leu Glu Gly Arg Ser Asp Arg Glu Ala Pro Gly Cys
                565                 570                 575

Arg Ala Asn Ser Glu Glu Phe Ile Pro Ile Phe Ala Asn Asn Pro Arg
            580                 585                 590

Glu Leu Lys Ala Phe Leu Glu His Met Ser Glu Val Gln Pro Asp Ser
            595                 600                 605

Pro Gln Gly Ile Tyr Asp Thr Leu Leu Glu Leu Arg Leu Gln Asn Trp
            610                 615                 620

Ala His Glu Lys Asp Pro Gln Val Lys Glu Lys Leu His Ala Glu Ala
625                 630                 635                 640

Ile Ser Leu Leu Lys Ser Gly Arg Phe Cys Asp Val Phe Asp Lys Ala
                645                 650                 655

Leu Val Leu Cys Gln Met His Asp Phe Gln Asp Gly Val Leu Tyr Leu
            660                 665                 670

Tyr Glu Gln Gly Lys Leu Phe Gln Gln Ile Met His Tyr His Met Gln
            675                 680                 685

His Glu Gln Tyr Arg Gln Val Ile Ser Val Cys Glu Arg His Gly Glu
            690                 695                 700

Gln Asp Pro Ser Leu Trp Glu Gln Ala Leu Ser Tyr Phe Ala Arg Lys
705                 710                 715                 720

Glu Glu Asp Cys Lys Glu Tyr Val Ala Ala Val Leu Lys His Ile Glu
                725                 730                 735

Asn Lys Asn Leu Met Pro Pro Leu Leu Val Val Gln Thr Leu Ala His
            740                 745                 750
```

```
Asn Ser Thr Ala Thr Leu Ser Val Ile Arg Asp Tyr Leu Val Gln Lys
            755                 760                 765

Leu Gln Lys Gln Ser Gln Gln Ile Ala Gln Asp Glu Leu Arg Val Arg
    770                 775                 780

Arg Tyr Arg Glu Glu Thr Thr Arg Ile Arg Gln Glu Ile Gln Glu Leu
785                 790                 795                 800

Lys Ala Ser Pro Lys Ile Phe Gln Lys Thr Lys Cys Ser Ile Cys Asn
                805                 810                 815

Ser Ala Leu Glu Leu Pro Ser Val His Phe Leu Cys Gly His Ser Phe
            820                 825                 830

His Gln His Cys Phe Glu Ser Tyr Ser Glu Ser Asp Ala Asp Cys Pro
    835                 840                 845

Thr Cys Leu Pro Glu Asn Arg Lys Val Met Asp Met Ile Arg Ala Gln
850                 855                 860

Glu Gln Lys Arg Asp Leu His Asp Gln Phe Gln His Gln Leu Lys Cys
865                 870                 875                 880

Ser Asn Asp Ser Phe Ser Val Ile Ala Asp Tyr Phe Gly Arg Gly Val
                885                 890                 895

Phe Asn Lys Leu Thr Leu Leu Thr Asp Pro Pro Thr Ala Arg Leu Thr
            900                 905                 910

Ser Ser Leu Glu Ala Gly Leu Gln Arg Asp Leu Leu Met His Ser Arg
    915                 920                 925

Arg Gly Thr
    930

<210> SEQ ID NO 11
<211> LENGTH: 875
<212> TYPE: PRT
<213> ORGANISM: Homo Sapiens

<400> SEQUENCE: 11

Met His Asp Ala Phe Glu Pro Val Pro Ile Leu Glu Lys Leu Pro Leu
1               5                   10                  15

Gln Ile Asp Cys Leu Ala Ala Trp Glu Glu Trp Leu Leu Val Gly Thr
            20                  25                  30

Lys Gln Gly His Leu Leu Tyr Arg Ile Arg Lys Asp Val Gly Cys
    35                  40                  45

Asn Arg Phe Glu Val Thr Leu Glu Lys Ser Asn Lys Asn Phe Ser Lys
50                  55                  60

Lys Ile Gln Gln Ile His Val Val Ser Gln Phe Lys Ile Leu Val Ser
65                  70                  75                  80

Leu Leu Glu Asn Asn Ile Tyr Val His Asp Leu Leu Thr Phe Gln Gln
            85                  90                  95

Ile Thr Thr Val Ser Lys Ala Lys Gly Ala Ser Leu Phe Thr Cys Asp
                100                 105                 110

Leu Gln His Thr Glu Thr Gly Glu Glu Val Leu Arg Met Cys Val Ala
            115                 120                 125

Val Lys Lys Lys Leu Gln Leu Tyr Phe Trp Lys Asp Arg Glu Phe His
    130                 135                 140

Glu Leu Gln Gly Asp Phe Ser Val Pro Asp Val Pro Lys Ser Met Ala
145                 150                 155                 160

Trp Cys Glu Asn Ser Ile Cys Val Gly Phe Lys Arg Asp Tyr Tyr Leu
                165                 170                 175

Ile Arg Val Asp Gly Lys Gly Ser Ile Lys Glu Leu Phe Pro Thr Gly
            180                 185                 190
```

```
Lys Gln Leu Glu Pro Leu Val Ala Pro Leu Ala Asp Gly Lys Val Ala
        195                 200                 205

Val Gly Gln Asp Asp Leu Thr Val Val Leu Asn Glu Glu Gly Ile Cys
    210                 215                 220

Thr Gln Lys Cys Ala Leu Asn Trp Thr Asp Ile Pro Val Ala Met Glu
225                 230                 235                 240

His Gln Pro Pro Tyr Ile Ile Ala Val Leu Pro Arg Tyr Val Glu Ile
                245                 250                 255

Arg Thr Phe Glu Pro Arg Leu Val Gln Ser Ile Glu Leu Gln Arg
                260                 265                 270

Pro Arg Phe Ile Thr Ser Gly Gly Ser Asn Ile Ile Tyr Val Ala Ser
                275                 280                 285

Asn His Phe Val Trp Arg Leu Ile Pro Val Pro Met Ala Thr Gln Ile
    290                 295                 300

Gln Gln Leu Leu Gln Asp Lys Gln Phe Glu Leu Ala Leu Gln Leu Ala
305                 310                 315                 320

Glu Met Lys Asp Asp Ser Asp Ser Glu Lys Gln Gln Ile His His
                325                 330                 335

Ile Lys Asn Leu Tyr Ala Phe Asn Leu Phe Cys Gln Lys Arg Phe Asp
                340                 345                 350

Glu Ser Met Gln Val Phe Ala Lys Leu Gly Thr Asp Pro Thr His Val
            355                 360                 365

Met Gly Leu Tyr Pro Asp Leu Leu Pro Thr Asp Tyr Arg Lys Gln Leu
    370                 375                 380

Gln Tyr Pro Asn Pro Leu Pro Val Leu Ser Gly Ala Glu Leu Glu Lys
385                 390                 395                 400

Ala His Leu Ala Leu Ile Asp Tyr Leu Thr Gln Lys Arg Ser Gln Leu
                405                 410                 415

Val Lys Lys Leu Asn Asp Ser Asp His Gln Ser Ser Thr Ser Pro Leu
                420                 425                 430

Met Glu Gly Thr Pro Thr Ile Lys Ser Lys Lys Leu Leu Gln Ile
    435                 440                 445

Ile Asp Thr Thr Leu Leu Lys Cys Tyr Leu His Thr Asn Val Ala Leu
    450                 455                 460

Val Ala Pro Leu Leu Arg Leu Glu Asn Asn His Cys His Ile Glu Glu
465                 470                 475                 480

Ser Glu His Val Leu Lys Lys Ala His Lys Tyr Ser Glu Leu Ile Ile
                485                 490                 495

Leu Tyr Glu Lys Lys Gly Leu His Glu Lys Ala Leu Gln Val Leu Val
            500                 505                 510

Asp Gln Ser Lys Lys Ala Asn Ser Pro Leu Lys Gly His Glu Arg Thr
            515                 520                 525

Val Gln Tyr Leu Gln His Leu Gly Thr Glu Asn Leu His Leu Ile Phe
    530                 535                 540

Ser Tyr Ser Val Trp Val Leu Arg Asp Phe Pro Glu Asp Gly Leu Lys
545                 550                 555                 560

Ile Phe Thr Glu Asp Leu Pro Glu Val Glu Ser Leu Pro Arg Asp Arg
                565                 570                 575

Val Leu Gly Phe Leu Ile Glu Asn Phe Lys Gly Leu Ala Ile Pro Tyr
            580                 585                 590

Leu Glu His Ile Ile His Val Trp Glu Glu Thr Gly Ser Arg Phe His
    595                 600                 605
```

Asn Cys Leu Ile Gln Leu Tyr Cys Glu Lys Val Gln Gly Leu Met Lys
610                 615                 620

Glu Tyr Leu Leu Ser Phe Pro Ala Gly Lys Thr Pro Val Pro Ala Gly
625                 630                 635                 640

Glu Glu Glu Gly Glu Leu Gly Glu Tyr Arg Gln Lys Leu Leu Met Phe
            645                 650                 655

Leu Glu Ile Ser Ser Tyr Tyr Asp Pro Gly Arg Leu Ile Cys Asp Phe
            660                 665                 670

Pro Phe Asp Gly Leu Leu Glu Arg Ala Leu Leu Leu Gly Arg Met
            675                 680                 685

Gly Lys His Glu Gln Ala Leu Phe Ile Tyr Val His Ile Leu Lys Asp
690                 695                 700

Thr Arg Met Ala Glu Glu Tyr Cys His Lys His Tyr Asp Arg Asn Lys
705                 710                 715                 720

Asp Gly Asn Lys Asp Val Tyr Leu Ser Leu Leu Arg Met Tyr Leu Ser
            725                 730                 735

Pro Pro Ser Ile His Cys Leu Gly Pro Ile Lys Leu Glu Leu Leu Glu
            740                 745                 750

Pro Lys Ala Asn Leu Gln Ala Ala Leu Gln Val Leu Glu Leu His His
            755                 760                 765

Ser Lys Leu Asp Thr Thr Lys Ala Leu Asn Leu Leu Pro Ala Asn Thr
770                 775                 780

Gln Ile Asn Asp Ile Arg Ile Phe Leu Glu Lys Val Leu Glu Glu Asn
785                 790                 795                 800

Ala Gln Lys Lys Arg Phe Asn Gln Val Leu Lys Asn Leu Leu His Ala
            805                 810                 815

Glu Phe Leu Arg Val Gln Glu Glu Arg Ile Leu His Gln Gln Val Lys
            820                 825                 830

Cys Ile Ile Thr Glu Glu Lys Val Cys Met Val Cys Lys Lys Lys Ile
            835                 840                 845

Gly Asn Ser Ala Phe Ala Arg Tyr Pro Asn Gly Val Val Val His Tyr
850                 855                 860

Phe Cys Ser Lys Glu Val Asn Pro Ala Asp Thr
865                 870                 875

<210> SEQ ID NO 12
<211> LENGTH: 186
<212> TYPE: PRT
<213> ORGANISM: Artificial Sequence
<220> FEATURE:
<223> OTHER INFORMATION: T34N substitution, GDP-binding

<400> SEQUENCE: 12

Met Leu Ala Leu Ile Ser Arg Leu Leu Asp Trp Phe Arg Ser Leu Phe
1               5                   10                  15

Trp Lys Glu Glu Met Glu Leu Thr Leu Val Gly Leu Gln Tyr Ser Gly
            20                  25                  30

Lys Asn Thr Phe Val Asn Val Ile Ala Ser Gly Gln Phe Ser Glu Asp
            35                  40                  45

Met Ile Pro Thr Val Gly Phe Asn Met Arg Lys Val Thr Lys Gly Asn
50                  55                  60

Val Thr Ile Lys Ile Trp Asp Ile Gly Gly Gln Pro Arg Phe Arg Ser
65                  70                  75                  80

Met Trp Glu Arg Tyr Cys Arg Gly Val Asn Ala Ile Val Tyr Met Ile
            85                  90                  95

Asp Ala Ala Asp Arg Glu Lys Ile Glu Ala Ser Arg Asn Glu Leu His
            100                 105                 110

Asn Leu Leu Asp Lys Pro Gln Leu Gln Gly Ile Pro Val Leu Val Leu
        115                 120                 125

Gly Asn Lys Arg Asp Leu Pro Asn Ala Leu Asp Glu Lys Gln Leu Ile
130                 135                 140

Glu Lys Met Asn Leu Ser Ala Ile Gln Asp Arg Glu Ile Cys Cys Tyr
145                 150                 155                 160

Ser Ile Ser Cys Lys Glu Lys Asp Asn Ile Asp Ile Thr Leu Gln Trp
                165                 170                 175

Leu Ile Gln His Ser Lys Ser Arg Arg Ser
            180                 185

<210> SEQ ID NO 13
<211> LENGTH: 186
<212> TYPE: PRT
<213> ORGANISM: Artificial Sequence
<220> FEATURE:
<223> OTHER INFORMATION: Q75L substitution, GTP-binding

<400> SEQUENCE: 13

Met Leu Ala Leu Ile Ser Arg Leu Leu Asp Trp Phe Arg Ser Leu Phe
1               5                   10                  15

Trp Lys Glu Glu Met Glu Leu Thr Leu Val Gly Leu Gln Tyr Ser Gly
            20                  25                  30

Lys Thr Thr Phe Val Asn Val Ile Ala Ser Gly Gln Phe Ser Glu Asp
        35                  40                  45

Met Ile Pro Thr Val Gly Phe Asn Met Arg Lys Val Thr Lys Gly Asn
50                  55                  60

Val Thr Ile Lys Ile Trp Asp Ile Gly Gly Leu Pro Arg Phe Arg Ser
65                  70                  75                  80

Met Trp Glu Arg Tyr Cys Arg Gly Val Asn Ala Ile Val Tyr Met Ile
                85                  90                  95

Asp Ala Ala Asp Arg Glu Lys Ile Glu Ala Ser Arg Asn Glu Leu His
            100                 105                 110

Asn Leu Leu Asp Lys Pro Gln Leu Gln Gly Ile Pro Val Leu Val Leu
        115                 120                 125

Gly Asn Lys Arg Asp Leu Pro Asn Ala Leu Asp Glu Lys Gln Leu Ile
130                 135                 140

Glu Lys Met Asn Leu Ser Ala Ile Gln Asp Arg Glu Ile Cys Cys Tyr
145                 150                 155                 160

Ser Ile Ser Cys Lys Glu Lys Asp Asn Ile Asp Ile Thr Leu Gln Trp
                165                 170                 175

Leu Ile Gln His Ser Lys Ser Arg Arg Ser
            180                 185

<210> SEQ ID NO 14
<211> LENGTH: 1327
<212> TYPE: DNA
<213> ORGANISM: Artificial Sequence
<220> FEATURE:
<223> OTHER INFORMATION: GFP labelled Arl8bWT

<400> SEQUENCE: 14
ttccccaaat tataggagca gagctctctg gctactagag aacccactgc ttactggctt     60
atcgaaatta atacgactca ctatagggag acccaagctg gctagttaag cttggtaccg    120
agctcggatc cactagtcca gtgtggtgga attgcccttc accatgctgg cgctcatctc    180

| ccgcctgctg gactggttcc gttcgctctt ctggaaggaa gagatggagc tgacgctcgt | 240 |
| gggggctgcag tactcgggca agaccacctt cgtcaatgtc atcgcgtcag gtcaattcag | 300 |
| tgaagatatg atacccacag tgggcttcaa catgaggaag gtaactaaag gtaacgtcac | 360 |
| aataaagatc tgggacatag gaggacaacc ccgattcgaa agcatgtggg agcggtattg | 420 |
| cagaggagtc aatgctattg tttacatgat agatgctgca gatcgtgaaa agatagaagc | 480 |
| ttcccgaaat gagctacata atcttctaga taaaccacag ttacaaggaa ttccagtgct | 540 |
| agtgcttgga aacaagagag atcttcctaa tgccttggat gagaaacagc taattgaaaa | 600 |
| aatgaatctg tctgctattc aggatagaga aatttgctgc tattcaattt cttgcaaaga | 660 |
| aaaggataat atagatatca cacttcagtg gcttattcag cattcaaaat ctagaagaag | 720 |
| cgaagggcaa ttctgcagat atccagcaca gtggcggccg ctcgagtcta gaatggctag | 780 |
| caaaggagaa gaacttttca ctggagttgt cccaattctt gtttgaatta gatggtgatg | 840 |
| ttaatgggca caaattttct gtcagtggag agggtgaagg tgaatgctac atacggaaag | 900 |
| cttaccctta aatttatttt gcactactgg aaaactacct gttccatggg ccaatacttg | 960 |
| tcactacttt ctcttatgtt gtccatgctt tttcccgtta ccggataat atgaaacggc | 1020 |
| atgacttttc cagagtgcca tggcccgaag ggttatgttc taggaacgca cttatatctt | 1080 |
| tcaagatgac gggaactaac aagaacccgt gctgaagtca gtttgaagg ggataccttg | 1140 |
| gtttatcgta cgagtttaaa gggtattgat tttaaagaaa taggaatacc atcctccgga | 1200 |
| ctcctacttc tgtagttcca ctctattacc tccccaccat tgtgttatat tccatgtgcc | 1260 |
| ggctcaccaa gtgaatggta ttactaagct aatactctca tcaatcttcc tccaccaaca | 1320 |
| cactgag | 1327 |

<210> SEQ ID NO 15
<211> LENGTH: 1250
<212> TYPE: DNA
<213> ORGANISM: Artificial Sequence
<220> FEATURE:
<223> OTHER INFORMATION: mcherry labelled Arl8bWT

<400> SEQUENCE: 15

| cacccaagac aaaagcagag ctggtttagt gaccgtcaga tccgctagcg ctaccggact | 60 |
| cagatctcga gatgctggcg ctcatctccc gcctgctgga ctggttccgt tcgctcttct | 120 |
| ggaaggaaga gatggagctg acgctcgtgg ggctgcagta ctcgggcaag accaccttcg | 180 |
| tcaatgtcat cgcgtcaggt caattcagtg aagatatgat acccacagtg ggcttcaaca | 240 |
| tgaggaaggt aactaaaggt aacgtcacaa taaagatctg ggacataggga ggacaacccc | 300 |
| gatttcgaag catgtgggag cggtattgca gaggagtcaa tgctattgtt tacatgatag | 360 |
| atgctgcaga tcgtgaaaag atagaagctt cccgaaatga gctacataat cttctagata | 420 |
| aaccacagtt acaaggaatt ccagtgctag tgcttggaaa caagagagat cttcctaatg | 480 |
| ccttggatga gaaacagcta attgaaaaaa tgaatctgtc tgctattcag gatagagaaa | 540 |
| tttgctgcta ttcaatttct tgcaaagaaa aggataatat agatatcaca cttcagtggc | 600 |
| ttattcagca ttcaaaatct agaagaagcc gggatccgat ggtgagcaag ggcgaggagg | 660 |
| ataacatggc catcatcaag gagttcatgc gcttcaaggt gcacatggag ggctccgtga | 720 |
| acggccacga gttcgagatc gagggcgagg gcgagggccg cccctacgag ggcacccaga | 780 |
| ccgccaagct gaaggtgacc aagggtggcc ccctgccctt cgcctgggac atcctgtccc | 840 |

-continued

| | |
|---|---|
| ctcagttcat gtacggctcc aaggcctacg tgaagcaccc cgccgacatc cccgactact | 900 |
| tgaagctgtc cttccccgag ggcttcaagt gggagcgcgt gatgaacttc gaggacggcg | 960 |
| gcgtggtgac cgtgacccag gactcctccc tgcaggacgg cgagttcatc tacaagtgaa | 1020 |
| gctgcgcggc accaacttcc cctccgacgg ccccgtaatg cagaagagga ccatgggctg | 1080 |
| gaggcctcct cgagcgatgt accccgagga cgcgccctga ggcgagatca gcagaggctg | 1140 |
| agctgagacg ccgccactac gacgctgagt cagaactact acaagtcaga gccggcagct | 1200 |
| gctggcctac acgtcacttc agtggaactt aacttcacaa agcgaggaac | 1250 |

<210> SEQ ID NO 16
<211> LENGTH: 1193
<212> TYPE: DNA
<213> ORGANISM: Artificial Sequence
<220> FEATURE:
<223> OTHER INFORMATION: mcherry labelled Arl8bQ75L

<400> SEQUENCE: 16

| | |
|---|---|
| tttcaacgga atacaaatag cgagctggtt tagtgaccgt cagatccgct agcgctaccg | 60 |
| gactcagatc tcgagatgct ggcgctcatc tcccgcctgc tggactggtt ccgttcgctc | 120 |
| ttctggaagg aagagatgga gctgacgctc gtggggctgc agtactcggg caagaccacc | 180 |
| ttcgtcaatg tcatcgcgtc aggtcaattc agtgaagata tgatacccac agtgggcttc | 240 |
| aacatgagga aggtaactaa aggtaacgtc acaataaaga tctgggacat aggaggacta | 300 |
| ccccgatttc gaagcatgtg ggagcggtat tgcagaggag tcaatgctat tgtttacatg | 360 |
| atagatgctg cagatcgtga aaagatagaa gcttcccgaa atgagctaca taatcttcta | 420 |
| gataaaccac agttacaagg aattccagtg ctagtgcttg aaacaagag atcttcct | 480 |
| aatgccttgg atgagaaaca gctaattgaa aaaatgaatc tgtctgctat tcaggataga | 540 |
| gaaatttgct gctattcaat ttcttgcaaa gaaaaggata atatagatat cacacttcag | 600 |
| tggcttattc agcattcaaa atctagaaga agccggatc cgatggtgag caagggcgag | 660 |
| gaggataaca tggccatcat caaggagttc atgcgcttca aggtgcacat ggagggctcc | 720 |
| gtgaacggcc acgagttcga gatcgagggc gaggcgagg ccgcccta cgagggcacc | 780 |
| cagaccgcca agctgaaggt gaccaagggt ggccccctgc ccttcgcctg gacatcctg | 840 |
| tcccctcagt tcatgtacgg ctccaaggcc tacgtgaagc accccgccga catccccgac | 900 |
| tacttgaagc tgtccttccc cgagggcttc aagtgggagc gcgtgatgaa cttcgaggac | 960 |
| ggcggcgtgg tgaccgtgac ccaggactcc tccctgcagg acggcgagtt catctacagt | 1020 |
| gaagctgcgc ggcaccaact tcccctccga cgctcgtatg cagagagaca tgggctggga | 1080 |
| gctctcgagc gatgtacccg agacgcgcct gaggcgagat cagcagagct gagctgagga | 1140 |
| cgcgcactac gacgctgaag tcagacacta cagtcagaag ccgttcagct gcc | 1193 |

<210> SEQ ID NO 17
<211> LENGTH: 1311
<212> TYPE: DNA
<213> ORGANISM: Artificial Sequence
<220> FEATURE:
<223> OTHER INFORMATION: mcherry labelled Arl8bT34N

<400> SEQUENCE: 17

| | |
|---|---|
| ataaccccaa tacaaaagca gagctggttt agtgaccgtc agatccgcta gcgctaccgg | 60 |
| actcagatct cgagatgctg gcgctcatct cccgcctgct ggactggttc cgttcgctct | 120 |
| tctggaagga agagatggag ctgacgctcg tggggctgca gtactcgggc aagaacacct | 180 |

```
tcgtcaatgt catcgcgtca ggtcaattca gtgaagatat gatacccaca gtgggcttca      240
acatgaggaa ggtaactaaa ggtaacgtca caataaagat ctgggacata ggaggacaac      300
cccgatttcg aagcatgtgg gagcggtatt gcagaggagt caatgctatt gtttacatga      360
tagatgctgc agatcgtgaa aagatagaag cttcccgaaa tgagctacat aatcttctag      420
ataaaccaca gttacaagga attccagtgc tagtgcttgg aaacaagaga gatcttccta      480
atgccttgga tgagaaacag ctaattgaaa agatgaatct gtctgctatt caggatagag      540
aaatttgctg ctattcaatt tcttgcaaag aaaaggataa tatagatatc acacttcagt      600
ggcttattca gcattcaaaa tctagaagaa gccgggatcc gatggtgagc aagggcgagg      660
aggataacat ggccatcatc aaggagttca tgcgcttcaa ggtgcacatg gagggctccg      720
tgaacggcca cgagttcgag atcgagggcg agggcgaggg ccgcccctac gagggcaccc      780
agaccgccaa gctgaaggtg accaagggtg gccccctgcc cttcgcctgg gacatcctgt      840
cccctcagtt catgtacggc tccaaggcct acgtgaagca cccgccgac atccccgact      900 acttgaagct gtccttcccc gagggcttca gtgggagcg cgtgatgaac ttccaggacg      960
gcggcgtggt gaccgtgacc caggacttcc tccctgcag acggcgagt tcatctacaa     1020 agtgaagctg cgcgggcacc aacttccccc tccgacggcc ccgtaatgca gaagaaagac     1080
catgggcctg gaaggccttc ctcgagcgat gttacccgaa gacggcgtcc ctgaaaggcg     1140
agatatcagc atgaagctga agcttgaaga tcggcgtcac ttacgtactg ccttgagtca     1200
tagaccaact tacaagccat agaagtcggt gcagcttgtc ctgtccttta cacatgctct     1260
ataactatct aagtttggaa acattcacta cggtctacac agcaggatga c              1311

<210> SEQ ID NO 18
<211> LENGTH: 1250
<212> TYPE: DNA
<213> ORGANISM: Artificial Sequence
<220> FEATURE:
<223> OTHER INFORMATION: MG1021 vector

<400> SEQUENCE: 18
cacccaagac aaaagcagag ctggtttagt gaccgtcaga tccgctagcg ctaccggact       60
cagatctcga gatgctggcg ctcatctccc gcctgctgga ctggttccgt tcgctcttct      120
ggaaggaaga gatggagctg acgctcgtgg ggctgcagta ctcgggcaag accaccttcg      180
tcaatgtcat cgcgtcaggt caattcagtg aagatatgat acccacagtg gcttcaaca      240 tgaggaaggt aactaaaggt aacgtcacaa taaagatctg gacatagga ggacaacccc      300 gatttcgaag catgtgggag cggtattgca gaggagtcaa tgctattgtt tacatgatag      360
atgctgcaga tcgtgaaaag atagaagctt cccgaaatga gctacataat cttctagata      420
aaccacagtt acaaggaatt ccagtgctag tgcttggaaa caagagagat cttcctaatg      480
ccttggatga gaaacagcta attgaaaaaa tgaatctgtc tgctattcag gatagagaaa      540
tttgctgcta ttcaatttct tgcaaagaaa aggataatat agatatcaca cttcagtggc      600
ttattcagca ttcaaaatct agaagaagcc gggatccgat ggtgagcaag ggcgaggagg      660
ataacatggc catcatcaag gagttcatgc gcttcaaggt gcacatggag ggctccgtga      720
acggccacga gttcgagatc gagggcgagg gcgagggccg ccctacgag gcacccaga      780 ccgccaagct gaaggtgacc aagggtggcc cctgcccctt cgcctgggac atcctgtccc      840
ctcagttcat gtacggctcc aaggcctacg tgaagcaccc cgccgacatc cccgactact      900
```

| tgaagctgtc cttccccgag ggcttcaagt gggagcgcgt gatgaacttc gaggacggcg | 960 |
| gcgtggtgac cgtgacccag gactcctccc tgcaggacgg cgagttcatc tacaagtgaa | 1020 |
| gctgcgcggc accaacttcc cctccgacgg ccccgtaatg cagaagagga ccatgggctg | 1080 |
| gaggcctcct cgagcgatgt accccgagga cgcgccctga ggcgagatca gcagaggctg | 1140 |
| agctgagacg ccgccactac gacgctgagt cagaactact acaagtcaga gccggcagct | 1200 |
| gctggcctac acgtcacttc agtggaactt aacttcacaa agcgaggaac | 1250 |

```
<210> SEQ ID NO 19
<211> LENGTH: 1193
<212> TYPE: DNA
<213> ORGANISM: Artificial Sequence
<220> FEATURE:
<223> OTHER INFORMATION: MG1022 vector

<400> SEQUENCE: 19
```

| tttcaacgga atacaaatag cgagctggtt tagtgaccgt cagatccgct agcgctaccg | 60 |
| gactcagatc tcgagatgct ggcgctcatc tcccgcctgc tggactggtt ccgttcgctc | 120 |
| ttctggaagg aagagatgga gctgacgctc gtggggctgc agtactcggg caagaccacc | 180 |
| ttcgtcaatg tcatcgcgtc aggtcaattc agtgaagata tgatacccac agtgggcttc | 240 |
| aacatgagga aggtaactaa aggtaacgtc acaataaaga tctgggacat aggaggacta | 300 |
| ccccgatttc gaagcatgtg ggagcggtat tgcagaggag tcaatgctat tgtttacatg | 360 |
| atagatgctg cagatcgtga aaagatagaa gcttcccgaa atgagctaca taatcttcta | 420 |
| gataaaccac agttacaagg aattccagtg ctagtgcttg aaacaagag agatcttcct | 480 |
| aatgccttgg atgagaaaca gctaattgaa aaatgaatc tgtctgctat tcaggataga | 540 |
| gaaatttgct gctattcaat ttcttgcaaa gaaaaggata atatagatat cacacttcag | 600 |
| tggcttattc agcattcaaa atctagaaga agccgggatc cgatggtgag caagggcgag | 660 |
| gaggataaca tggccatcat caaggagttc atgcgcttca aggtgcacat ggagggctcc | 720 |
| gtgaacggcc acgagttcga atcgagggc gagggcgagg ccgcccccta cgagggcacc | 780 |
| cagaccgcca agctgaaggt gaccaagggt ggccccctgc ccttcgcctg ggacatcctg | 840 |
| tcccctcagt tcatgtacgg ctccaaggcc tacgtgaagc accccgccga catccccgac | 900 |
| tacttgaagc tgtccttccc cgagggcttc aagtgggagc gcgtgatgaa cttcgaggac | 960 |
| ggcggcgtgg tgaccgtgac ccaggactcc tccctgcagg acggcgagtt catctacagt | 1020 |
| gaagctgcgc ggcaccaact tcccctccga cgctcgtatg cagagagaca tgggctggga | 1080 |
| gctctcgagc gatgtacccg agacgcgcct gaggcgagat cagcagagct gagctgagga | 1140 |
| cgcgcactac gacgctgaag tcagacacta cagtcagaag ccgttcagct gcc | 1193 |

```
<210> SEQ ID NO 20
<211> LENGTH: 1311
<212> TYPE: DNA
<213> ORGANISM: Artificial Sequence
<220> FEATURE:
<223> OTHER INFORMATION: MG1023 vector

<400> SEQUENCE: 20
```

| ataaccccaa tacaaaagca gagctggttt agtgaccgtc agatccgcta gcgctaccgg | 60 |
| actcagatct cgagatgctg gcgctcatct cccgcctgct ggactggttc cgttcgctct | 120 |
| tctggaagga agagatggag ctgacgctcg tggggctgca gtactcgggc aagaacacct | 180 |
| tcgtcaatgt catcgcgtca ggtcaattca gtgaagatat gatacccaca gtgggcttca | 240 |

-continued

```
acatgaggaa ggtaactaaa ggtaacgtca caataaagat ctgggacata ggaggacaac    300
cccgatttcg aagcatgtgg gagcggtatt gcagaggagt caatgctatt gtttacatga    360
tagatgctgc agatcgtgaa aagatagaag cttcccgaaa tgagctacat aatcttctag    420
ataaaccaca gttacaagga attccagtgc tagtgcttgg aaacaagaga gatcttccta    480
atgccttgga tgagaaacag ctaattgaaa agatgaatct gtctgctatt caggatagag    540
aaatttgctg ctattcaatt tcttgcaaag aaaaggataa tatagatatc acacttcagt    600
ggcttattca gcattcaaaa tctagaagaa gccgggatcc gatggtgagc aagggcgagg    660
aggataacat ggccatcatc aaggagttca tgcgcttcaa ggtgcacatg gagggctccg    720
tgaacggcca cgagttcgag atcgagggcg agggcgaggg ccgcccctac gagggcaccc    780
agaccgccaa gctgaaggtg accaaggggtg gcccctgcc cttcgcctgg gacatcctgt    840
cccctcagtt catgtacggc tccaaggcct acgtgaagca ccccgccgac atccccgact    900
acttgaagct gtccttcccc gagggcttca gtgggagcg cgtgatgaac ttccaggacg    960
gcggcgtggt gaccgtgacc caggacttcc tcccctgcag gacggcgagt tcatctacaa   1020
agtgaagctg cgcgggcacc aacttccccc tccgacggcc ccgtaatgca gaagaaagac   1080
catgggcctg gaaggccttc ctcgagcgat gttacccgaa gacggcgtcc ctgaaaggcg   1140
agatatcagc atgaagctga agcttgaaga tcggcgtcac ttacgtactg ccttgagtca   1200
tagaccaact tacaagccat agaagtcggt gcagcttgtc ctgtccttta cacatgctct   1260
ataactatct aagtttggaa acattcacta cggtctacac agcaggatga c             1311
```

What is claimed is:

1. A method of increasing lysosome-mediated microautophagy of a lipid or protein substrate in a hepatic cell comprising administering a polypeptide consisting of the amino acid sequence:

(Arl8b$^{T34N}$; SEQ ID NO: 12)
MLALISRLLDWFRSLFWKEEMELTLVGLQYSGKNTFVNVIASGQFSEDMI

PTVGFNMRKVTKGNVTIKIWDIGGQPRFRSMWERYCRGVNAIVYMIDAAD

REKIEASRNELHNLLDKPQLQGIPVLVLGNKRDLPNALDEKQLIEKMNLS

AIQDREICCYSISCKEKDNIDITLQWLIQHSKSRRS.

2. A method for treating hypertriglyceridemia, hepatosteatosis, non-alcoholic fatty liver disease (NAFLD), hepatitis C virus (HCV) infection, hyperglycemia, hepatic insulin insensitivity, or obesity comprising administering to a subject in need thereof a polypeptide comprising the amino acid sequence:

(Arl8b$^{T34N}$; SEQ ID NO: 12)
MLALISRLLDWFRSLFWKEEMELTLVGLQYSGKTTFVNVIASGQFSEDMI

PTVGFNMRKVTKGNVTIKIWDIGGLPRFRSMWERYCRGVNAIVYMIDAAD

REKIEASRNELHNLLDKPQLQUPVLVLGNKRDLPNALDEKQLIEKMNLSA

IQDREICCYSISCKEKDNIDITLQWLIQHSKSRRS.

* * * * *

UNITED STATES PATENT AND TRADEMARK OFFICE
CERTIFICATE OF CORRECTION

PATENT NO. : 11,298,402 B2
APPLICATION NO. : 15/743213
DATED : April 12, 2022
INVENTOR(S) : Mohsen Amir Alipour et al.

It is certified that error appears in the above-identified patent and that said Letters Patent is hereby corrected as shown below:

In the Claims

In Claim 1, at Column 123, Line 41, the text: "(Arl8b$^{T34N}$; SEQ ID NO: 12)" should be replaced with: --(Arl8b$^{T34N}$; SEQ ID NO: 12)--.

In Claim 2, at Column 124, Lines 40-47, the text: "(Arl8b$^{T34N}$; SEQ ID NO: 12) MLALISRLLDWFRSLFWKEEMELTLVGLQYSGKTTFVNVIASGQFSEDMI PTVGFNMRKVTKGNVTIKIWDIGGLPRFRSMWERYCRGVNAIVYMIDAAD REKIEASRNELHNLLDKPQLQUPVLVLGNKRDLPNALDEKQLIEKMNLSA IQDREICCYSISCKEKDNIDITLQWLIQHSKSRRS" should be replaced with: --MLALISRLLDWFRSLFWKEEMELTLVGLQYSGKNTFVNVIASGQFSEDMIPTVGFNMRKV TKGNVTIKIWDIGGQPRFRSMWERYCRGVNAIVYMIDAADREKIEASRNELHNLLDKPQL QGIPVLVLGNKRDLPNALDEKQLIEKMNLSAIQDREICCYSISCKEKDNIDITLQWLIQHSK SRRS (Arl8b$^{T34N}$; SEQ ID NO: 12)--.

Signed and Sealed this
Ninth Day of August, 2022

*Katherine Kelly Vidal*

Katherine Kelly Vidal
*Director of the United States Patent and Trademark Office*